United States Patent
Catalano et al.

(10) Patent No.: US 12,221,444 B2
(45) Date of Patent: Feb. 11, 2025

(54) 5,6,7,7A-TETRAHYDROCYCLOPENTA[F]PYRIDO[1,2-H][1,7]NAPHTHYRIDIN-11(4BH)-ONE COMPOUNDS AND METHODS OF USE

(71) Applicant: GLAXOSMITHKLINE INTELLECTUAL, Middlesex (GB)

(72) Inventors: John G. Catalano, Research Triangle Park, NC (US); Pek Yoke Chong, Research Triangle Park, NC (US); Hamilton D. Dickson, Research Triangle Park, NC (US); Martin R. Leivers, Research Triangle Park, NC (US); Jason Gordon Weatherhead, Research Triangle Park, NC (US)

(73) Assignee: GlaxoSmithKline Intellectual Property Development Limited (GB)

( * ) Notice: Subject to any disclaimer, the term of this patent is extended or adjusted under 35 U.S.C. 154(b) by 638 days.

(21) Appl. No.: 17/509,769

(22) Filed: Oct. 25, 2021

(65) Prior Publication Data

US 2022/0144834 A1 May 12, 2022

Related U.S. Application Data

(63) Continuation of application No. 16/753,645, filed as application No. PCT/IB2018/057767 on Oct. 5, 2018, now abandoned.

(60) Provisional application No. 62/683,859, filed on Jun. 12, 2018, provisional application No. 62/681,146, filed on Jun. 6, 2018, provisional application No. 62/570,509, filed on Oct. 10, 2017, provisional application No. 62/568,633, filed on Oct. 5, 2017.

(51) Int. Cl.
*C07D 471/14* (2006.01)
*A61P 31/20* (2006.01)
*C07D 471/20* (2006.01)

(52) U.S. Cl.
CPC ............ *C07D 471/14* (2013.01); *A61P 31/20* (2018.01)

(58) Field of Classification Search
CPC ............................... C07D 471/14; A61P 31/20
USPC ......................................................... 514/278
See application file for complete search history.

(56) References Cited

FOREIGN PATENT DOCUMENTS

| | | |
|---|---|---|
| CN | 108727378 | 4/2017 |
| WO | 2015/173164 A1 | 11/2015 |
| WO | 2016/071215 A1 | 5/2016 |
| WO | 2018/047109 A1 | 3/2018 |
| WO | 2018/085619 A1 | 5/2018 |

OTHER PUBLICATIONS

Internal Search Report issued on Internal Application No. PCT/IB2018/057767, 2018.

*Primary Examiner* — Kristin A Vajda
(74) *Attorney, Agent, or Firm* — Hao Yin

(57) ABSTRACT

Compounds, specifically hepatitis B virus and/or hepatitis D virus inhibitors, more specifically compounds that inhibit HBe antigen and HBs antigen in a subject, for the treatment of viral infections, and methods of preparing and using such compounds.

9 Claims, No Drawings

5,6,7,7A-TETRAHYDROCYCLOPENTA[F]PYRIDO[1,2-H][1,7]NAPHTHYRIDIN-11(4BH)-ONE COMPOUNDS AND METHODS OF USE

FIELD OF THE INVENTION

The present invention relates to compounds useful for treatment of HBV in animals, and more particularly for treatment of HBV in humans.

BACKGROUND OF THE INVENTION

Hepatitis B is a viral disease transmitted parenterally by contaminated material such as blood and blood products, contaminated needles, sexually and vertically from infected or carrier mothers to their offspring. In those areas of the world where the disease is common vertical transmission at an early age results in a high proportion of infected individuals becoming chronic carriers of hepatitis B. It is estimated by the World Health Organization that more than 2 billion people have been infected worldwide, with about 4 million acute cases per year, 1 million deaths per year, and 350-400 million chronic carriers. Approximately 25% of carriers die from chronic hepatitis, cirrhosis, or liver cancer and nearly 75% of chronic carriers are Asian. Hepatitis B virus (HBV) is the second most significant carcinogen behind tobacco, causing from 60% to 80% of all primary liver cancer. HBV is 100 times more contagious than HIV.

HBV is transmitted through percutaneous or parenteral contact with infected blood, body fluids, and by sexual intercourse. HBV is able to remain on any surface it comes into contact with for about a week, e.g. table-tops, razor blades, blood stains, without losing infectivity. However, HBV cannot cross the skin or the mucous membrane barrier. Some break in this barrier, which can be minimal and insignificant, is required for transmission.

HBV is a small enveloped DNA virus belonging to the hepadnavirus family. The virus replicates through an RNA intermediate form by reverse transcription, which in practice relates them to retroviruses, like HIV. Although replication takes place in the liver, the virus spreads to the blood where viral proteins and antibodies against them are found in infected people. HBV is many times more infectious than HIV due to the greater concentrations of HBV virus found in the bloodstream at any given time.

HBV infection results in the production of two different particles: 1) the HBV virus itself (or Dane particle) which includes a viral capsid assembled from the HBV core antigen protein (HBcAg) and is covered by the hepatitis B surface antigen (HBsAg) and is capable of reinfecting cells and 2) subviral particles (or SVPs) which are high density lipoprotein-like particles comprised of lipids, cholesterol, cholesterol esters and the small and medium forms of the hepatitis B surface antigen (HBsAg) which are non-infectious. For each viral particle produced, 1,000-10,000 SVPs are released into the blood. As such SVPs (and the HBsAg protein they carry) represent the overwhelming majority of viral protein in the blood. HBV infected cells also secrete a soluble proteolytic product of the pre-core protein called the HBV e-antigen (HBeAg).

The hepatitis D virus (HDV) uses HBsAg to form its viral structure (Taylor, 2006, Virology, 344: 71-76) and as such, HDV infection can only occur in subjects with concomitant HBV infection. While the incidence of HDV co-infection in asymptomatic HBV carriers and chronic HBV-related liver disease is low in countries with a low incidence of HBV infection, it is a significant complication in HBV-infected subjects in countries with a high incidence of HBV infection and can increase the rate of progression of liver disease to fulminant hepatitis. As such, the clear unmet medical need in HBV infection is even more pressing in HBV/HDV co-infected subjects.

The current conventional methods of treatment for HBV include interferon or thymosin α1-based immunotherapies and the suppression of viral production by inhibition of the HBV polymerase (e.g., "nucs"). HBV polymerase inhibitors are effective in reducing viral production, but have little to no effect in rapidly reducing HBsAg blood levels or can slowly reduce HBsAg with long term treatment in a limited number of patients (as is the case with tenofovir disoproxil fumarate). Interferon based immunotherapy can achieve a reduction of both viral production and early removal of HBsAg from the blood but only in a small percentage of treated subjects. The generally accepted role of HBsAg in the blood is to sequester anti-HBsAg antibodies and allow infectious viral particles to escape immune detection which is likely one of the reasons why HBV infection remains a chronic condition. In addition HBsAg, HBeAg and HBcAg all have immuno-inhibitory properties as discussed below and the persistence of these viral proteins in the blood of patients following the administration of any of the currently available treatments for HBV as described above is likely having a significant impact in preventing patients from achieving immunological control of their HBV infection.

Although the three primary HBV proteins (HBsAg, HBeAg and HBcAg) all have immunoinhibitory properties (see below), HBsAg comprises the overwhelming majority of HBV protein in the circulation of HBV infected subjects. Additionally, while the removal (via seroconversion) of HBeAg or reductions in serum viremia are not correlated with the development of sustained control of HBV infection off treatment, the removal of serum HBsAg from the blood (and seroconversion) in HBV infection is a well-recognized excellent prognostic indicator of antiviral response on treatment which will lead to control of HBV infection off treatment (although this only occurs in a small fraction of patients receiving immunotherapy). Thus, while reduction of all three major HBV proteins (HBsAg, HBeAg and HBcAg) may result in the optimal removal of inhibitory effect, the removal of HBsAg alone may be sufficient in and of itself to remove the bulk of the viral inhibition of immune function in subjects with HBV infection.

Therefore, in the absence of any current treatment regimen which can restore immunological control of HBV in a large proportion of patients, there is a need to be provided with an effective treatment against HBV infection and HBV/HDV co-infection which can restore immunological control in the majority of patients.

Hepatitis B viral infections, in conjunction with Hepatitis D viral infections, are a continuing medical problem because, like any rapidly-replicating infectious agent, there are continuing mutations that help some sub-populations of HBV become resistant to current treatment regimens. At the present time there are no effective therapeutic agents for treating humans infected with HBV and/or Hepatitis D virus (HDV) infections which result in seroconversion to the virus in the body, or which effect a 90% reduction of antigen, compared to baseline numbers before treatment, in persons suffering from a hepatitis B viral infection. Currently the recommended therapies for chronic HBV and/or HDV infection by the American Association for the Study of Liver Diseases (AASLD) and the European Association for the Study of the Liver (EASL) include interferon alpha (INFα), pegylated interferon alpha-2a (Peg-IFN2a), entecavir, and tenofovir. However, typical interferon therapy is 48-weeks and results in serious and unpleasant side effects, and HBeAg seroconversion, 24 weeks after therapy has ceased, ranges from only 27-36%. Seroconversion of HBsAg is even lower—only 3% observed immediately after treatment ceases, with an increase to upwards of 12% after 5 years.

The nucleoside and nucleotide therapies entecavir and tenofovir are successful at reducing viral load, but the rates of HBeAg seroconversion and HBsAg loss are even lower than those obtained using IFNα therapy. Other similar therapies, including lamivudine (3TC), telbivudine (LdT), and adefovir are also used, but for nucleoside/nucleotide therapies in general, the emergence of resistance limits therapeutic efficacy.

Recent clinical research has found a correlation between seroconversion and reductions in HBeAg (Fried et al (2008) Hepatology 47:428) and reductions in HBsAg (Moucari et al (2009) Hepatology 49:1151). Reductions in antigen levels may have allowed immunological control of HBV infection because high levels of antigens are thought to induce immunological tolerance. Current nucleoside therapies for HBV are capable of dramatic reductions in serum levels of HBV but have little impact on HBeAg and HBsAg levels. Antisense therapy differs from nucleoside therapy in that it can directly target the transcripts for the antigens and thereby reduce serum HBeAg and HBsAg levels. But antisense therapy is expensive and requires intravenous delivery.

Thus, there is a need in the art to discover and develop new anti-viral therapies. More particularly, there is a need for new anti-HBV therapies capable of increasing HBeAg and HBsAg seroconversion rates. These serum markers are indicative of immunological control of HBV infection and leads to an improved prognosis, i.e. prevention of liver disease and progression to cirrhosis, prevention of liver failure, prevention of hepatocellular cancer (HCC), prevention of liver disease-related transplantation, and prevention of death.

SUMMARY OF THE INVENTION

Embodiments of the present invention features compounds of Formula I:

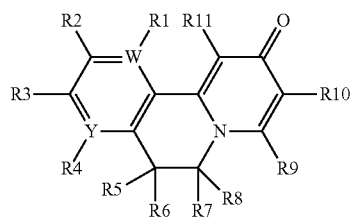

Formula I wherein
W and Y are independently C or N, with the proviso that W and Y are not both C;
wherein
if W is C, then $R^1$ is hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N—$C_xH_{2x}$-phenyl wherein x is 0, 1, 2, 3, 4, 5, 6; or —$OR^{12}$; and if Y is C, then $R^4$ is hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N—$C_xH_{2x}$-phenyl wherein x is 0, 1, 2, 3, 4, 5, 6; or —$OR^{12}$;
wherein
if W is N, then $R^1$ is absent; and
if Y is N, then $R^4$ is absent;
$R^2$ and $R^3$ are independently selected from hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N—$C_xH_{2x}$-phenyl wherein x is 0, 1, 2, 3, 4, 5, 6; or —$OR^{12}$; $R^5$ and $R^6$ are independently hydrogen, hydroxy, halogen, cyano, amino alkyl or substituted alkyl, alkoxy or substituted alkoxy, cycloalkyl or substituted cycloalkyl, alkenyl or substituted alkenyl; aryl or substituted aryl, heteroaryl or substituted aryl, —$C_xH_{2x}$-phenyl or —O—$C_xH_{2x}$-phenyl wherein x is 0, 1, 2, 3, 4, 5 or 6;
$R^7$ and $R^8$ are independently hydrogen, hydroxy, halogen, cyano, amino, alkyl or substituted alkyl, alkoxy or substituted alkoxy, cycloalkyl or substituted cycloalkyl, alkenyl or substituted alkenyl; aryl or substituted aryl, heteroaryl, —$C_xH_{2x}$-phenyl or —O—$C_xH_{2x}$-phenyl wherein x is 0, 1, 2, 3, 4, 5 or 6;
or $R^5$ and $R^6$ together form a 3- to 8-membered cycloalkyl ring or 3- to 8-membered heterocycloalkyl ring, wherein the heteroatom in the heterocycloalkyl ring is O, N, $NR^{22}$, S, $SR^{22}$ or $SR^{22}R^{22'}$, wherein the 3- to 8-membered heterocycloalkyl ring is optionally substituted with $R^{13}$, $R^{13'}$, $R^{14}$ and/or $R^{14'}$;
or $R^6$ and $R^7$ together form a 3- to 8-membered cycloalkyl ring or heterocycloalkyl ring comprising one heteroatom or two or more heteroatoms, optionally substituted with $R^{15}$, $R^{15'}$, $R^{16}$ and/or $R^{16'}$, wherein the one heteroatom in the heteroalkyl ring is $NR^{20}$ and the two or more heteroatoms are selected from N, $NR^{22}$, O, S, $SR^{22}$ and $SR^{22}R^{22'}$;
or $R^7$ and $R^8$ together form a 3- to 8-membered cycloalkyl ring or 3- to 8-membered heterocycloalkyl ring, optionally substituted with $R^{17}$, $R^{17'}$, $R^{18}$ and/or $R^{18'}$ wherein the heteroatom in the heterocycloalkyl ring is O, N, $NR^{22}$, S, $SR^{22}$ or $SR^{22}R^{22'}$;
$R^9$ is a bond, hydrogen, hydroxy, halogen, cyano, amino, alkyl or substituted alkyl, alkoxy or substituted alkoxy, cycloalkyl or substituted cycloalkyl, alkenyl or substituted alkenyl, heterocycloalkyl or substituted heterocycloalkyl, aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6;

$R^{10}$ is a substituent shown in Table 2 or a tautomer thereof;

or $R^9$ is a bond and $R^9$ and $R^{10}$ together form an oxaborole ring;

$R^{11}$ is hydrogen, hydroxy, halogen, cyano, amino, alkyl or substituted alkyl; alkenyl or substituted alkenyl; alkoxy or substituted alkoxy; cycloalkyl or substituted cycloalkyl; heterocycloalkyl or substituted heterocycloalkyl, aryl, heteroaryl, —$C_xH_{2x}$-phenyl or —O—$C_xH_{2x}$-phenyl wherein x is 0, 1, 2, 3, 4, 5 or 6;

$R^{12}$ is hydrogen; alkyl or substituted alkyl, alkoxy or substituted alkoxy, cycloalkyl or substituted cycloalkyl, heterocycloalkyl or substituted heterocycloalkyl, aryl or substituted aryl, heteroaryl or substituted heteroaryl;

$R^{13}$, $R^{13'}$, $R^{14}$ and $R^{14'}$ are independently hydrogen, hydroxy, halogen, amino, aminoalkyl, cyano, $C_{1-6}$alkyl, $C_{1-6}$alkoxy, carbonyl, carboxamide, amide; or $R^{13}$ and $R^{13'}$ or $R^{14}$ and $R^{14'}$ together form a 3- to 8-membered cycloalkyl ring or 3- to 8-membered heterocycloalkyl ring, optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;

$R^{15}$, $R^{15'}$, $R^{16}$ and $R^{16'}$ are independently hydrogen, hydroxy, halogen, amino, cyano, $C_{1-6}$alkyl, or $C_{1-6}$alkoxy; or $R^{15}$ and $R^{15'}$ or $R^{16}$ and $R^{16'}$ together form a 3- to 8-membered cycloalkyl ring or 3- to 8-membered heterocycloalkyl ring optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;

$R^{17}$, $R^{17'}$, $R^{18}$ and $R^{18'}$ are independently hydrogen, hydroxy, halogen, amino, cyano, $C_{1-6}$alkyl, or $C_{1-6}$alkoxy; or $R^{17}$ and $R^{18}$ or $R^{17'}$ and $R^{18'}$ together form a 3- to 8-membered cycloalkyl ring or 3- to 8-membered heterocycloalkyl ring, optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;

$R^{19}$, $R^{19'}$ and $R^{19''}$ are independently hydrogen, $C_{1-6}$alkyl, $C_{3-8}$cycloalkyl, $C_{2-6}$alkenyl, $C_{1-6}$alkoxy, phenyl, $C_{1-6}$alkylimidizole, $C_{1-6}$alkyltriazole, $C_{1-6}$alkyltetrazole, $C_{1-6}$alkylthiazole, $C_{1-6}$alkyloxazole, $C_{1-6}$alkyldioxazole; $C_{1-6}$alkyloxazolidone; and $R^{20}$ and $R^{21}$ are independently hydrogen, $C_{1-6}$alkyl, $C_{3-8}$cycloalkyl, $C_{2-6}$alkenyl, $C_{1-6}$alkoxy, phenyl, $C_{1-6}$alkylimidizole, $C_{1-6}$alkyltriazole, $C_{1-6}$alkyltetrazole, $C_{1-6}$alkylthiazole, $C_{1-6}$alkyloxazole, $C_{1-6}$alkyldioxazole, $C_{1-6}$alkyloxazolidone, or $R^{20}$ and $R^{21}$ together with the nitrogen to which they are attached form unsubstituted pyrrolidinyl, unsubstituted piperidinyl, or unsubstituted morpholinyl; or form carboxyl-substituted pyrrolidinyl, carboxyl-substituted piperidinyl or carboxyl-substituted morpholinyl; and $R^{22}$ and $R^{22'}$ are independently selected from hydrogen, oxygen, $C_{1-6}$alkyl or substituted $C_{1-6}$alkyl, $C_{1-6}$alkoxy or substituted $C_{1-6}$alkoxy, $C_{3-8}$cycloalkyl or substituted $C_{3-8}$cycloalkyl, $C_{2-6}$alkenyl or substituted $C_{2-6}$alkenyl, aryl or substituted aryl, including substituted or unsubstituted $C_{1-6}$alkylimidizole, substituted or unsubstituted $C_{1-6}$alkyltriazole, $C_{1-6}$alkyltetrazole, $C_{1-6}$alkylthiazole, substituted or unsubstituted $C_{1-6}$alkyloxazole, $C_{1-6}$alkyldioxazole; $C_{1-6}$alkyloxazolidone; —$COR^{19}$, —$COOR^{19'}$, —$CSOR^{19''}$, —$CONR^{20}R^{21}$, or a pharmaceutically acceptable salt thereof.

Another embodiment provides a compound of Formula IA or Formula IB:

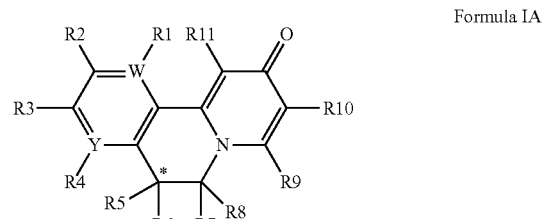

Formula IA

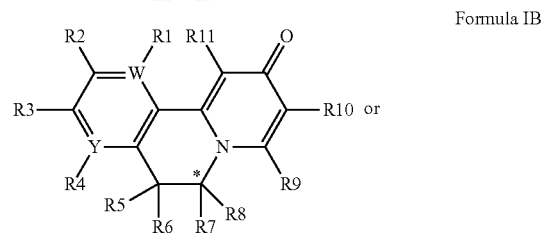

Formula IB wherein

C* is a carbon atom stereocenter which has a configuration which is (R) or (S);

W and Y are independently C or N, with the proviso that W and Y are not both C;

wherein if W is C, then $R^1$ is hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N—$C_xH_{2x}$-phenyl wherein x is 0, 1, 2, 3, 4, 5, 6; or —$OR^{12}$; and if Y is C, then $R^4$ is hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N— $C_xH_{2x}$-phenyl wherein x is 0, 1, 2, 3, 4, 5, 6; or —$OR^{12}$;

wherein if W is N, then $R^1$ is absent; and if Y is N, then $R^4$ is absent;

$R^2$ and $R^3$ are independently selected from hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N— $C_xH_{2x}$-phenyl wherein x is 0, 1, 2, 3, 4, 5, 6; or —$OR^{12}$;

$R^5$ and $R^6$ are independently hydrogen, hydroxy, halogen, cyano, amino alkyl or substituted alkyl, alkoxy or substituted alkoxy, cycloalkyl or substituted cycloalkyl, alkenyl or substituted alkenyl; aryl or substituted aryl, heteroaryl or substituted aryl, —$C_xH_{2x}$-phenyl or —O—$C_xH_{2x}$-phenyl wherein x is 0, 1, 2, 3, 4, 5 or 6;

$R^7$ and $R^8$ are independently hydrogen, hydroxy, halogen, cyano, amino, alkyl or substituted alkyl, alkoxy or substituted alkoxy, cycloalkyl or substituted cycloalkyl, alkenyl or substituted alkenyl; aryl or substituted aryl, heteroaryl, —$C_xH_{2x}$-phenyl or —O—$C_xH_{2x}$-phenyl wherein x is 0, 1, 2, 3, 4, 5 or 6;

or $R^5$ and $R^6$ together form a 3- to 8-membered cycloalkyl ring or 3- to 8-membered heterocycloalkyl ring, wherein the heteroatom in the heterocycloalkyl ring is O, N, $NR^{22}$, S, $SR^{22}$ or $SR^{22}R^{22'}$, wherein the 3- to 8-membered heterocycloalkyl ring is optionally substituted with $R^{13}$, $R^{13'}$, $R^{14}$ and/or $R^{14'}$;

or $R^6$ and $R^7$ together form a 3- to 8-membered cycloalkyl ring or heterocycloalkyl ring comprising one heteroatom or two or more heteroatoms, optionally substituted with $R^{15}$, $R^{15'}$, $R^{16}$ and/or $R^{16'}$, wherein the one heteroatom in the heteroalkyl ring is $NR^{20}$ and the two or more heteroatoms are selected from N, $NR^{22}$, O, S, $SR^{22}$ and $SR^{22}R^{22'}$;

or $R^7$ and $R^8$ together form a 3- to 8-membered cycloalkyl ring or 3- to 8-membered heterocycloalkyl ring, optionally substituted with $R^{17}$, $R^{17'}$, $R^{18}$ and/or $R^{18'}$, wherein the heteroatom in the heterocycloalkyl ring is O, N, $NR^{22}$, S, $SR^{22}$ or $SR^{22}R^{22'}$;

$R^9$ is a bond, hydrogen, hydroxy, halogen, cyano, amino, alkyl or substituted alkyl, alkoxy or substituted alkoxy, cycloalkyl or substituted cycloalkyl, alkenyl or substituted alkenyl, heterocycloalkyl or substituted heterocycloalkyl, aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6;

$R^{10}$ is a substituent shown in Table 2 or a tautomer thereof;

or $R^9$ is a bond and $R^9$ and $R^{10}$ together form an oxaborole ring;

$R^{11}$ is hydrogen, hydroxy, halogen, cyano, amino, alkyl or substituted alkyl; alkenyl or substituted alkenyl; alkoxy or substituted alkoxy; cycloalkyl or substituted cycloalkyl; heterocycloalkyl or substituted heterocycloalkyl, aryl, heteroaryl, —$C_xH_{2x}$-phenyl or —O—$C_xH_{2x}$-phenyl wherein x is 0, 1, 2, 3, 4, 5 or 6;

$R^{12}$ is hydrogen; alkyl or substituted alkyl, alkoxy or substituted alkoxy, cycloalkyl or substituted cycloalkyl, heterocycloalkyl or substituted heterocycloalkyl, aryl or substituted aryl, heteroaryl or substituted heteroaryl;

$R^{13}$, $R^{13'}$, $R^{14}$ and $R^{14'}$ are independently hydrogen, hydroxy, halogen, amino, aminoalkyl, cyano, $C_{1-6}$alkyl, $C_{1-6}$alkoxy, carbonyl, carboxamide, amide; or $R^{13}$ and $R^{13'}$ or $R^{14}$ and $R^{14'}$ together form a 3- to 8-membered cycloalkyl ring or 3- to 8-membered heterocycloalkyl ring, optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;

$R^{15}$, $R^{15'}$, $R^{16}$ and $R^{16'}$ are independently hydrogen, hydroxy, halogen, amino, cyano, $C_{1-6}$alkyl, or $C_{1-6}$alkoxy; or $R^{15}$ and $R^{15'}$ or $R^{16}$ and $R^{16'}$ together form a 3- to 8-membered cycloalkyl ring or 3- to 8-membered heterocycloalkyl ring optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;

$R^{17}$, $R^{17'}$, $R^{18}$ and $R^{18'}$ are independently hydrogen, hydroxy, halogen, amino, cyano, $C_{1-6}$alkyl, or $C_{1-6}$alkoxy; or $R^{17}$ and $R^{18}$ or $R^{17'}$ and $R^{18'}$ together form a 3- to 8-membered cycloalkyl ring or 3- to 8-membered heterocycloalkyl ring, optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;

$R^{19}$, $R^{19''}$ and $R^{19'''}$ are independently hydrogen, $C_{1-6}$alkyl, $C_{3-8}$cycloalkyl, $C_{2-6}$alkenyl, $C_{1-6}$alkoxy, phenyl, $C_{1-6}$alkylimidizole, $C_{1-6}$alkyltriazole, $C_{1-6}$alkyltetrazole, $C_{1-6}$alkylthiazole, $C_{1-6}$alkyloxazole, $C_{1-6}$alkyldioxazole; $C_{1-6}$alkyloxazolidone; and $R^{20}$ and $R^{21}$ are independently hydrogen, $C_{1-6}$alkyl, $C_{3-8}$cycloalkyl, $C_{2-6}$alkenyl, $C_{1-6}$alkoxy, phenyl, $C_{1-6}$alkylimidizole, $C_{1-6}$alkyltriazole, $C_{1-6}$alkyltetrazole, $C_{1-6}$alkylthiazole, $C_{1-6}$alkyloxazole, $C_{1-6}$alkyldioxazole; $C_{1-6}$alkyloxazolidone, or $R^{20}$ and $R^{21}$ together with the nitrogen to which they are attached form unsubstituted pyrrolidinyl, unsubstituted piperidinyl, or unsubstituted morpholinyl; or form carboxyl-substituted pyrrolidinyl, carboxyl-substituted piperidinyl or carboxyl-substituted morpholinyl; and $R^{22}$ and $R^{22'}$ are independently selected from hydrogen, oxygen, $C_{1-6}$alkyl or substituted $C_{1-6}$alkyl, $C_{1-6}$alkoxy or substituted $C_{1-6}$alkoxy, $C_{3-8}$cycloalkyl or substituted $C_{3-8}$cycloalkyl, $C_{2-6}$alkenyl or substituted $C_{2-6}$alkenyl, aryl or substituted aryl, including substituted or unsubstituted $C_{1-6}$alkylimidizole, substituted or unsubstituted $C_{1-6}$ alkyltriazole, $C_{1-6}$alkyltetrazole, $C_{1-6}$alkylthiazole, substituted or unsubstituted $C_{1-6}$ alkyloxazole, $C_{1-6}$alkyldioxazole; $C_{1-6}$alkyloxazolidone; —$COR^{19}$, —$COOR^{19'}$, —$CSOR^{19''}$, —$CONR^{20}R^{21}$, or a pharmaceutically acceptable salt thereof.

In another particular embodiment of the invention there are provided compounds of Formula I, Formula IA or Formula IB as described herein, including salts and prodrugs thereof, wherein $R^{10}$ is selected from —$CO_2H$, —$B(OH)_2$, —$NHSO_2R^{25'}$, —$NCO_2R^{25}$,

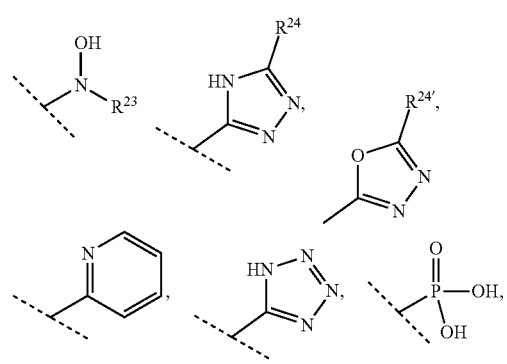

-continued

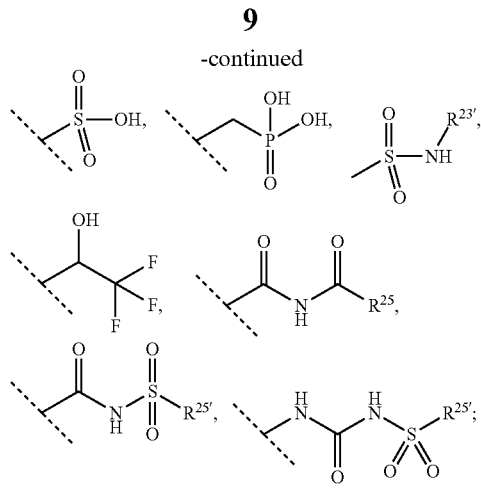

wherein
$R^{23}$ and $R^{23'}$ are independently selected from H, alkyl or substituted alkyl, cycloalkyl or substituted cycloalkyl, alkenyl or substituted alkenyl, heterocycloalkyl or substituted heterocycloalkyl, aryl or substituted aryl, heteroaryl or substituted heteroaryl,

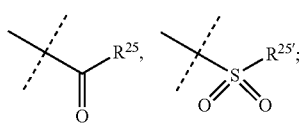

$R^{24}$ and $R^{24'}$ are independently selected from H, hydroxyl, amino or substituted amino, alkyl or substituted alkyl, cycloalkyl or substituted cycloalkyl, alkenyl or substituted alkenyl, thiol or thioalkyl, heterocycloalkyl or substituted heterocycloalkyl, aryl or substituted aryl, heteroaryl or substituted heteroaryl; and $R^{25}$ and $R^{25'}$ are independently selected from H, OH, alkyl or substituted alkyl, cycloalkyl or substituted cycloalkyl, alkenyl or substituted alkenyl, heterocycloalkyl or substituted heterocycloalkyl, aryl or substituted aryl and heteroaryl or substituted heteroaryl; or a pharmaceutically acceptable salt thereof.

In another particular embodiment of the invention there are provided compounds of Formula I, Formula IA or Formula IB, including salts and prodrugs thereof, wherein
$R^1$, $R^2$, $R^3$, $R^4$, $R^5$, $R^6$, $R^7$, $R^9$ and $R^{11}$ are as described herein;
$R^8$ is isopropyl; and
$R^{10}$ is selected from $—CO_2H$, $—B(OH)_2$, $—NHSO_2R^{25'}$, $—NCO_2R^{25}$,

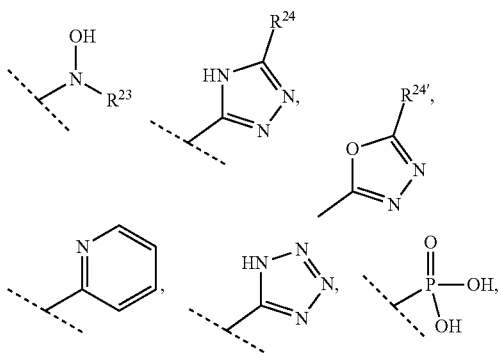

-continued

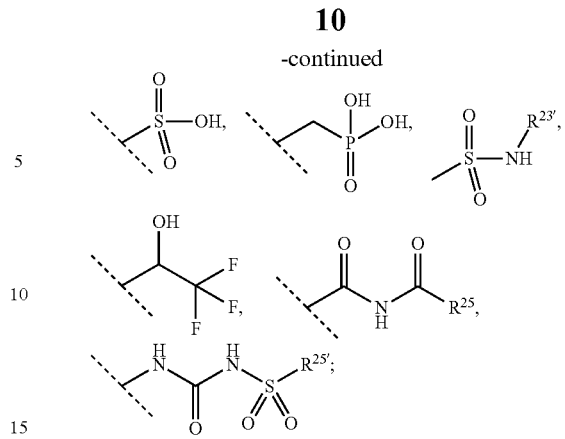

wherein
$R^{23}$ and $R^{23'}$ are independently selected from H, alkyl or substituted alkyl, cycloalkyl or substituted cycloalkyl, alkenyl or substituted alkenyl, heterocycloalkyl or substituted heterocycloalkyl, aryl or substituted aryl, heteroaryl or substituted heteroaryl,

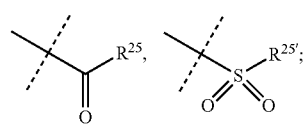

$R^{24}$ and $R^{24'}$ are independently selected from H, hydroxyl, amino or substituted amino, alkyl or substituted alkyl, cycloalkyl or substituted cycloalkyl, alkenyl or substituted alkenyl, thiol or thioalkyl, heterocycloalkyl or substituted heterocycloalkyl, aryl or substituted aryl, heteroaryl or substituted heteroaryl; and $R^{25}$ and $R^{25'}$ are independently selected from H, OH, alkyl or substituted alkyl, cycloalkyl or substituted cycloalkyl, alkenyl or substituted alkenyl, heterocycloalkyl or substituted heterocycloalkyl, aryl or substituted aryl and heteroaryl or substituted heteroaryl; or a pharmaceutically acceptable salt thereof.

In another embodiment there is provided a compound of Formula I, Formula IA or Formula IB, including salts and prodrugs thereof, wherein
$R^1$, $R^2$, $R^3$, $R^4$, $R^9$ and $R^{11}$ are as described;
$R^5$, $R^6$ and $R^7$ are H;
$R^8$ is isopropyl;
$R^{10}$ is selected from $—CO_2H$, $—B(OH)_2$, $—NHSO_2R^{25'}$, $—NCO_2R^{25}$,

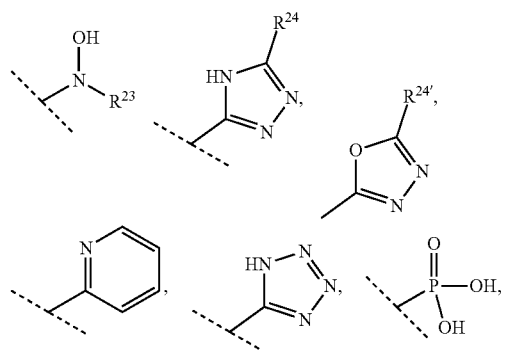

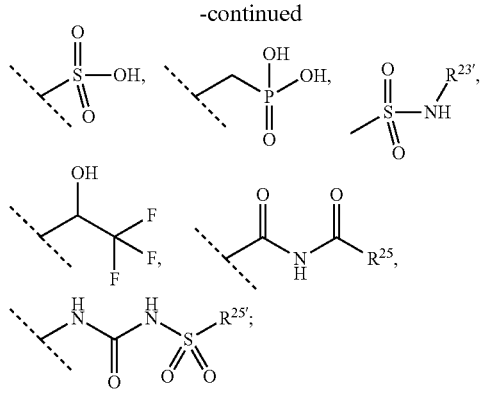

wherein
R$^{23}$ and R$^{23'}$ are independently selected from H, alkyl or substituted alkyl, cycloalkyl or substituted cycloalkyl, alkenyl or substituted alkenyl, heterocycloalkyl or substituted heterocycloalkyl, aryl or substituted aryl, heteroaryl or substituted heteroaryl,

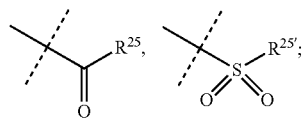

R$^{24}$ and R$^{24'}$ are independently selected from H, hydroxyl, amino or substituted amino, alkyl or substituted alkyl, cycloalkyl or substituted cycloalkyl, alkenyl or substituted alkenyl, thiol or thioalkyl, heterocycloalkyl or substituted heterocycloalkyl, aryl or substituted aryl, heteroaryl or substituted heteroaryl; and R$^{25}$ and R$^{25'}$ are independently selected from H, OH, alkyl or substituted alkyl, cycloalkyl or substituted cycloalkyl, alkenyl or substituted alkenyl, heterocycloalkyl or substituted heterocycloalkyl, aryl or substituted aryl and heteroaryl or substituted heteroaryl; or a pharmaceutically acceptable salt thereof.

In particular embodiments, there is provided a method for the treatment of a hepatitis B infection or hepatitis B/hepatitis D co-infection, particularly a method for the treatment of a hepatitis B infection or hepatitis B/hepatitis D co-infection in a human, the method comprising administering to a subject in need of such treatment a compound of Formula I, IA or IB as described herein.

In yet another embodiment, the present invention provides a method for the treatment of a hepatitis B infection or hepatitis B/hepatitis D co-infection, particularly a method for the treatment of a hepatitis B infection or hepatitis B/hepatitis D co-infection in a human, the method comprising administering to a subject in need of such treatment a first pharmaceutically acceptable agent comprising a compound of Formula I, Formula IA or Formula IB as described herein, in combination with a second pharmaceutically acceptable agent that stimulates immune function and a third pharmaceutically acceptable agent comprising an antiviral compound.

In still other embodiments, the administration of a compound of Formula I, IA or IB as described herein inhibits the release of hepatitis B surface antigen (HBsAg), HB core antigen protein (HBcAg), and/or hepatitis B pre-core protein known as the HBV e-antigen antigen (HBeAg) from infected hepatocytes.

Embodiments of the present invention features compounds that inhibit levels of HBe and/or HBs antigens in a subject infected with hepatitis B virus, and therefore are useful for treating human hepatitis B virus infections, and disease and symptoms associated with such virus infections. The foregoing features of the invention will be more readily understood by reference to the following detailed description, taken with reference to the accompanying Tables, in which:

Table 1 is a listing of compounds of Formula I described herein.

Table 2 is a listing of R$^{10}$ substituents for compounds of Formula I as described herein.

Table 3 is summary of HepAD38 cells—HBsAg ELISA and cytotoxicity assays showing EC$_{50}$ values measured for a tested compound against HBs antigens (HBsAg).

DETAILED DESCRIPTION OF SPECIFIC EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

As used herein unless otherwise specified, "alkyl" refers to a monovalent saturated aliphatic hydrocarbyl group having from 1 to 14 carbon atoms and, in some embodiments, from 1 to 6 carbon atoms The term "alkyl" includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—). Alkyl groups may also be substituted, for example, with one or more alkyl, cycloalkyl, heterocycloalkyl, alkoxy, amino, aminoalkyl, thiol, thioalkyl, aryl, heteroaryl, halo or haloalkyl substituents.

"Alkoxy" or "alkoxyl" refers to the group —O-alkyl wherein alkyl is defined herein. Alkoxy includes, by way of example, methoxy, ethoxy, n-propoxy, isopropoxy, n-butoxy, t-butoxy, sec-butoxy, n-pentoxy, morpholinylpropoxy, piperidinylethoxy. Alkoxyl groups may also be substituted, for example, with one or more alkyl, cycloalkyl, heterocycloalkyl, alkoxy, amino, aminoalkyl, thiol, thioalkyl, aryl, heteroaryl, halo or haloalkyl substituents.

"Amino" refers to the group —NR$^a$R$^b$ where R$^a$ and R$^b$ are independently selected from hydrogen, hydroxy, alkyl or substituted alkyl, alkenyl or substituted alkenyl, aryl or substituted aryl, cycloalkyl or substituted cycloalkyl, heterocycloalkyl or substituted heterocycloalkyl, heteroaryl or substituted heteroaryl, and wherein R$^a$ and R$^b$ are optionally joined together with the nitrogen bound thereto to form a heterocyclic group. When R$^a$ is hydrogen and R$^b$ is alkyl, the amino group is sometimes referred to herein as alkylamino or aminoalkyl. When R$^a$ and R$^b$ are alkyl, the amino group is sometimes referred to herein as dialkylamino. When referring to a monosubstituted amino, it is meant that either $R^a$ or $R^b$ is hydrogen but not both. When referring to a disubstituted amino, it is meant that neither $R^a$ nor $R^b$ are hydrogen.

"Aryl" refers to an aromatic group of from 5 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring). Aryl groups may also be substituted, for example, with one or more alkyl, cycloalkyl, heterocycloalkyl, alkoxy, amino, aminoalkyl, thiol, thioalkyl, aryl, heteroaryl, halo or haloalkyl substituents.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "Cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Cycloalkyl groups may also be substituted, for example, with one or more alkyl, cycloalkyl, heterocycloalkyl, alkoxy, amino, aminoalkyl, thiol, thioalkyl, aryl, heteroaryl, halo or haloalkyl substituents.

"Halo" or "halogen" refers to fluoro, chloro, bromo, and iodo.

"Haloalkyl" refers to substitution of alkyl groups with 1 to 9 (e.g. when the alkyl group has 3 carbon atoms, such as a t-butyl group fully-substituted with halogen) or in some embodiments 1 to 3 halo groups (e.g. trifluoromethyl).

"Hydroxy" or "hydroxyl" refers to the group —OH.

"Heteroaryl" refers to an aromatic group of from 1 to 14 carbon atoms and 1 to 6 heteroatoms selected from oxygen, nitrogen, sulfur, phosphorus, silicon and boron, and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthyl, naphthylpryidyl, oxazolyl, quinolyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl. Heteroaryl groups may also be substituted, for example, with one or more alkyl, cycloalkyl, heterocycloalkyl, alkoxy, amino, aminoalkyl, thiol, thioalkyl, aryl, heteroaryl, halo or haloalkyl substituents.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms. Heterocyclyl or heterocycloalkyl groups may also be substituted, for example, with one or more alkyl, cycloalkyl, heterocycloalkyl, alkoxy, amino, aminoalkyl, thiol, thioalkyl, aryl, heteroaryl, halo or haloalkyl substituents.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, naphthalene, oxazole, oxopyrrolidine, piperidine, piperazine, indoline, phthalimide, quinoline, 1,2,3,4-tetrahydroisoquinoline, 4,5,6,7-tetrahydrobenzo[b]thiophene, thiazole, cyclopentathiazole, thiazolidine, thiophene, benzo[b]thiophene, morpholine, thiomorpholine (also referred to as thiamorpholine), piperidine, pyrrolidine, and tetrahydrofuranyl.

"Fused heterocyclic" or "fused heterocyclyl" refers to a 3 to 10 member cyclic substituent formed by the replacement of two hydrogen atoms at different carbon atoms in a cycloalkyl ring structure, as exemplified by the following cyclopentathiazole structure:

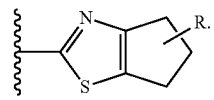

Fused heterocyclyl groups may also be substituted, for example, with one or more alkyl, cycloalkyl, heterocycloalkyl, alkoxy, amino, aminoalkyl, thiol, thioalkyl, aryl, heteroaryl, halo or haloalkyl substituents.

"Fused aryl and fused heteroaryl" refers to a 5 to 6 member aryl structure or heteroaryl structure fused with a 5- to 6-member aryl, heteroaryl or cycloalkyl ring at different carbon atoms in the aryl structure or the heteroaryl structure, which may be substituted at one of the carbons in the fused aryl or fused heteroaryl and connected to the core molecule at another of the carbons, as exemplified by the following cyclopentylthiazole, quinoline or naphthalene structures:

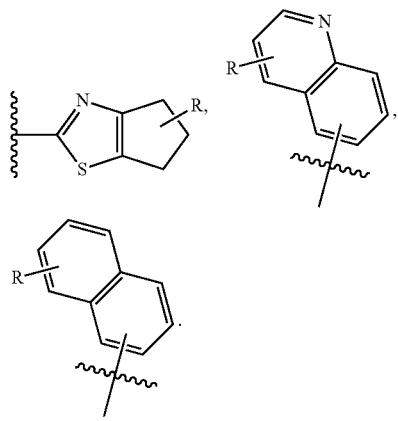

Fused aryl and fused heteroaryl groups may also be substituted, for example, with one or more alkyl, cycloalkyl, heterocycloalkyl, alkoxy, amino, aminoalkyl, thiol, thioalkyl, aryl, heteroaryl, halo or haloalkyl substituents.

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of nitrogen, such as N(O) {N$^+$—O$^-$} and sulfur such as S(O) and S(O)$_2$, and the quaternized form of any basic nitrogen.

"Oxazole" and "oxazolyl" refers to a 5-membered heterocyclic ring containing one nitrogen and one oxygen as heteroatoms and also contains three carbons and may be substituted at one of the three carbons and may be connected to another molecule at another of the three carbons, as exemplified by any of the following structures, wherein the oxazolidinone groups shown here are bonded to a parent molecule, which is indicated by a wavy line in the bond to the parent molecule:

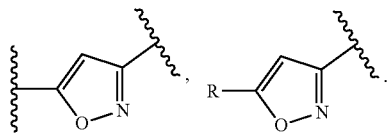

"Oxopyrrolidine" and "oxopyrrolidinyl" refers to a 5-membered heterocyclic ring containing nitrogen and 4 carbons that is substituted at one of the carbons in the heterocyclic ring by a carbonyl and may be connected to another substituent at another carbon in the heterocyclic ring, as exemplified by the structure below:

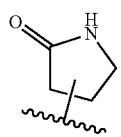

"Pyridine" and "pyridinyl" refers to a 6-membered heteroaryl ring containing one nitrogen and 5 carbons that may also be substituted at one or more of the carbons in the heteroaryl ring, and may be connected to another substituent at another carbon in the heteroaryl ring, as exemplified by the structures below:

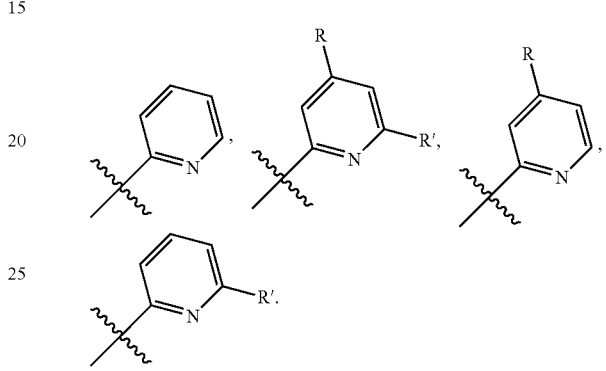

"Thiazole" and "thiazolyl" refers to a 5-membered heteroaryl containing one sulfur and one nitrogen in the heteroaryl ring and 3 carbons in the heteroaryl ring that may also be substituted at one or more of the carbons in the heteroaryl ring, and may be connected to another substituent at another carbon in the heteroaryl ring, as exemplified by the structures below:

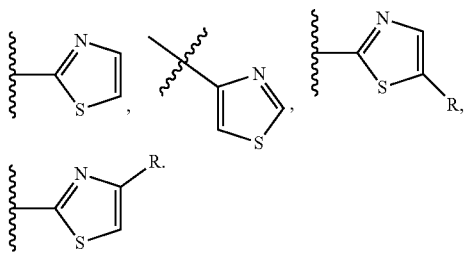

"Pyrimidine" and "pyrimidinyl" refers to a 6-membered heteroaryl ring containing two nitrogens in the heteroaryl ring and 4 carbons in the heteroaryl ring that may be substituted at one or more of the carbons in the heteroaryl ring, and may be connected to another substituent at another carbon in the heteroaryl ring, as exemplified by the structures below:

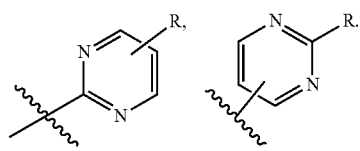

"Racemates" refers to a mixture of enantiomers. In an embodiment of the invention, the compounds of Formulas I, or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Thio" or "thiol" refers to the group —SR where R is selected from hydrogen, alkyl, alkenyl, aryl, cycloalkyl, heterocycloalkyl, heteroaryl, heterocyclic. When R is H the thio group is sometimes referred to herein as a thiol group, and when R is alkyl the thio group is sometimes referred to herein as a thioalkyl group or alkylthio. The sulfur may also bound to another carbon or atom in the same molecule to form a heterocyclic group.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" or "subject" refers to mammals and includes humans and non-human mammals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Wherever dashed lines occur adjacent to single bonds denoted by solid lines, then the dashed line represents an optional double bond at that position. Likewise, wherever dashed circles appear within ring structures denoted by solid lines or solid circles, then the dashed circles represent one to three optional double bonds arranged according to their proper valence taking into account whether the ring has any optional substitutions around the ring as will be known by one of skill in the art. For example, the dashed line in the structure below could either indicate a double bond at that position or a single bond at that position:

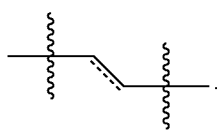

Similarly, ring A below could be a cyclohexyl ring without any double bonds or it could also be a phenyl ring having three double bonds arranged in any position that still depicts the proper valence for a phenyl ring. Likewise, in ring B below, any of $X^1$-$X^5$ could be selected from: C, CH, or $CH_2$, N, or NH, and the dashed circle means that ring B could be a cyclohexyl or phenyl ring or a N-containing heterocycle with no double bonds or a N-containing heteroaryl ring with one to three double bonds arranged in any position that still depicts the proper valence:

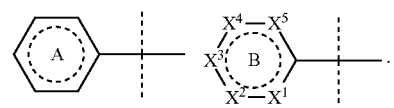

Where specific compounds or generic formulas are drawn that have aromatic rings, such as aryl or heteroaryl rings, then it will understood by one of still in the art that the particular aromatic location of any double bonds are a blend of equivalent positions even if they are drawn in different locations from compound to compound or from formula to formula. For example, in the two pyridine rings (A and B) below, the double bonds are drawn in different locations, however, they are known to be the same structure and compound:

A

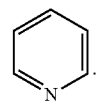

B

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—C($R^x$)$_2$—", it should be understood that the two $R^x$ groups can be the same, or they can be different if $R^x$ is defined as having more than one possible identity. In addition, certain substituents are drawn as —$R^xR^y$, where the "–" indicates a bond adjacent to the parent molecule and $R^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

In accordance with one embodiment of the present invention, there are provided compounds of Formula I or a salt or prodrug thereof,

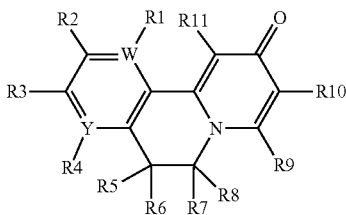

Formula I wherein
W and Y are independently C or N, with the proviso that W and Y are not both C;
wherein
if W is C, then $R^1$ is hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N—$C_xH_{2x}$-phenyl wherein x is 0, 1, 2, 3, 4, 5, 6; or —$OR^{12}$; and
if Y is C, then $R^4$ is hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N—$C_xH_{2x}$-phenyl wherein x is 0, 1, 2, 3, 4, 5, 6; or —$OR^{12}$;
wherein
if W is N, then $R^1$ is absent; and
if Y is N, then $R^4$ is absent;
$R^2$ and $R^3$ are independently selected from hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N—$C_xH_{2x}$-phenyl wherein x is 0, 1, 2, 3, 4, 5, 6; or —$OR^{12}$;
$R^5$ and $R^6$ are independently hydrogen, hydroxy, halogen, cyano, amino alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6;
$R^7$ and $R^8$ are independently hydrogen, hydroxy, halogen, cyano, amino, alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6;
or $R^5$ and $R^6$ together form a 3- to 8-membered cycloalkyl ring or 3- to 8-membered heterocycloalkyl ring, wherein the heteroatom in the heterocycloalkyl ring is O, N, $NR^{22}$, S, $SR^{22}$ or $SR^{22}R^{22'}$, wherein the 3- to 8-membered heterocycloalkyl ring is optionally substituted with $R^{13}$, $R^{13'}$, $R^{14}$ and/or $R^{14'}$;
or $R^6$ and $R^7$ together form a 3- to 8-membered cycloalkyl ring or heterocycloalkyl ring comprising one heteroatom or two or more heteroatoms, optionally substituted with $R^{15}$, $R^{15'}$, $R^{16}$ and/or $R^{16'}$, wherein the one heteroatom in the heteroalkyl ring is $NR^{20}$ and the two or more heteroatoms are selected from N, $NR^{22}$, O, S, $SR^{22}$ and $SR^{22}R^{22'}$;
or $R^7$ and $R^8$ together form a 3- to 8-membered cycloalkyl ring or 3- to 8-membered heterocycloalkyl ring, optionally substituted with $R^{17}$, $R^{17'}$, $R^{18}$ and/or $R^{18'}$, wherein the heteroatom in the heterocycloalkyl ring is O, N, $NR^{22}$, S, $SR^{22}$ or $SR^{22}R^{22'}$;
$R^9$ is a bond, hydrogen, hydroxy, halogen, cyano, amino, alkyl or substituted alkyl, alkoxy or substituted alkoxy, cycloalkyl or substituted cycloalkyl, alkenyl or substituted alkenyl, heterocycloalkyl or substituted heterocycloalkyl, aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6;
$R^{10}$ is a substituent shown in Table 2 or a tautomer thereof;
or $R^9$ is a bond and $R^9$ and $R^{10}$ together form an oxaborole ring;
$R^{11}$ is hydrogen, hydroxy, halogen, cyano, amino, alkyl or substituted alkyl; alkenyl or substituted alkenyl; alkoxy or substituted alkoxy; cycloalkyl or substituted cycloalkyl; heterocycloalkyl or substituted heterocycloalkyl, aryl, heteroaryl, —$C_xH_{2x}$-phenyl or —O—$C_xH_{2x}$-phenyl wherein x is 0, 1, 2, 3, 4, 5 or 6;
$R^{12}$ is hydrogen; alkyl or substituted alkyl, alkoxy or substituted alkoxy, cycloalkyl or substituted cycloalkyl, heterocycloalkyl or substituted heterocycloalkyl, aryl or substituted aryl, heteroaryl or substituted heteroaryl;
$R^{13}$, $R^{13'}$, $R^{14}$ and $R^{14'}$ are independently hydrogen, hydroxy, halogen, amino, aminoalkyl, cyano, $C_{1-6}$alkyl, $C_{1-6}$alkoxy, carbonyl, carboxamide, amide; or $R^{13}$ and $R^{13'}$ or $R^{14}$ and $R^{14'}$ together form a 3- to 8-membered cycloalkyl ring or 3- to 8-membered heterocycloalkyl ring, optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;
$R^{15}$, $R^{15'}$, $R^{16}$ and $R^{16'}$ are independently hydrogen, hydroxy, halogen, amino, cyano, $C_{1-6}$alkyl, or $C_{1-6}$alkoxy; or $R^{15}$ and $R^{15'}$ or $R^{16}$ and $R^{16'}$ together form a 3- to 8-membered cycloalkyl ring or 3- to 8-membered heterocycloalkyl ring optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;
$R^{17}$, $R^{17'}$, $R^{18}$ and $R^{18'}$ are independently hydrogen, hydroxy, halogen, amino, cyano, $C_{1-6}$alkyl, or $C_{1-6}$alkoxy; or $R^{17}$ and $R^{18}$ or $R^{17'}$ and $R^{18'}$ together form a 3- to 8-membered cycloalkyl ring or 3- to 8-membered heterocycloalkyl ring, optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;

$R^{19}$, $R^{19'}$ and $R^{19''}$ are independently hydrogen, $C_{1-6}$alkyl, $C_{3-8}$cycloalkyl, $C_{2-6}$alkenyl, $C_{1-6}$alkoxy, phenyl, $C_{1-6}$alkylimidizole, $C_{1-6}$alkyltriazole, $C_{1-6}$ alkyltetrazole, $C_{1-6}$alkylthiazole, $C_{1-6}$alkyloxazole, $C_{1-6}$alkyldioxazole; $C_{1-6}$alkyloxazolidone; and $R^{20}$ and $R^{21}$ are independently hydrogen, $C_{1-6}$alkyl, $C_{3-8}$cycloalkyl, $C_{2-6}$alkenyl, $C_{1-6}$alkoxy, phenyl, $C_{1-6}$alkylimidizole, $C_{1-6}$alkyltriazole, $C_{1-6}$alkyltetrazole, $C_{1-6}$alkylthiazole, $C_{1-6}$alkyloxazole, $C_{1-6}$alkyldioxazole; $C_{1-6}$alkyloxazolidone, or $R^{20}$ and $R^{21}$ together with the nitrogen to which they are attached form unsubstituted pyrrolidinyl, unsubstituted piperidinyl, or unsubstituted morpholinyl; or form carboxyl-substituted pyrrolidinyl, carboxyl-substituted piperidinyl or carboxyl-substituted morpholinyl; and $R^{22}$ and $R^{22'}$ are independently selected from hydrogen, oxygen, $C_{1-6}$alkyl or substituted $C_{1-6}$alkyl, $C_{1-6}$alkoxy or substituted $C_{1-6}$alkoxy, $C_{3-8}$cycloalkyl or substituted $C_{3-8}$cycloalkyl, $C_{2-6}$alkenyl or substituted $C_{2-6}$alkenyl, aryl or substituted aryl, including substituted or unsubstituted $C_{1-6}$alkylimidizole, substituted or unsubstituted $C_{1-6}$alkyltriazole, $C_{1-6}$alkyltetrazole, $C_{1-6}$alkylthiazole, substituted or unsubstituted $C_{1-6}$alkyloxazole, $C_{1-6}$alkyldioxazole; $C_{1-6}$alkyloxazolidone; —$COR^{19}$, —$COOR^{19'}$, —$CSOR^{19''}$, —$CONR^{20}R^{21}$, or a pharmaceutically acceptable salt thereof.

One particular embodiment provides a compound according of Formula I, Formula IA or Formula IB as described herein, wherein:

$R^1$ is selected from hydrogen, hydroxy, halogen, cyano, amino, pyrrolidinyl, unsubstituted $C_{1-6}$alkyl or halo-substituted $C_{1-6}$alkyl, unsubstituted $C_{1-6}$alkoxy or halo-substituted $C_{1-6}$alkyoxy; $C_{3-7}$cycloalkyl or halo-substituted $C_{3-7}$cycloalkyl; N-containing monocyclic heterocycloalkyl, pyrrolidinyl, —$C_xH_{2x}$-phenyl, —O—$C_xH_{2x}$-phenyl, or —$(C_{1-6}$alkyl$)N$—$C_xH_{2x}$-phenyl wherein x is 0, 1, 2, 3, 4, 5 or 6; or —$OR^{12}$;

$R^2$ and $R^3$ are independently $OR^{12}$;

$R^4$ is selected from hydrogen, hydroxy, halogen, cyano, amino, pyrrolidinyl, unsubstituted $C_{1-6}$alkyl or halo-substituted $C_{1-6}$alkyl, unsubstituted $C_{1-6}$alkoxy or halo-substituted $C_{1-6}$alkyoxy; $C_{3-7}$cycloalkyl or halo-substituted $C_{3-7}$cycloalkyl; N-containing monocyclic heterocycloalkyl, pyrrolidinyl, —$C_xH_{2x}$-phenyl, —O—$C_xH_{2x}$-phenyl, or —$(C_{1-6}$alkyl$)N$—$C_xH_{2x}$-phenyl wherein x is 0, 1, 2, 3, 4, 5 or 6; or —$OR^{12}$;

$R^6$ and $R^7$ together form a 3- to 8-membered cycloalkyl ring or 3- to 8-membered heterocycloalkyl ring comprising one heteroatom or two or more heteroatoms, optionally substituted with $R^{15}$, $R^{15'}$, $R^{16}$ and/or $R^{16'}$, wherein the one heteroatom in the heteroalkyl ring is $NR^{20}$ and the two or more heteroatoms are selected from N, $NR^{22}$, O, S, $SR^{22}$ and $SR^{22}R^{22'}$; $R^{11}$ is hydrogen; $R^{12}$ is as described herein; and $R^{15}$ and $R^{16}$ or $R^{15'}$ and $R^{16'}$ together form a 3- to 8-membered cycloalkyl ring or heterocycloalkyl ring optionally substituted with oxygen, halogen, hydroxy, amino, cyano, $C_{1-6}$alkyl, $C_{3-8}$cycloalkyl, $C_{2-6}$alkenyl or $C_{1-6}$alkoxy wherein the heteroatom in the heteroalkyl ring is O, N, $NR^{22}$, S, $SR^{22}$ or $SR^{22}R^{22'}$, or a pharmaceutically acceptable salt thereof.

Another embodiment provides a compound of Formula I, Formula IA or

Formula IB as described herein, $R^9$ is as described herein and $R^{10}$ is a substituent shown in Table 2, or $R^9$ is a bond and $R^9$ and $R^{10}$ together form an oxaborole ring; or a pharmaceutically acceptable salt thereof.

Another particular embodiment provides a compound of Formula I, Formula IA or Formula IB as described herein, $R^9$ is as described herein and $R^{10}$ is a substituent shown in Table 2, or $R^9$ is a bond and $R^9$ and $R^{10}$ together form an oxaborole ring; and $R^{12}$ is unsubstituted $C_{1-6}$alkyl; or a pharmaceutically acceptable salt thereof.

Another particular embodiment provides a compound of Formula I, Formula IA or Formula IB as described herein, wherein W and Y are as described herein, $R^1$, $R^2$, $R^3$ and $R^4$ are independently $OR^{12}$; $R^9$ is as described herein and $R^{10}$ is a substituent shown in Table 2, or $R^9$ is a bond and $R^9$ and $R^{10}$ together form an oxaborole ring; and $R^{12}$ is as described herein; or a pharmaceutically acceptable salt thereof.

Another embodiment of the invention provides a compound of Formula I, Formula IA or Formula IB or a pharmaceutically acceptable salt thereof, as described herein, wherein $R^9$ is a bond and $R^9$ and $R^{10}$ together form an oxaborole ring.

Yet another embodiment of the invention provides a compound of Formula I, Formula IA or Formula IB or a pharmaceutically acceptable salt thereof, as described herein, wherein W and Y are as described herein;

$R^1$ and $R^4$, are as described;

$R^2$ and $R^3$ are independently selected from hydrogen, hydroxy, halogen, cyano, amino, thio, $C_{1-6}$alkyl or substituted $C_{1-6}$alkyl, $C_{1-6}$alkoxy or substituted $C_{1-6}$ alkoxy; $C_{3-8}$cycloalkyl or substituted $C_{3-8}$cycloalkyl; $C_{2-8}$alkenyl or substituted $C_{2-8}$alkenyl; 3- to 8-membered heterocycloalkyl or substituted 3- to 8-membered heterocycloalkyl, aryl or substituted aryl, heteroaryl or substituted heteroaryl, or —$OR^{12}$;

$R^5$ and $R^6$ are independently hydrogen, hydroxy, halogen, cyano, amino, $C_{1-6}$alkyl or substituted $C_{1-6}$alkyl, $C_{1-6}$alkoxy or substituted $C_{1-6}$alkoxy, $C_{3-8}$cycloalkyl or substituted $C_{3-8}$cycloalkyl, $C_{2-8}$alkenyl or substituted $C_{2-8}$alkenyl; aryl or substituted aryl, heteroaryl or substituted aryl, —$C_xH_{2x}$-phenyl or —O—$C_xH_{2x}$-phenyl wherein x is 0, 1, 2, 3, 4, 5 or 6;

$R^7$ and $R^8$ are independently hydrogen, hydroxy, halogen, cyano, amino, $C_{1-6}$alkyl or substituted $C_{1-6}$alkyl, $C_{1-6}$alkoxy or substituted $C_{1-6}$alkoxy, $C_{3-8}$cycloalkyl or substituted $C_{3-8}$cycloalkyl, $C_{2-8}$alkenyl or substituted $C_{2-8}$alkenyl; aryl or substituted aryl, heteroaryl or substituted aryl, —$C_xH_{2x}$-phenyl or —O—$C_xH_{2x}$-phenyl wherein x is 0, 1, 2, 3, 4, 5 or 6;

or $R^5$ and $R^6$ together form a 3- to 8-membered cycloalkyl ring or 3- to 8-membered heterocycloalkyl ring, wherein the heteroatom in the heterocycloalkyl ring is O, N, $NR^{22}$, S, $SR^{22}$ or $SR^{22}R^{22'}$, wherein the 3- to 8-membered heterocycloalkyl ring is optionally substituted with $R^{13}$, $R^{13'}$, $R^{14}$ and/or $R^{14'}$;

or $R^6$ and $R^7$ together form a 3- to 8-membered cycloalkyl ring or heterocycloalkyl ring comprising one heteroatom or two or more heteroatoms, optionally substituted with $R^{15}$, $R^{15'}$, $R^{16}$ and/or $R^{16'}$, wherein the one heteroatom in the heteroalkyl ring is $NR^{20}$ and the two or more heteroatoms are selected from N, $NR^{22}$, O, S, $SR^{22}$ and $SR^{22}R^{22'}$;

or $R^7$ and $R^8$ together form a 3- to 8-membered cycloalkyl ring or 3- to 8-membered heterocycloalkyl ring, optionally substituted with $R^{17}$, $R^{17'}$, $R^{18}$ and/or $R^{18'}$, wherein the heteroatom in the heterocycloalkyl ring is O, N, $NR^{22}$, S, $SR^{22}$ or $SR^{22}R^{22'}$;

$R^9$ is a bond, hydrogen, hydroxy, halogen, cyano, amino, alkyl or substituted alkyl, alkoxy or substituted alkoxy, cycloalkyl or substituted cycloalkyl, alkenyl or substituted alkenyl, heterocycloalkyl or substituted heterocycloalkyl, aryl or substituted aryl, heteroaryl or substituted heteroaryl, $—C_xH_{2x}$-phenyl or $—O—C_xH_{2x}$-phenyl wherein x is 0, 1, 2, 3, 4, 5 or 6;

$R^{10}$ is a substituent shown in Table 2 or a tautomer thereof;

or $R^9$ is a bond and $R^9$ and $R^{10}$ together form an oxaborole ring;

$R^{11}$ is hydrogen, hydroxy, halogen, cyano, amino, $C_{1-6}$alkyl or substituted $C_{1-6}$alkyl, $C_{1-6}$alkoxy or substituted $C_{1-6}$alkoxy, $C_{3-8}$cycloalkyl or substituted $C_{3-8}$cycloalkyl, $C_{2-8}$alkenyl or substituted $C_{2-8}$alkenyl; aryl or substituted aryl, heteroaryl or substituted aryl, $—C_xH_{2x}$-phenyl or $—O—C_xH_{2x}$-phenyl wherein x is 0, 1, 2, 3, 4, 5 or 6;

$R^{12}$ is hydrogen; $C_{1-6}$alkyl or substituted $C_{1-6}$alkyl, $C_{1-6}$alkoxy or substituted $C_{1-6}$alkoxy, $C_{3-8}$cycloalkyl or substituted $C_{3-8}$cycloalkyl, $C_{3-8}$heterocycloalkyl or substituted $C_{3-8}$heterocycloalkyl, aryl or substituted aryl, heteroaryl or substituted heteroaryl; and $R^{22}$ and $R^{22'}$ are independently selected from hydrogen, oxygen, $C_{1-6}$alkyl or substituted $C_{1-6}$alkyl, $C_{1-6}$alkoxy or substituted $C_{1-6}$alkoxy, $C_{3-8}$cycloalkyl or substituted $C_{3-8}$cycloalkyl, $C_{2-6}$alkenyl or substituted $C_{2-6}$alkenyl, aryl or substituted aryl, $—COR^{19}$, $—COOR^{19'}$, $—CSOR^{19''}$, $—CONR^{20}R^{21}$.

Another embodiment of the invention provides a compound of Formula I, Formula IA or Formula IB or a pharmaceutically acceptable salt thereof, as described herein, wherein W and Y are each N.

A particular embodiment of the invention provides a compound of Formula I, Formula IA or Formula IB or a pharmaceutically acceptable salt thereof, as described herein, wherein W and Y are as described herein;

$R^1$, $R^2$, $R^3$ and $R^4$ are independently H or $OR^{12}$; and $R^5$ and $R^6$ together form a 3- to 8-membered cycloalkyl ring or 3- to 8-membered heterocycloalkyl ring, wherein the heteroatom in the heterocycloalkyl ring is O, N, $NR^{22}$, S, $SR^{22}$ or $SR^{22}R^{22'}$, wherein the 3- to 8-membered heterocycloalkyl ring is optionally substituted with $R^{13}$, $R^{13'}$, $R^{14}$ and/or $R^{14'}$.

Another particular embodiment of the invention provides a compound of Formula I, Formula IA or Formula IB or a pharmaceutically acceptable salt thereof, as described herein, wherein W and Y are as described herein;

$R^2$ and $R^3$ are independently H or $OR^{12}$; and $R^6$ and $R^7$ together form a 3- to 8-membered cycloalkyl ring or heterocycloalkyl ring comprising one heteroatom or two or more heteroatoms, optionally substituted with $R^{15}$, $R^{15'}$, $R^{16}$ and/or $R^{16'}$, wherein the one heteroatom in the heteroalkyl ring is $NR^{20}$ and the two or more heteroatoms are selected from N, $NR^{22}$, O, S, $SR^{22}$ and $SR^{22}R^{22'}$.

Another particular embodiment of the invention provides a compound of Formula I, Formula IA or Formula IB or a pharmaceutically acceptable salt thereof, as described herein, wherein $R^1$, $R^2$, $R^3$ and $R^4$ are independently H or $OR^{12}$; and $R^7$ and $R^8$ together form a 3- to 8-membered cycloalkyl ring or 3- to 8-membered heterocycloalkyl ring, optionally substituted with $R^{17}$ and $R^{18}$, wherein the heteroatom in the heterocycloalkyl ring is selected from O, N, $NR^{22}$, S, $SR^{22}$ or $SR^{22}R^{22'}$.

Another particular embodiment provides a compound of Formula I, Formula IA or Formula IB as described herein, wherein $R^2$ and $R^3$ are independently $OR^{12}$; $R^5$ and $R^6$ together form a 3- to 8-membered cycloalkyl ring or 3- to 8-membered heterocycloalkyl ring, optionally substituted with $R^{13}$ and $R^{14}$, wherein the heteroatom in the heteroalkyl ring is O, N, $NR^{22}$, S, $SR^{22}$ or $SR^{22}R^{22'}$; $R^{10}$ is a substituent shown in Table 2, or $R^9$ is a bond and $R^9$ and $R^{10}$ together form an oxaborole ring; $R^{11}$ is H; $R^{12}$ is unsubstituted $C_{1-6}$alkyl; and $R^{13}$ and $R^{14}$ or $R^{13'}$ and $R^{14'}$ together form a 3- to 8-membered cycloalkyl ring or 3- to 8-membered heterocycloalkyl ring, optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heteroalkyl ring is O, N, $NR^{22}$, S, $SR^{22}$ or $SR^{22}R^{22'}$; or a pharmaceutically acceptable salt thereof.

Still another particular embodiment provides a compound of Formula I, Formula IA or Formula IB as described herein, wherein $R^2$ and $R^3$ are independently $OR^{12}$; $R^7$ and $R^8$ together form a 3- to 8-membered ring, optionally substituted with $R^{17}$ and $R^{18}$; $R^{10}$ is a substituent shown in Table 2 or $R^9$ is a bond and $R^9$ and $R^{10}$ together form an oxaborole ring; $R^{11}$ is H; $R^{12}$ is unsubstituted $C_{1-6}$alkyl; and $R^{17}$ and $R^{18}$ or $R^{17'}$ and $R^{18'}$ together form a 3- to 8-membered cycloalkyl ring or 3- to 8-membered heterocycloalkyl ring, optionally substituted with oxygen, halogen, hydroxy, amino, cyano, $C_{1-6}$alkyl, $C_{3-6}$cycloalkyl, $C_{2-6}$alkenyl or $C_{1-6}$alkoxy, wherein the heteroatom in the heteroalkyl ring is O, N, $NR^{22}$, S, $SR^{22}$ or $SR^{22}R^{22'}$; or a pharmaceutically acceptable salt thereof.

Another particular embodiment provides a compound of Formula I, Formula IA or Formula IB as described herein, wherein $R^2$ and $R^3$ are independently $OR^{12}$; and $R^5$ and $R^6$ together form a 3- to 8-membered cycloalkyl ring or 3- to 8-membered heterocycloalkyl ring, optionally substituted with $R^{13}$, $R^{14}$, $R^{13'}$ and/or $R^{14'}$, wherein the heteroatom in the heteroalkyl ring is O, N, $NR^{22}$, S, $SR^{22}$ or $SR^{22}R^{22'}$, or a pharmaceutically acceptable salt thereof.

Another particular embodiment provides a compound of Formula I, Formula IA or Formula IB as described herein wherein $R^2$ and $R^3$ are independently $OR^{12}$; and $R^7$ and $R^8$ together form a 3- to 8-membered cycloalkyl ring or 3- to 8-membered heterocycloalkyl ring, optionally substituted with $R^{17}$, $R^{18}$, $R^{17'}$ and/or $R^{18'}$, wherein the heteroatom in the heteroalkyl ring is O, N, $NR^{22}$, S, $SR^{22}$ or $SR^{22}R^{22'}$, or a pharmaceutically acceptable salt thereof.

Still more particular embodiments provide compounds of Formula I, Formula IA or Formula IB or a pharmaceutically acceptable salt thereof as described herein, wherein $R^1$, $R^2$, $R^3$ and $R^4$ are as described; and (A) $R^5$ and $R^6$ are independently hydroxy, halogen, cyano, amino alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, $—C_xH_{2x}$-phenyl or $—O—C_xH_{2x}$-phenyl wherein x is 0, 1, 2, 3, 4, 5 or 6; or $R^5$ and $R^6$ together form a 3- to 8-membered cycloalkyl ring or 3- to 8-membered heterocycloalkyl ring, optionally substituted with $R^{13}$, $R^{13'}$, $R^{14}$ and/or $R^{14'}$, wherein the heteroatom in the heterocycloalkyl ring is selected from O, N, $NR^{22}$, S, $SR^{22}$ or $SR^{22}R^{22'}$; and $R^7$ and $R^8$ are independently hydrogen, hydroxy, halogen, cyano, amino, alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6; or (B) $R^5$ and $R^8$ are independently hydrogen, hydroxy, halogen, cyano, amino alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6; and $R^6$ and $R^7$ together form a 3- to 8-membered cycloalkyl ring or 3- to 8-membered heterocycloalkyl ring comprising one heteroatom or two or more heteroatoms, optionally substituted with $R^{15}$, $R^{15'}$, $R^{16}$ and/or $R^{16'}$, wherein the one heteroatom in the heteroalkyl ring is $NR^{20}$ and the two or more heteroatoms are selected from N, $NR^{22}$, O, S, $SR^{22}$ and $SR^{22}R^{22'}$; or (C) $R^5$ and $R^6$ are independently hydrogen, hydroxy, halogen, cyano, amino alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6; and $R^7$ and $R^8$ are independently hydroxy, halogen, cyano, amino, alkyl or substituted alkyl, alkoxy or substituted alkoxy, cycloalkyl or substituted cycloalkyl, alkenyl or substituted alkenyl; aryl or substituted aryl, heteroaryl, —$C_xH_{2x}$-phenyl or —O—$C_xH_{2x}$-phenyl wherein x is 0, 1, 2, 3, 4, 5 or 6; or $R^7$ and $R^8$ together form a 3- to 8-membered cycloalkyl ring or a 3- to 8-membered heterocycloalkyl ring, optionally substituted with $R^{17}$, $R^{18'}$, $R^{17}$ and/or $R^{18'}$, wherein the heteroatom in the heterocycloalkyl ring is selected from O, N, $NR^{22}$, S, $SR^{22}$ or $SR^{22}R^{22'}$.

In other particular embodiments, there is provided a compound of Formula I, Formula IA, or Formula IB as described, wherein the compound is selected from the compounds of Table 1, wherein $R^{10}$ is as described herein or a substituent shown in Table 2, or a tautomer thereof.

In particular embodiments there is provided a compound of Formula I or pharmaceutically acceptable salt thereof as described herein, wherein W is N; Y is C; $R^1$ is absent; $R^2$ and $R^3$ are independently selected from hydrogen, hydroxy, halogen, $C_{1-6}$alkyl or substituted $C_{1-6}$alkyl, $C_{1-6}$alkoxy or substituted $C_{1-6}$alkoxy, $C_{3-8}$cycloalkyl or substituted $C_{3-8}$cycloalkyl, $C_{2-8}$alkenyl or substituted $C_{2-8}$alkenyl, or —$OR^{12}$, $R^4$ is H; $R^6$ and $R^7$ together form a 3- to 8-membered cycloalkyl ring, optionally substituted with $R^{15}$, $R^{15'}$, $R^{16}$ and/or $R^{16'}$; $R^{11}$ is H; and $R^{15}$, $R^{15'}$, $R^{16}$ and/or $R^{16'}$ are independently hydrogen, hydroxy, halogen, amino, cyano, $C_{1-6}$alkyl, or $C_{1-6}$alkoxy.

In a particular embodiment, there is provided a compound of Formula I or a pharmaceutically acceptable salt thereof as described herein, wherein W is N; Y is C: $R^1$ is absent; $R^2$ is halogen; $R^3$ is $OR^{12}$; and $R^4$ is H.

In another particular embodiment there is provided a compound of Formula I or pharmaceutically acceptable salt thereof as described herein, wherein W is N; Y is C; $R^1$ is absent; $R^2$ is halogen and $R^3$ is —$OR^{12}$; $R^4$ is H; $R^6$ and $R^7$ together form a 3- to 8-membered cycloalkyl ring, optionally substituted with $R^{15}$, $R^{15'}$, $R^{16}$ and/or $R^{16'}$; $R^{11}$ is H; and $R^{15}$, $R^{15'}$, $R^{16}$ and/or $R^{16'}$ are independently $C_{1-6}$alkyl.

In another particular embodiment there is provided a compound of Formula I or pharmaceutically acceptable salt thereof as described herein, wherein: $R^6$ and $R^7$ together form a 3- to 8-membered cycloalkyl ring, optionally substituted with $R^{15}$, $R^{15'}$, $R^{16}$ and/or $R^{16'}$.

In another particular embodiment there is provided a compound of Formula I or pharmaceutically acceptable salt thereof as described herein, wherein: $R^7$ and $R^8$ together form a 3- to 8-membered cycloalkyl ring or 3- to 8-membered heterocycloalkyl ring, optionally substituted with $R^{17}$ and $R^{18}$, wherein the heteroatom in the heterocycloalkyl ring is selected from O, N, $NR^{22}$, S, $SR^{22}$ or $SR^{22}R^{22'}$.

In one particular embodiment there is provided a compound selected from the group consisting of:
(4bR,7aS)-2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid;
(4bS,7aR)-2-Chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid;
(4bR,7aS)-2-Cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid;
2-Cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid;
(7aR)-2-Cyclopropyl-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid;
(7aR)-2-Chloro-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid;
(7aR)-2-Chloro-4b-methoxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid;
(4bR,7aS)-2-Hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid;
(4bR,7aS)-2-Chloro-3-hydroxy-7,7-dimethyl-11-oxo-4b,5,6,7,7a,11-hexahydrocyclopenta[f]pyrido[1,2-h][1,7]naphthyridine-10-carboxylic acid;
2-Chloro-6-(1-hydroxy-2-methylpropan-2-yl)-3-(3-methoxypropoxy)-10-oxo-6,10-dihydro-5H-pyrido[1,2-h][1,7]naphthyridine-9-carboxylic acid;
(S)-6-(tert-butyl)-2-chloro-3-(3-methoxypropoxy)-10-oxo-6,10-dihydro-5H-pyrido[1,2-h][1,7]naphthyridine-9-carboxylic acid;
(S)-6-(tert-butyl)-3-(cyclopropylmethoxy)-2-methyl-10-oxo-6,10-dihydro-5H-pyrido[1,2-h][1,7]naphthyridine-9-carboxylic acid;
(S)-6-(tert-butyl)-3-(3-methoxypropoxy)-2-methyl-10-oxo-6,10-dihydro-5H-pyrido[1,2-h][1,7]naphthyridine-9-carboxylic acid;
(S)-6-(tert-butyl)-2-cyclopropyl-3-(cyclopropylmethoxy)-10-oxo-6,10-dihydro-5H-pyrido[1,2-h][1,7]naphthyridine-9-carboxylic acid;
(S)-6-(tert-butyl)-2-cyclopropyl-3-(3-methoxypropoxy)-10-oxo-6,10-dihydro-5H-pyrido[1,2-h][1,7]naphthyridine-9-carboxylic acid;
(R)-6-(tert-butyl)-3-(cyclopropylmethoxy)-2-methoxy-10-oxo-6,10-dihydro-5H-pyrido[1,2-h][1,7]naphthyridine-9-carboxylic acid;
(S)-6-(tert-butyl)-3-(cyclopropylmethoxy)-2-methoxy-10-oxo-6,10-dihydro-5H-pyrido[1,2-h][1,7]naphthyridine-9-carboxylic acid;
(S)-6-(tert-butyl)-3-(cyclopropylmethoxy)-2-hydroxy-10-oxo-6,10-dihydro-5H-pyrido[1,2-h][1,7]naphthyridine-9-carboxylic acid;

(S)-6-(tert-butyl)-2-methoxy-3-(3-methoxypropoxy)-10-oxo-6,10-dihydro-5H-pyrido[1,2-h][1,7]naphthyridine-9-carboxylic acid;

(S)-6-(tert-butyl)-2-hydroxy-3-(3-methoxypropoxy)-10-oxo-6,10-dihydro-5H-pyrido[1,2-h][1,7]naphthyridine-9-carboxylic acid;

(S)-6-(tert-butyl)-3-(3-methoxypropoxy)-10-oxo-2-(prop-1-en-2-yl)-6,10-dihydro-5H-pyrido[1,2-h][1,7]naphthyridine-9-carboxylic acid;

(S)-6-(tert-butyl)-2-isopropyl-3-(3-methoxypropoxy)-10-oxo-6,10-dihydro-5H-pyrido[1,2-h][1,7]naphthyridine-9-carboxylic acid;

(S)-6-(tert-butyl)-2-chloro-3-(3-methoxypropoxy)-8-methyl-10-oxo-6,10-dihydro-5H-pyrido[1,2-h][1,7]naphthyridine-9-carboxylic acid;

(S)-6-(tert-butyl)-2-(hydroxymethyl)-3-(3-methoxypropoxy)-10-oxo-5,10-dihydro-6H-pyrido[1,2-h][1,7]naphthyridine-9-carboxylic acid;

(S)-6-(tert-butyl)-2-cyclopropyl-11-hydroxy-3-(3-methoxypropoxy)-10-oxo-5,10-dihydro-6H-pyrido[1,2-h][1,7]naphthyridine-9-carboxylic acid;

(2-chloro-3-(cyclopropylmethoxy)-6-isopropyl-6-methyl-10-oxo-5,10-dihydro-6H-pyrido[1,2-h][1,7]naphthyridine-9-carboxylic acid;

(2-chloro-3-(cyclopropylmethoxy)-6-isopropyl-6-methyl-10-oxo-5,10-dihydro-6H-pyrido[1,2-h][1,7]naphthyridine-9-carboxylic acid;

2-cyclopropyl-6-isopropyl-3-(3-methoxypropoxy)-6-methyl-10-oxo-5,10-dihydro-6H-pyrido[1,2-h][1,7]naphthyridine-9-carboxylic acid;

2-cyclopropyl-6-isopropyl-3-(3-methoxypropoxy)-6-methyl-10-oxo-5,10-dihydro-6H-pyrido[1,2-h][1,7]naphthyridine-9-carboxylic acid;

6-(tert-butyl)-2-chloro-3-(cyclopropylmethoxy)-10-oxo-6,10-dihydro-5H-pyrido[1,2-h][1,7]naphthyridine-9-carboxylic acid;

2'-Chloro-3'-(cyclopropylmethoxy)-10'-oxo-5',10'-dihydrospiro[cyclobutane-1,6'-pyrido[1,2-h][1,7]naphthyridine]-9'-carboxylic acid;

2',3'-Dimethoxy-10'-oxo-5',10'-dihydrospiro[cyclobutane-1,6'-pyrido[1,2-h][1,7]naphthyridine]-9'-carboxylic acid;

6-Isopropyl-2,3-dimethyl-10-oxo-5,10-dihydro-6H-pyrido[2,1-f][1,6]naphthyridine-9-carboxylic acid;

2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid;

3'-(cyclopropylmethoxy)-2'-(difluoromethyl)-11'-fluoro-10'-oxo-5',10'-dihydrospiro[cyclobutane-1,6'-pyrido[1,2-h][1,7]naphthyridine]-9'-carboxylic acid;

2'-(difluoromethyl)-11'-fluoro-10'-oxo-3'-((tetrahydrofuran-3-yl)methoxy)-5',10'-dihydrospiro[cyclobutane-1,6'-pyrido[1,2-h][1,7]naphthyridine]-9'-carboxylic acid;

(S)-3-(cyclopropylmethoxy)-2-(difluoromethyl)-11-fluoro-6-isopropyl-6-methyl-10-oxo-6,10-dihydro-5H-pyrido[1,2-h][1,7]naphthyridine-9-carboxylic acid; and (6S)-2-(difluoromethyl)-11-fluoro-6-isopropyl-6-methyl-10-oxo-3-((tetrahydrofuran-3-yl)methoxy)-6,10-dihydro-5H-pyrido[1,2-h][1,7]naphthyridine-9-carboxylic acid; or a pharmaceutically acceptable salt or tautomer thereof.

In one particular embodiment there is provided a compound selected from:

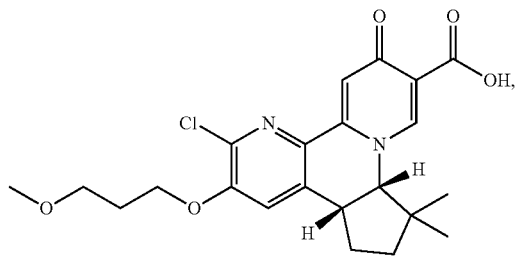

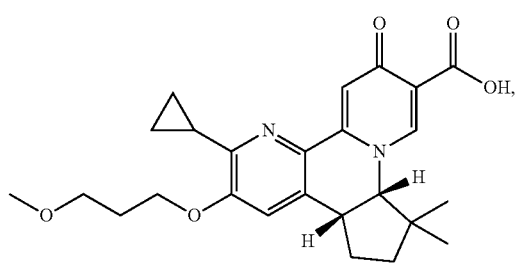

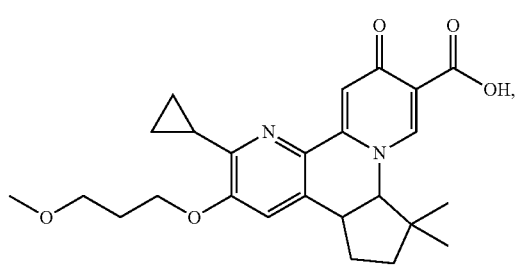

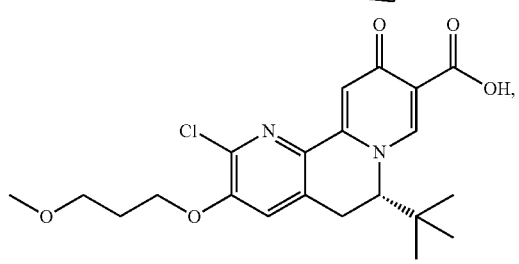

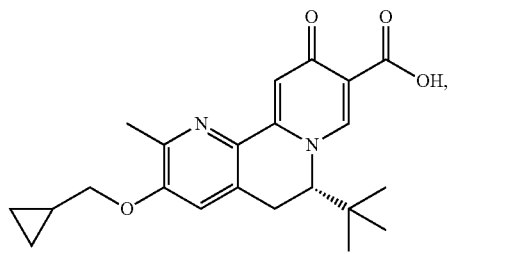

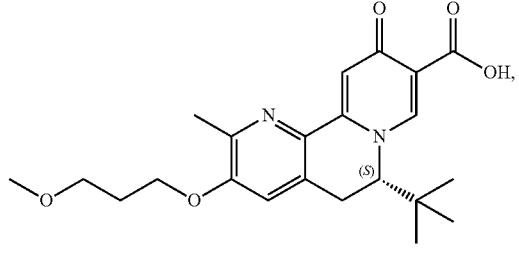

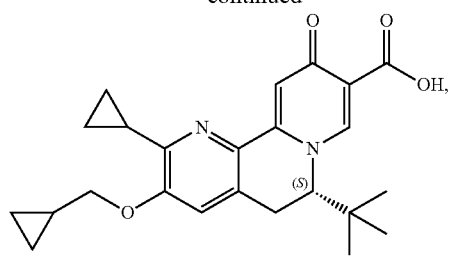
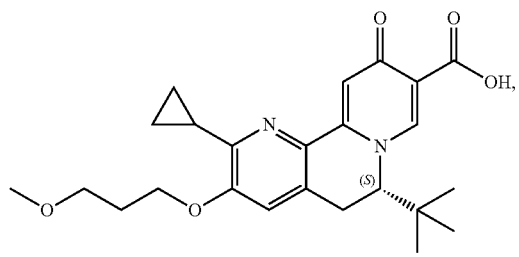
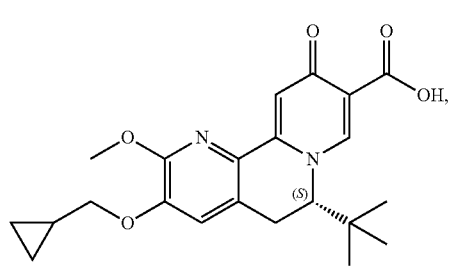
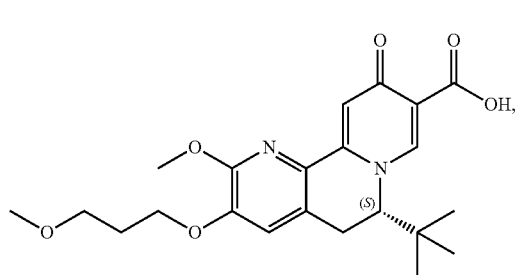
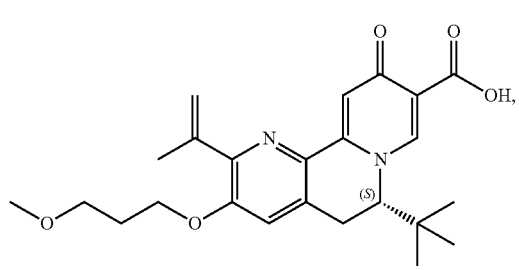
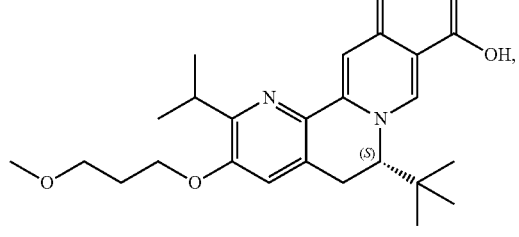
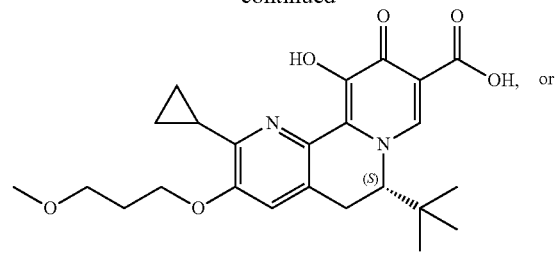
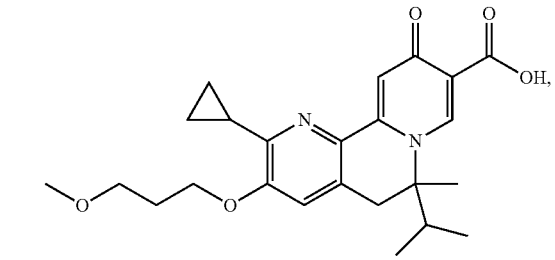
or a pharmaceutically acceptable salt thereof.
In a particular embodiment, there is provided a compound whose structure is:
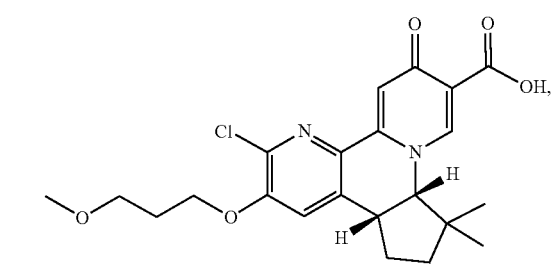 [SMILES: COCCCOc1cc2c(nc1Cl)-c1cc(=O)c(C(=O)O)cn1[C@H]1[C@@H]2CCC1(C)C]
or a pharmaceutically acceptable salt thereof.
In a particular embodiment, there is provided a compound whose structure is:
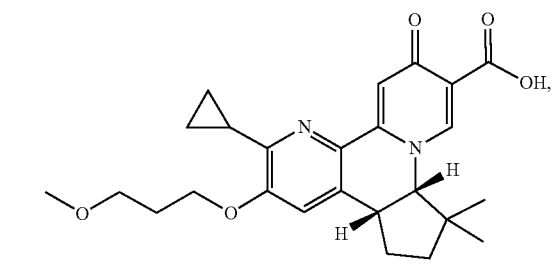 [SMILES: COCCCOc1cc2c(nc1C1CC1)-c1cc(=O)c(C(=O)O)cn1[C@H]1[C@@H]2CCC1(C)C]
or a pharmaceutically acceptable salt thereof.

In a particular embodiment, there is provided a compound whose structure is:

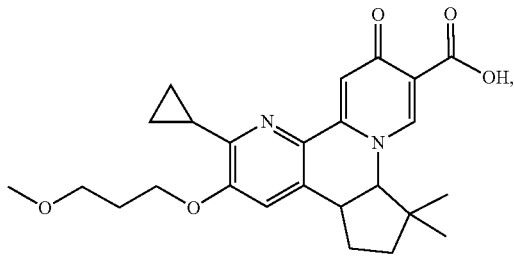 [SMILES: COCCCOc1cc2c(nc1C1CC1)-c1cc(=O)c(C(=O)O)cn1C1C2CCC1(C)C]

or a pharmaceutically acceptable salt thereof.

In a particular embodiment, there is provided a compound whose structure is:

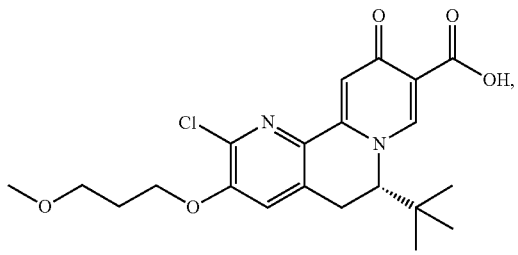 [SMILES: COCCCOc1cc2c(nc1Cl)-c1cc(=O)c(C(=O)O)cn1[C@H](C(C)(C)C)C2]

or a pharmaceutically acceptable salt thereof.

In a particular embodiment, there is provided a compound whose structure is:

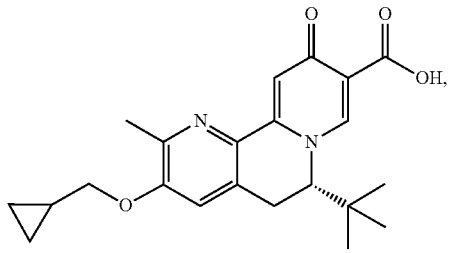 [SMILES: Cc1nc2c(cc1OCC1CC1)C[C@@H](C(C)(C)C)n1cc(C(=O)O)c(=O)cc1-2]

or a pharmaceutically acceptable salt thereof.

In a particular embodiment, there is provided a compound whose structure is:

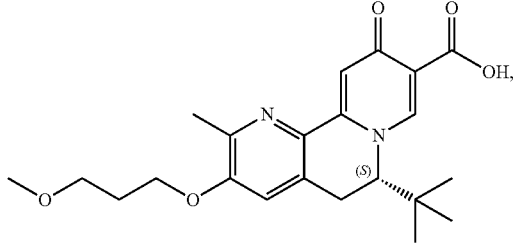

or a pharmaceutically acceptable salt thereof.

In a particular embodiment, there is provided a compound whose structure is:

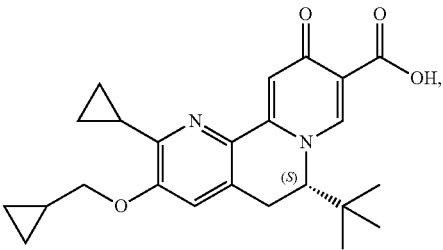

or a pharmaceutically acceptable salt thereof.

In a particular embodiment, there is provided a compound whose structure is:

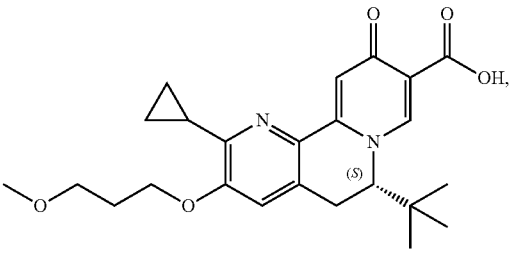

or a pharmaceutically acceptable salt thereof.

In a particular embodiment, there is provided a compound whose structure is:

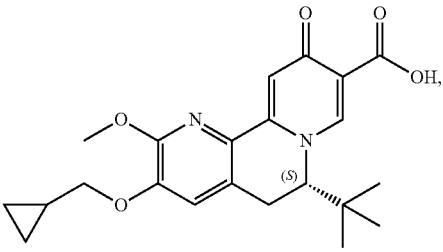

or a pharmaceutically acceptable salt thereof.

In a particular embodiment, there is provided a compound whose structure is:

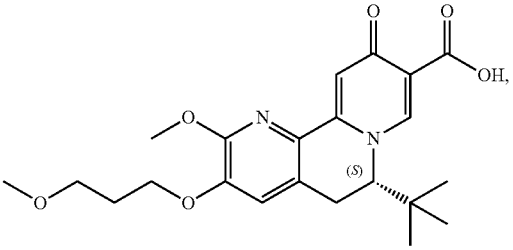

or a pharmaceutically acceptable salt thereof.

In a particular embodiment, there is provided a compound whose structure is:

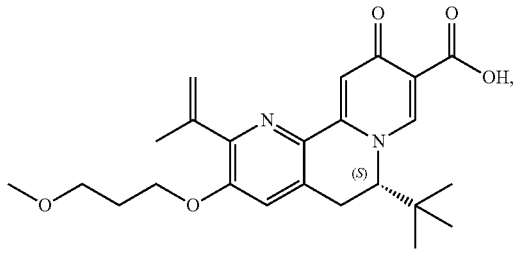

or a pharmaceutically acceptable salt thereof.

In a particular embodiment, there is provided a compound whose structure is:

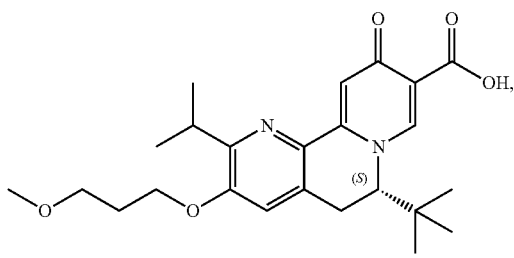

or a pharmaceutically acceptable salt thereof.

In a particular embodiment, there is provided a compound whose structure is:

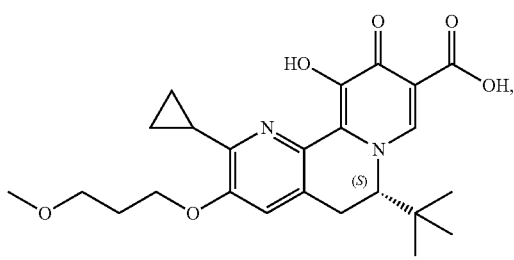

or a pharmaceutically acceptable salt thereof.

In a particular embodiment, there is provided a compound whose structure is:

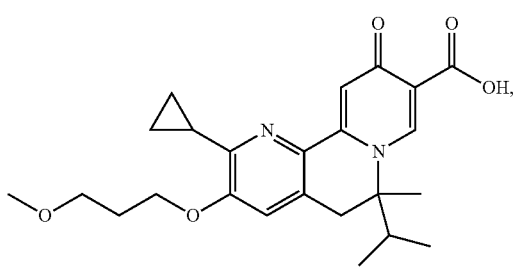 [SMILES: COCCCOc1cc2c(nc1C1CC1)-c1cc(=O)c(C(=O)O)cn1C(C)(C(C)C)C2]

or a pharmaceutically acceptable salt thereof.

In accordance with one embodiment of the present invention, there is provided a compound having the structure of Formula I, IA or IB wherein the compounds are selected from:

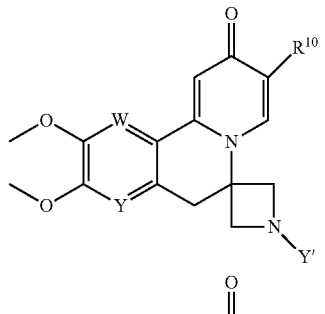

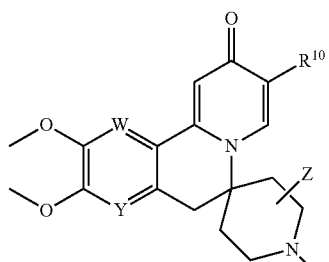

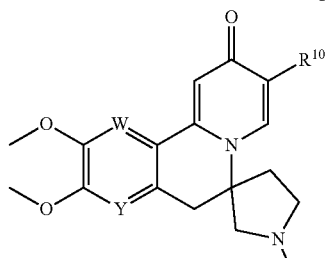

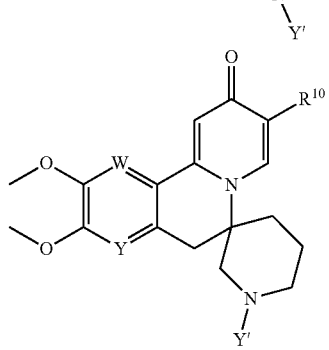

wherein W and Y are independently N or C, with the proviso that W and Y are not both C, and wherein $R^{10}$ is as described herein or a substituent shown in Table 2 and Y' is

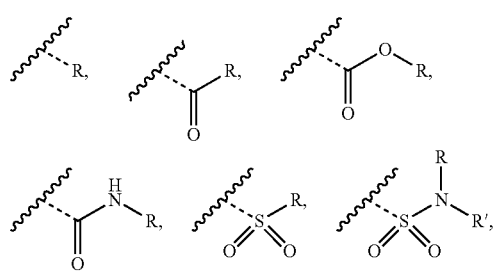

heterocycle or substituted heterocycle, heteroaryl or substituted heteroaryl, wherein R and R' are independently alkyl or substituted alkyl.

In particular embodiments there are provided compounds of Formula I, IA or IB wherein the compounds are selected from:

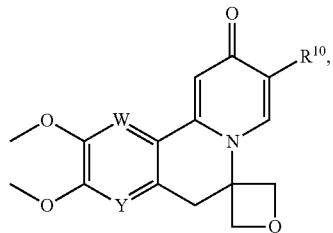

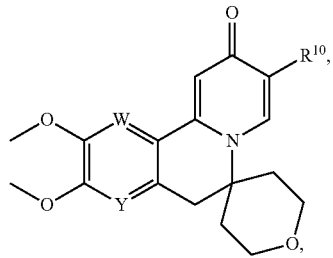

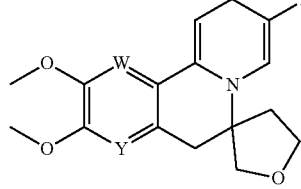

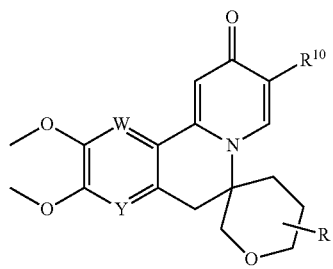

wherein W and Y are independently N or C, with the proviso that W and Y are not both C, and wherein $R^{10}$ is as described herein or a substituent shown in Table 2.

In other particular embodiments there are provided compounds of Formula I, IA or IB wherein the compounds are selected from:

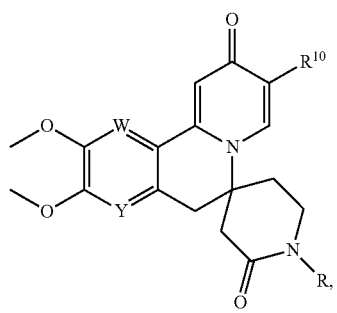

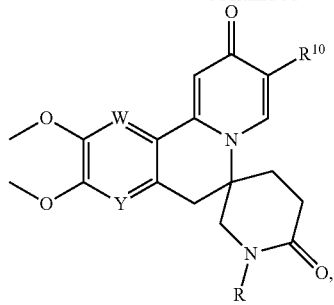

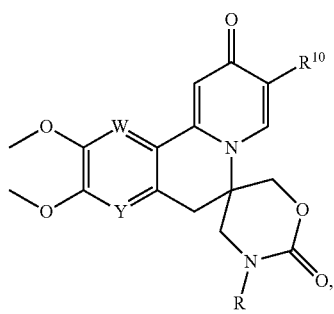

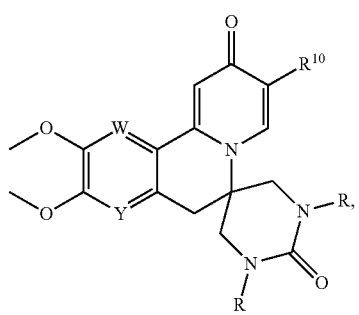

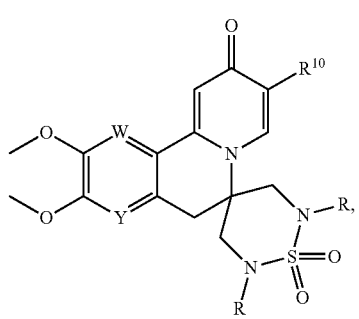

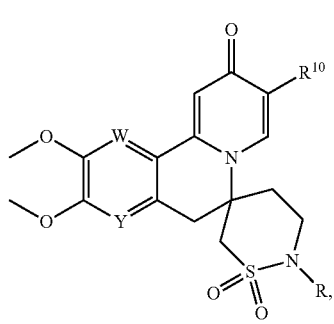

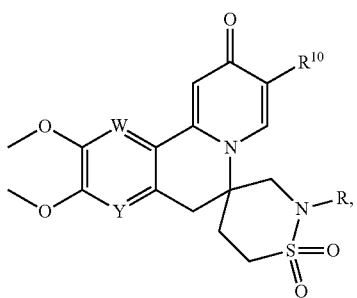
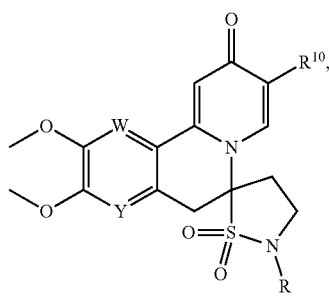
wherein W and Y are independently N or C, with the proviso that W and Y are not both C, and wherein $R^{10}$ is a substituent as described herein or a substituent shown in Table 2, and R is H, alkyl or substituted alkyl.
In another embodiment of the present invention, compounds of Formula I, Formula IA or Formula IB are selected from:
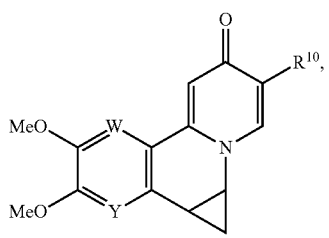
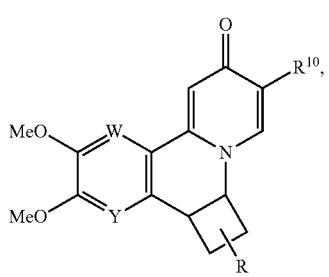

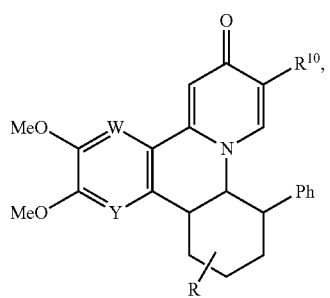

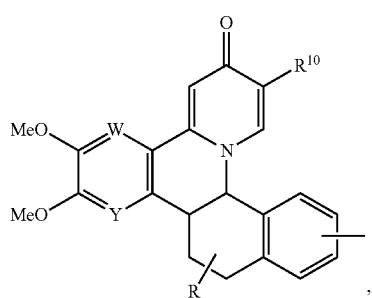

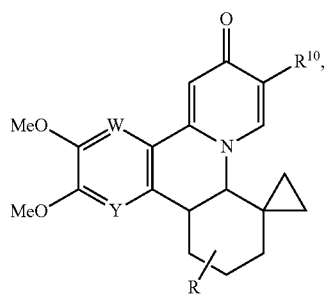

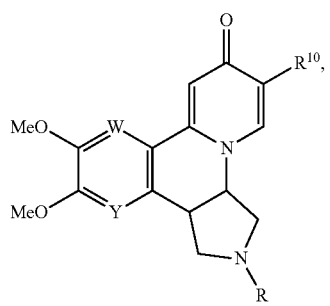

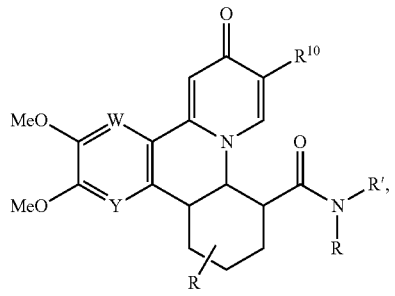

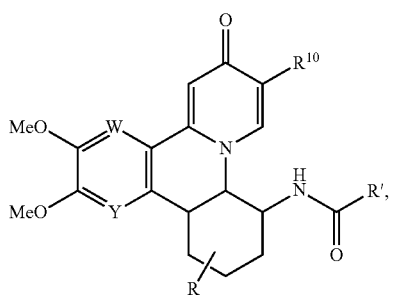

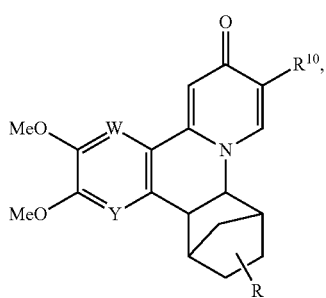

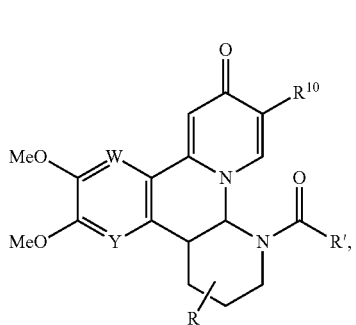

wherein W and Y are independently N or C, with the proviso that W and Y are not both C, and wherein $R^{10}$ is a substituent as described herein or a substituent shown in Table 2, and R is hydrogen, hydroxy,

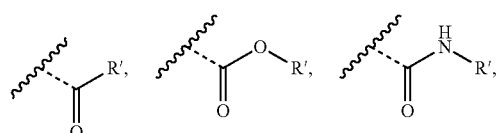

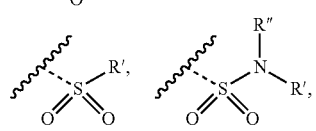

heterocycloalkyl or substituted heterocycloalkyl, heteroaryl or substituted heteroaryl, wherein R' and R" are independently alkyl or substituted alkyl.

In another embodiment of the present invention there is provided a compound of Formula I, Formula IA or Formula IB as shown:

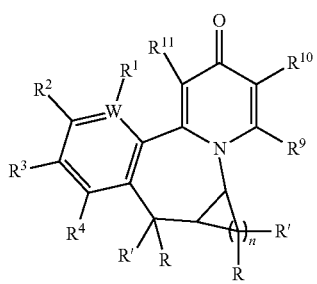

or

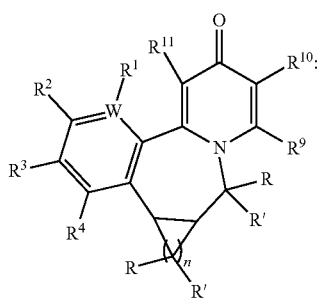

wherein $R^1$, $R^2$, $R^3$, $R^4$, $R^9$ and $R^{11}$ are as described, W and Y are independently N or C, with the proviso that W and Y are not both C, and wherein $R^{10}$ is as described herein or selected from the substituents shown in Table 2, and R' and R are independently selected from hydrogen, hydroxyl, halo, alkyl or substituted alkyl, alkylene or substituted alkylene, carbocycle or substituted carbocycle, heterocycloalkyl or substituted heterocycloalkyl, aryl or substituted aryl, heteroaryl or substituted heteroaryl, wherein said substituted R and R' groups may be substituted with hydroxyl, halo, alkyl, alkylene, cycloalkyl, heterocycle, aryl, heteroaryl,

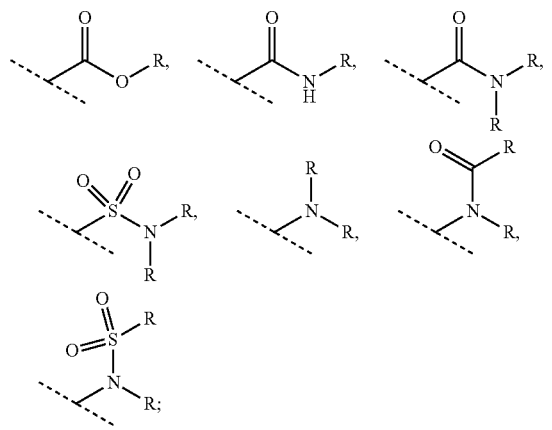

or R and R' together form a spiro, fused or bridged carbocylic or heterocyclic ring.

In another embodiment of the present invention, there is provided a compound having the structure of Formula I, IA or IB, wherein the compound is selected from:

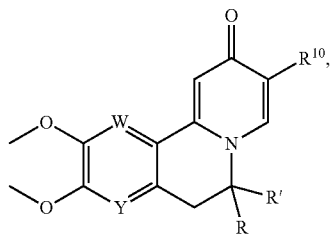

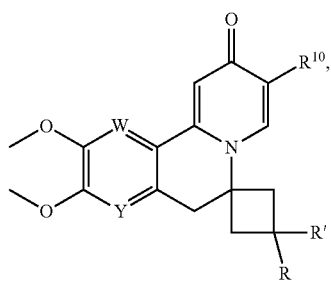

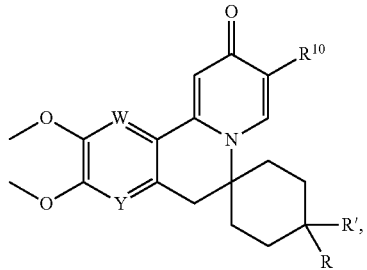

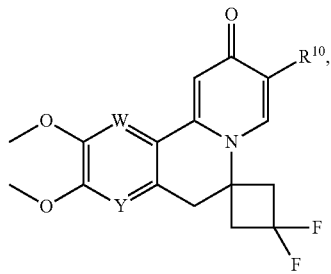

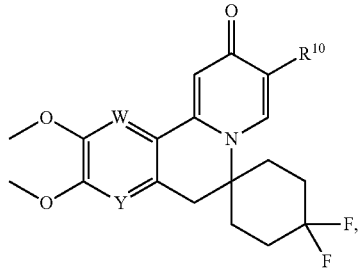

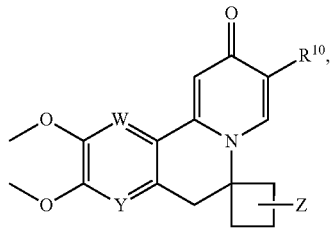

-continued

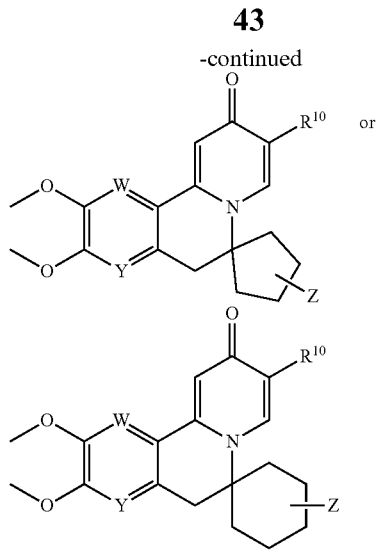

wherein W and Y are independently N or C, with the proviso that W and Y are not both C, and wherein $R^{10}$ is as described herein or is selected from the substituents shown in Table 2, R and R' are independently H, hydroxyl, alkyl or substituted alkyl, acyl, ester, carbamoyl, sulfonyl urea, or urea, and wherein Z is H, OH, $NH_2$, SH, or substituted C, O, N or S.

In another particular embodiment, there is provided a compound of Formula I, IA or IB as indicated:

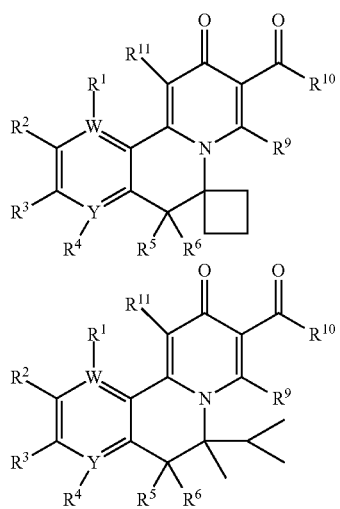

wherein $R^4$, $R^5$, $R^6$, $R^9$, and $R^{11}$ are as described, W and Y are independently N or C, with the proviso that W and Y are not both C, and wherein $R^{10}$ is as described herein or is selected from the substituents shown in Table 2, $R^1$ is as described, $R^2$ and $R^3$ are independently selected from:

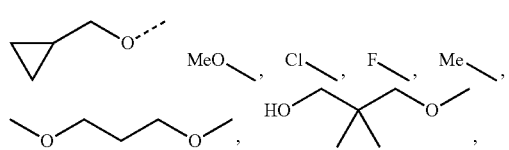

-continued

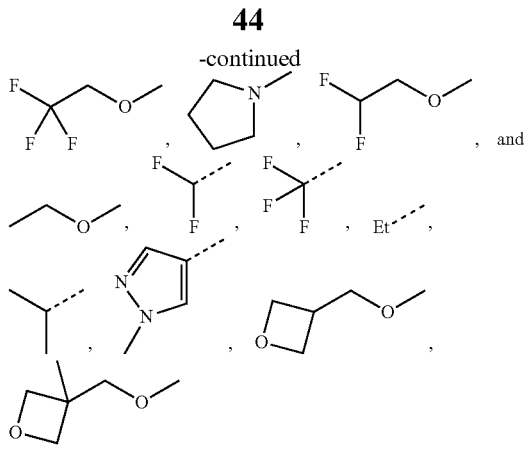

In an embodiment there is provided a compound of Formula I, Formula IA or Formula IB as described herein or a pharmaceutically acceptable salt thereof, wherein:

(A) $R^5$ and $R^6$ are independently hydroxy, halogen, cyano, amino alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6; or $R^5$ and $R^6$ together form a 3- to 8-membered cycloalkyl ring or 3- to 8-membered heterocycloalkyl ring, optionally substituted with $R^{13}$, $R^{13'}$, $R^{14}$ and/or $R^{14'}$, wherein the heteroatom in the heterocycloalkyl ring is selected from O, N, $NR^{22}$, S, $SR^{22}$ or $SR^{22}R^{22'}$; and $R^7$ and $R^8$ are independently hydrogen, hydroxy, halogen, cyano, amino, alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6; or (B) $R^5$ and $R^8$ are independently hydrogen, hydroxy, halogen, cyano, amino alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6; and $R^6$ and $R^7$ together form a 3- to 8-membered cycloalkyl ring or 3- to 8-membered heterocycloalkyl ring comprising one heteroatom or two or more heteroatoms, optionally substituted with $R^{15}$, $R^{15'}$, $R^{16}$ and/or $R^{16'}$, wherein the one heteroatom in the heteroalkyl ring is $NR^{20}$ and the two or more heteroatoms are selected from N, $NR^{22}$, O, S, $SR^{22}$ and $SR^{22}R^{22'}$; or (C) $R^5$ and $R^6$ are independently hydrogen, hydroxy, halogen, cyano, amino alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6; and $R^7$ and $R^8$ are independently hydroxy, halogen, cyano, amino, alkyl or substituted alkyl, alkoxy or substituted alkoxy, cycloalkyl or substituted cycloalkyl, alkenyl or substituted alkenyl; aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6; or $R^7$ and $R^8$ together form a 3- to 8-membered cycloalkyl ring or a 3- to 8-membered heterocycloalkyl ring, optionally substituted with $R^{17}$, $R^{18'}$, $R^{17}$ and/or $R^{18}$, wherein the heteroatom in the heterocycloalkyl ring is selected from O, N, $NR^{22}$, S, $SR^{22}$ or $SR^{22}R^{22'}$.

In one embodiment there is provided a compound of Formula I, Formula IA or Formula IB according as described herein or a pharmaceutically acceptable salt thereof, wherein the compound is selected from the compounds of Table 1, and wherein $R^{10}$ is as described herein or is a substituent shown in Table 2, or a tautomer thereof.

In one embodiment there is provided a method of treating or preventing a virus infection in a subject susceptible to or suffering from the virus infection comprising administering to the subject an inhibitor of a HBe or HBs antigen wherein the inhibitor is a compound of Formula I, Formula IA or Formula IB as described herein.

In one embodiment there is provided a method of treating or preventing a hepatitis B virus infection in a subject susceptible to or suffering from the hepatitis B virus infection, comprising administering to the subject an inhibitor of a HBe or HBs antigen wherein the inhibitor is a compound of Formula I, Formula IA or Formula IB as described herein.

In one embodiment there is provided a method of treating or preventing a hepatitis B virus infection in a subject susceptible to or suffering from the hepatitis B virus infection comprising administering to the subject an inhibitor of a HBe or HBs antigen wherein the inhibitor comprises a compound from Table 1 wherein $R^{10}$ is a substituent shown in Table 2 or tautomer thereof, or wherein the inhibitor is a compound from Table IB.

In one embodiment there is provided a method of inhibiting the level of HBe or HBs antigen in a mammal, comprising administering to said mammal a therapeutically effective amount of a compound of Formula I, Formula IA or Formula IB as described herein or a pharmaceutically acceptable salt, solvate or hydrate thereof.

In a particular embodiment, there is provided a method of inhibiting the level of HBe or HBs antigen in a mammal, comprising administering to said mammal a therapeutically effective amount of a compound of Formula I, Formula IA or Formula IB as described herein, or a pharmaceutically acceptable salt, solvate or hydrate thereof, wherein the mammal is a human.

In one embodiment there is provided a pharmaceutical composition comprising a pharmaceutically acceptable diluent and a therapeutically effective amount of a compound of Formula I, Formula IA or Formula IB as described herein.

In one embodiment there is provided a compound of Formula I, Formula IA or Formula IB as described herein, or a pharmaceutical composition thereof, for use in therapy.

In one embodiment there is provided a compound of Formula I, Formula IA or Formula IB as described herein, or a pharmaceutical composition thereof, for use in the treatment of a viral infection.

In one embodiment there is provided a compound of Formula I, Formula IA or Formula IB as described herein, or a pharmaceutical composition thereof, for use in the treatment of a viral infection, wherein the viral infection is a hepatitis B viral infection.

In one embodiment there is provided use of a compound of Formula I, Formula IA or Formula IB as described herein, or a pharmaceutical composition thereof, in the manufacture of a medicament for use in the treatment of a hepatitis B viral infection in a human.

In one embodiment there is provided a compound of Formula I, Formula IA or Formula IB as described herein, or a pharmaceutical composition thereof, for use in medical therapy.

In one embodiment there is provided a compound of Formula I, Formula IA or Formula IB as described herein, or a pharmaceutical composition thereof, for use in the treatment of prevention of a hepatitis B viral infection in a human.

In one embodiment there is provided a compound of Formula I, Formula IA or Formula IB as described herein, or a pharmaceutical composition thereof, for use in inhibiting the level of HBe or HBs antigen in a mammal HBsAg in vitro.

Compounds described herein can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formula I, Formula IA or Formula IB for use in therapy.

In another embodiment of the intention, there is provided a compound of Formula I, Formula IA or Formula IB, for use in the treatment of a viral infection.

In another embodiment of the invention, there is provided a use of a compound of Formula I, Formula IA or Formula IB in the manufacture of a medicament for use in the treatment of a viral infection in a human.

In another embodiment of the invention, there is provided a pharmaceutical composition comprising a pharmaceutically acceptable diluent and a therapeutically effective amount of a compound as defined in Formula I, Formula IA or Formula IB.

In one embodiment, the pharmaceutical formulation containing a compound of Formula I, Formula IA or Formula IB or a salt thereof is a formulation adapted for parenteral administration. In another embodiment, the formulation is a long-acting parenteral formulation. In a further embodiment, the formulation is a nano-particle formulation.

In one embodiment, the pharmaceutical formulation containing a compound of Formula I, Formula IA or Formula IB or a salt thereof is a formulation adapted for oral, rectal, topical or intravenous formulation, wherein the pharmaceutical formulation optionally comprises any one or more of a pharmaceutically acceptable carrier, adjuvant or vehicle.

In one embodiment, the compounds of Formula I, Formula IA or Formula IB are formulated for oral administration, and can be administered as a conventional preparation, for example, as any dosage form of a solid agent such as tablets, powders, granules, capsules and the like; an aqueous agent; an oily suspension; or a liquid agent such as syrup and elixir. In one embodiment, the compounds of Formula I, Formula IA or Formula IB are formulated for parenteral administration, and can be administered as an aqueous or oily suspension injectable, or a nasal drop. Upon preparation of a parenteral formulation with a compound of Formula I, Formula IA or Formula IB, conventional excipients, binders, lubricants, aqueous solvents, oily solvents, emulsifiers, suspending agents, preservatives, stabilizers and the like may be arbitrarily used. As an anti-viral-drug, particularly, an oral agent is preferable. A preparation of a compound of Formula I, Formula IA or Formula IB may be prepared by combining (e.g. mixing) a therapeutically effective amount of a compound of Formula I, Formula IA or Formula IB with a pharmaceutically acceptable carrier or diluent.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the compound of Formula I, Formula IA or Formula IB can be combined with an oral, non-toxic pharmaceutically acceptable inert carrier such as ethanol, glycerol, water and the like. Powders are prepared by comminuting the compound of Formula I, Formula IA or Formula IB to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulations of compounds of Formula I, Formula IA or Formula IB can also be prepared to prolong or sustain the release of the compound, as for example by coating or embedding particulate material in polymers, wax or the like.

The compounds of Formula I, Formula IA or Formula IB or salts, solvates or hydrates thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula I, Formula IA or Formula IB or salts, solvates or hydrates thereof, may also be delivered by the use of monoclonal antibodies as individual carriers to which the compound molecules are coupled. The compounds may also be coupled with soluble polymers as targetable drug carriers. Such polymers can include polyvinylpyrrolidone, pyrancopolymer, polyhydroxypropylmethacrylamide-phenol, polyhydroxyethylaspartamide-phenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the compounds of Formula I, Formula IA or Formula IB may be delivered from a patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers or insufflators.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations described herein may include other agents conventional in the art having regard to the type of formulation in question, for example those suitable for oral administration may include flavouring agents.

A therapeutically effective amount of a compound of Formula I, Formula IA or Formula IB will depend upon a number of factors including, for example, the age and weight of the human or other animal, the precise condition requiring treatment and its severity, the nature of the formulation, and the route of administration, and will ultimately be at the discretion of the attendant physician or veterinarian. An effective amount of a salt or hydrate thereof may be determined as a proportion of the effective amount of the compound of Formula I, Formula IA or Formula IB or salts, solvates or hydrates thereof per se.

Embodiments of the present invention provide administration of a compound of Formula I, Formula IA or Formula IB to a healthy or virus-infected patient, either as a single agent or in combination with (a) another agent that is effective in treating or preventing hepatitis B virus of hepatitis D virus, (b) another agent that improves immune response and robustness, or (c) another agent that reduces inflammation and/or pain.

The compounds of Formula I, Formula IA or Formula IB or salts, solvates or hydrates thereof, are believed to have activity in preventing, halting or reducing the effects of hepatitis B virus by inhibiting the HBe and/or HBs antigens, thereby interfering with or preventing the virus from remaining in the host cell and rendering the virus unable to replicate.

Accordingly, there is provided a method of treating a hepatitis B virus and/or hepatitis D virus by administering a therapeutically effective amount of a compound of Formula I, Formula IA or Formula IB to a mammal, or a pharmaceutically acceptable salt, solvate or hydrate thereof. In one embodiment, the mammal is a human.

In another aspect of the present invention, there is provided a method of reducing HBe and/or HBs antigens in a mammal by administering to said mammal a therapeutically effective amount of a compound of Formula I, Formula IA or Formula IB or a pharmaceutically acceptable salt, solvate or hydrate thereof. In one embodiment, the mammal is a human.

In other embodiments, the compounds of the present invention may be used in combination with one or more antiviral therapeutic agents or anti-inflammatory agents useful in the prevention or treatment of viral diseases or associated pathophysiology. Thus, the compounds of the present invention and their salts, solvates, or other pharmaceutically acceptable derivatives thereof, may be employed alone or in combination with other antiviral or anti-inflammatory therapeutic agents.

The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds.

Alternatively, the combination may be administered separately in a sequential manner wherein one treatment agent is administered first and the other second or vice versa. Such sequential administration may be close in time or remote in time. The amounts of the compound(s) of Formula I, Formula IA or Formula IB or salts thereof and the other pharmaceutically active agent(s) and the relative timings of administration will be selected in order to achieve the desired combined therapeutic effect.

More particularly, embodiments provide a method as described comprising administering an additional agent selected from an antiviral agent, an antibiotic, an analgesic, a non-steroidal anti-inflammatory (NSAID) agent, an antifungal agent, an antiparasitic agent, an anti-nausea agent, an anti-diarrheal agent, or an immunosuppressant agent. In certain embodiments, the antiviral agent is an anti-hepatitis B agent or an anti-hepatitis C agent. Still more particularly, the additional agent is administered as part of a single dosage form of said pharmaceutical formulation, or as a separate dosage form.

The present invention is directed to compounds, compositions and pharmaceutical compositions that have utility as novel treatments and/or preventative therapies for virus infections. While not wanting to be bound by any particular theory, it is thought that the present compounds are able to inhibit the levels of HBe and HBs antigens in a subject infected with hepatitis B virus or suffering from a chronic hepatitis B viral infection. By reducing the levels of HBe and HBs antigens in a subject infected with hepatitis B virus, compounds described herein are effective at treating hepatitis B infections, and secondary disorders such as liver cirrhosis, liver failure and liver cancer which are often associated with hepatitis B virus infections.

Therefore, in another embodiment of the present invention, there is provided a method of treating or preventing a hepatitis B virus infection in a subject suffering from the HBV infection comprising administering to the subject an inhibitor of HBe and/or HBs antigens, wherein the inhibitor is a compound of Formula I, Formula IA or Formula IB.

In another embodiment of the present invention, there is provided a method of treating a hepatitis B virus infection and/or a hepatitis D virus infection in a subject suffering from the virus infection comprising administering to the subject compound from Table 1.

In some embodiments, provided is a method for treating a viral infection in a subject mediated at least in part by a virus in the hepatitis B family and or the hepatitis D family, comprising administering to the subject a composition comprising a compound of any of Formula I, Formula IA or Formula IB, or a pharmaceutically acceptable salt thereof.

In yet another aspect, another embodiment of the present invention provides a method of inhibiting progression of a viral infection in a subject at risk for infection with a hepatitis B virus and/or a hepatitis D virus, comprising administering to the subject a therapeutically effective amount of the compound of Formula I, Formula IA or Formula IB, or a pharmaceutically acceptable salt thereof.

In yet another aspect, another embodiment of the present invention provides a method of preventing a viral infection in a subject at risk for infection from a hepatitis B virus and/or a hepatitis D virus comprising administering to the subject a therapeutically effective amount of the compound of Formula I or Formula IA, or a pharmaceutically acceptable salt thereof.

In yet another aspect, another embodiment of the present invention provides a method of treating a virus infection in a subject suffering from said virus infection, comprising administering to the subject a therapeutically effective amount of the compound of Formula I, Formula IA or Formula IB, or a pharmaceutically acceptable salt thereof.

Compounds, methods and pharmaceutical compositions for treating viral infections, by administering compounds of Formula I, Formula IA or Formula IB in therapeutically effective amounts are disclosed. Methods for preparing compounds of Formula I, Formula IA or Formula IB and methods of using the compounds and pharmaceutical compositions thereof are also disclosed. In particular, the treatment and prophylaxis of viral infections such as those caused by hepatitis B and/or hepatitis D are disclosed.

In other embodiments, the compounds described herein are useful for treating infections in a subject wherein the infection is caused by a multi-drug resistant strain of the hepatitis B virus and/or a hepatitis D virus.

In further embodiments, the compound of the present invention, or a pharmaceutically acceptable salt thereof, is chosen from the compounds set forth in Table 1.

EXAMPLES

Synthetic Schemes

The compounds of the present invention having Formula I, Formula IA or Formula IB

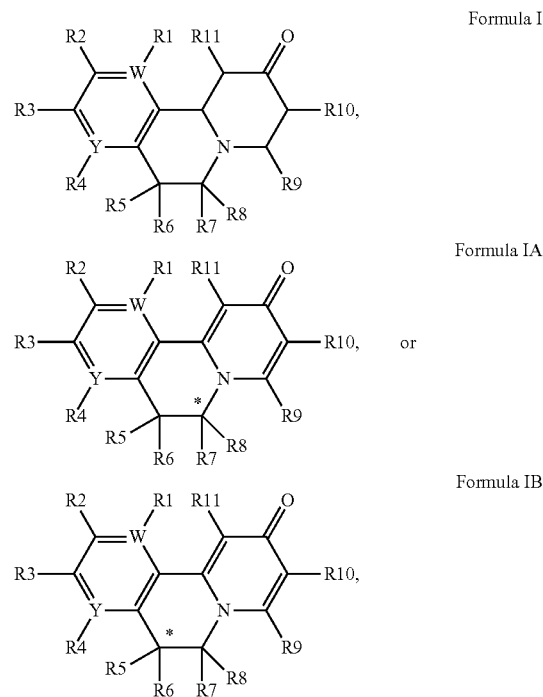

or corresponding pharmaceutically acceptable salts thereof, are prepared using conventional organic syntheses, wherein:

C* is a carbon atom stereocenter which has a configuration which is (R) or (S);

W and Y are independently C or N, with the proviso that W and Y are not both C;

wherein if W is C, then $R^1$ is hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N—$C_xH_{2x}$-phenyl wherein x is 0, 1, 2, 3, 4, 5, 6; or —$OR^{12}$; and if Y is C, then $R^4$ is hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N—$C_xH_{2x}$-phenyl wherein x is 0, 1, 2, 3, 4, 5, 6; or —$OR^{12}$;

wherein if W is N, then $R^1$ is absent; and if Y is N, then $R^4$ is absent;

$R^2$ and $R^3$ are independently selected from hydrogen, hydroxy, halogen, cyano, amino or substituted amino, thio or substituted thio, alkyl or substituted alkyl, alkoxy or substituted alkoxy; cycloalkyl or substituted cycloalkyl; alkenyl or substituted alkenyl; 3- to 8-membered heterocycloalkyl or substituted 3- to 8-membered heterocycloalkyl, aryl or substituted aryl, heteroaryl or substituted heteroaryl, pyrrolidinyl, —$C_xH_{2x}$-phenyl, —O—$C_xH_{2x}$-phenyl, or —($C_{1-6}$alkyl)N—$C_xH_{2x}$-phenyl wherein x is 0, 1, 2, 3, 4, 5, 6; or —$OR^{12}$;

$R^5$ and $R^6$ are independently hydrogen, hydroxy, halogen, cyano, amino alkyl or substituted alkyl, alkoxy or substituted alkoxy, cycloalkyl or substituted cycloalkyl, alkenyl or substituted alkenyl; aryl or substituted aryl, heteroaryl or substituted aryl, —$C_xH_{2x}$-phenyl or —O—$C_xH_{2x}$-phenyl wherein x is 0, 1, 2, 3, 4, 5 or 6;

$R^7$ and $R^8$ are independently hydrogen, hydroxy, halogen, cyano, amino, alkyl or substituted alkyl, alkoxy or substituted alkoxy, cycloalkyl or substituted cycloalkyl, alkenyl or substituted alkenyl; aryl or substituted aryl, heteroaryl, —$C_xH_{2x}$-phenyl or —O—$C_xH_{2x}$-phenyl wherein x is 0, 1, 2, 3, 4, 5 or 6;

or $R^5$ and $R^6$ together form a 3- to 8-membered cycloalkyl ring or 3- to 8-membered heterocycloalkyl ring, wherein the heteroatom in the heterocycloalkyl ring is O, N, $NR^{22}$, S, $SR^{22}$ or $SR^{22}R^{22'}$, wherein the 3- to 8-membered heterocycloalkyl ring is optionally substituted with $R^{13}$, $R^{13'}$, $R^{14}$ and/or $R^{14'}$;

or $R^6$ and $R^7$ together form a 3- to 8-membered cycloalkyl ring or heterocycloalkyl ring comprising one heteroatom or two or more heteroatoms, optionally substituted with $R^{15}$, $R^{15'}$, $R^{16}$ and/or $R^{16'}$, wherein the one heteroatom in the heteroalkyl ring is $NR^{20}$ and the two or more heteroatoms are selected from N, $NR^{22}$, O, S, $SR^{22}$ and $SR^{22}R^{22'}$;

or $R^7$ and $R^8$ together form a 3- to 8-membered cycloalkyl ring or 3- to 8-membered heterocycloalkyl ring, optionally substituted with $R^{17}$, $R^{17'}$, $R^{18}$ and/or $R^{18'}$, wherein the heteroatom in the heterocycloalkyl ring is O, N, $NR^{22}$, S, $SR^{22}$ or $SR^{22}R^{22'}$;

$R^9$ is a bond, hydrogen, hydroxy, halogen, cyano, amino, alkyl or substituted alkyl, alkoxy or substituted alkoxy, cycloalkyl or substituted cycloalkyl, alkenyl or substituted alkenyl, heterocycloalkyl or substituted heterocycloalkyl, aryl or substituted aryl, heteroaryl or substituted heteroaryl, —$C_xH_{2x}$-phenyl or —O—$C_xH_{2x}$-phenyl wherein x is 0, 1, 2, 3, 4, 5 or 6;

$R^{10}$ is a substituent shown in Table 2 or a tautomer thereof;

or $R^9$ is a bond and $R^9$ and $R^{10}$ together form an oxaborole ring;

$R^{11}$ is hydrogen, hydroxy, halogen, cyano, amino, alkyl or substituted alkyl; alkenyl or substituted alkenyl; alkoxy or substituted alkoxy; cycloalkyl or substituted cycloalkyl; heterocycloalkyl or substituted heterocycloalkyl, aryl, heteroaryl, —$C_xH_{2x}$-phenyl or —O—$C_xH_{2x}$-phenyl wherein x is 0, 1, 2, 3, 4, 5 or 6;

$R^{12}$ is hydrogen; alkyl or substituted alkyl, alkoxy or substituted alkoxy, cycloalkyl or substituted cycloalkyl, heterocycloalkyl or substituted heterocycloalkyl, aryl or substituted aryl, heteroaryl or substituted heteroaryl;

$R^{13}$, $R^{13'}$, $R^{14}$ and $R^{14'}$ are independently hydrogen, hydroxy, halogen, amino, aminoalkyl, cyano, $C_{1-6}$alkyl, $C_{1-6}$alkoxy, carbonyl, carboxamide, amide; or $R^{13}$ and $R^{13'}$ or $R^{14}$ and $R^{14'}$ together form a 3- to 8-membered cycloalkyl ring or 3- to 8-membered heterocycloalkyl ring, optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;

$R^{15}$, $R^{15'}$, $R^{16}$ and $R^{16'}$ are independently hydrogen, hydroxy, halogen, amino, cyano, $C_{1-6}$alkyl, or $C_{1-6}$alkoxy; or $R^{15}$ and $R^{15'}$ or $R^{16}$ and $R^{16'}$ together form a 3- to 8-membered cycloalkyl ring or 3- to 8-membered heterocycloalkyl ring optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;

$R^{17}$, $R^{17'}$, $R^{18}$ and $R^{18'}$ are independently hydrogen, hydroxy, halogen, amino, cyano, $C_{1-6}$alkyl, or $C_{1-6}$alkoxy; or $R^{17}$ and $R^{18}$ or $R^{17'}$ and $R^{18'}$ together form a 3- to 8-membered cycloalkyl ring or 3- to 8-membered heterocycloalkyl ring, optionally substituted with oxygen, halogen, hydroxy, amino, cyano, $C_{1-6}$alkyl, $C_{3-8}$cycloalkyl, $C_{2-6}$alkenyl or $C_{1-6}$alkoxy, wherein the heteroatom in the heterocycloalkyl ring is O, N, $NR^{22}$, S, $SR^{22}$ or $SR^{22}R^{22'}$;

$R^{19}$, $R^{19'}$ and $R^{19''}$ are independently hydrogen, $C_{1-6}$alkyl, $C_{3-8}$cycloalkyl, $C_{2-6}$alkenyl, $C_{1-6}$alkoxy, phenyl, $C_{1-6}$alkylimidizole, $C_{1-6}$alkyltriazole, $C_{1-6}$alkyltetrazole, $C_{1-6}$alkylthiazole, $C_{1-6}$alkyloxazole, $C_{1-6}$alkyldioxazole; $C_{1-6}$alkyloxazolidone; and $R^{20}$ and $R^{21}$ are independently hydrogen, $C_{1-6}$alkyl, $C_{3-8}$cycloalkyl, $C_{2-6}$alkenyl, $C_{1-6}$alkoxy, phenyl, $C_{1-6}$alkylimidizole, $C_{1-6}$alkyltriazole, $C_{1-6}$alkyltetrazole, $C_{1-6}$alkylthiazole, $C_{1-6}$alkyloxazole, $C_{1-6}$alkyldioxazole; $C_{1-6}$alkyloxazolidone, or $R^{20}$ and $R^{21}$ together with the nitrogen to which they are attached form unsubstituted pyrrolidinyl, unsubstituted piperidinyl, or unsubstituted morpholinyl; or form carboxyl-substituted pyrrolidinyl, carboxyl-substituted piperidinyl or carboxyl-substituted morpholinyl; and $R^{22}$ and $R^{22'}$ are independently selected from hydrogen, oxygen, $C_{1-6}$alkyl or substituted $C_{1-6}$alkyl, $C_{1-6}$alkoxy or substituted $C_{1-6}$alkoxy, $C_{3-8}$cycloalkyl or substituted $C_{3-8}$cycloalkyl, $C_{2-6}$alkenyl or substituted $C_{2-6}$alkenyl, aryl or substituted aryl, including substituted or unsubstituted $C_{1-6}$alkylimidizole, substituted or unsubstituted $C_{1-6}$alkyltriazole, $C_{1-6}$alkyltetrazole, $C_{1-6}$alkylthiazole, substituted or unsubstituted $C_{1-6}$alkyloxazole, $C_{1-6}$alkyldioxazole; $C_{1-6}$alkyloxazolidone; —$COR^{19}$, —$COOR^{19'}$, —$CSOR^{19''}$, —$CONR^{20}R^{21}$, or a pharmaceutically acceptable salt thereof.

Other embodiments provide compounds of Formula I, Formula IA or Formula IB or a pharmaceutically acceptable salt thereof as described herein, wherein:

$R^5$ and $R^6$ together form a 3- to 8-membered cycloalkyl ring or 3- to 8-membered heterocycloalkyl ring, wherein the heteroatom in the heterocycloalkyl ring is O, N, $NR^{22}$, S, $SR^{22}$ or $SR^{22}R^{22'}$, wherein the 3- to 8-membered heterocycloalkyl ring is optionally substituted with $R^{13}$, $R^{13'}$, $R^{14}$ and/or $R^{14'}$.

Other particular embodiments provide compounds of Formula I, Formula IA or Formula IB or a pharmaceutically acceptable salt thereof as described herein, wherein:

$R^6$ and $R^7$ together form a 3- to 8-membered cycloalkyl ring or heterocycloalkyl ring comprising one heteroatom or two or more heteroatoms, optionally substituted with $R^{15}$, $R^{15'}$, $R^{16}$ and/or $R^{16'}$, wherein the one heteroatom in the heteroalkyl ring is $NR^{20}$ and the two or more heteroatoms are selected from N, $NR^{22}$, O, S, $SR^{22}$ and $SR^{22}R^{22'}$.

Other particular embodiments provide compounds of Formula I, Formula IA or Formula IB or a pharmaceutically acceptable salt thereof as described herein, wherein:

$R^7$ and $R^8$ together form a 3- to 8-membered cycloalkyl ring or 3- to 8-membered heterocycloalkyl ring, optionally substituted with $R^{17}$, $R^{17'}$, $R^{18}$ and/or $R^{18'}$, wherein the heteroatom in the heterocycloalkyl ring is O, N, $NR^{22}$, S, $SR^{22}$ or $SR^{22}R^{22'}$.

Suitable synthetic routes are depicted below in the following general reaction schemes. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

Abbreviations

In describing the examples, chemical elements are identified in accordance with the Periodic Table of the Elements. Abbreviations and symbols utilized herein are in accordance with the common usage of such abbreviations and symbols by those skilled in the chemical arts. The following abbreviations are used herein:

AcOH acetic acid
$Ac_2O$ acetic anhydride
aq aqueous
B4 (S)-2-(((benzyloxy)carbonyl)amino)-3-(4-(trifluoromethyl)piperidin-1-yl)propanoic acid
BOC (Boc)N-tert-butoxycarbonyl or tert-butyloxycarbonyl
CBz carboxybenzyl
dba dibenzylideneacetone or dibenzalacetone
DCE dichloroethane
DCM dichloromethane
DCM/EA dichloromethane/ethanol
DDQ 2,3-dichloro-5,6-dicyanobenzoquinone
DIPEA (or DIEA) N,N-diisopropylethylamine, or Hünig's base
DME dimethoxyethane
DMEM Dulbecco's Modified Eagle Medium
DMF dimethylformamide
DMP Dess-Martin periodinane
DMSO-d6 deuterated dimethylsulfoxide
DMSO dimethylsulfoxide
DPPA diphenyl phosphoryl azide
$EC_{50}$ 50% effective concentration
EDTA ethylenediaminetetraacetic acid
Et ethyl
$Et_2O$ diethyl ether
EtOH ethanol
EtOAc, EA, AcOEt ethyl acetate
GlutaMAX™ cell culture supplement from Life Technologies
h hour(s)
HEPES 4-(2-hydroxyethyl)-1-piperazineethanesulfonic acid
HPLC high performance liquid chromatography
$IC^{50}$ 50% inhibition concentration
iPrOH isopropyl alcohol or isopropanol
LCMS Liquid chromatography mass spectroscopy
LDA lithium di-isopropyl amide
Me methyl
MeOH methanol
NBS N-bromosuccinimide
NCS N-chlorosuccinimide
NIS N-iodosuccinimide
NXS N-halosuccinimide
$NaBH(OAc)_3$ sodium triacetoxyborohydride
NMR Nuclear Magnetic Resonance spectroscopy
$Pd_2(dba)_3$ Tris(dibenzylideneacetone)dipalladium(0)
PE petroleum ether
$PPh_3$ triphenylphosphine
Pr propyl
RB round bottom
rt or r.t. room temperature
RT retention time
SFC supercritical fluid chromatography
$SO_3pyr$ sulfur trioxide pyridine complex—formula $C_5H_5NSO_3$
SPhos 2-dicyclohexyl phosphine-2',6'-dimethoxybiphenyl or dicyclohexyl(2',6'-dimethoxy-[1,1'-biphenyl]-2-yl)
t-BuOMe methyl t-butyl ether
T3P 1-Propanephosphonic anhydride solution, 2,4,6-Tripropyl-1,3,5,2,4,6-trioxatriphosphorinane-2,4,6-trioxide
TFA trifluoroacetic acid
THF tetrahydrofuran
uv ultraviolet Unless otherwise noted, all starting materials were obtained from commercial suppliers and used without further purification. Unless otherwise indicated, all temperatures are expressed in ° C. (degrees Centigrade). Unless otherwise indicated, all reactions are conducted under an inert atmosphere at ambient temperature.

All temperatures are given in degrees Celsius, all solvents are highest available purity and all reactions run under anhydrous conditions in an argon (Ar) or nitrogen ($N_2$) atmosphere where necessary.

The following examples illustrate the invention. These examples are not intended to limit the scope of the present invention, but rather to provide guidance to the skilled artisan to prepare and use the compounds, compositions, and methods of the present invention.

While particular embodiments of the present invention are described, the skilled artisan will appreciate that various changes and modifications can be made without departing from the spirit and scope of the invention.

As used herein the symbols and conventions used in these processes, schemes and examples are consistent with those used in the contemporary scientific literature, for example, the *Journal of the American Chemical Society or the Journal of Biological Chemistry*. Unless otherwise noted, all starting materials were obtained from commercial suppliers and used without further purification.

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are highest available purity unless otherwise indicated.

¹H NMR (hereinafter also "NMR") spectra were recorded on a Varian Unity-400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Flash chromatography was run over Merck Silica gel 60 (230-400 mesh), or using a Teledyne Isco Combiflash® Companion with normal phase, disposable Redi-Sep® flash columns. Mass spectra were run on an open access LC-MS system using electrospray ionization. The analytical low-resolution mass spectra (MS) were recorded on Waters SQD instrument with UPLC analysis was conducted on a Phenomenex® Kinetex® 1.7 um, 2.1×50 mm XB-C18 column at 40CSQ using a gradient elution method. Solvent A: 0.2% formic acid (FA) in water; Solvent B: 0.15% FA in acetonitrile; 1%-99% Solvent B gradient over 1.1 minutes and holding steady at 99% solvent B for another 0.4 minutes, at 1 ml/min flow rate.

Synthetic Preparation of Compounds

General Protocols for Making Compounds as Described Herein are Shown Below in Schemes 1-15.

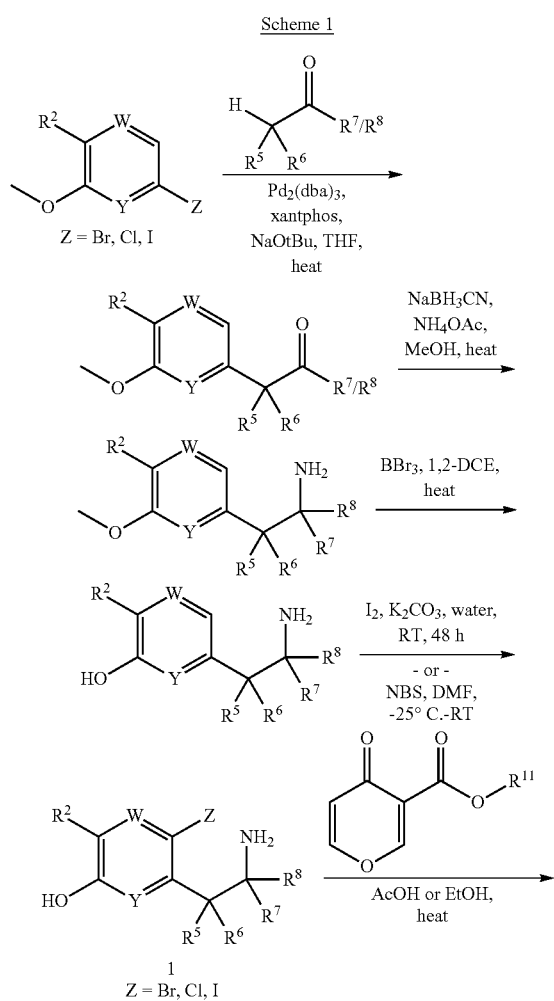

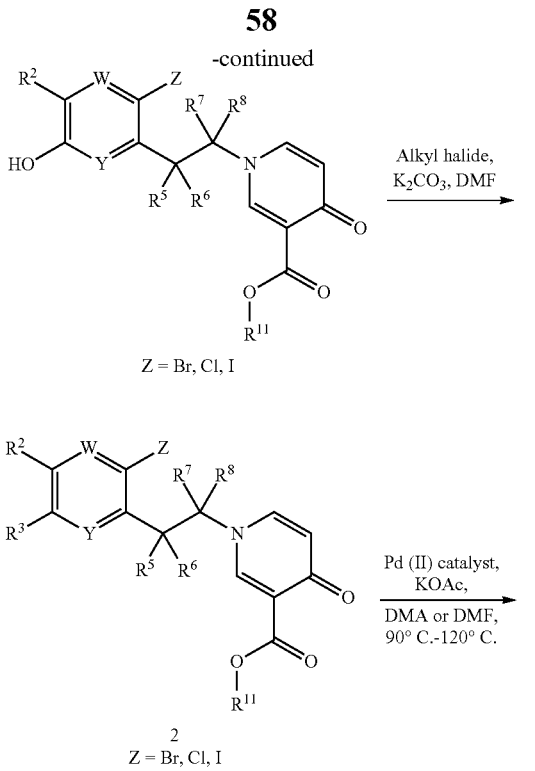

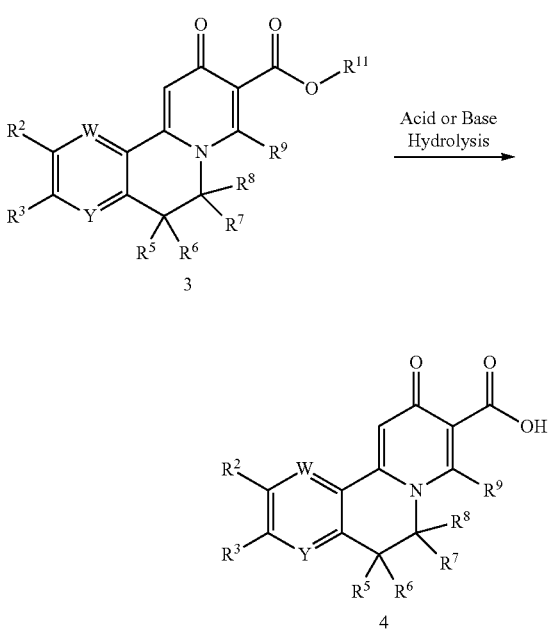

Particular compounds disclosed herein may be made according to Scheme 1. For example, compound 4 can be prepared by reacting compound 1 with an appropriately substituted 4-pyranone, as shown, in acetic acid or ethanol, with heat. Reductive cyclisation of 2 by treatment of compound 2 with Pd(II) catalyst with an appropriate base such as potassium acetate in an appropriate solvent such as N,N-dimethylacetamide (DMA) or N,N-dimethylformamide (DMF) at 90-120° C., yields fused tricyclic carboxylate compound 3. Compound 3 is then subjected to hydrolysis of the ester under acid or base conditions to yield the carboxylic acid 4. Further chemical manipulation of the carboxylic acid can lead to additional $R^{10}$ groups.

Alternatively, compounds described herein may be prepared according to Scheme 2.

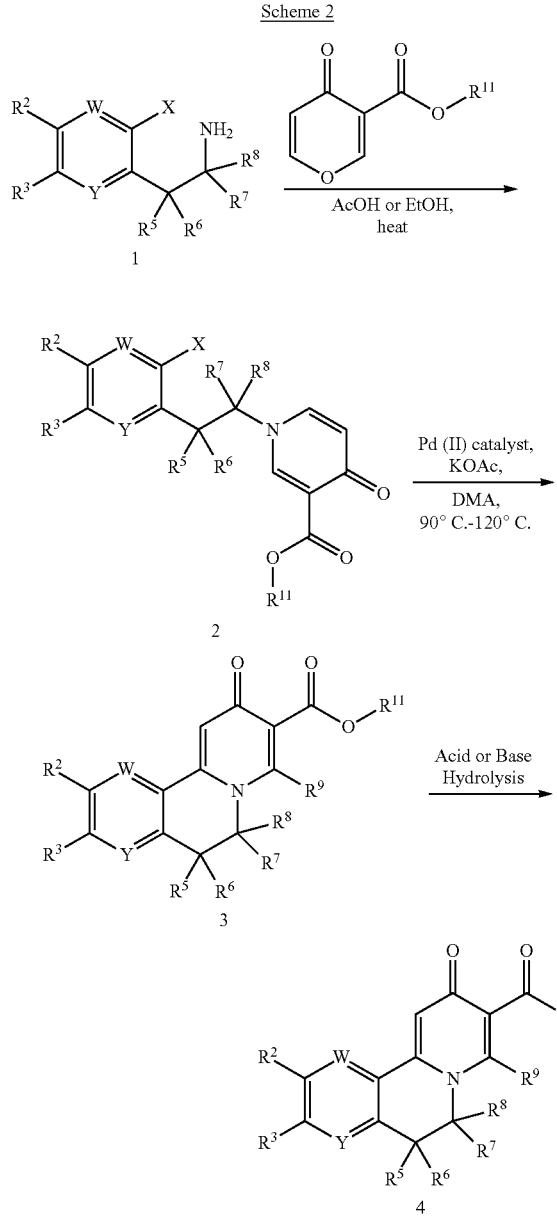

wherein X is Br or I, and W, Y, $R^5$, $R^6$, $R^7$ and $R^8$ are as described herein.

As shown in Scheme 2, compound 2 can be prepared by reacting compound 1 with an appropriately substituted 4-pyranone, as shown, in acetic acid or ethanol, with heat. Reductive cyclisation of 2 by treatment of compound 2 with Pd(II) catalyst with an appropriate base such as potassium acetate in an appropriate solvent such as N,N-dimethylacetamide (DMA) or N,N-dimethylformamide (DMF) at 90-120° C., yields fused tricyclic carboxylate compound 3. Compound 3 is then subjected to hydrolysis of the ester under acid or base conditions to yield the carboxylic acid 4. As with Scheme 1, further chemical manipulation of the carboxylic acid can lead to additional $R^{10}$ groups.

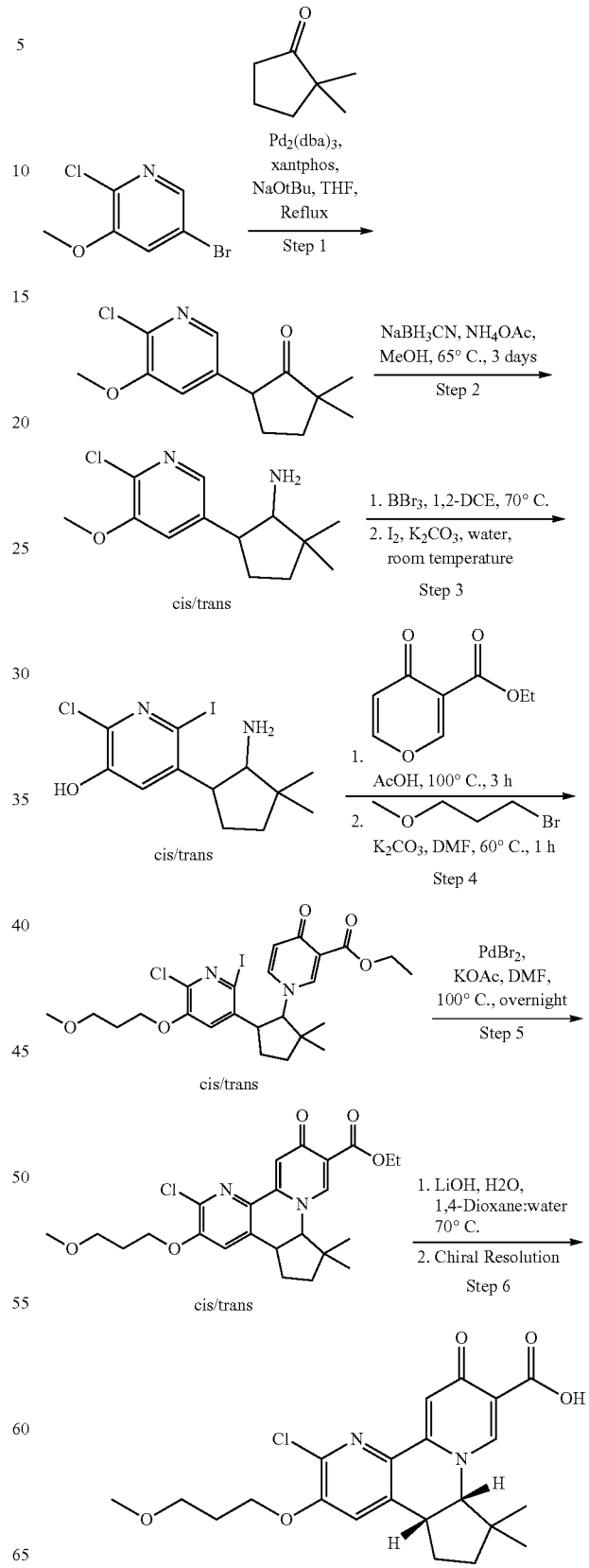

Example 1 Preparation A (Compound 220)

(4bR,7aS)-2-Chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid

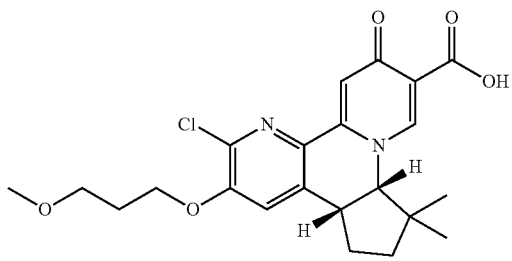 [SMILES: COCCCOc1cc2c(nc1Cl)-c1cc(=O)c(C(=O)O)cn1[C@H]1[C@@H]2CCC1(C)C]

Step 1: 5-(6-Chloro-5-methoxypyridin-3-yl)-2,2-dimethylcyclopentanone

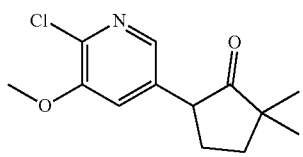

A flask was charged with a stir bar, 5-bromo-2-chloro-3-methoxypyridine (16.5 g, 74.2 mmol), tris(dibenzylideneacetone)dipalladium(0) (1.02 g, 1.11 mmol), xantphos (1.16 g, 2.00 mmol), and sodium tert-butoxide (12.6 g, 131 mmol). The flask was purged with a stream of nitrogen for 30 minutes. Tetrahydrofuran (THF) (300 ml) was degassed with nitrogen for 30 minutes. 2,2-dimethylcyclopentan-1-one (11.2 ml, 89 mmol) was added to the degassed tetrahydrofuran (THF) (300 ml) and this solution added to the nitrogen-purged flask that contained the initial substrate. The mixture was heated to reflux under nitrogen for 3 hours. The mixture was allowed to cool to room temperature and filtered through a silica plug over nitrogen. The plug was washed with tetrahydrofuran and the filtrate concentrated. The residue was dissolved in minimal dichloromethane and injected onto a silica column. The column was eluted 1 minute with hexanes and then a quick gradient (3 minutes) to 20% ethyl acetate/hexanes, and then isocratic at 20% ethyl acetate/hexanes until the product eluted. Fractions were concentrated to give 5-(6-chloro-5-methoxypyridin-3-yl)-2,2-dimethylcyclopentan-1-one (10.7 g, 42.1 mmol, 56.8% yield) as an oil. LCMS (ESI) m/z 254.2 (M+1).

Step 2: 5-(6-Chloro-5-methoxypyridin-3-yl)-2,2-dimethylcyclopentanamine (trans/cis mixture)

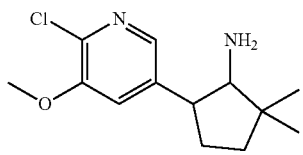

A stirring mixture of 5-(6-chloro-5-methoxypyridin-3-yl)-2,2-dimethylcyclopentan-1-one (trans/cis mixture) (10.7 g, 42.2 mmol) and ammonium acetate (32.5 g, 422 mmol) in methanol (200 mL) was degassed with a stream of nitrogen for 25 minutes. Sodium cyanoborohydride (5.30 g, 84 mmol) was added and the mixture heated at 65° C. over the weekend. The reflux condenser was removed and the oil bath heated to 80° C., allowing the reaction mixture to concentrate to ~70% of original volume over 4 hours. The reflux condenser was attached again and the mixture heated at strong reflux overnight (oil bath at 80° C.). The mixture was concentrated and the residue slurried in ~300 mL of dichloromethane. The mixture was stirred vigorously for ~30 minutes. Solids were filtered off and the filter cake washed with dichloromethane. The filtrate was concentrated to give 22 g of crude 5-(6-chloro-5-methoxypyridin-3-yl)-2,2-dimethylcyclopentan-1-amine (trans/cis mixture). The crude material was purified by silica chromatography eluting with a gradient of 0% to 10% 2M ammonia/methanol in dichloromethane. Fractions were concentrated to give 5-(6-chloro-5-methoxypyridin-3-yl)-2,2-dimethylcyclopentan-1-amine (trans/cis mixture) (9.04 g, 35.5 mmol, 84% yield). LCMS (ESI) m/z 255.2 (M+1).

Step 3: 5-(2-Amino-3,3-dimethylcyclopentyl)-2-chloro-6-iodopyridin-3-ol (trans/cis mixture)

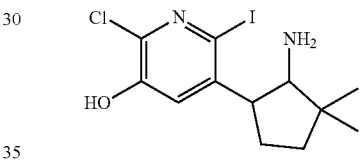

Boron tribromide (6.71 mL, 71.0 mmol) was added slowly dropwise to a vigorously stirring solution of 5-(6-chloro-5-methoxypyridin-3-yl)-2,2-dimethylcyclopentan-1-amine (trans/cis mixture) (9.04 g, 35.5 mmol) in 1,2-dichloroethane (DCE) (175 mL). The mixture was stirred at room temperature for 30 minutes and then heated at 70° C. overnight. The mixture was cooled in an ice bath and then carefully quenched with slow addition of methanol. Additional methanol (100 mL) was added. The mixture was warmed to room temperature, stirred for 30 minutes, and concentrated to leave ~17 g of crude 5-(2-amino-3,3-dimethylcyclopentyl)-2-chloropyridin-3-ol (trans/cis mixture). Water (200 mL) was added to the crude material and stirred with a stir bar. Potassium carbonate (24.5 g, 177 mmol) was added slowly and carefully portion-wise in order to control effervescence. The mixture was stirred for 10 minutes after complete addition of the potassium carbonate. The aqueous mixture was tested with pH paper to assure that the mixture was basic. The aqueous mixture was extracted 1 time with 100 mL of dichloromethane. LC-MS indicated only impurities in the organic layer and only 5-(2-amino-3,3-dimethylcyclopentyl)-2-chloropyridin-3-ol (trans/cis mixture) in the aqueous layer. The organic phase was discarded and the aqueous layer transferred from the separatory funnel to a round bottom flask before Iodine (18.0 g, 71.0 mmol) was added. The mixture was stirred overnight at room temperature. Excess sodium sulfite (~4 eq) was added portion wise. 2-Methyltetrahydrofuran (100 mL) was added and the mixture stirred. Excess acetic acid was added carefully to neutralize the aqueous layer while controlling effervescence. Solid sodium chloride was added to the aqueous phase. The mixture was extracted 3 times with 2-methyltetrahydrofuran. The combined organic layers were washed 2 times with brine. The organic phase was dried over sodium sulfate and concentrated to give 12.6 g of crude material. The material was purified by silica chromatography eluting with a gradient of 0% to 20% 2M ammonia/methanol in dichloromethane. Fractions were concentrated to give 5-(2-amino-3,3-dimethylcyclopentyl)-2-chloro-6-iodopyridin-3-ol (trans/cis mixture) (6.6 g, 18 mmol, 50.7% yield). LCMS (ESI) m/z 367.1 (M+1).

Step 4: Ethyl 1-(5-(6-chloro-2-iodo-5-(3-methoxypropoxy)pyridin-3-yl)-2,2-dimethylcyclopentyl)-4-oxo-1,4-dihydropyridine-3-carboxylate (trans/cis mixture)

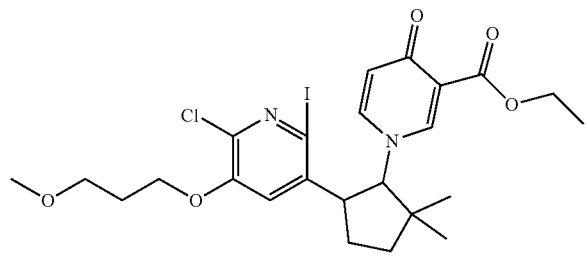 [SMILES: CCOC(=O)c1cn(C2C(c3cc(OCCCOC)c(Cl)nc3I)CCC2(C)C)ccc1=O]

5-(2-Amino-3,3-dimethylcyclopentyl)-2-chloro-6-iodopyridin-3-ol (trans/cis mixture) (6.6 g, 18 mmol) and ethyl 4-oxo-4H-pyran-3-carboxylate (3.94 g, 23.4 mmol) in acetic acid (150 mL) were stirred at 100° C. for 3 hours. The mixture was allowed to cool to room temperature and concentrated to dryness under vacuum. Toluene was added and rotovaped several times to help get rid of remaining acetic acid. Final evaporation gave crude ethyl 1-(5-(6-chloro-5-hydroxy-2-iodopyridin-3-yl)-2,2-dimethylcyclopentyl)-4-oxo-1,4-dihydropyridine-3-carboxylate. LCMS (ESI) m/z 517.1 (M+1). Crude ethyl 1-(5-(6-chloro-5-hydroxy-2-iodopyridin-3-yl)-2,2-dimethylcyclopentyl)-4-oxo-1,4-dihydropyridine-3-carboxylate was dissolved in N,N-dimethylformamide (DMF) (75 mL) before potassium carbonate (12.4 g, 90 mmol) and 1-bromo-3-methoxypropane (4.05 mL, 36.0 mmol) were added. The mixture was allowed to stir at room temperature for 15 minutes and then was heated to 60° C. for 1 hour. The reaction mixture was cooled in an ice bath and quenched with water. A solid precipitated. The mixture was extracted 3 times with ethyl acetate. A solid was floating at the phase interface and so the mixture was extracted 1 time with dichloromethane. Solids dissolved and product was observed in the organic phase. The combined organic layers were washed 2 times with 5% lithium chloride, washed 1 time with brine, dried over sodium sulfate, and concentrated. The residue was slurried in ethyl ether and the precipitate collected by filtration. The solid was air dried to give ethyl 1-(5-(6-chloro-2-iodo-5-(3-methoxypropoxy)pyridin-3-yl)-2,2-dimethylcyclopentyl)-4-oxo-1,4-dihydropyridine-3-carboxylate (racemic trans) (5.21 g, 8.85 mmol, 49.1% yield) as a pale tan solid. LCMS (ESI) m/z 589.2 (M+1). The filtrate was concentrated and the residue purified by silica chromatography eluting with a gradient or 0% to 10% methanol in dichloromethane. Fractions were concentrated to give ethyl 1-(5-(6-chloro-2-iodo-5-(3-methoxypropoxy)pyridin-3-yl)-2,2-dimethylcyclopentyl)-4-oxo-1,4-dihydropyridine-3-carboxylate (trans/cis mixture) (2.59 g, 3.08 mmol, 17.1% yield, 70% pure). LCMS (ESI) m/z 589.2 (M+1).

Step 5: Ethyl 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylate (trans/cis Mixture)

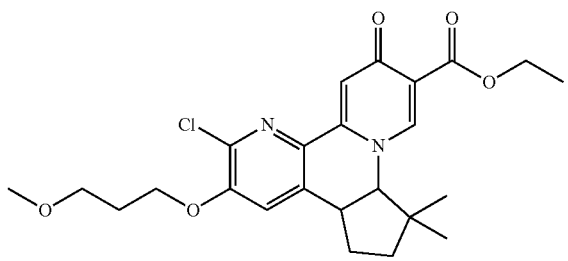 [SMILES: CCOC(=O)c1cn2c(cc1=O)-c1nc(Cl)c(OCCCOC)cc1C1CCC(C)(C)C12]

A round bottom flask containing a stir bar, ethyl 1-(5-(6-chloro-2-iodo-5-(3-methoxypropoxy)pyridin-3-yl)-2,2-dimethylcyclopentyl)-4-oxo-1,4-dihydropyridine-3-carboxylate (trans/cis mixture) (5.57 g, 9.46 mmol), potassium acetate (4.64 g, 47.3 mmol), and palladium(II) bromide (0.504 g, 1.89 mmol) was purged with nitrogen for 20 minutes using a septum with needle-in/needle-out. N,N-Dimethylformamide (DMF) (75 mL) was purged with nitrogen for 20 minutes before being added to the reaction vessel. The reaction vessel was placed into an oil bath that was preheated to 100° C. and the mixture stirred overnight. The mixture was allowed to cool to room temperature and filtered through a pad of celite. The celite pad was washed with dichloromethane and the filtrate concentrated. The residue was purified by silica chromatography eluting with a gradient of 0% to 10% methanol in dichloromethane. Fractions were concentrated to give ethyl 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylate (trans/cis mixture) (3.15 g, 6.83 mmol, 72.2% yield) as a pale tan solid. LCMS (ESI) m/z 461.3 (M+1).

Step 6: (4bR,7aS)-2-Chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid

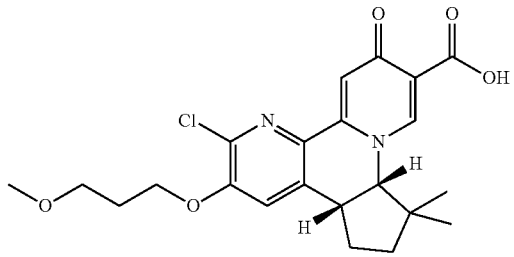 [SMILES: COCCCOc1cc2c(nc1Cl)-c1cc(=O)c(C(=O)O)cn1[C@H]1[C@@H]2CCC1(C)C]

To a solution of ethyl 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylate (trans/cis mixture) (3.15 g, 6.83 mmol) in 1,4-dioxane (40 mL) was added a solution of lithium hydroxide monohydrate (1.434 g, 34.2 mmol) in water (30 mL). The mixture was heated at 70° C. for 3 hours. LC-MS indicated complete conversion to the desired racemic cis product. The mixture was allowed to cool to room temperature and diluted with 0.5M hydrochloric acid (100 mL). The precipitate was collected by filtration and the filter cake thoroughly washed with water. The filter cake was air dried for several hours with vacuum on a Buchner funnel until solids no longer appeared moist by visual inspection. The filter cake was dissolved in 150 mL of dichloromethane. Full dissolution required stirring for several minutes. The solution was dried over sodium sulfate and concentrated to give 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (racemic cis) (2.6 g, 6.01 mmol, 88% yield).

The racemate was purified in several batches using the following conditions: Column=Chiralpak IC, 10 mm×250 mm (5 u); Mobile phase=3:1 MeOH/EtOH+0.1% TFA; Flow rate=10 mL/min; Injection volume=500 uL (30 mg/mL conc., DCM used as injection solvent); Collection wavelength=254 nm. Fractions corresponding to peak 1 were concentrated. The residues were slurried in ethyl ether, sonicated, stirred for 10 minutes, and then the stirring mixture cooled in an ice bath. Solids were collected by vacuum filtration, air dried, and dried under high vacuum to give (4bR,7aS)-2-Chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (1.24 g, 2.87 mmol, 42% yield) as white solids. LCMS (ESI) m/z 433.2 (M+1). $^1$H NMR (400 MHz, DMSO-$d_6$) δ ppm 8.62 (s, 1H), 7.63 (s, 1H), 7.43 (s, 1H), 4.72 (d, J=8.98 Hz, 1H), 4.19-4.39 (m, 2H), 3.94 (td, J=8.68, 3.32 Hz, 1H), 3.51 (t, J=6.05 Hz, 2H), 3.26 (s, 3H), 2.35-2.46 (m, 1H), 2.19-2.31 (m, 1H), 2.03 (quin, J=6.25 Hz, 2H), 1.55-1.67 (m, 1H), 1.40-1.50 (m, 1H), 1.15 (s, 3H), 0.40 (s, 3H).

Scheme 4 - Alternative Synthesis of Compound 220, Example 1

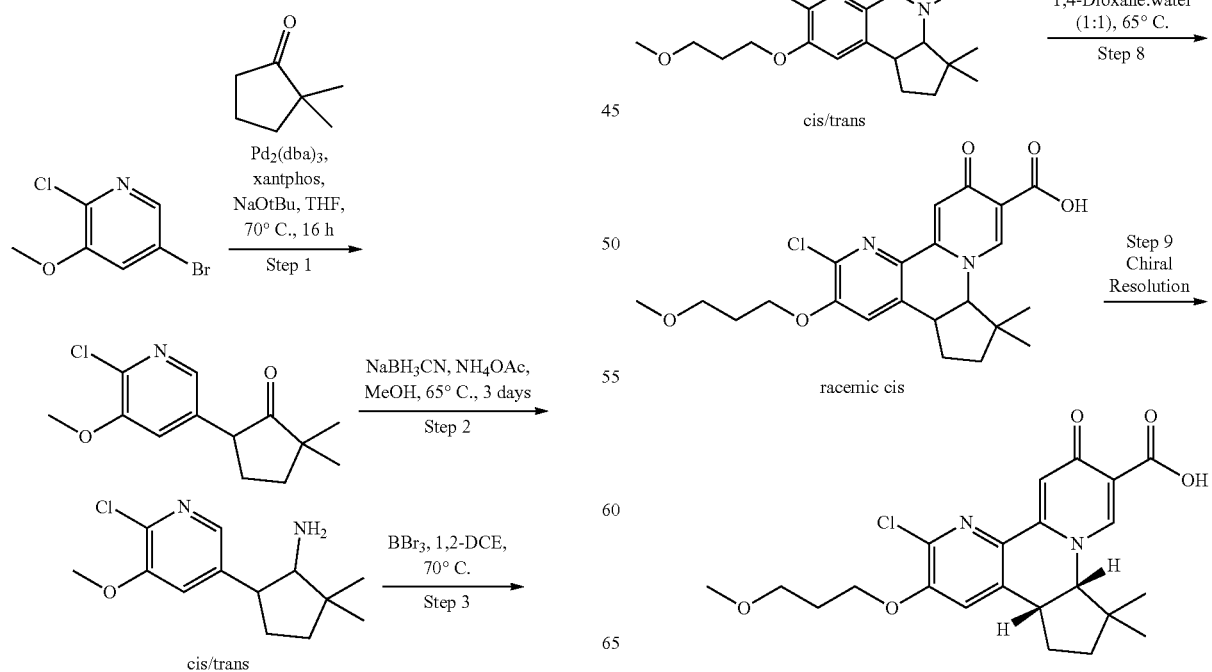

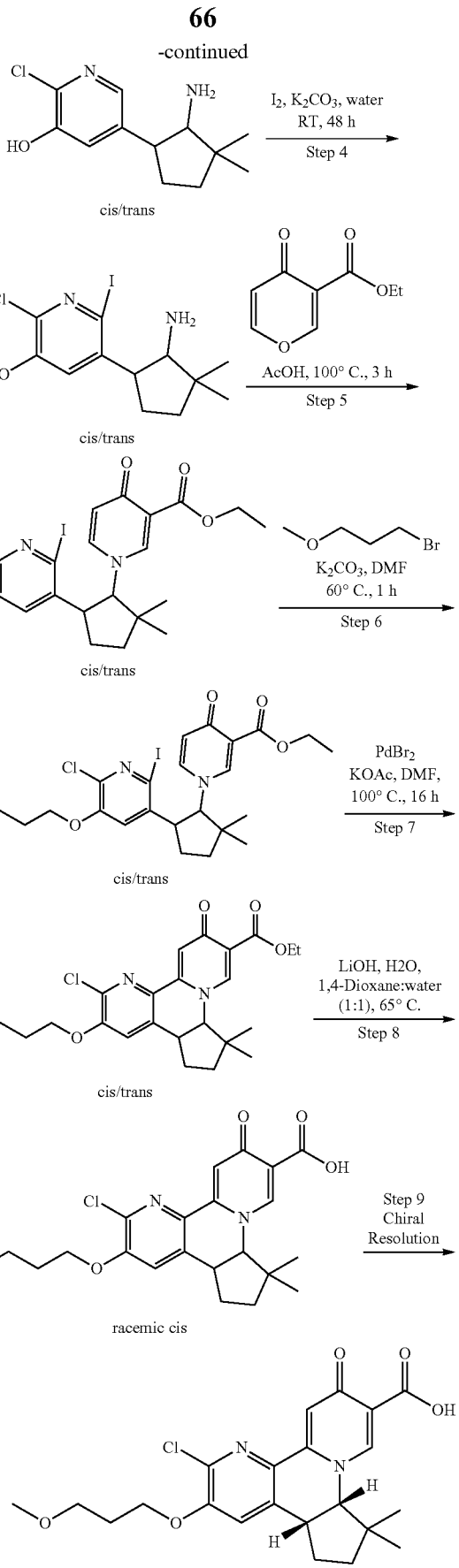

Example 1 Preparation B (Compound 220)

(4bR,7aS)-2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid

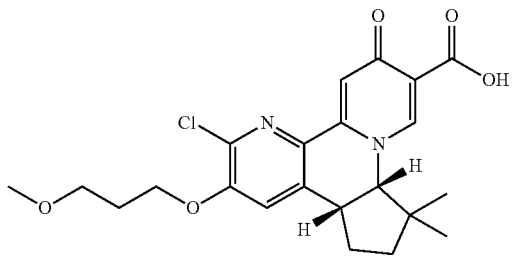 [SMILES: COCCCOc1cc2c(nc1Cl)-c1cc(=O)c(C(=O)O)cn1[C@H]1[C@@H]2CCC1(C)C]

Step 1: 5-(6-Chloro-5-methoxypyridin-3-yl)-2,2-dimethylcyclopentan-1-one

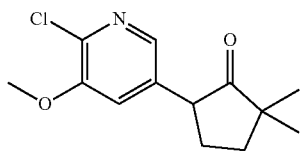

To a solution of 5-bromo-2-chloro-3-methoxypyridine (100 g, 449 mmol) in THF (2 L) was added NaOtBu (76.02 g, 791 mmol), Xantphos (7.01 g, 12.1 mmol) and 2,2-dimethylcyclopentan-1-one (65.56 g, 584.6 mmol). The reaction mixture was degassed with nitrogen for 30 minutes. Pd$_2$(dba)$_3$ was added to the reaction and the reaction mixture was stirred at 70° C. for 3 h. After completion of the reaction, the reaction mixture was filtered through silica gel (60-120) pad and washed with THF. The solvent was removed under reduced pressure and the crude product was purified by column chromatography (230-400 silica gel) using 0-30% ethyl acetate in petroleum ether as an eluent. Fractions were collected and concentrated to afford the title compound (61 g, 54% yield), LCMS (ESI) m/z 253.9 (M+1).

Step 2: 5-(6-Chloro-5-methoxypyridin-3-yl)-2,2-dimethylcyclopentan-1-amine (trans/cis mixture)

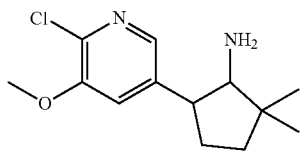

To a solution of 5-(6-chloro-5-methoxypyridin-3-yl)-2,2-dimethylcyclopentan-1-one (60 g, 236.5 mmol) in methanol (1.2 L) was added NH$_4$OAc (182 g, 2365 mmol). The reaction mixture was degassed with nitrogen for 30 minutes. NaBH$_3$CN was added (29.7 g, 473 mmol) to the reaction mixture and the reaction mixture was stirred at 65° C. for 3 days. After completion of the reaction, the solvent was removed under reduced pressure to afford the crude title compound (55 g). LCMS (ESI) m/z: 255.7 (M+1). This was taken for next step without further purification.

Step 3: Preparation of 5-(2-amino-3,3-dimethylcyclopentyl)-2-chloro-6-iodopyridin-3-ol (trans/cis mixture)

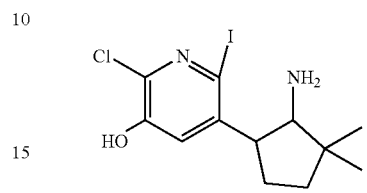

To a solution of 5-(6-chloro-5-methoxypyridin-3-yl)-2,2-dimethylcyclopentan-1-amine (60 g, 236 mmol) in 1,2-Dichloroethane (DCE) (1300 mL), BBr$_3$ (22.27 mL, 236 mmol) was added and the reaction mixture was stirred at 70° C. for 16 h. After completion of the reaction, methanol (1.5 L) was added to reaction mixture slowly dropwise at 0° C. and stirred at room temperature for 30 minutes. The reaction mixture was concentrated and the residue was taken in water (1 L) and adjusted the pH at basic using potassium carbonate (325 g, 2355 mmol). The aqueous layer was washed with DCM (200 mL). To the aqueous layer iodine (120 g, 471 mmol) was added and stirred at room temperature for 16 h. After completion of the reaction, sodium sulfite (200 g) was added to quench the excess Iodine. Acetic acid (250 mL) was added and extracted with 2-methyl THF (2*1 L). The organic layer was separated and dried over sodium sulfate. The solvent was removed under reduced pressure and the crude product was triturated with 20% dichloromethane in hexane (2*600 mL). The solid obtained was filtered and dried to afford the title compound (35 g, 21.89% yield). LCMS (54%) (ESI) m/z: 367 (M+1).

Step 4: Ethyl 1-(5-(6-chloro-5-hydroxy-2-iodopyridin-3-yl)-2,2-dimethylcyclopentyl)-4-oxo-1,4-dihydropyridine-3-carboxylate (trans/cis mixture)

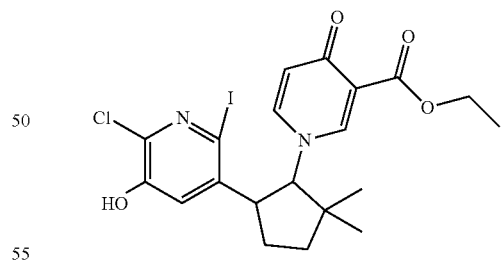

A suspension of 5-(2-amino-3,3-dimethylcyclopentyl)-2-chloro-6-iodopyridin-3-ol (87 g, 237 mmol), ethyl 4-oxo-4H-pyran-3-carboxylate (45.9 g, 273 mmol) and acetic acid (1.8 L) was stirred at 100° C. for 3 h. After completion of the reaction, the reaction mixture was concentrated and co-evaporated with toluene (4*200 mL) and the residue was purified by column chromatography (230-400 silica gel) using 10-15% MeOH in DCM as an eluent. Fractions were collected and concentrated to afford the title compound (51 g, 22% yield) as dark brown solid. LCMS (53%) (ESI) m/z: 517 (M+1).

Step 5: Ethyl 1-(5-(6-chloro-2-iodo-5-(3-methoxy-propoxy)pyridin-3-yl)-2,2-dimethylcyclopentyl)-4-oxo-1,4-dihydropyridine-3-carboxylate (trans/cis mixture)

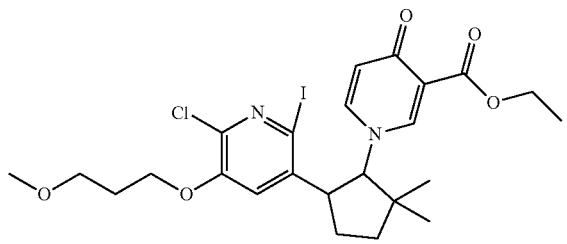 [SMILES: CCOC(=O)c1cn(C2C(c3cc(OCCCOC)c(Cl)nc3I)CCC2(C)C)ccc1=O]

To a solution of ethyl 1-(5-(6-chloro-5-hydroxy-2-iodopyridin-3-yl)-2,2-dimethylcyclopentyl)-4-oxo-1,4-dihydropyridine-3-carboxylate (51 g, 99 mmol) in N,N-Dimethylformamide (580 mL) was added K2CO3 (68.2 g, 493 mmol) and 1-bromo-3-methoxypropane (30.2 g, 197 mmol). The reaction mixture was stirred at 60° C. for 1 h. After completion of the reaction, the reaction mixture was quenched with ice cold water (1500 mL) and extracted with DCM (2 L). The combined organic layers were washed with brine (500 mL), dried over Na2SO4 and concentrated. The crude was purified by column chromatography (230-400 silica gel) using 0-10% Methanol in DCM as an eluent. Fractions were collected and concentrated to afford the title compound (52 g, 84% yield). LCMS (ESI) m/z: 588.8 (M+1).

Step 6: Ethyl 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylate (trans/cis mixture)

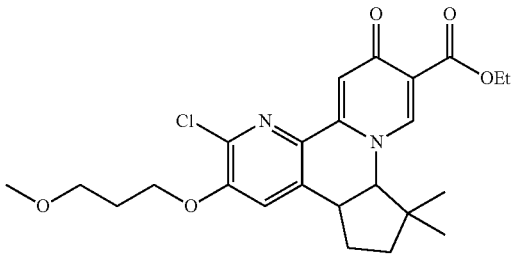

To a solution of ethyl 1-(5-(6-chloro-2-iodo-5-(3-methoxypropoxy) pyridin-3-yl)-2,2-dimethylcyclopentyl)-4-oxo-1,4-dihydropyridine-3-carboxylate (52 g, 88 mmol) in N, N-Dimethylformamide (550 mL) was added potassium acetate (43.3 g, 442 mmol). The reaction mixture was degassed with nitrogen for 20 minutes. Palladium(II) bromide (4.70 g, 17.66 mmol) was added to the reaction mixture and the reaction mixture was stirred at 100° C. for 16 h. After completion of the reaction, the reaction mixture was filtered through celite and washed with DCM. The organic phase was washed with water (250 mL), dried over Na2SO4 and concentrated. The crude was purified by column chromatography (230-400 silica gel) using 2-5% MeOH in DCM as an eluent. Fractions were collected and concentrated to afford the title compound (20 g, 42% yield). LCMS (ESI) m/z: 461.1 (M+1).

Step 7: (4bR,7aS)-2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid

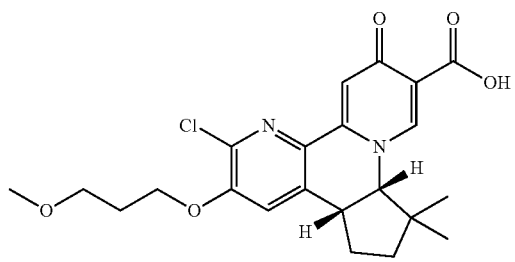 [SMILES: COCCCOc1cc2c(nc1Cl)-c1cc(=O)c(C(=O)O)cn1[C@H]1[C@@H]2CCC1(C)C]

To a solution of Ethyl 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylate (17.5 g, 38 mmol) in 1.4-Dioxane (150 mL) and water (150 mL) was added lithium hydroxide.H$_2$O (7.9 g, 190.14 mmol). The reaction mixture was heated to 70° C. for 2 h. After completion of the reaction, the reaction mixture was concentrated and the residue was taken in DCM (250 mL). 1.5N HCl was added to this mixture until pH=6. The organic layer was separated and dried over Na$_2$SO$_4$ and concentrated to get 15 g (yield: 91%) of racemic mixture. This racemic mixture was purified by prep. HPLC using to afford the title compound (5.5 g, 73% yield) as pale yellow solid. Chiral HPLC method: Chiral pak IC (21*250), 5 mics, Mobile phase A: 0.1% TFA in Methanol, B: 0.1% TFA in Ethanol; A:B: 75:25, Flow rate: 25 ml/min. First peak rt: 5.4. $^1$H NMR 400 MHz, DMSO-d$_6$: δ8.62 (s, 1H), 7.63 (s, 1H), 7.43 (s, 1H), 4.73 (d, J=8.96 Hz, 1H), 4.33-4.28 (m, 2H), 3.95-3.94 (m, 1H), 3.53-3.50 (m, 2H), 3.27 (s, 3H), 2.39-2.38 (m, 1H), 2.28-2.27 (m, 1H), 2.04-2.01 (m, 2H), 1.61-1.60 (m, 1H), 1.47-1.44 (m, 1H), 1.15 (s, 3H), 0.40 (s, 3H). LCMS (ESI) m/z: 432.9 (M+1).

Example 2 (Compound 221)

(4bS,7aR)-2-Chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid

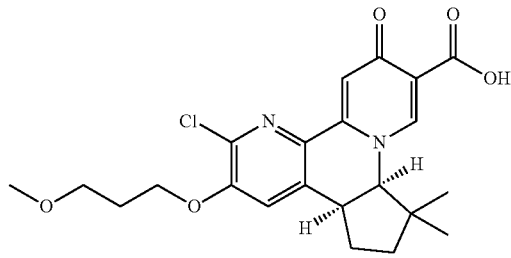 [SMILES: COCCCOc1cc2c(nc1Cl)-c1cc(=O)c(C(=O)O)cn1[C@@H]1[C@H]2CCC1(C)C]

Step 1: (4bS,7aR)-2-Chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid 2-Chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (racemic cis) (500 mg) was purified by chiral chromatography. Column=Chiralpak IC, 10 mm×250 mm (5 u), Mobile phase=3:1 MeOH/EtOH+ 0.1% TFA, Flow rate=10 mL/min, Injection volume=500 uL (30 mg/mL conc.); DCM used as injection solvent, Collection wavelength=254 nm. Peak 2 was concentrated to give (4bS,7aR)-2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (190 mg, 0.438 mmol, 38% yield) as a white solid. LCMS (ESI) m/z 433.3 (M+1). $^1$H NMR (400 MHz, DMSO-$d_6$) δ ppm 8.59 (s, 1H), 7.60 (s, 1H), 7.40 (s, 1H), 4.69 (d, J=8.98 Hz, 1H), 4.18-4.36 (m, 2H), 3.84-3.96 (m, 1H), 3.48 (t, J=6.25 Hz, 2H), 3.23 (s, 3H), 2.30-2.43 (m, 1H), 2.18-2.28 (m, 1H), 2.00 (quin, J=6.15 Hz, 2H), 1.53-1.64 (m, 1H), 1.37-1.48 (m, 1H), 1.12 (s, 3H), 0.37 (s, 3H).

Example 3: (Compound 222)

(4bR,7aS)-2-Cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid

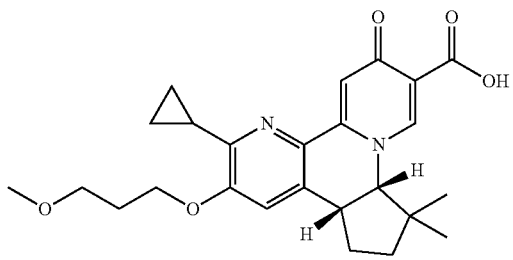 [SMILES: COCCCOc1cc2c(nc1C1CC1)-c1cc(=O)c(C(=O)O)cn1[C@H]1[C@@H]2CCC1(C)C]

Step 1: (4bR,7aS)-2-Cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid A reaction vial containing a stir bar, (4bR,7aS)-2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (81 mg, 0.19 mmol), potassium carbonate (103 mg, 0.748 mmol), cyclopropylboronic acid (32.1 mg, 0.374 mmol), and tetrakis(triphenylphosphine)palladium(0) (43.2 mg, 0.037 mmol) was purged thoroughly with a stream of nitrogen (needle in/needle out). 1,4-Dioxane (2 mL) was added and the reaction vial placed into a heating block that was preheated to 100° C. The mixture was heated at 100° C. overnight. The reaction mixture was allowed to cool to room temperature and then diluted with 2-methyltetrahydrofuran and water. Acetic acid was added slowly and carefully (effervescence) until the aqueous phase was neutralized. The mixture was extracted 2 times with 2-methyltetrahydrofuran. The combined organic layers were washed with brine and concentrated. The residue was purified by medium pressure reverse phase chromatography (C18/acetonitrile/water/0.1% formic acid/10% to 100% gradient). Fractions were combined and concentrated until a white precipitate was observed. A small amount of acetonitrile was added and the solution became clear. The solution was lyophilized to give (4bR,7aS)-2-cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (67 mg, 0.151 mmol, 81% yield) as a white powder. LCMS (ESI) m/z 439.1 (M+1). $^1$H NMR (400 MHz, DMSO-$d_6$) δ ppm 8.54 (s, 1H), 7.46 (s, 1H), 7.31 (s, 1H), 4.64 (d, J=8.98 Hz, 1H), 4.08-4.33 (m, 2H), 3.79-3.91 (m, 1H), 3.50 (t, J=6.25 Hz, 2H), 3.24 (s, 3H), 2.39-2.45 (m, 1H), 2.16-2.38 (m, 2H), 2.01 (quin, J=6.15 Hz, 2H), 1.51-1.63 (m, 1H), 1.32-1.45 (m, 1H), 1.12 (s, 3H), 0.92-1.05 (m, 4H), 0.34 (s, 3H).

Example 4: (Compound 223)

2-Cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (racemic cis)

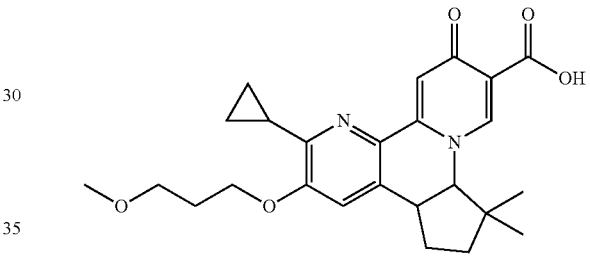

Step 1: 2-Cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (racemic cis)

A reaction vial containing a stir bar, ethyl 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylate (racemic cis) (200 mg, 0.434 mmol), potassium carbonate (240 mg, 1.74 mmol), cyclopropylboronic acid (74.5 mg, 0.868 mmol), and tetrakis(triphenylphosphine)palladium(0) (100 mg, 0.087 mmol) was purged thoroughly with a stream of nitrogen (needle in/needle out). 1,4-Dioxane (4 mL) was added and the reaction vial placed into a heating block that was preheated to 100° C. The mixture was heated at 100° C. for 3 hours. Additional cyclopropylboronic acid (74.5 mg, 0.868 mmol) and tetrakis(triphenylphosphine)palladium(0) (100 mg, 0.087 mmol) were added and the mixture continued to heat at 100° C. for 2 hours. The mixture was allowed to cool and was filtered through a celite plug. The celite plug was washed with ethyl acetate. The filtrate was concentrated to give crude ethyl 2-cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylate. The crude intermediate was dissolved in methanol (2 mL) before a solution of lithium hydroxide monohydrate (182 mg, 4.34 mmol) in water (2 mL) was added. The mixture was heated at 60° C. for 3 hours and cooled to room temperature. The mixture was purified by medium pressure reverse phase chromatography (C18/acetonitrile/water/0.1% formic acid/ 10% to 100% gradient). Fractions were lyophilized to give 2-cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (racemic cis) (50 mg, 0.114 mmol, 26.3% yield) as a pale tan powder. LCMS (ESI) m/z 439.3 (M+1). $^1$H NMR (400 MHz, DMSO-$d_6$) δ ppm 8.54 (s, 1H), 7.46 (s, 1H), 7.31 (s, 1H), 4.64 (d, J=8.98 Hz, 1H), 4.11-4.28 (m, 2H), 3.79-3.91 (m, 1H), 3.50 (t, J=6.25 Hz, 2H), 3.24 (s, 3H), 2.39-2.45 (m, 1H), 2.16-2.38 (m, 2H), 1.96-2.04 (m, 2H), 1.51-1.64 (m, 1H), 1.34-1.44 (m, 1H), 1.12 (s, 3H), 0.93-1.06 (m, 4H), 0.34 (s, 3H).

Scheme 5 - Preparation of Compounds Such as Example 5

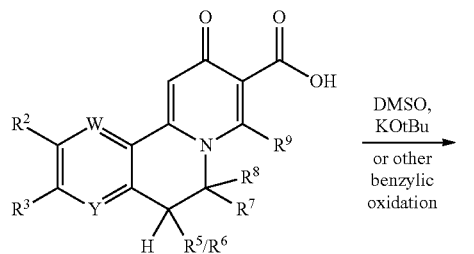

DMSO, KOtBu or other benzylic oxidation

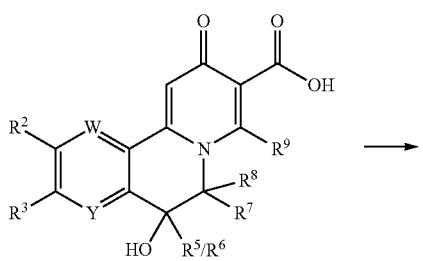

Where $R^5$ = OR and $R^6$ = not hydrogen, and where $R^6$ can cyclize with $R^7$ or $R^8$ to form a ring.

Example 5: (Compound 224)

(7aR)-2-Cyclopropyl-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid

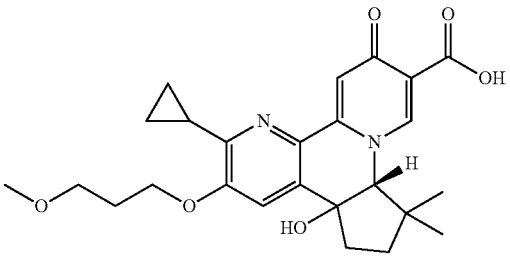 [SMILES: COCCCOc1cc2c(nc1C1CC1)-c1cc(=O)c(C(=O)O)cn1[C@@H]1C(C)(C)CCC21O]

Step 1: (7aR)-2-Cyclopropyl-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid Potassium tert-butoxide (13.3 mg, 0.119 mmol) was added to a solution of (4bR,7aS)-2-cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (13 mg, 0.030 mmol) in dimethyl sulfoxide (DMSO) (0.5 mL) at room temperature and stirred overnight. The mixture was injected onto a medium pressure reverse phase column and eluted (C18/acetonitrile/water/ 0.1% formic acid/10% to 100% gradient). Fractions were lyophilized to give (7aR)-2-cyclopropyl-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (single isomer) (6 mg, 0.013 mmol, 43.6% yield) as an off-white powder. LC-MS and NMR were consistent with desired product. LCMS (ESI) m/z 455.3 (M+1). $^1$H NMR (400 MHz, DMSO-$d_6$) δ ppm 8.68 (s, 1H), 7.50 (s, 2H), 6.11 (s, 1H), 4.62 (s, 1H), 4.12-4.35 (m, 2H), 3.51 (t, J=6.05 Hz, 2H), 3.24 (s, 3H), 2.57-2.68 (m, 1H), 2.11-2.24 (m, 1H), 2.02 (quin, J=6.15 Hz, 2H), 1.56-1.70 (m, 1H), 1.13-1.26 (m, 4H), 0.97-1.10 (m, 4H), 0.24 (s, 3H).

Example 6: (Compound 225)

(7aR)-2-Chloro-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid

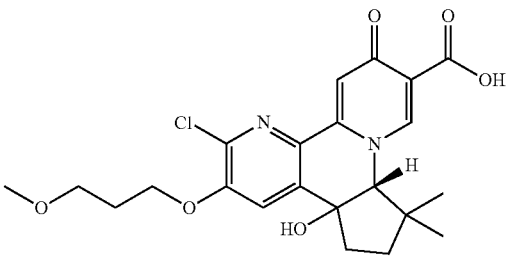 [SMILES: COCCCOc1cc2c(nc1Cl)-c1cc(=O)c(C(=O)O)cn1[C@@H]1C(C)(C)CCC21O]

Step 1: (7aR)-2-Chloro-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid Potassium tert-butoxide (15.5 mg, 0.139 mmol) was added to a solution of (4bR,7aS)-2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (15 mg, 0.035 mmol) in dimethyl sulfoxide (DMSO) (1 mL) at room temperature and stirred for 2 hours. The mixture was injected onto a medium pressure reverse phase column and eluted (C18/acetonitrile/water/0.1% formic acid/10% to 100% gradient). Fractions were lyophilized to give (7aR)-2-chloro-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (7 mg, 0.015 mmol, 44.6% yield) as a white powder. LCMS (ESI) m/z 449.1 (M+1). $^1$H NMR (400 MHz, DMSO-d$_6$) δ ppm 8.74 (s, 1H), 7.78 (s, 1H), 7.44 (s, 1H), 6.28 (s, 1H), 4.70 (s, 1H), 4.18-4.43 (m, 2H), 3.49 (t, J=6.25 Hz, 2H), 3.24 (s, 3H), 2.59-2.73 (m, 1H), 2.21 (dt, J=13.47, 8.88 Hz, 1H), 2.01 (quin, J=6.15 Hz, 2H), 1.58-1.71 (m, 1H), 1.21-1.29 (m, 1H), 1.18 (s, 3H), 0.27 (s, 3H).

Example 7: (Compound 226)

(7aR)-2-Chloro-4b-methoxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid

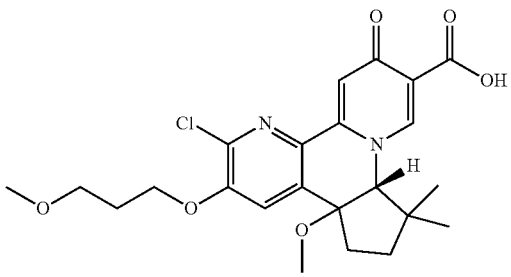 [SMILES: COCCCOc1cc2c(nc1Cl)-c1cc(=O)c(C(=O)O)cn1[C@@H]1C(C)(C)CCC21OC]

Step 1: (7aR)-2-Chloro-4b-methoxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid Sodium hydride (60% in mineral oil) (1.87 mg, 0.047 mmol) was added to a stirring solution of (7aR)-2-chloro-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (7 mg, 0.016 mmol) and methyl iodide (2.9 μl, 0.047 mmol) in N,N-dimethylformamide (DMF) (0.5 mL). The mixture was stirred for 2 hours. The mixture was heated to 80° C. for 2 hours. The mixture was allowed to cool to room temperature and quenched with water. The mixture stirred for 20 minutes. The mixture was injected onto a medium pressure reverse phase chromatography (C18/acetonitrile/water/0.1% formic acid/10% to 100% gradient). Fractions were lyophilized to give (4bS,7aR)-2-chloro-4b-methoxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid as an off-white powder. LCMS (ESI) m/z 463.2 (M+1). $^1$H NMR (400 MHz, DMSO-d$_6$) δ ppm 8.79 (s, 1H), 7.78 (s, 1H), 7.46 (s, 1H), 4.92 (s, 1H), 4.26-4.42 (m, 2H), 3.49 (t, J=6.25 Hz, 2H), 3.24 (s, 3H), 2.94 (s, 3H), 2.66 (dt, J=13.56, 6.68 Hz, 1H), 2.19-2.33 (m, 1H), 2.01 (quin, J=6.15 Hz, 2H), 1.63-1.74 (m, 1H), 1.28-1.40 (m, 1H), 1.19 (s, 3H), 0.29 (s, 3H).

Example 8 (Compound 227) and Example 9 (Compound 228)

(4bR,7aS)-2-Hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (4bR,7aS)-2-Chloro-3-hydroxy-7,7-dimethyl-11-oxo-4b,5,6,7,7a,11-hexahydrocyclopenta[f]pyrido[1,2-h][1,7]naphthyridine-10-carboxylic acid

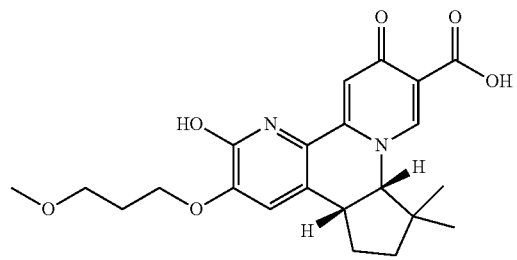

Example 8

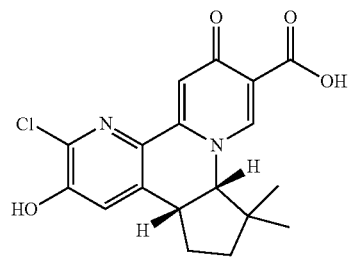

Example 9

A mixture of (4bR,7aS)-2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (61 mg, 0.141 mmol) in sodium hydroxide (2M) (4 mL, 8 mmol) was heated at 150° C. in a microwave reactor for 1 hour. The mixture was injected onto a medium pressure reverse phase column and eluted (C18/acetonitrile/water/0.1% formic acid/0% to 100% gradient). 2 sets of fractions were lyophilized separately to give:

Example 8: (4bR,7aS)-2-Hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (20 mg, 0.048 mmol, 34% yield). LCMS (ESI) m/z 415.2 (M+1). $^1$H NMR (400 MHz, DMSO-d$_6$) δ ppm 11.15-11.71 (m, 1H), 8.53 (s, 1H), 7.44 (s, 1H), 6.97-7.27 (m, 1H), 4.61 (d, J=8.98 Hz, 1H), 4.00-4.19 (m, 2H), 3.73 (br. s., 1H), 3.45 (t, J=6.05 Hz, 2H), 3.23 (s, 3H), 2.11-2.33 (m, 2H), 1.96 (quin, J=6.25 Hz, 2H), 1.50-1.61 (m, 1H), 1.31-1.45 (m, 1H), 1.11 (s, 3H), 0.42 (s, 3H).

Example 9: (4bR,7aS)-2-Chloro-3-hydroxy-7,7-dimethyl-11-oxo-4b,5,6,7,7a,11-hexahydrocyclopenta[f]pyrido[1,2-h][1,7]naphthyridine-10-carboxylic acid (8 mg, 0.022 mmol, 15.6% yield). LCMS (ESI) m/z 361.1 (M+1). $^1$H NMR (400 MHz, DMSO-$d_6$) δ ppm 11.85 (br. s, 1H), 8.57 (s, 1H), 7.37 (s, 1H), 7.24 (s, 1H), 4.66 (d, J=8.98 Hz, 1H), 3.80-3.94 (m, 1H), 2.25-2.43 (m, 2H), 1.94-2.08 (m, 1H), 1.52-1.64 (m, 1H), 1.38-1.49 (m, 1H), 1.11 (s, 3H), 0.37 (s, 3H).

Example 10: (Compound 229)

2-Chloro-6-(1-hydroxy-2-methylpropan-2-yl)-3-(3-methoxypropoxy)-10-oxo-6,10-dihydro-5H-pyrido[1,2-h][1,7]naphthyridine-9-carboxylic acid

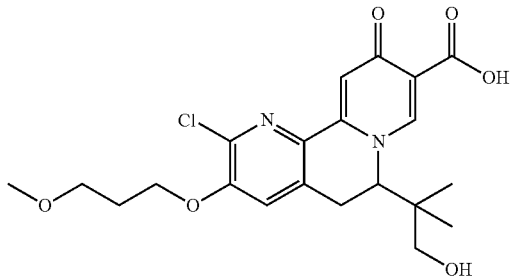 [SMILES: COCCCOc1cc2c(nc1Cl)-c1cc(=O)c(C(=O)O)cn1C(C(C)(C)CO)C2]

Step 1: 4-(Benzyloxy)-1-(6-chloro-5-methoxypyridin-3-yl)-3,3-dimethylbutan-2-one

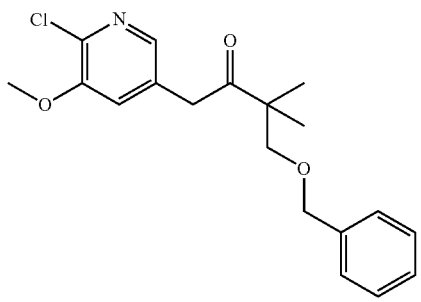 [SMILES: COc1cc(CC(=O)C(C)(C)COCc2ccccc2)cnc1Cl]

A flask was charged with a stir bar, 5-bromo-2-chloro-3-methoxypyridine (5.8 g, 26 mmol), tris(dibenzylideneacetone)dipalladium(0) (0.358 g, 0.391 mmol), and sodium tert-butoxide (4.41 g, 45.9 mmol). The flask was purged with a stream of nitrogen before 4-(benzyloxy)-3,3-dimethylbutan-2-one (5.45 g, 26.4 mmol) in tetrahydrofuran (THF) (100 ml) was added. The mixture was heated to reflux for 3 hours. The mixture was allowed to cool to room temperature and diluted with water. The mixture was extracted 3 times with ethyl acetate. The combined organic layers were washed with brine, dried over sodium sulfate, and concentrated. The residue was purified by silica chromatography eluting with a gradient of 0% to 50% ethyl acetate in hexanes. The fractions were concentrated to give 4-(benzyloxy)-1-(6-chloro-5-methoxypyridin-3-yl)-3,3-dimethylbutan-2-one (5.62 g, 16.2 mmol, 62% yield) as a pale yellow oil. LCMS (ESI) m/z 348.2 (M+1). $^1$H NMR (400 MHz, CHLOROFORM-d) δ ppm 7.70 (d, J=1.95 Hz, 1H), 7.21-7.39 (m, 5H), 7.01 (d, J=1.56 Hz, 1H), 4.49 (s, 2H), 3.79 (s, 5H), 3.52 (s, 2H), 1.22 (s, 6H).

Step 2: 4-(Benzyloxy)-1-(6-chloro-5-methoxypyridin-3-yl)-3,3-dimethylbutan-2-amine

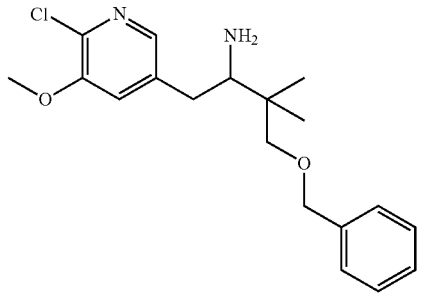 [SMILES: COc1cc(CC(N)C(C)(C)COCc2ccccc2)cnc1Cl]

A mixture of 4-(benzyloxy)-1-(6-chloro-5-methoxypyridin-3-yl)-3,3-dimethylbutan-2-one (3 g, 8.6 mmol) and ammonium acetate (9.97 g, 129 mmol) in methanol (50 mL) were stirred at room temperature overnight. Sodium cyanoborohydride (1.08 g, 17.3 mmol) was added and the mixture heated at 60° C. overnight. The mixture was allowed to cool to room temperature, concentrated to ~15 mL, quenched with 1M sodium hydroxide, and extracted 3 times with ethyl acetate. The combined organic layers were washed with brine, dried over sodium sulfate, and concentrated to give crude 4-(benzyloxy)-1-(6-chloro-5-methoxypyridin-3-yl)-3,3-dimethylbutan-2-amine (2.84 g, 5.62 mmol, 65% yield). LCMS (ESI) m/z 349.3 (M+1).

Step 3: 5-(2-Amino-4-hydroxy-3,3-dimethylbutyl)-2-chloropyridin-3-ol

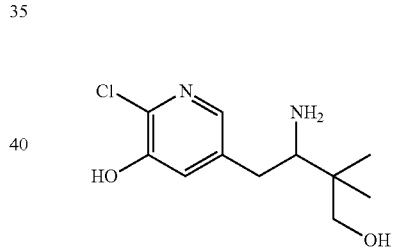

Boron tribromide (2.66 mL, 28.1 mmol) was added dropwise to a solution of 4-(benzyloxy)-1-(6-chloro-5-methoxypyridin-3-yl)-3,3-dimethylbutan-2-amine (2.84 g, 5.62 mmol) in 1,2-dichloroethane (DCE) (100 mL) at 0° C. The mixture was allowed to warm to room temperature and stirred for 4 hours. An oily solid precipitated on the bottom of the flask. The solids were scraped off the walls of the flask and the mixture stirred vigorously at room temperature overnight. An oily solid precipitate coated the bottom of the flask. The liquid phase was decanted and poured into ice. The precipitate in the original reaction flask was slurried in fresh 1,2-dichloroethane (DCE) (100 mL) and stirred while 1 mL (~2 eq) of fresh boron tribromide was added dropwise at room temperature. The mixture was heated at 70° C. for 4 hours and then allowed to cool to room temperature. The mixture was cooled with an ice bath, quenched with slow careful addition of 100 mL of methanol, warmed to room temperature, and stirred for 1 hour. The mixture was concentrated and the residue purified by medium pressure reverse phase chromatography (C18/acetonitrile/water/0.1% formic acid/0% to 20% gradient). Fractions were lyophilized to give 5-(2-amino-4-hydroxy-3,3-dimethylbutyl)-2-chloropyridin-3-ol (910 mg, 3.72 mmol, 66.2% yield) as a white powder. LCMS (ESI) m/z 245.2 (M+1). ¹H NMR (400 MHz, DMSO-d$_6$) δ ppm 7.80 (d, J=1.95 Hz, 1H), 7.59 (br. s., 3H), 7.25 (d, J=1.95 Hz, 1H), 3.31-3.38 (m, 2H), 3.19-3.29 (m, 1H), 2.92-3.02 (m, 1H), 2.53-2.63 (m, 1H), 0.95 (s, 3H), 0.90 (s, 3H).

Step 4: 5-(2-Amino-4-hydroxy-3,3-dimethylbutyl)-2-chloro-6-iodopyridin-3-ol

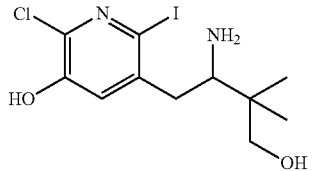 [SMILES: CC(C)(CO)C(N)Cc1cc(O)c(Cl)nc1I]

Iodine (233 mg, 0.919 mmol) was added to a stirring mixture of 5-(2-amino-4-hydroxy-3,3-dimethylbutyl)-2-chloropyridin-3-ol (225 mg, 0.919 mmol) and potassium carbonate (381 mg, 2.76 mmol) in water (10 mL). The mixture was stirred at room temperature for 2 hours. Solid sodium sulfite was added portion wise to the mixture until color dissipated. The aqueous mixture was injected onto a medium pressure reverse phase C18 column and then eluted with acetonitrile/water/0.1% formic acid/0% to 50% gradient. Combined fractions were lyophilized to give 5-(2-amino-4-hydroxy-3,3-dimethylbutyl)-2-chloro-6-iodopyridin-3-ol (164 mg, 0.443 mmol, 48.1% yield) as a white solid. LCMS (ESI) m/z 371.0 (M+1). ¹H NMR (400 MHz, DMSO-d$_6$) δ ppm 8.23 (s, 1H), 7.20 (s, 1H), 3.13-3.41 (m, 2H), 2.70-2.88 (m, 2H), 2.29-2.39 (m, 1H), 0.92 (s, 3H), 0.84 (s, 3H).

Step 5: Ethyl 1-(4-acetoxy-1-(6-chloro-5-hydroxy-2-iodopyridin-3-yl)-3,3-dimethylbutan-2-yl)-4-oxo-1,4-dihydropyridine-3-carboxylate

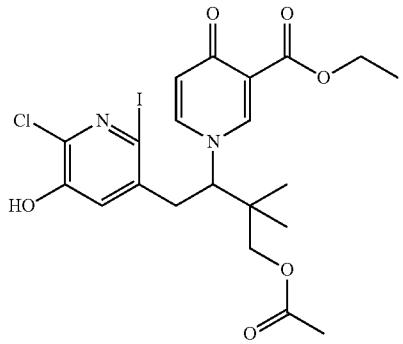 [SMILES: CCOC(=O)c1cn(C(Cc2cc(O)c(Cl)nc2I)C(C)(C)COC(C)=O)ccc1=O]

5-(2-Amino-4-hydroxy-3,3-dimethylbutyl)-2-chloro-6-iodopyridin-3-ol (164 mg, 0.443 mmol) and ethyl 4-oxo-4H-pyran-3-carboxylate (83 mg, 0.494 mmol) in acetic acid (4 mL) were stirred at 100° C. for 4 hours. The mixture was allowed to cool to room temperature and concentrated. The residue was purified by medium pressure reverse phase chromatography (C18/acetonitrile/water/0.1% formic acid/ 0% to 100% gradient). 2 sets of fractions were concentrated separately to give ethyl 1-(1-(6-chloro-5-hydroxy-2-iodopyridin-3-yl)-4-hydroxy-3,3-dimethylbutan-2-yl)-4-oxo-1,4-dihydropyridine-3-carboxylate (83 mg, 0.16 mmol, 36% yield) and ethyl 1-(4-acetoxy-1-(6-chloro-5-hydroxy-2-iodopyridin-3-yl)-3,3-dimethylbutan-2-yl)-4-oxo-1,4-dihydropyridine-3-carboxylate (27 mg, 0.048 mmol, 11% yield). LCMS (ESI) m/z 563.2 (M+1).

Step 6: Ethyl 1-(4-acetoxy-1-(6-chloro-2-iodo-5-(3-methoxypropoxy)pyridin-3-yl)-3,3-dimethylbutan-2-yl)-4-oxo-1,4-dihydropyridine-3-carboxylate

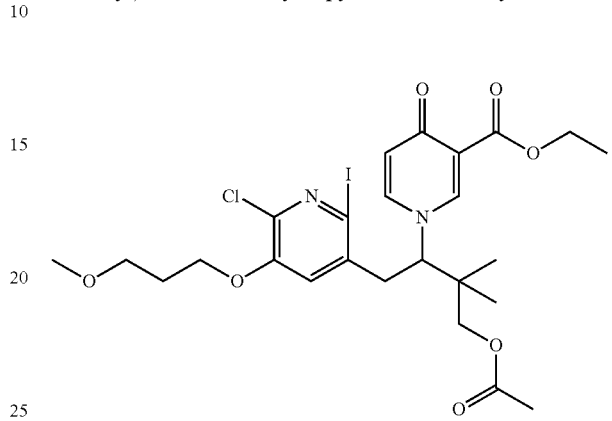

Ethyl 1-(4-acetoxy-1-(6-chloro-5-hydroxy-2-iodopyridin-3-yl)-3,3-dimethylbutan-2-yl)-4-oxo-1,4-dihydropyridine-3-carboxylate (27 mg, 0.048 mmol), potassium carbonate (26.5 mg, 0.192 mmol), and 1-bromo-3-methoxypropane (19 mg, 0.124 mmol) were stirred at room temperature overnight. The mixture was quenched with water and extracted 2 times with ethyl acetate. The combined organic layers were washed with brine, washed with 5% lithium chloride (aq), and concentrated. The residue was purified by medium pressure reverse phase chromatography (C18/acetonitrile/water/0.1% formic acid/10% to 100% gradient). Fractions were lyophilized to give ethyl 1-(4-acetoxy-1-(6-chloro-2-iodo-5-(3-methoxypropoxy)pyridin-3-yl)-3,3-dimethylbutan-2-yl)-4-oxo-1,4-dihydropyridine-3-carboxylate (15 mg, 0.024 mmol, 49.2% yield) as a white powder. LCMS (ESI) m/z 635.9 (M+1).

Step 7: 2-Chloro-6-(1-hydroxy-2-methylpropan-2-yl)-3-(3-methoxypropoxy)-10-oxo-6,10-dihydro-5H-pyrido[1,2-h][1,7]naphthyridine-9-carboxylic acid

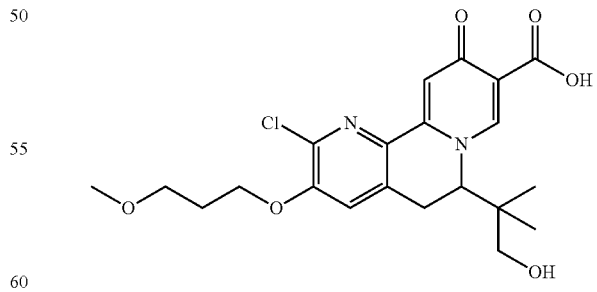

A round bottom flask containing a stir bar, ethyl 1-(4-acetoxy-1-(6-chloro-2-iodo-5-(3-methoxypropoxy)pyridin-3-yl)-3,3-dimethylbutan-2-yl)-4-oxo-1,4-dihydropyridine-3-carboxylate (14 mg, 0.022 mmol), potassium acetate (4.33 mg, 0.044 mmol), and palladium(II) bromide (1.2 mg, 4.4 µmol) was purged with nitrogen for 15 minutes. N,N-

Dimethylacetamide (DMA) (1 mL) was purged with nitrogen for 5 minutes before being added to the reaction vessel. The reaction vessel was placed into an oil bath that was preheated to 90° C. and the mixture stirred for 3 hours. The mixture was allowed to cool to room temperature, filtered through celite, and the filtrate purified by medium pressure reverse phase chromatography (C18/acetonitrile/water/0.1% formic acid/10% to 100% gradient). Fractions were combined and basified with 1M sodium hydroxide. The mixture was heated at 60° C. overnight, cooled to room temperature, and concentrated. The residue was dissolved in water and acidified to pH=3-4 with 1M hydrochloric acid. The mixture was purified by medium pressure reverse phase chromatography (C18/acetonitrile/water/0.1% formic acid/0% to 100% gradient). Fractions were lyophilized to give 2-chloro-6-(1-hydroxy-2-methylpropan-2-yl)-3-(3-methoxypropoxy)-10-oxo-5,10-dihydro-6H-pyrido[1,2-h][1,7]naphthyridine-9-carboxylic acid (3 mg, 6.9 μmol, 31% yield). LCMS (ESI) m/z 437.2 (M+1).

General Scheme 6 for Preparation of Compounds of Examples 11-25

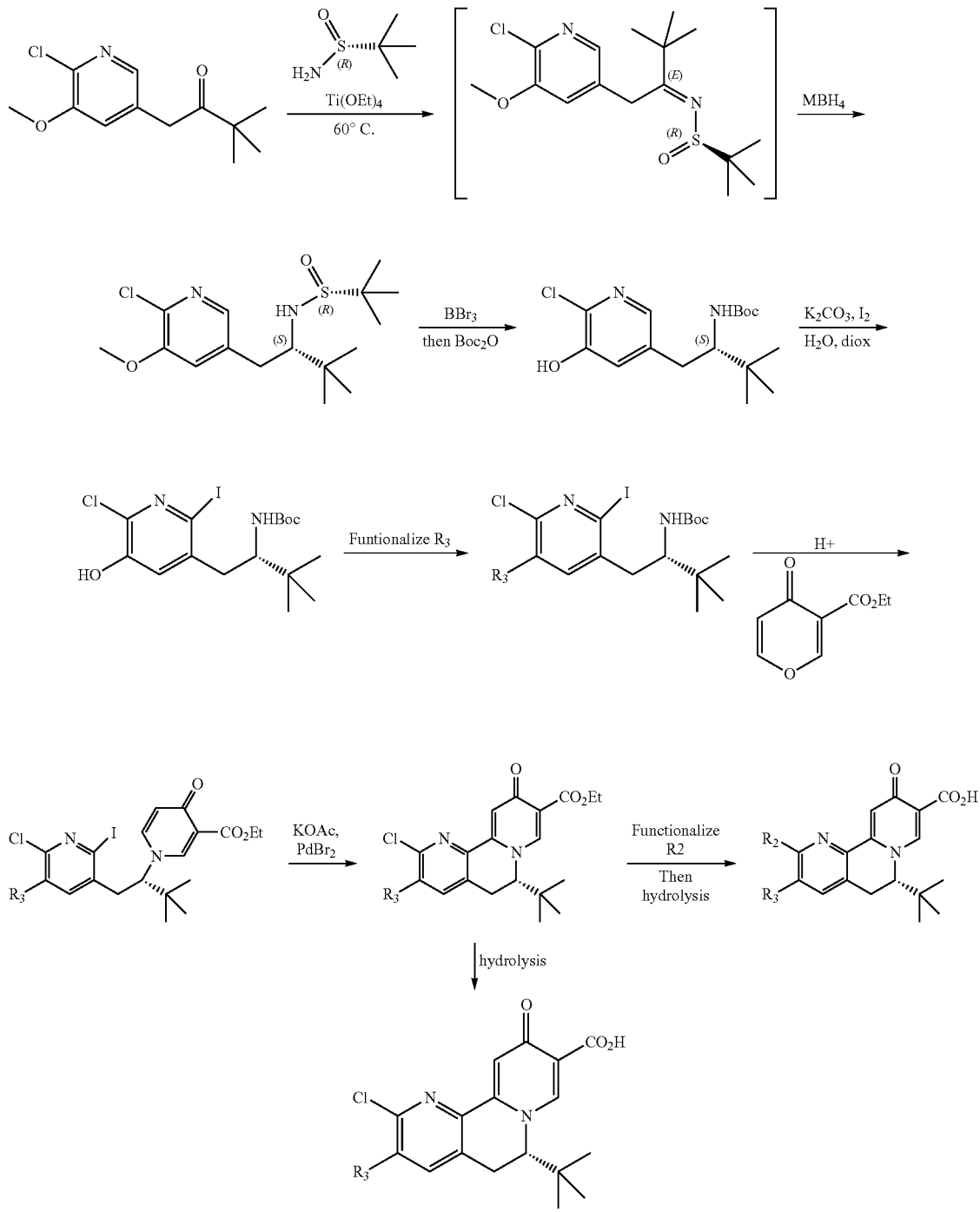

Example 11 (Compound 230)

(S)-6-(tert-Butyl)-2-chloro-3-(3-methoxypropoxy)-10-oxo-6,10-dihydro-5H-pyrido[1,2-h][1,7]naphthyridine-9-carboxylic acid

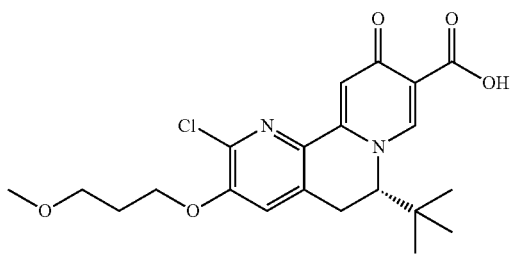 [SMILES: COCCCOc1cc2c(nc1Cl)-c1cc(=O)c(C(=O)O)cn1[C@H](C(C)(C)C)C2]

Step 1: (R)—N—((S)-1-(6-Chloro-5-methoxypyridin-3-yl)-3,3-dimethylbutan-2-yl)-2-methylpropane-2-sulfinamide

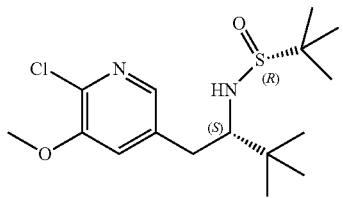

A solution of 1-(6-chloro-5-methoxypyridin-3-yl)-3,3-dimethylbutan-2-one (2.54 g, 10.50 mmol), (R)-2-methylpropane-2-sulfinamide (2.55 g, 21.00 mmol) and Ti(OEt)$_4$ (5.99 g, 26.3 mmol) in toluene (8.5 mL) was stirred for 10 mins at 60° C. and the vessel was then evacuated. The reaction mixture was stirred at 60° C. under vacuum for 24 h. The vessel was re-pressurized with nitrogen and toluene (5 mL) and THF (35 mL) were added. A solution of LiBH$_4$ (15.8 mL, 2M in THF, 31.5 mmol) was added slowly. The reaction mixture was stirred at RT overnight. The reaction mixture was diluted with THF (130 mL) and brine (3 mL), stirred for 30 mins, and then filtered through celite. The filtrate was evaporated and purified by silica gel chromatography (0-100% EtOAc/hexanes) to afford (R)—N—((S)-1-(6-chloro-5-methoxypyridin-3-yl)-3,3-dimethylbutan-2-yl)-2-methylpropane-2-sulfinamide (2.58 g, 71%) as the major diastereomer. LCMS (m/z, ES+)=346.9, 348.1 (M+1).

Step 2: (S)-5-(2-Amino-3,3-dimethylbutyl)-2-chloropyridin-3-ol

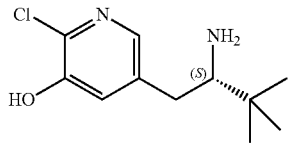

A solution of (R)—N—((S)-1-(6-chloro-5-methoxypyridin-3-yl)-3,3-dimethylbutan-2-yl)-2-methylpropane-2-sulfinamide (2.56 g, 7.38 mmol) in 1,2-dichloroethane (36.9 mL) was stirred at 0° C. Boron tribromide (4.88 mL, 51.7 mmol) was added slowly. The reaction mixture was removed from the cooling bath and stirred overnight at RT. The solution was cooled to 0° C. and quenched by careful addition of MeOH. The resulting suspension was evaporated. EtOAc was added and the solid was collected by filtration, washed with EtOAc, and dried to afford (S)-5-(2-amino-3,3-dimethylbutyl)-2-chloropyridin-3-ol, as the bis HBr salt. (2.89 g, quant.) LCMS (m/z, ES+)=229.1, 231.1 (M+1).

Step 3: (S)-tert-Butyl (1-(6-chloro-5-hydroxypyridin-3-yl)-3,3-dimethylbutan-2-yl)carbamate

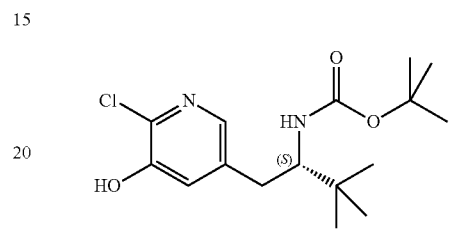

Triethylamine (0.95 mL, 6.85 mmol) was added to a stirred suspension of (S)-5-(2-amino-3,3-dimethylbutyl)-2-chloropyridin-3-ol. 2HBr (1.36 g, 3.42 mmol) and Boc-anhydride (0.87 mL, 3.73 mmol) in THF (34.2 mL) and the reaction mixture was stirred at 60° C. for 1 h and then evaporated to dryness. The solid was suspended in diethyl ether, isolated by filtration and then partitioned between EtOAc and water. The aqueous layer was extracted with CH$_2$Cl$_2$ (4×) and the combined organic phases were dried (Na$_2$SO$_4$), filtered and evaporated to provide (S)-tert-butyl (1-(6-chloro-5-hydroxypyridin-3-yl)-3,3-dimethylbutan-2-yl)carbamate (assumed quant.). LCMS (m/z, ES+)=329.6, 331.2 (M+1).

Step 4: (S)-tert-Butyl (1-(6-chloro-5-hydroxy-2-iodopyridin-3-yl)-3,3-dimethylbutan-2-yl)carbamate

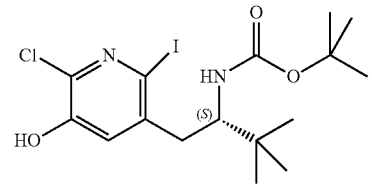

Iodine (0.87 g, 3.42 mmol) was added to a stirred solution of tert-butyl (S)-(1-(6-chloro-5-hydroxypyridin-3-yl)-3,3-dimethylbutan-2-yl)carbamate (1.13 g, 3.42 mmol) and K$_2$CO$_3$ (1.42 g, 10.26 mmol) in water (8.6 mL) and 1,4-dioxane (8.6 mL). The reaction mixture was stirred overnight at rt. More iodine (0.20 g, 0.79 mmol) and K$_2$CO$_3$ (0.40 g, 7.23 mmol) were added and the reaction mixture was heated at 40° C. for 5 h. Solid Na$_2$SO$_3$ was added while stirring until the solution was no longer dark brown. The solution was diluted with brine and EtOAc. The aqueous phase was extracted with EtOAc. The combined organic layers were dried (Na$_2$SO$_4$), filtered and evaporated to provide (S)-tert-butyl (1-(6-chloro-5-hydroxy-2-iodopyridin-3-yl)-3,3-dimethylbutan-2-yl)carbamate as a yellow foam (1.56 g, quant.). LCMS (m/z, ES+)=455.1, 457.1 (M+1).

Step 5: (S)-tert-Butyl (1-(6-chloro-2-iodo-5-(3-methoxypropoxy)pyridin-3-yl)-3,3-dimethylbutan-2-yl)carbamate

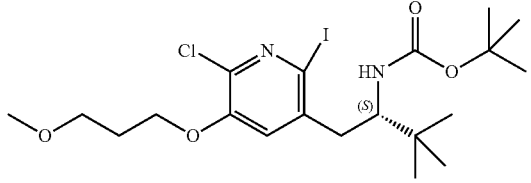

A solution of tert-butyl (S)-(1-(6-chloro-5-hydroxy-2-iodopyridin-3-yl)-3,3-dimethylbutan-2-yl)carbamate (0.83 g, 1.84 mmol), K₂CO₃ (0.76 g, 5.51 mmol), and 1-bromo-3-methoxypropane (0.56 g, 3.67 mmol) in DMF (12.2 mL) was heated at 80° C. for 3 h. The reaction mixture was evaporated to dryness and the residue was taken up in CH₂Cl₂ and H₂O. The aqueous phase was extracted CH₂Cl₂ (2×) and the combined organic layers were dried (Na₂SO₄), filtered, and evaporated to afford tert-butyl (S)-(1-(6-chloro-2-iodo-5-(3-methoxypropoxy)pyridin-3-yl)-3,3-dimethylbutan-2-yl)carbamate (0.97 g, quant.) as an off-white solid. LCMS (m/z, ES+)=527.2, 529.2 (M+1).

Step 6: (S)-Ethyl 1-(1-(6-chloro-2-iodo-5-(3-methoxypropoxy)pyridin-3-yl)-3,3-dimethylbutan-2-yl)-4-oxo-1,4-dihydropyridine-3-carboxylate

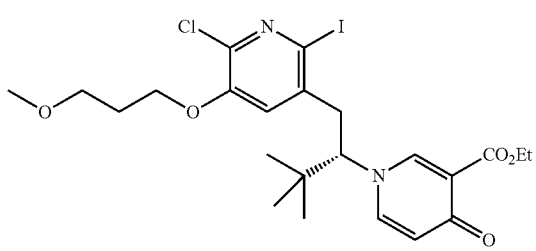 [SMILES: CCOC(=O)c1cn([C@@H](Cc2cc(OCCCOC)c(Cl)nc2I)C(C)(C)C)ccc1=O]

4 M Hydrogen chloride in dioxane (6.89 mL, 27.5 mmol) was added to a solution of tert-butyl (S)-(1-(6-chloro-2-iodo-5-(3-methoxypropoxy)pyridin-3-yl)-3,3-dimethylbutan-2-yl)carbamate (967 mg, 1.84 mmol) in CH₂Cl₂ (7 mL). The reaction mixture was stirred at rt for 3 h and evaporated to dryness. The solid was dissolved in CH₂Cl₂ (1 mL) and Et₃N (1 mL) and then evaporated to dryness. The residue was taken up in saturated NaHCO₃ and CH₂Cl₂. The aqueous phase was extracted with CH₂Cl₂ (2×) and the combined organic layers were dried (Na₂SO₄), filtered, and evaporated to afford (S)-1-(6-chloro-2-iodo-5-(3-methoxypropoxy)pyridin-3-yl)-3,3-dimethylbutan-2-amine. A solution of the above amine and ethyl 4-oxo-4H-pyran-3-carboxylate (340 mg, 2.02 mmol) in acetic acid (18.4 mL) was stirred at 100° C. for 7 h. The reaction mixture was evaporated to dryness and the residue was purified by reverse phase chromatography (10-100% CH₃CN/H₂O (0.1% formic acid)) to afford ethyl (S)-1-(1-(6-chloro-2-iodo-5-(3-methoxypropoxy)pyridin-3-yl)-3,3-dimethylbutan-2-yl)-4-oxo-1,4-dihydropyridine-3-carboxylate (593 mg, 56%) as a tan solid. LCMS (m/z, ES+)=577.7, 579.2 (M+1).

Step 7: (S)-Ethyl 6-(tert-butyl)-2-chloro-3-(3-methoxypropoxy)-10-oxo-6,10-dihydro-5H-pyrido[1,2-h][1,7]naphthyridine-9-carboxylate

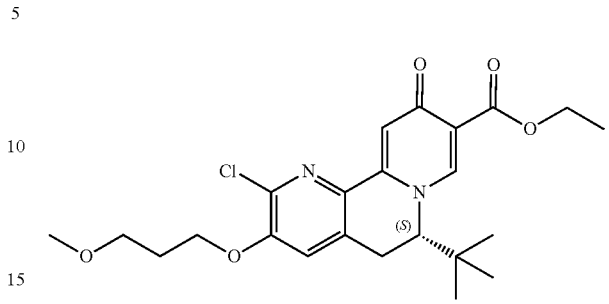

A flask containing of ethyl (S)-1-(1-(6-chloro-2-iodo-5-(3-methoxypropoxy)pyridin-3-yl)-3,3-dimethylbutan-2-yl)-4-oxo-1,4-dihydropyridine-3-carboxylate (0.59 g, 1.03 mmol), potassium acetate (0.20 g, 2.06 mmol), and palladium(II) bromide (0.055 g, 0.21 mmol) was purged with nitrogen. Degassed N,N-dimethylacetamide (DMA) (10.3 mL) was added and the reaction mixture was heated at 90° C. for 24 h. The solvent was removed by evaporation and the residue was purified by reverse phase chromatography (5-100% CH₃CN/H₂O (0.1% formic acid)) to afford ethyl (S)-6-(tert-butyl)-2-chloro-3-(3-methoxypropoxy)-10-oxo-5,10-dihydro-6H-pyrido[1,2-h][1,7]naphthyridine-9-carboxylate (326 mg, 71%) as an off-white solid. ¹H NMR (400 MHz, CDCl₃) δ ppm 8.18 (s, 1H), 7.49 (s, 1H), 7.02 (s, 1H), 4.40 (q, J=7.0 Hz, 2H), 4.13-4.26 (m, 2H), 3.93 (d, J=6.6 Hz, 1H), 3.62 (m, 2H), 3.42-3.51 (m, 1H), 3.38 (s, 3H), 3.17-3.25 (m, 1H), 2.15 (quin, J=6.0 Hz, 2H), 1.41 (t, J=7.2 Hz, 3H), 0.86 (s, 9H); LCMS (m/z, ES+)=449.3, 451.3 (M+1).

Step 8: (S)-6-(tert-Butyl)-2-chloro-3-(3-methoxypropoxy)-10-oxo-6,10-dihydro-5H-pyrido[1,2-h][1,7]naphthyridine-9-carboxylic acid

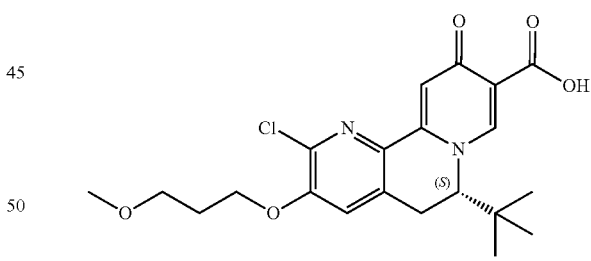

A solution of ethyl (S)-6-(tert-butyl)-2-chloro-3-(3-methoxypropoxy)-10-oxo-5,10-dihydro-6H-pyrido[1,2-h][1,7]naphthyridine-9-carboxylate (42 mg, 0.094 mmol) in 1 M LiOH (1.7 mL) and MeOH (1.7 mL) was stirred at 50° C. for 1.5 h. 1 M Citric acid (2 mL) was added and the reaction mixture was stirred for several mins. The white solid was collected by filtration, washed with water, and dried to afford (S)-6-(tert-butyl)-2-chloro-3-(3-methoxypropoxy)-10-oxo-5,10-dihydro-6H-pyrido[1,2-h][1,7]naphthyridine-9-carboxylic acid (35.5 mg, 90%) as a white solid. ¹H NMR (400 MHz, DMSO-d₆) δ ppm 16.31 (s, 1H), 8.81 (s, 1H), 7.75 (s, 1H), 7.30 (s, 1H), 4.68 (d, J=6.3 Hz, 1H), 4.19-4.32 (m, 2H), 3.40-3.60 (m, 4H), 3.26 (s, 3H), 2.04 (quin, J=6.2 Hz, 2H), 0.75 (s, 9H); LCMS (m/z, ES+)=421.3, 423.2 (M+1).

Example 12 (Compound 231)

(S)-6-(tert-Butyl)-3-(cyclopropylmethoxy)-2-methyl-10-oxo-6,10-dihydro-5H-pyrido[1,2-h][1,7]naphthyridine-9-carboxylic acid

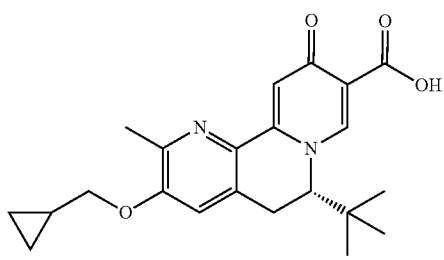

Step 1: (S)-tert-Butyl (1-(6-chloro-5-(cyclopropylmethoxy)-2-iodopyridin-3-yl)-3,3-dimethylbutan-2-yl)carbamate

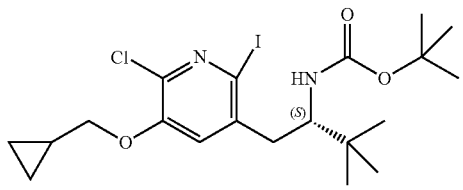

A solution of tert-butyl (S)-(1-(6-chloro-5-hydroxy-2-iodopyridin-3-yl)-3,3-dimethylbutan-2-yl)carbamate (0.73 g, 1.60 mmol), $K_2CO_3$ (0.66 g, 4.78 mmol), and (bromomethyl)cyclopropane (0.43 g, 3.19 mmol) in DMF (10.6 mL) was heated at 80° C. for 3 h. The reaction mixture was evaporated to dryness and the residue was taken up in $CH_2Cl_2$ and $H_2O$. The aqueous phase was extracted with $CH_2Cl_2$ (2×) and the combined organic layers were dried ($Na_2SO_4$), filtered, and evaporated to afford tert-butyl (S)-(1-(6-chloro-5-(cyclopropylmethoxy)-2-iodopyridin-3-yl)-3,3-dimethylbutan-2-yl)carbamate (0.81 g, quant.) as an off-white solid. LCMS (m/z, ES+)=508.8, 511.1 (M+1).

Step 2: (S)-Ethyl 1-(1-(6-chloro-5-(cyclopropylmethoxy)-2-iodopyridin-3-yl)-3,3-dimethylbutan-2-yl)-4-oxo-1,4-dihydropyridine-3-carboxylate

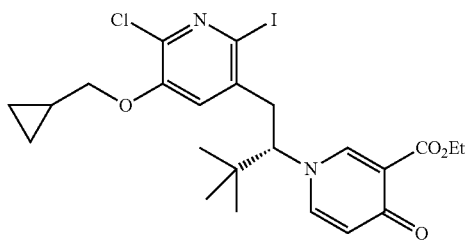 [SMILES: CCOC(=O)c1cn([C@@H](Cc2cc(OCC3CC3)c(Cl)nc2I)C(C)(C)C)ccc1=O]

4 M Hydrogen chloride in dioxane (5.98 mL, 23.9 mmol) was added to a solution of tert-butyl (S)-(1-(6-chloro-5-(cyclopropylmethoxy)-2-iodopyridin-3-yl)-3,3-dimethylbutan-2-yl)carbamate (812 mg, 1.60 mmol) in $CH_2Cl_2$ (6 mL). The reaction mixture was stirred at rt for 3 h and evaporated to dryness. The solid was dissolved in $CH_2Cl_2$ (1 mL) and $Et_3N$ (1 mL) and then evaporated to dryness. The residue was taken up in saturated $NaHCO_3$ and $CH_2Cl_2$. The aqueous phase was extracted with $CH_2Cl_2$ (2×) and the combined organic layers were dried ($Na_2SO_4$), filtered, and evaporated to afford (S)-1-(6-chloro-2-iodo-5-(cyclopropylmethoxy)pyridin-3-yl)-3,3-dimethylbutan-2-amine. LCMS (m/z, ES+)=409.1, 411.1 (M+1).

A solution of the above amine and ethyl 4-oxo-4H-pyran-3-carboxylate (295 mg, 1.76 mmol) in acetic acid (16.0 mL) was stirred at 100° C. for 7 h. The reaction mixture was evaporated to dryness and the residue was purified by reverse phase chromatography (5-100% $CH_3CN/H_2O$ (0.1% formic acid)) to afford ethyl (S)-1-(1-(6-chloro-5-(cyclopropylmethoxy)-2-iodopyridin-3-yl)-3,3-dimethylbutan-2-yl)-4-oxo-1,4-dihydropyridine-3-carboxylate (453 mg, 51%) as a tan solid. LCMS (m/z, ES+)=559.4, 561.1 (M+1).

Step 3: (S)-Ethyl 6-(tert-butyl)-2-chloro-3-(cyclopropylmethoxy)-10-oxo-6,10-dihydro-5H-pyrido[1,2-h][1,7]naphthyridine-9-carboxylate

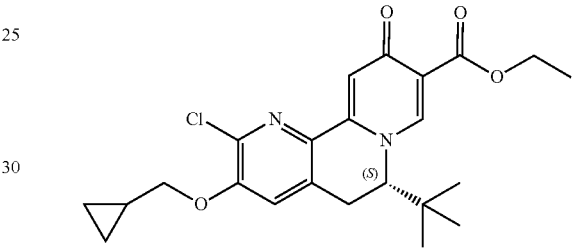

A flask containing ethyl (S)-1-(1-(6-chloro-5-(cyclopropylmethoxy)-2-iodopyridin-3-yl)-3,3-dimethylbutan-2-yl)-4-oxo-1,4-dihydropyridine-3-carboxylate (0.45 g, 0.81 mmol), potassium acetate (0.16 g, 1.62 mmol), and palladium(II) bromide (0.043 g, 0.16 mmol) was purged with nitrogen. Degassed N,N-dimethylacetamide (DMA) (8.1 mL) was added and the reaction mixture was heated at 90° C. for 24 h. The solvent was removed by evaporation and the residue was taken up in $CH_2Cl_2$ and water and filtered through celite. The organic phase was evaporated to dryness and the residue was purified by reverse phase chromatography (10-100% $CH_3CN/H_2O$ (0.1% formic acid)) to afford ethyl (S)-6-(tert-butyl)-2-chloro-3-(cyclopropylmethoxy)-10-oxo-5,10-dihydro-6H-pyrido[1,2-h][1,7]naphthyridine-9-carboxylate (216 mg, 62%) as an off-white solid. LCMS (m/z, ES+)=431.2, 433.2 (M+1); >97% e.e. by chiral HPLC.

Step 4: (S)-6-(tert-Butyl)-3-(cyclopropylmethoxy)-2-methyl-10-oxo-6,10-dihydro-5H-pyrido[1,2-h][1,7]naphthyridine-9-carboxylic acid

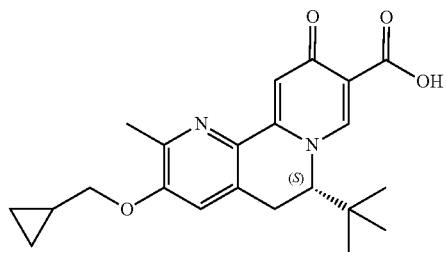

A solution of ethyl (S)-6-(tert-butyl)-2-chloro-3-(cyclopropylmethoxy)-10-oxo-5,10-dihydro-6H-pyrido[1,2-h][1,7]naphthyridine-9-carboxylate (52.7 mg, 0.12 mmol), Pd(PPh₃)₄ (28 mg, 0.024 mmol), potassium carbonate (34 mg, 0.25 mmol), and trimethylboroxine (46 mg, 0.37 mmol) in 1,4-dioxane (0.61 mL) was heated at 100° C. overnight. The reaction mixture was diluted with CH₂Cl₂ and filtered through celite. The filtrate was evaporated and the residue was purified by reverse phase chromatography (5-100% CH₃CN/H₂O (0.1% formic acid)) to afford (S)-ethyl 6-(tert-butyl)-3-(cyclopropylmethoxy)-2-methyl-10-oxo-6,10-dihydro-5H-pyrido[1,2-h][1,7]naphthyridine-9-carboxylate (36.5 mg, 73%). ¹H NMR (400 MHz, CDCl₃) δ ppm 8.18 (s, 1H), 7.56 (s, 1H), 6.80 (s, 1H), 4.40 (q, J=7.0 Hz, 2H), 3.87 (s, 3H), 3.39-3.48 (m, 1H), 3.10-3.18 (m, 1H), 2.50 (s, 3H), 1.41 (t, J=7.0 Hz, 3H), 0.69 (m, 2H), 0.40 (m, 2H); LCMS (m/z, ES+)=411.4 (M+1).

A solution of the above ester in 1M LiOH (0.9 mL) and MeOH (0.9 mL) was heated at 50° C. for 1.5 h. 1 M citric acid (1.2 mL) was added and the reaction mixture was stirred for 15 mins. The solid was collected by filtration, washed with water, and dried to afford (S)-6-(tert-butyl)-3-(cyclopropylmethoxy)-2-methyl-10-oxo-6,10-dihydro-5H-pyrido[1,2-h][1,7]naphthyridine-9-carboxylic acid (27.7 mg, 59% for 2 steps) as a white solid. ¹H NMR (400 MHz, DMSO-d₆) δ ppm 16.53 (br. s., 1H), 8.77 (s, 1H), 7.44 (s., 1H), 7.42 (s, 1H), 4.58-4.69 (m, 1H), 3.98 (m, 2H), 3.46-3.55 (m, 2H), 2.43 (s, 3H), 1.22-1.36 (m, 1H), 0.73 (s, 9H), 0.65-0.55 (m, 2H), 0.33-0.44 (m, 2H); LCMS (m/z, ES+)=383.2 (M+1).

Example 13 (Compound 232)

(S)-6-(tert-Butyl)-3-(3-methoxypropoxy)-2-methyl-10-oxo-6,10-dihydro-5H-pyrido[1,2-h][1,7]naphthyridine-9-carboxylic acid

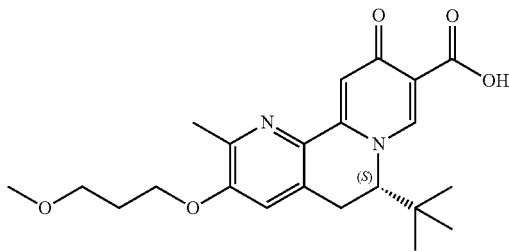

A solution of ethyl (S)-6-(tert-butyl)-2-chloro-3-(3-methoxypropoxy)-10-oxo-5,10-dihydro-6H-pyrido[1,2-h][1,7]naphthyridine-9-carboxylate (47.7 mg, 0.11 mmol), Pd(PPh₃)₄ (25 mg, 0.021 mmol), potassium carbonate (29 mg, 0.21 mmol), and trimethylboroxine (40 mg, 0.32 mmol) in 1,4-dioxane (0.53 mL) was heated at 100° C. overnight. The reaction mixture was diluted with CH₂Cl₂ and filtered through celite. The filtrate was evaporated and the residue was purified by silica gel chromatography (0-100% (3:1 EtOAc:EtOH) in hexanes) to afford (S)-ethyl 6-(tert-butyl)-3-(3-methoxypropoxy)-2-methyl-10-oxo-6,10-dihydro-5H-pyrido[1,2-h][1,7]naphthyridine-9-carboxylate (41.3 mg, 91%) as a white solid. ¹H NMR (400 MHz, CDCl₃) δ ppm 8.17 (s, 1H), 7.27 (s, 1H), 6.86 (m, 1H), 4.39 (q, J=7.0 Hz, 2H), 4.05-4.17 (m, 2H), 3.91 (d, J=6.6 Hz, 1H), 3.63-3.55 (m, 2H), 3.49-3.41 (m, 1H), 3.38 (s, 3H), 3.15 (d, J=16.8 Hz, 1H), 2.46 (s, 3H), 2.12 (quin, J=6.1 Hz, 2H), 1.40 (t, J=7.0 Hz, 3H), 0.84 (s, 9H); LCMS (m/z, ES+)=429.4 (M+1).

A solution of the above ester in 1M LiOH (1 mL) and MeOH (1 mL) was heated at 50° C. for 1.5 h. 1 M citric acid (1.2 mL) was added and the reaction mixture was stirred for 15 mins. The solid was collected by filtration, washed with water, and dried to afford (S)-6-(tert-butyl)-3-(3-methoxypropoxy)-2-methyl-10-oxo-5,10-dihydro-6H-pyrido[1,2-h][1,7]naphthyridine-9-carboxylic acid (27.6 mg, 65% for 2 steps) as a white solid. ¹H NMR (400 MHz, DMSO-d₆) δ ppm 16.53 (s, 1H), 8.77 (s, 1H), 7.46 (s, 1H), 7.44 (s, 1H), 4.64 (d, J=6.3 Hz, 1H), 4.09-4.23 (m, 2H), 3.47-3.56 (m, 3H), 3.38-3.32 (m, 1H), 3.26 (s, 3H), 2.42 (s, 3H), 2.02 (quin, J=6.2 Hz, 2H), 0.74 (s, 9H); LCMS (m/z, ES+)=401.2 (M+1).

Example 14 (Compound 233)

(S)-6-(tert-Butyl)-2-cyclopropyl-3-(cyclopropylmethoxy)-10-oxo-6,10-dihydro-5H-pyrido[1,2-h][1,7]naphthyridine-9-carboxylic acid

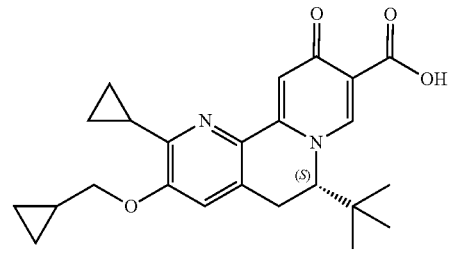

A solution of ethyl (S)-6-(tert-butyl)-2-chloro-3-(cyclopropylmethoxy)-10-oxo-5,10-dihydro-6H-pyrido[1,2-h][1,7]naphthyridine-9-carboxylate (53 mg, 0.12 mmol), Pd(PPh₃)₄ (28 mg, 0.025 mmol), potassium carbonate (51 mg, 0.37 mmol), and cyclopropylboronic acid (21 mg, 0.25 mmol) in 1,4-dioxane (1.2 mL) was heated at 100° C. overnight. The reaction mixture was diluted with CH₂Cl₂ and filtered through celite. The filtrate was evaporated and the residue was purified by silica gel chromatography (0-100% (3:1 EtOAc:EtOH) in hexanes) to afford (S)-ethyl 6-(tert-butyl)-2-cyclopropyl-3-(cyclopropylmethoxy)-10-oxo-6,10-dihydro-5H-pyrido[1,2-h][1,7]naphthyridine-9-carboxylate (53.3 mg, 99%) as a white solid. ¹H NMR (400 MHz, CDCl₃) δ ppm 8.14 (s, 1H), 7.42 (s, 1H), 6.77 (s, 1H), 4.38 (q, J=7.3 Hz, 2H), 3.88 (m, J=6.8, 2.1 Hz, 2H), 3.43 (dd, J=16.8, 7.0 Hz, 1H), 3.11 (d, J=16.8 Hz, 1H), 2.56-2.47 (m, 1H), 1.39 (t, J=7.0 Hz, 3H), 1.35-1.29 (m, 1H), 1.22-1.29 (m, 1H), 1.04-1.19 (m, 2H), 0.93-1.01 (m, 2H), 0.82 (s, 9H), 0.63-0.73 (m, 2H), 0.44-0.38 (m, 2H); LCMS (m/z, ES+)=437.4 (M+1).

A solution of the above ester in 1M LiOH (1.2 mL) and MeOH (1.2 mL) was heated at 50° C. for 2 h. 1 M citric acid (1.5 mL) was added and the reaction mixture was stirred for 15 mins. The solid was collected by filtration, washed with water, and dried to afford (S)-6-(tert-butyl)-2-cyclopropyl-3-(cyclopropylmethoxy)-10-oxo-5,10-dihydro-6H-pyrido[1,2-h][1,7]naphthyridine-9-carboxylic acid (38.8 mg, 77% for 2 steps) as a white solid. ¹H NMR (400 MHz, DMSO-d₆) δ ppm 16.53 (s, 1H), 8.76 (s, 1H), 7.38 (s, 1H), 7.35 (s, 1H), 4.62 (d, J=6.3 Hz, 1H), 4.05-3.94 (m, 2H), 3.42-3.55 (m, 1H), 3.30-3.28 (m, 1H), 1.26-1.44 (m, 1H), 0.93-1.06 (m, 4H), 0.72 (s, 9H), 0.65-0.59 (m, 2H), 0.43-0.5 (m, 2H); LCMS (m/z, ES+)=409.2 (M+1).

Example 15 (Compound 234)

(S)-6-(tert-Butyl)-2-cyclopropyl-3-(3-methoxypropoxy)-10-oxo-6,10-dihydro-5H-pyrido[1,2-h][1,7]naphthyridine-9-carboxylic acid

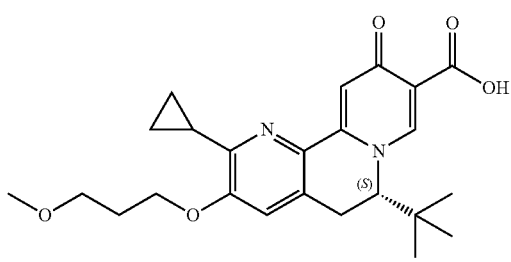

A solution of ethyl (S)-6-(tert-butyl)-2-chloro-3-(3-methoxypropoxy)-10-oxo-5,10-dihydro-6H-pyrido[1,2-h][1,7]naphthyridine-9-carboxylate (46 mg, 0.10 mmol), Pd(PPh₃)₄, (24 mg, 0.020 mmol), potassium carbonate (42 mg, 0.31 mmol), and cyclopropylboronic acid (18 mg, 0.21 mmol) in 1,4-dioxane (1.0 mL) was heated at 100° C. overnight. The reaction mixture was diluted with CH₂Cl₂ and filtered through celite. The filtrate was evaporated and the residue was purified by silica gel chromatography (0-100% (3:1 EtOAc:EtOH) in hexanes) to afford (S)-ethyl 6-(tert-butyl)-2-cyclopropyl-3-(3-methoxypropoxy)-10-oxo-6,10-dihydro-5H-pyrido[1,2-h][1,7]naphthyridine-9-carboxylate (43.6 mg, 94%) as a white solid. ¹H NMR (400 MHz, CDCl₃) δ ppm 8.16 (s, 1H), 7.45 (s, 1H), 6.83 (s, 1H), 4.39 (q, J=7.0 Hz, 2H), 4.13 (m, 2H), 3.89 (d, J=6.6 Hz, 1H), 3.62 (m, 2H), 3.39-3.46 (m, 1H), 3.38 (s, 3H), 3.13 (d, J=16.8 Hz, 1H), 2.40-2.50 (m, 1H), 2.15 (quin, J=6.1 Hz, 2H), 1.40 (t, J=7.0 Hz, 3H), 1.14-1.22 (m, 1H), 1.04-1.12 (m, 1H), 0.93-1.02 (m, 2H), 0.83 (s, 9H); LCMS (m/z, ES+)=455.5 (M+1).

A solution of the above ester in 1M LiOH (1.2 mL) and MeOH (1.2 mL) was heated at 50° C. for 2 h. 1 M citric acid (1.5 mL) was added and the reaction mixture was stirred for 15 mins. The solid was collected by filtration, washed with water, and dried to afford (S)-6-(tert-butyl)-2-cyclopropyl-3-(3-methoxypropoxy)-10-oxo-5,10-dihydro-6H-pyrido[1,2-h][1,7]naphthyridine-9-carboxylic acid (27.2 mg, 62%) as a white solid. ¹H NMR (400 MHz, DMSO-d₆) δ ppm 16.53 (s, 1H), 8.76 (s, 1H), 7.43 (s, 1H), 7.35 (s, 1H), 4.62 (d, J=6.3 Hz, 1H), 4.11-4.24 (m, 2H), 3.42-3.57 (m, 4H), 3.26 (s, 3H), 2.41-2.46 (m, 1H), 2.05 (quin, J=6.2 Hz, 2H), 0.94-1.06 (m, 4H), 0.73 (s, 9H); LCMS (m/z, ES+)=427.2 (M+1).

Example 16 (Compound 235)

(R)-6-(tert-Butyl)-3-(cyclopropylmethoxy)-2-methoxy-10-oxo-6,10-dihydro-5H-pyrido[1,2-h][1,7]naphthyridine-9-carboxylic acid

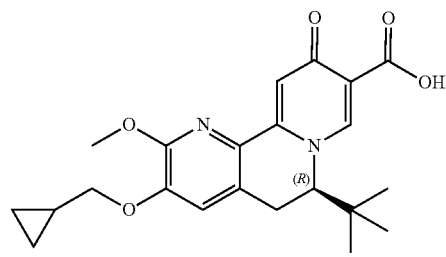

Step 1: (S)—N—((R)-1-(6-Chloro-5-methoxypyridin-3-yl)-3,3-dimethylbutan-2-yl)-2-methylpropane-2-sulfinamide and (S)—N—((S)-1-(6-Chloro-5-methoxypyridin-3-yl)-3,3-dimethylbutan-2-yl)-2-methylpropane-2-sulfinamide

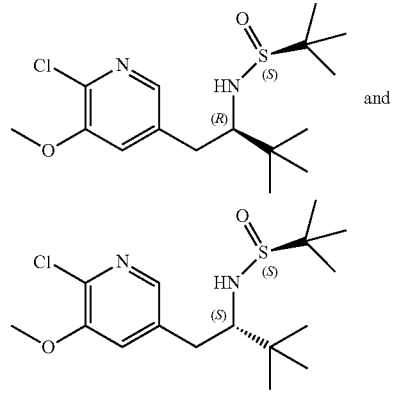

A solution of 1-(6-chloro-5-methoxypyridin-3-yl)-3,3-dimethylbutan-2-one (2.56 g, 10.57 mmol), (S)-2-methylpropane-2-sulfinamide (2.56 g, 21.14 mmol), Ti(OEt)₄ (6.03 g, 26.4 mmol) in toluene (8.5 mL) was stirred for 10 mins at 60° C. and the vessel was then evacuated. The reaction mixture was stirred at 60° C. under vacuum for 24 h. The vessel was re-pressurized with nitrogen, toluene (5 mL) and Ti(OEt)₄ (2.4 g, 10.5 mmol) were added and the reaction mixture was stirred under vacuum for 4 h. The vessel was re-pressurized with nitrogen, toluene (5 mL) was added and the reaction mixture was stirred under vacuum for another 3 h. The thick reaction mixture was then taken up in THF (70.5 mL), additional Ti(OEt)₄ (2.4 g, 10.5 mmol) was added, and the solution was cooled to −30° C. NaBH₄ (1.20 g, 31.7 mmol) was added portion wise. The reaction mixture was then allowed to warm slowly to rt overnight. The reaction mixture was diluted with THF (130 mL) and brine (3 mL), stirred for 30 mins, and then filtered through celite. The filtrate was evaporated and purified by silica gel chromatography to afford the two diastereomers.

Major diastereomer is a white solid: (S)—N—((R)-1-(6-chloro-5-methoxypyridin-3-yl)-3,3-dimethylbutan-2-yl)-2-methylpropane-2-sulfinamide (1.8 g, 50%). ¹H NMR (400

MHz, CDCl₃) δ ppm 7.81 (d, J=2.0 Hz, 1H), 7.40 (d, J=2.0 Hz, 1H), 3.97 (s, 3H), 3.26 (m, 1H), 3.06-3.15 (m, 2H), 2.72 (dd, J=14.8, 8.2 Hz, 1H), 1.17 (s, 9H), 0.99 (s, 9H); LCMS (m/z, ES+)=346.8, 348.5 (M+1).

Minor diastereomer is a clear oil: (S)—N—((S)-1-(6-chloro-5-methoxypyridin-3-yl)-3,3-dimethylbutan-2-yl)-2-methylpropane-2-sulfinamide (1.2 g, 33%). ¹H NMR (400 MHz, CDCl₃) δ ppm 7.77 (d, J=1.6 Hz, 1H), 7.07 (d, J=1.6 Hz, 1H), 3.93 (s, 3H), 3.19-3.33 (m, 2H), 3.02 (dd, J=14.1, 2.7 Hz, 1H), 2.55 (dd, J=14.1, 10.5 Hz, 1H), 1.08 (s, 9H), 0.98 (s, 9H); LCMS (m/z, ES+)=346.8, 348.0 (M+1).

Step 2: (R)-5-(2-Amino-3,3-dimethylbutyl)-2-chloropyridin-3-ol

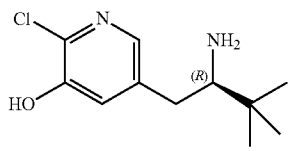

A solution of (S)—N—((R)-1-(6-chloro-5-methoxypyridin-3-yl)-3,3-dimethylbutan-2-yl)-2-methylpropane-2-sulfinamide (1.82 g, 5.26 mmol) in 1,2-dichloroethane (26.3 mL) was stirred at 0° C. Boron tribromide (3.48 mL, 36.8 mmol) was added slowly. The reaction mixture was removed from the cooling bath and stirred overnight at RT. The solution was cooled to 0° C. and quenched by careful addition of MeOH. The resulting suspension was evaporated. EtOAc was added and the solid was collected by filtration, washed with EtOAc, and dried to afford (S)-5-(2-amino-3,3-dimethylbutyl)-2-chloropyridin-3-ol, as the bis HBr salt. (2.1 g, quant.) LCMS (m/z, ES+)=229.2, 231.2 (M+1).

Step 3: (R)-tert-Butyl (1-(6-chloro-5-hydroxypyridin-3-yl)-3,3-dimethylbutan-2-yl)carbamate

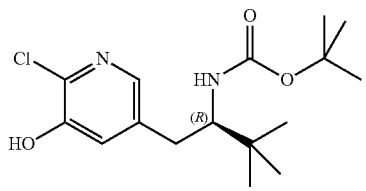

A stirred suspension of (R)-5-(2-amino-3,3-dimethylbutyl)-2-chloropyridin-3-ol. 2HBr (1.0 g, 2.51 mmol) and Boc-anhydride (0.80 g, 3.67 mmol) in THF (25.1 mL) was stirred at 60° C. for 1.5 h. THF (10 mL) and triethylamine (0.35 mL, 2.51 mmol) were added and the reaction mixture was stirred for another 30 mins. Additional triethylamine (0.35 mL, 2.51 mmol) was added and the reaction mixture was stirred at 60° C. for 1 h. The solution was then evaporated to dryness. The solid was suspended in diethyl ether, isolated by filtration and washed with additional diethyl ether. The solid was taken up in EtOAc and washed with dilute aqueous NaHCO₃, and brine. The organic phase was dried (Na₂SO₄), filtered and evaporated to provide (R)-tert-butyl (1-(6-chloro-5-hydroxypyridin-3-yl)-3,3-dimethylbutan-2-yl)carbamate (1.01 g, 99%) as a light yellow solid. LCMS (m/z, ES+)=329.2, 331.2 (M+1).

Step 4: (R)-tert-Butyl (1-(6-chloro-5-hydroxy-2-iodopyridin-3-yl)-3,3-dimethylbutan-2-yl)carbamate

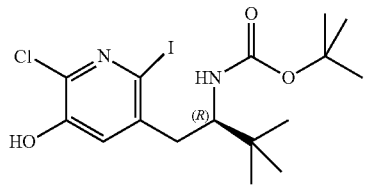

Iodine (0.64 g, 2.51 mmol) was added to a stirred solution of tert-butyl (R)-(1-(6-chloro-5-hydroxypyridin-3-yl)-3,3-dimethylbutan-2-yl)carbamate (0.83 g, 2.51 mmol) and K₂CO₃ (1.04 g, 7.53 mmol) in water (6.3 mL) and 1,4-dioxane (6.3 mL). The reaction mixture was stirred at RT for 1.5 h.

Solid Na2SO3 was added while stirring until the solution was no longer dark brown. The solution was diluted with brine and EtOAc. The aqueous phase was extracted with EtOAc. The combined organic phases were dried (Na2SO4), filtered and evaporated to provide (R)-tert-butyl (1-(6-chloro-5-hydroxy-2-iodopyridin-3-yl)-3,3-dimethylbutan-2-yl)carbamate as a yellow foam (0.38 g, 34%). LCMS (m/z, ES+)=455.4, 457.1 (M+1).

Step 5: (R)-tert-Butyl (1-(6-chloro-5-(cyclopropylmethoxy)-2-iodopyridin-3-yl)-3,3-dimethylbutan-2-yl)carbamate

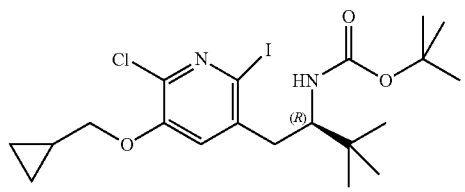

A solution of tert-butyl (R)-(1-(6-chloro-5-hydroxy-2-iodopyridin-3-yl)-3,3-dimethylbutan-2-yl)carbamate (0.3819 g, 0.840 mmol), K₂CO₃ (0.35 g, 2.52 mmol), and (bromomethyl)cyclopropane (0.23 g, 1.68 mmol) in DMF (5.6 mL) was heated at 80° C. for 3 h. The reaction mixture was evaporated to dryness and the residue was taken up in CH₂Cl₂ and H₂O. The aqueous phase was extracted CH₂Cl₂ (2×) and the combined organic layers were dried (Na₂SO₄), filtered, and evaporated to afford tert-butyl (R)-(1-(6-chloro-5-(cyclopropylmethoxy)-2-iodopyridin-3-yl)-3,3-dimethylbutan-2-yl)carbamate (415.4 mg, 97%) as an off-white solid. LCMS (m/z, ES+)=509.2, 511.2 (M+1).

Step 6: Ethyl (R)-1-(1-(6-chloro-5-(cyclopropylmethoxy)-2-iodopyridin-3-yl)-3,3-dimethylbutan-2-yl)-4-oxo-1,4-dihydropyridine-3-carboxylate

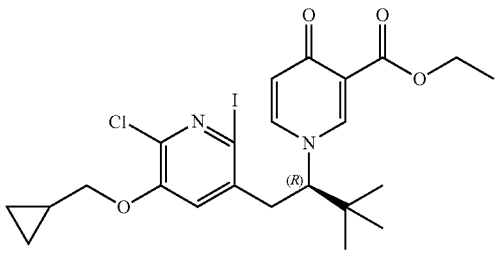

4 M Hydrogen chloride in dioxane (3.06 mL, 12.25 mmol) was added to a solution of tert-butyl (R)-(1-(6-chloro-5-(cyclopropylmethoxy)-2-iodopyridin-3-yl)-3,3-dimethylbutan-2-yl)carbamate (0.42 g, 0.82 mmol) in $CH_2Cl_2$ (3 mL). The reaction mixture was stirred at rt for 3 h and evaporated to dryness. The solid was dissolved in $CH_2Cl_2$ (1 mL) and $Et_3N$ (1 mL), stirred, and then evaporated to dryness. The residue was taken up in saturated $NaHCO_3$ and $CH_2Cl_2$. The aqueous phase was extracted with $CH_2Cl_2$ (2×) and the combined organic layers were dried ($Na_2SO_4$), filtered, and evaporated to afford (R)-1-(6-chloro-5-(cyclopropylmethoxy)-2-iodopyridin-3-yl)-3,3-dimethylbutan-2-amine. A solution of the above amine and ethyl 4-oxo-4H-pyran-3-carboxylate (151 mg, 0.90 mmol) in acetic acid (8.2 mL) was stirred at 100° C. for 7 h. The reaction mixture was evaporated to dryness and the residue was purified by reverse phase chromatography (5-100% $CH_3CN/H_2O$ (0.1% formic acid)) to afford ethyl (R)-1-(1-(6-chloro-5-(cyclopropylmethoxy)-2-iodopyridin-3-yl)-3,3-dimethylbutan-2-yl)-4-oxo-1,4-dihydropyridine-3-carboxylate (389 mg, 85%) as a light tan solid. LCMS (m/z, ES−)=575.2, 577.2 (M−1).

Step 7: (R)-Ethyl 6-(tert-butyl)-2-chloro-3-(cyclopropylmethoxy)-10-oxo-6,10-dihydro-5H-pyrido[1,2-h][1,7]naphthyridine-9-carboxylate

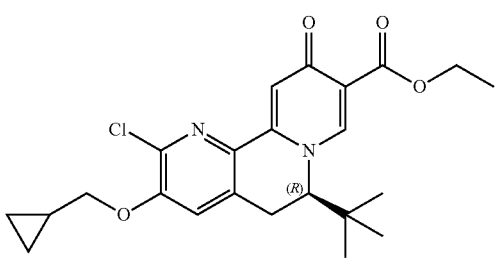

A flask containing of ethyl (R)-1-(1-(6-chloro-5-(cyclopropylmethoxy)-2-iodopyridin-3-yl)-3,3-dimethylbutan-2-yl)-4-oxo-1,4-dihydropyridine-3-carboxylate (0.39 g, 0.70 mmol), potassium acetate (0.14 g, 1.39 mmol), and palladium(II) bromide (0.037 g, 0.14 mmol) was purged with nitrogen. Degassed N,N-dimethylacetamide (DMA) (7.0 mL) was added and the reaction mixture was heated at 90° C. for 24 h. The solution was purified by reverse phase chromatography (10-100% $CH_3CN/H_2O$ (0.1% formic acid)) to afford ethyl (R)-6-(tert-butyl)-2-chloro-3-(cyclopropylmethoxy)-10-oxo-5,10-dihydro-6H-pyrido[1,2-h][1,7]naphthyridine-9-carboxylate (167 mg, 56%). $^1$H NMR (400 MHz, $CDCl_3$) δ ppm 8.18 (s, 1H), 7.49 (s, 1H), 6.96 (s, 1H), 4.40 (q, J=7.3 Hz, 2H), 3.96 (d, J=7.0 Hz, 2H), 3.93 (d, J=6.6 Hz, 1H), 3.46 (dd, J=17.0, 6.8 Hz, 1H), 3.19 (d, J=16.8 Hz, 1H), 1.41 (t, J=7.0 Hz, 3H), 1.30-1.37 (m, 1H), 0.85 (s, 9H), 0.76-0.70 (m, 2H), 0.41-0.48 (m, 2H); LCMS (m/z, ES−)=429.4, 431.4 (M−1).

Step 8: (R)-6-(tert-Butyl)-3-(cyclopropylmethoxy)-2-methoxy-10-oxo-6,10-dihydro-5H-pyrido[1,2-h][1,7]naphthyridine-9-carboxylic acid

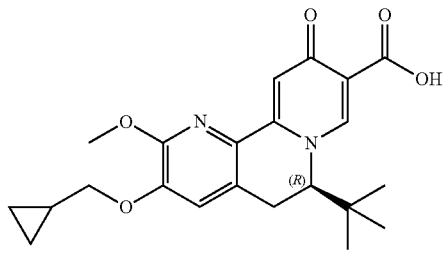

A solution of ethyl (R)-6-(tert-butyl)-2-chloro-3-(cyclopropylmethoxy)-10-oxo-5,10-dihydro-6H-pyrido[1,2-h][1,7]naphthyridine-9-carboxylate (33 mg, 0.077 mmol), NaB(OMe)$_4$ (36 mg, 0.23 mmol), tBuXPhos (6.5 mg, 0.015 mmol) and $Pd_2(dba)_3$ (7.0 mg, 7.66 μmol) in DMF (0.77 mL) was heated at 80° C. for 2 h. The reaction mixture was filtered through celite and the celite was rinsed with EtOAc and $CH_2Cl_2$. The filtrate was evaporated and the residue was purified by silica gel chromatography (0-100% (3:1 EtOAc: EtOH) in hexanes) to afford ethyl (R)-6-(tert-butyl)-3-(cyclopropylmethoxy)-2-methoxy-10-oxo-5,10-dihydro-6H-pyrido[1,2-h][1,7]naphthyridine-9-carboxylate (27 mg, 83%). $^1$H NMR (400 MHz, $CDCl_3$) δ ppm 8.17 (s, 1H), 7.42 (s, 1H), 6.80 (s, 1H), 4.39 (q, J=7.0 Hz, 2H), 4.05 (s, 3H), 3.94-3.85 (m, 3H), 3.42 (dd, J=16.6, 6.8 Hz, 1H), 3.09 (d, J=16.8 Hz, 1H), 1.37-1.40 (t, J=7.2 Hz, 4H), 1.27-1.37 (m, 1H), 0.85 (s, 9H), 0.66-0.75 (m, 2H), 0.42-0.37 (m, 2H); LCMS (m/z, ES+)=427.4 (M+1).

A solution of the above ester in 1M LiOH (1 mL) and MeOH (1 mL) was heated at 50° C. for 2 h. The reaction mixture was filtered through an acrodisc filter to remove fine particulates and 1 M citric acid (1 mL) was added to the clear filtrate. The precipitate was collected by filtration, washed with water, and dried to afford (R)-6-(tert-butyl)-3-(cyclopropylmethoxy)-2-methoxy-10-oxo-5,10-dihydro-6H-pyrido[1,2-h][1,7]naphthyridine-9-carboxylic acid (19 mg, 62% for 2 steps) as an off-white solid. $^1$H NMR (400 MHz, DMSO-$d_6$) δ ppm 16.53 (s, 1H), 8.77 (s, 2H), 7.40 (s, 2H), 7.36 (s, 2H), 4.62 (d, J=6.8 Hz, 1H), 3.97 (s, 3H), 3.96-3.89 (m, 2H), 3.49-3.40 (m, 1H), 1.22-1.32 (m, 1H), 0.75 (s, 9H), 0.57-0.65 (m, 2H), 0.31-0.40 (m, 2H); LCMS (m/z, ES+)= 399.2 (M+1).

Example 17 (Compound 236)

(S)-6-(tert-Butyl)-3-(cyclopropylmethoxy)-2-methoxy-10-oxo-6,10-dihydro-5H-pyrido[1,2-h][1,7]naphthyridine-9-carboxylic acid

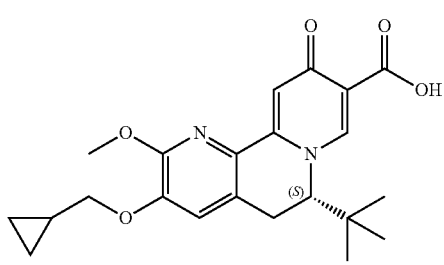

A solution of ethyl (S)-6-(tert-butyl)-2-chloro-3-(cyclopropylmethoxy)-10-oxo-5,10-dihydro-6H-pyrido[1,2-h][1,7]naphthyridine-9-carboxylate (52 mg, 0.12 mmol), NaB(OMe)$_4$ (57 mg, 0.36 mmol), tBuXPhos (10.3 mg, 0.024 mmol) and Pd$_2$(dba)$_3$ (11.0 mg, 0.012 mmol) in DMF (1.2 mL) was heated at 80° C. for 2 h. The reaction mixture was filtered through celite and the celite was rinsed with EtOAc and CH$_2$Cl$_2$. The filtrate was evaporated and the residue was purified by silica gel chromatography (0-100% (3:1 EtOAc:EtOH) in hexanes) to afford ethyl (S)-6-(tert-butyl)-3-(cyclopropylmethoxy)-2-methoxy-10-oxo-5,10-dihydro-6H-pyrido[1,2-h][1,7]naphthyridine-9-carboxylate (32 mg, 62%). $^1$H NMR (400 MHz, CDCl$_3$) δ ppm 8.17 (s, 1H), 7.44 (s, 1H), 6.80 (s, 1H), 4.40 (q, J=7.2 Hz, 2H), 4.06 (s, 3H), 3.89 (m, 3H), 3.42 (dd, J=16.8, 7.0 Hz, 1H), 3.09 (d, J=16.4 Hz, 1H), 1.40 (t, J=7.0 Hz, 3H), 1.31-1.37 (m, 1H), 0.84 (s, 9H), 0.68-0.75 (m, 2H), 0.36-0.43 (m, 2H); LCMS (m/z, ES+)=427.4 (M+1).

A solution of the above ester in 1M LiOH (0.75 mL) and MeOH (0.75 mL) was heated at 50° C. for 2 h. 1 M citric acid (0.75 mL) was added to the reaction mixture and the precipitate was collected by filtration, washed with water, and dried to afford (S)-6-(tert-butyl)-3-(cyclopropylmethoxy)-2-methoxy-10-oxo-6,10-dihydro-5H-pyrido[1,2-h][1,7]naphthyridine-9-carboxylic acid (26.5 mg, 55% for 2 steps) as a white solid. $^1$H NMR (400 MHz, CDCl$_3$) δ ppm 16.11 (s, 1H), 8.45 (s, 1H), 7.65 (s, 1H), 6.83 (s, 1H), 4.08 (s, 3H), 4.04 (d, J=6.8 Hz, 1H), 3.92 (m, 2H), 3.48 (dd, J=17.1, 7.3 Hz, 1H), 3.16 (d, J=17.1 Hz, 1H), 1.31-1.43 (m, 1H), 0.86 (s, 9H), 0.69-0.78 (m, 2H), 0.41 (m, 2H); LCMS (m/z, ES+)=399.3 (M+1).

Example 18 (Compound 237)

(S)-6-(tert-Butyl)-3-(cyclopropylmethoxy)-2-hydroxy-10-oxo-6,10-dihydro-5H-pyrido[1,2-h][1,7]naphthyridine-9-carboxylic acid

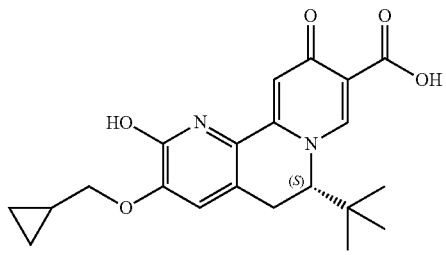

The demethylated product was formed as a by-product of the reaction that produced ethyl (S)-6-(tert-butyl)-3-(cyclopropylmethoxy)-2-methoxy-10-oxo-5,10-dihydro-6H-pyrido[1,2-h][1,7]naphthyridine-9-carboxylate and was collected as mixed fractions that were combined. Re-purification by reverse phase chromatography (10-100% CH$_3$CN/H$_2$O (0.1% formic acid)) afforded (S)-ethyl 6-(tert-butyl)-3-(cyclopropylmethoxy)-2-hydroxy-10-oxo-6,10-dihydro-5H-pyrido[1,2-h][1,7]naphthyridine-9-carboxylate (8.3 mg, 17%). $^1$H NMR (400 MHz, CDCl$_3$) δ ppm 8.18 (s, 1H), 6.85 (s, 1H), 6.55 (s, 1H), 4.37 (q, J=7.0 Hz, 2H), 3.83-3.97 (m, 3H), 3.33 (dd, J=16.8, 6.6 Hz, 1H), 2.95 (d, J=17.2 Hz, 1H), 1.33-1.42 (m, 4H), 0.65-0.74 (m, 2H), 0.40 (m, 2H); LCMS (m/z, ES+)=413.3 (M+1).

A solution of the above ester in 1M LiOH (0.5 mL) and MeOH (0.5 mL) was heated at 50° C. for 2 h. 1 M citric acid (0.5 mL) was added to the reaction mixture and the solution was purified by reverse phase chromatography (5-100% CH$_3$CN/H$_2$O (0.1% formic acid)) to afford (S)-6-(tert-butyl)-3-(cyclopropylmethoxy)-2-hydroxy-10-oxo-5,10-dihydro-6H-pyrido[1,2-h][1,7]naphthyridine-9-carboxylic acid (6.4 mg, 14% for 2 steps) as a yellow solid. $^1$H NMR (400 MHz, CDCl$_3$) δ ppm 15.72 (br. s., 1H), 8.44 (s, 1H), 7.38 (s, 1H), 6.66 (s, 1H), 4.04 (d, J=4.9 Hz, 1H), 3.96 (d, J=6.8 Hz, 2H), 3.40-3.53 (m, 1H), 3.04 (d, J=17.1 Hz, 1H), 1.34-1.45 (m, 1H), 0.89 (s, 9H), 0.77-0.72 (m, 2H), 0.47-0.42 (m, 2H); LCMS (m/z, ES+)=385.2 (M+1).

Example 19 (Compound 238)

(S)-6-(tert-Butyl)-2-methoxy-3-(3-methoxypropoxy)-10-oxo-6,10-dihydro-5H-pyrido[1,2-h][1,7]naphthyridine-9-carboxylic acid

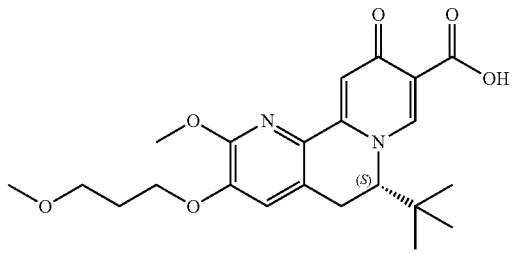

A solution of ethyl (S)-6-(tert-butyl)-2-chloro-3-(3-methoxypropoxy)-10-oxo-5,10-dihydro-6H-pyrido[1,2-h][1,7]naphthyridine-9-carboxylate (46.8 mg, 0.10 mmol), NaB(OMe)₄ (49 mg, 0.31 mmol), tBuXPhos (8.9 mg, 0.021 mmol) and Pd₂(dba)₃ (9.6 mg, 0.010 mmol) in DMF (1.0 mL) was heated at 80° C. for 2 h. The reaction mixture was filtered through celite and the celite was rinsed with CH₂Cl₂. The filtrate was evaporated and the residue was re-subjected to the reaction conditions with more reagents: NaB(OMe)₄ (49 mg, 0.31 mmol), tBuXPhos (8.9 mg, 0.021 mmol) and Pd₂(dba)₃ (9.6 mg, 0.010 mmol) in DMF (1.0 mL) at 80° C. for another 3 h. The reaction mixture was filtered through celite and the celite was rinsed with CH₂Cl₂. The filtrate was evaporated and the residue was purified by silica gel chromatography (0-100% (3:1 EtOAc:EtOH) in hexanes) to afford ethyl (S)-6-(tert-butyl)-2-methoxy-3-(3-methoxypropoxy)-10-oxo-5,10-dihydro-6H-pyrido[1,2-h][1,7]naphthyridine-9-carboxylate as a tan solid. ¹H NMR (400 MHz, CDCl₃) δ ppm 8.18 (s, 1H), 7.44 (s, 1H), 6.86 (s, 1H), 4.40 (q, J=7.3 Hz, 2H), 4.19-4.12 (m, 2H), 4.05 (s, 3H), 3.90 (d, J=6.6 Hz, 1H), 3.61-3.55 (m, 2H), 3.42 (dd, J=16.8, 7.0 Hz, 1H), 3.37 (s, 3H), 3.11 (d, J=16.8 Hz, 1H), 2.15 (quin, J=6.2 Hz, 2H), 1.40 (t, J=7.0 Hz, 3H), 0.86 (s, 9H); LCMS (m/z, ES+)=445.0 (M+1).

A solution of the above ester in 1M LiOH (0.75 mL) and MeOH (0.75 mL) was heated at 50° C. for 2 h. 1 M citric acid (0.75 mL) was added to the reaction mixture and the solution was purified by reverse phase chromatography (5-100% CH₃CN/H₂O (0.1% formic acid)) to afford (S)-6-(tert-butyl)-2-methoxy-3-(3-methoxypropoxy)-10-oxo-5,10-dihydro-6H-pyrido[1,2-h][1,7]naphthyridine-9-carboxylic acid (19.6 mg, 45% for 2 steps) as a white solid. ¹H NMR (400 MHz, CDCl₃) δ ppm 16.12 (s, 1H), 8.46 (s, 1H), 7.65 (s, 1H), 6.90 (s, 1H), 4.24-4.13 (m, 2H), 4.06 (s, 1H), 3.63-3.55 (m, 2H), 3.49 (dd, J=16.6, 6.3 Hz, 1H), 3.38 (s, 3H), 3.18 (d, J=17.1 Hz, 1H), 2.16 (quin, J=6.1 Hz, 2H), 0.87 (s, 9H); LCMS (m/z, ES+)=417.2 (M+1).

Example 20 (Compound 239)

(S)-6-(tert-Butyl)-2-hydroxy-3-(3-methoxypropoxy)-10-oxo-6,10-dihydro-5H-pyrido[1,2-h][1,7]naphthyridine-9-carboxylic acid

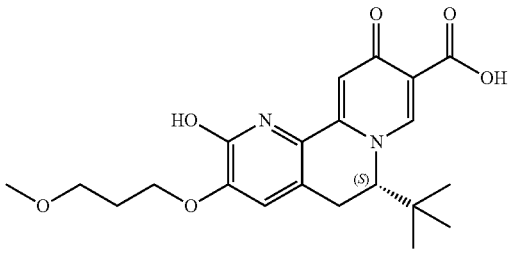

The demethylated product was formed as a by-product of the reaction that produced ethyl (S)-6-(tert-butyl)-2-methoxy-3-(3-methoxypropoxy)-10-oxo-5,10-dihydro-6H-pyrido[1,2-h][1,7]naphthyridine-9-carboxylate and was collected as mixed fractions that were combined and subjected to hydrolysis conditions without further purification. A solution of the ester in 1 M LiOH (0.5 mL) and MeOH (0.5 mL) was heated at 50° C. for 2 h. 1 M citric acid (0.5 mL) was added to the reaction mixture and the solution was purified by reverse phase chromatography (5-100% CH₃CN/H₂O (0.1% formic acid)) to afford (S)-6-(tert-butyl)-2-hydroxy-3-(3-methoxypropoxy)-10-oxo-5,10-dihydro-6H-pyrido[1,2-h][1,7]naphthyridine-9-carboxylic acid (3.4 mg, 8% for 2 steps) as a yellow solid. ¹H NMR (400 MHz, CDCl₃) δ ppm 15.76 (br. s., 1H), 8.42 (s, 1H), 7.47 (s, 1H), 6.70 (s, 1H), 4.20 (t, J=6.1 Hz, 2H), 4.04 (d, J=6.3 Hz, 1H), 3.61-3.76 (m, 2H), 3.48 (dd, J=17.1, 6.8 Hz, 1H), 3.41 (s, 3H), 3.04 (d, J=17.1 Hz, 1H), 2.21 (quin, J=6.0 Hz, 2H), 0.89 (s, 9H); LCMS (m/z, ES+)=403.2 (M+1).

Example 21 (Compound 240)

(S)-6-(tert-Butyl)-3-(3-methoxypropoxy)-10-oxo-2-(prop-1-en-2-yl)-6,10-dihydro-5H-pyrido[1,2-h][1,7]naphthyridine-9-carboxylic acid

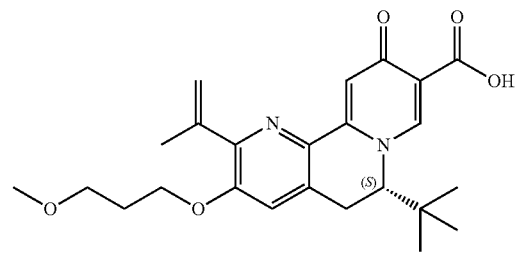

Step 1: (S)-Ethyl 6-(tert-butyl)-3-(3-methoxypropoxy)-10-oxo-2-(prop-1-en-2-yl)-6,10-dihydro-5H-pyrido[1,2-h][1,7]naphthyridine-9-carboxylate

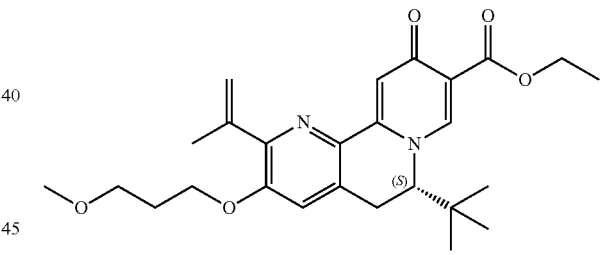

A solution of ethyl (S)-6-(tert-butyl)-2-chloro-3-(3-methoxypropoxy)-10-oxo-5,10-dihydro-6H-pyrido[1,2-h][1,7]naphthyridine-9-carboxylate (88.4 mg, 0.20 mmol), potassium isopropenyltrifluoroborate (58 mg, 0.39 mmol), sodium carbonate (63 mg, 0.59 mmol) and Pd(PPh₃)₄ (23 mg, 0.020 mmol) in ethanol (2.0 mL) was stirred at 80° C. overnight. The reaction mixture was diluted with CH₂Cl₂ and filtered through celite. The filtrate was evaporated and the residue was purified by silica gel chromatography (0-100% (3:1 EtOAc:EtOH) in hexanes) to afford ethyl (S)-6-(tert-butyl)-3-(3-methoxypropoxy)-10-oxo-2-(prop-1-en-2-yl)-5,10-dihydro-6H-pyrido[1,2-h][1,7]naphthyridine-9-carboxylate (87.5 mg, 98%) as a white solid. ¹H NMR (400 MHz, CDCl₃) δ ppm 8.18 (s, 1H), 7.54 (s, 1H), 7.00 (s, 1H), 5.91 (s, 1H), 5.54 (s, 1H), 4.39 (q, J=7.0 Hz, 2H), 4.07-4.22 (m, 2H), 3.93 (d, J=6.6 Hz, 1H), 3.61-3.56 (m, 2H), 3.48 (dd, J=17.0, 6.8 Hz, 1H), 3.37 (s, 3H), 3.19 (d, J=16.8 Hz, 1H), 2.25 (s, 3H), 2.13 (quin, J=6.1 Hz, 2H), 1.40 (t, J=7.2 Hz, 3H), 0.85 (s, 9H); LCMS (m/z, ES+)=455.9 (M+1).

Step 2: (S)-6-(tert-Butyl)-3-(3-methoxypropoxy)-10-oxo-2-(prop-1-en-2-yl)-6,10-dihydro-5H-pyrido[1,2-h][1,7]naphthyridine-9-carboxylic acid

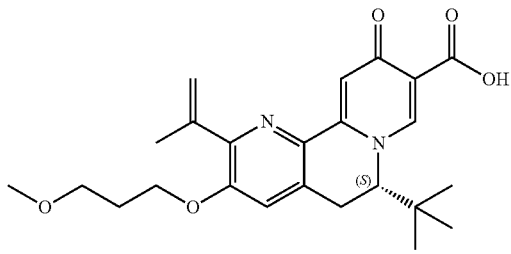

The title compound was isolated as a side-product by base-promoted hydrolysis during an oxidation reaction of ethyl (S)-6-(tert-butyl)-3-(3-methoxypropoxy)-10-oxo-2-(prop-1-en-2-yl)-5,10-dihydro-6H-pyrido[1,2-h][1,7]naphthyridine-9-carboxylate (30.3 mg, 0.067 mmol) with trimethylsulfoxonium iodide (31 mg, 0.14 mmol) and KOtBu (15 mg, 0.13 mmol) in DMSO (0.64 mL) and THF (0.27 mL). Purification of the reaction mixture by reverse phase chromatography (5-100% CH₃CN/H₂O (0.1% formic acid)) afforded (S)-6-(tert-butyl)-3-(3-methoxypropoxy)-10-oxo-2-(prop-1-en-2-yl)-6,10-dihydro-5H-pyrido[1,2-h][1,7]naphthyridine-9-carboxylic acid (4.8 mg, 17%) as a white solid. ¹H NMR (400 MHz, CDCl₃) δ ppm 16.16 (s, 1H), 8.47 (s, 1H), 7.78 (s, 1H), 7.04 (s, 1H), 5.95 (s, 1H), 5.59 (s, 1H), 4.26-4.12 (m, 2H), 4.07 (d, J=6.8 Hz, 1H), 3.62-3.57 (m, 2H), 3.53 (dd, J=17.3, 7.1 Hz, 1H), 3.38 (s, 3H), 3.26 (d, J=17.1 Hz, 1H), 2.26 (s, 3H), 2.15 (quin, J=6.0 Hz, 2H), 0.87 (s, 9H); LCMS (m/z, ES+)=427.3 (M+1).

Example 22: (Compound 241)

(S)-6-(tert-Butyl)-2-isopropyl-3-(3-methoxypropoxy)-10-oxo-6,10-dihydro-5H-pyrido[1,2-h][1,7]naphthyridine-9-carboxylic acid

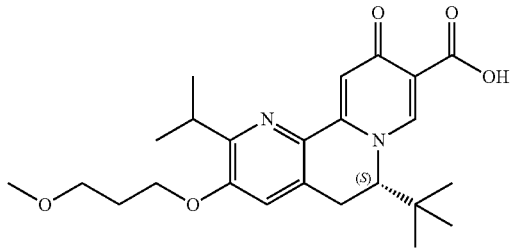

A solution of ethyl (S)-6-(tert-butyl)-3-(3-methoxypropoxy)-10-oxo-2-(prop-1-en-2-yl)-5,10-dihydro-6H-pyrido[1,2-h][1,7]naphthyridine-9-carboxylate (11.9 mg, 0.026 mmol) and 10% Pd/C (catalytic) in MeOH (1 mL) was stirred under 60 psi H₂ for 1.5 h. The reaction mixture was filtered through celite and evaporated to dryness to afford the crude (S)-ethyl 6-(tert-butyl)-2-isopropyl-3-(3-methoxypropoxy)-10-oxo-6,10-dihydro-5H-pyrido[1,2-h][1,7]naphthyridine-9-carboxylate, which was used without further purification.

A solution of the above ester in 1M LiOH (0.7 mL) and MeOH (0.7 mL) was heated at 50° C. for 2 h. 1 M citric acid (0.8 mL) was added and the reaction mixture was stirred for 15 mins. The precipitate was collected by filtration, washed with water, and dried to afford (S)-6-(tert-butyl)-2-isopropyl-3-(3-methoxypropoxy)-10-oxo-5,10-dihydro-6H-pyrido[1,2-h][1,7]naphthyridine-9-carboxylic acid (9.3 mg, 83% for two steps) as an off-white solid. ¹H NMR (400 MHz, CDCl₃) δ ppm 16.26 (s, 1H), 8.46 (s, 1H), 7.83 (s, 1H), 6.91 (s, 1H), 4.08-4.21 (m, 2H), 4.05 (d, J=6.8 Hz, 1H), 3.66-3.58 (m, 2H), 3.41-3.55 (m, 2H), 3.38 (s, 3H), 3.22 (d, J=17.1 Hz, 1H), 2.14 (quin, J=6.0 Hz, 2H), 1.27 (d, J=6.8 Hz, 6H), 0.85 (s, 9H); LCMS (m/z, ES+)=429.3 (M+1).

Example 23: (Compound 243)

(S)-6-(tert-Butyl)-2-chloro-3-(3-methoxypropoxy)-8-methyl-10-oxo-6,10-dihydro-5H-pyrido[1,2-h][1,7]naphthyridine-9-carboxylic acid

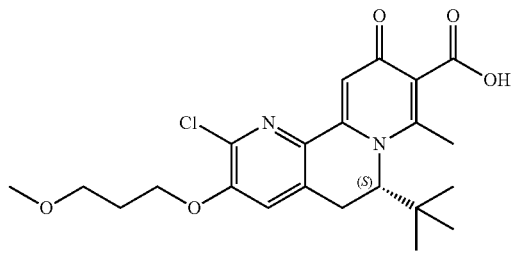

Step 1: Ethyl 2-methyl-4-oxo-4H-pyran-3-carboxylate

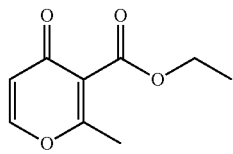

A solution of ethyl 3-oxobutanoate (3.64 g, 28 mmol) in 20 mL THF was added by syringe pump (dropwise) to a vessel containing NaH (60% dispersion in mineral oil) (1.176 g, 29.4 mmol) that was cooled at 0° C. during the addition. The reaction mixture was stirred at RT for 1 h after addition was complete, and then cooled back down to 0° C. A solution of 3-chloroacryloyl chloride (3.50 g, 28 mmol) in 20 mL THF was slowly added to the cooled reaction mixture by syringe pump over 1 h. After addition was complete, the reaction mixture was stirred at RT overnight and then heated under reflux for 2.5 h. The reaction mixture was diluted with water and extracted with Et₂O (4×) and CH₂Cl₂ (2×). The combined organic extracts were dried (Na₂SO₄), filtered, evaporated and purified by silica gel chromatography (0-100% EtOAc/hexanes) to afford ethyl 2-methyl-4-oxo-4H-pyran-3-carboxylate (2.65 g, 52%) as a brown liquid. ¹H NMR (400 MHz, CDCl₃) δ ppm 7.66 (d, J=5.9 Hz, 1H), 6.36 (d, J=5.9 Hz, 1H), 4.39 (q, J=7.3 Hz, 2H), 2.38 (s, 3H), 1.38 (t, J=7.2 Hz, 3H); LCMS (m/z, ES+)=183.1 (M+1).

Step 2: (S)-Ethyl 1-(1-(6-chloro-2-iodo-5-(3-methoxypropoxy)pyridin-3-yl)-3,3-dimethylbutan-2-yl)-2-methyl-4-oxo-1,4-dihydropyridine-3-carboxylate

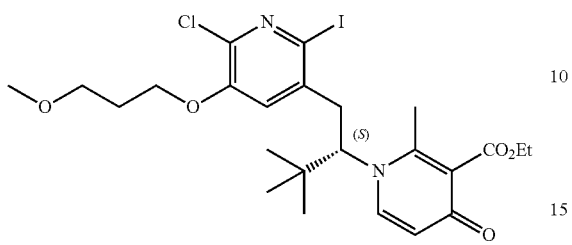

A solution of (S)-1-(6-chloro-2-iodo-5-(3-methoxypropoxy)pyridin-3-yl)-3,3-dimethylbutan-2-amine, Hydrochloride (196 mg, 0.42 mmol) and ethyl 2-methyl-4-oxo-4H-pyran-3-carboxylate (0.23 g, 1.27 mmol) in HOAc (4.2 mL) was stirred at 100° C. for 10 h. The reaction mixture was evaporated to dryness, taken up in $CH_2Cl_2$ and saturated $NaHCO_3$ and stirred for 1 h. The organic layer was isolated, dried ($Na_2SO_4$), filtered and evaporated. The residue was stirred with additional ethyl 2-methyl-4-oxo-4H-pyran-3-carboxylate (200 mg, 1.10 mmol) in HOAc (4.2 mL) at 100° C. overnight. The reaction mixture was evaporated to dryness and the residue was purified by reverse phase chromatography (5-100% $CH_3CN/H_2O$ (0.1% formic acid)) to afford ethyl (S)-1-(1-(6-chloro-2-iodo-5-(3-methoxypropoxy)pyridin-3-yl)-3,3-dimethylbutan-2-yl)-2-methyl-4-oxo-1,4-dihydropyridine-3-carboxylate (67.4 mg, 27%) as a brown solid. LCMS (m/z, ES+)=591.2, 593.2 (M+1).

Step 3: (S)-Ethyl 6-(tert-butyl)-2-chloro-3-(3-methoxypropoxy)-8-methyl-10-oxo-6,10-dihydro-5H-pyrido[1,2-h][1,7]naphthyridine-9-carboxylate

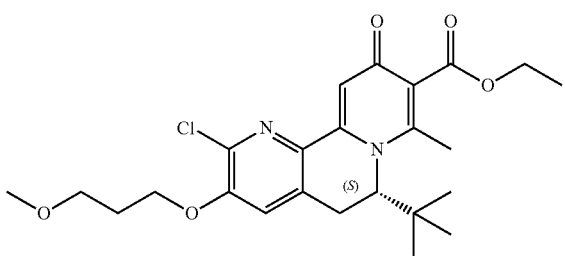

A flask containing ethyl (S)-1-(1-(6-chloro-2-iodo-5-(3-methoxypropoxy)pyridin-3-yl)-3,3-dimethylbutan-2-yl)-2-methyl-4-oxo-1,4-dihydropyridine-3-carboxylate (67.4 mg, 0.11 mmol), potassium acetate (22 mg, 0.23 mmol), and palladium(II) bromide (6.1 mg, 0.023 mmol) was purged with nitrogen. Degassed DMF (1.1 mL) was added and the reaction mixture was heated at 90° C. for 24 h. The solution was cooled to RT, additional palladium(II) bromide (6.1 mg, 0.023 mmol) was added and the reaction mixture was heated at 90° C. for another 6 h. The solvent was removed by evaporation and the residue was purified by silica gel chromatography (0-100% 3:1 (EtOAc/EtOH) in hexanes) to afford ethyl (S)-6-(tert-butyl)-2-chloro-3-(3-methoxypropoxy)-8-methyl-10-oxo-5,10-dihydro-6H-pyrido[1,2-h][1,7]naphthyridine-9-carboxylate (12.1 mg, 23%) as a brown oil. $^1H$ NMR (400 MHz, $CDCl_3$) δ ppm 7.48 (s, 1H), 7.00 (s, 1H), 4.34-4.45 (m, 3H), 4.13-4.24 (m, 2H), 3.65-3.58 (m, 2H), 3.31-3.41 (m, 4H), 3.15 (d, J=16.8 Hz, 1H), 2.45 (s, 3H), 2.12-2.19 (m, 2H), 1.38 (t, J=7.2 Hz, 3H), 0.80 (s, 9H); LCMS (m/z, ES+)=463.3, 465.3 (M+1).

Step 4: (S)-6-(tert-Butyl)-2-chloro-3-(3-methoxypropoxy)-8-methyl-10-oxo-6,10-dihydro-5H-pyrido[1,2-h][1,7]naphthyridine-9-carboxylic acid

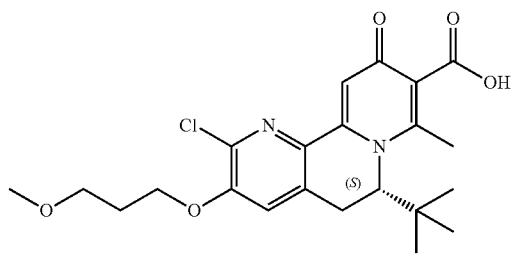

A solution of (S)-ethyl 6-(tert-butyl)-2-chloro-3-(3-methoxypropoxy)-8-methyl-10-oxo-6,10-dihydro-5H-pyrido[1,2-h][1,7]naphthyridine-9-carboxylate (12.1 mg, 0.026 mmol) in 1 M LiOH (0.5 mL) and MeOH (0.5 mL) was heated at 50° C. for 2 h and then 60° C. for 2 h. 1 M citric acid (0.7 mL) was added to the reaction mixture. The solution was evaporated to dryness and the residue was purified by reverse phase chromatography (5-90% $CH_3CN/H_2O$ (0.1% formic acid)) to afford (S)-6-(tert-butyl)-2-chloro-3-(3-methoxypropoxy)-8-methyl-10-oxo-5,10-dihydro-6H-pyrido[1,2-h][1,7]naphthyridine-9-carboxylic acid (7.0 mg, 62%) as a white solid. $^1H$ NMR (400 MHz, $CDCl_3$) δ ppm 17.61 (br. s., 1H), 7.82 (s, 1H), 7.05 (s, 1H), 4.81 (d, J=5.4 Hz, 1H), 4.15-4.28 (m, 2H), 3.67-3.57 (m, 2H), 3.49-3.41 (m, 1H), 3.38 (s, 3H), 3.25 (d, J=17.6 Hz, 1H), 3.18 (s, 3H), 2.17 (quin, J=6.0 Hz, 2H), 0.81 (s, 9H); LCMS (m/z, ES+)=435.2, 437.2 (M+1).

Example 24: (Compound 243)

(S)-6-(tert-Butyl)-2-(hydroxymethyl)-3-(3-methoxypropoxy)-10-oxo-5,10-dihydro-6H-pyrido[1,2-h][1,7]naphthyridine-9-carboxylic acid

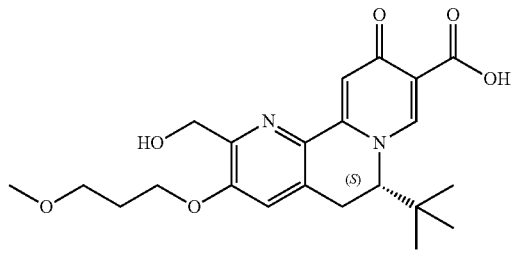

Step 1: (S)-tert-Butyl (1-(5-(benzyloxy)-6-chloro-2-iodopyridin-3-yl)-3,3-dimethylbutan-2-yl)carbamate

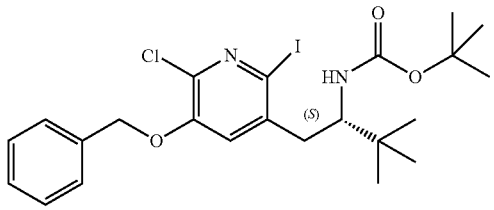

A solution of tert-butyl (S)-(1-(6-chloro-5-hydroxy-2-iodopyridin-3-yl)-3,3-dimethylbutan-2-yl)carbamate (2.18 g, 4.79 mmol), K$_2$CO$_3$ (1.99 g, 14.38 mmol), (bromomethyl)benzene (0.86 mL, 7.19 mmol) in DMF (32.0 mL) was heated at 80° C. for 3 h. The reaction mixture was evaporated to dryness and the residue was taken up in CH$_2$Cl$_2$ and water. The aqueous layer was extracted with CH$_2$Cl$_2$ (2×) and the combined organic phases were dried (Na$_2$SO$_4$), filtered, and evaporated to afford tert-butyl (S)-(1-(5-(benzyloxy)-6-chloro-2-iodopyridin-3-yl)-3,3-dimethylbutan-2-yl)carbamate (assumed quant), which was taken on to the next step without further purification. LCMS (m/z, ES+)= 545.4, 547.0 (M+1).

Step 2: Ethyl (S)-1-(1-(5-(benzyloxy)-6-chloro-2-iodopyridin-3-yl)-3,3-dimethylbutan-2-yl)-4-oxo-1,4-dihydropyridine-3-carboxylate

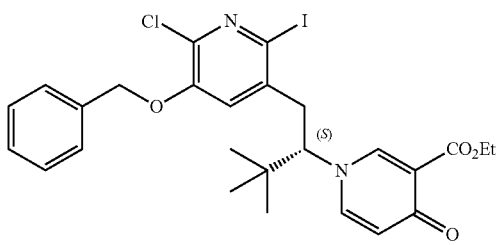

HCl (4M in dioxane) (11.98 mL, 47.9 mmol) was added to a solution of tert-butyl (S)-(1-(5-(benzyloxy)-6-chloro-2-iodopyridin-3-yl)-3,3-dimethylbutan-2-yl)carbamate (2.61 g, 4.79 mmol) in CH$_2$Cl$_2$ (6 mL) and the reaction mixture was stirred at RT for 3 h. The mixture was evaporated to dryness and the residue was taken up in saturated NaHCO$_3$ and CH$_2$Cl$_2$. The aqueous layer was extracted with CH$_2$Cl$_2$ (2×) and the combined organic phases were dried (Na$_2$SO$_4$), filtered, and evaporated to give a brown oil.

A solution of the above amine and ethyl 4-oxo-4H-pyran-3-carboxylate (0.89 g, 5.27 mmol) in HOAc (24 mL) was stirred at 100° C. for 7 h. The reaction mixture was evaporated, the residue was taken up in CH$_2$Cl$_2$ and saturated NaHCO$_3$, and the solution was stirred vigorously for 30 mins. The aqueous phase was extracted with CH$_2$Cl$_2$ (5×10 mL), and the combined organic phases were dried (Na$_2$SO$_4$), filtered, evaporated and purified by silica gel chromatography (0-100% (3:1 EtOAc:EtOH) in hexanes) to afford ethyl (S)-1-(1-(5-(benzyloxy)-6-chloro-2-iodopyridin-3-yl)-3,3-dimethylbutan-2-yl)-4-oxo-1,4-dihydropyridine-3-carboxylate (1.39 g, 49%) as a brown solid. LCMS (m/z, ES+)= 596.1, 597.2 (M+1).

Step 3: Ethyl (S)-3-(benzyloxy)-6-(tert-butyl)-2-chloro-10-oxo-5,10-dihydro-6H-pyrido[1,2-h][1,7]naphthyridine-9-carboxylate

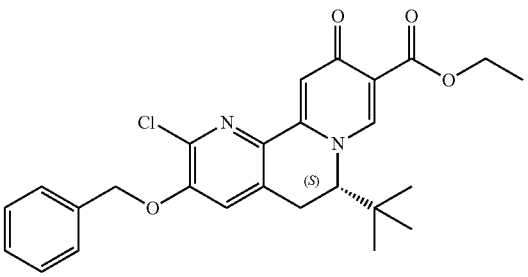

A flask containing ethyl (S)-1-(1-(5-(benzyloxy)-6-chloro-2-iodopyridin-3-yl)-3,3-dimethylbutan-2-yl)-4-oxo-1,4-dihydropyridine-3-carboxylate (1.39 g, 2.34 mmol), potassium acetate (460 mg, 4.68 mmol), and palladium(II) bromide (125 mg, 0.47 mmol) was purged with nitrogen. Degassed DMF (23.4 mL) was added and the reaction mixture was heated at 90° C. for 24 h. The solvent was removed by evaporation and the residue was dissolved in CH$_2$Cl$_2$, filtered through celite and purified by silica gel chromatography (0-100% 3:1 (EtOAc/EtOH) in hexanes) to afford ethyl (S)-3-(benzyloxy)-6-(tert-butyl)-2-chloro-10-oxo-5,10-dihydro-6H-pyrido[1,2-h][1,7]naphthyridine-9-carboxylate (706 mg, 65%) as a brown solid. LCMS (m/z, ES+)=467.3, 469.3 (M+1).

Step 4: Ethyl (S)-3-(benzyloxy)-6-(tert-butyl)-10-oxo-2-vinyl-5,10-dihydro-6H-pyrido[1,2-h][1,7]naphthyridine-9-carboxylate

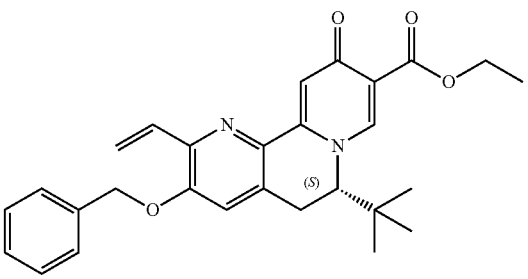

A solution of ethyl (S)-3-(benzyloxy)-6-(tert-butyl)-2-chloro-10-oxo-5,10-dihydro-6H-pyrido[1,2-h][1,7]naphthyridine-9-carboxylate (0.34 g, 0.74 mmol), trifluoro(vinyl)-14-borane potassium salt (0.20 g, 1.48 mmol), sodium carbonate (0.24 g, 2.22 mmol) and Pd(PPh$_3$)$_4$ (85 mg, 0.074 mmol) in EtOH (7.4 mL) was stirred at 80° C. overnight. The reaction mixture was diluted with CH$_2$Cl$_2$, filtered through celite, and evaporated. The residue was purified by silica gel chromatography (0-100% 3:1 (EtOAc/EtOH) in hexanes) to afford ethyl (S)-3-(benzyloxy)-6-(tert-butyl)-10-oxo-2-vinyl-5,10-dihydro-6H-pyrido[1,2-h][1,7]naphthyridine-9-carboxylate (251 mg, 74%) as an off-white foam. $^1$H NMR (400 MHz, CDCl$_3$) δ ppm 8.21 (s, 1H), 7.39-7.73 (m, 7H), 7.00 (s, 1H), 6.59 (d, J=6.6 Hz, 1H), 5.54 (d, J=10.5 Hz, 1H), 5.09-5.24 (m, 2H), 4.40 (q, J=7.0 Hz, 2H), 3.90-4.01

(m, 1H), 3.39-3.55 (m, 1H), 3.13-3.24 (m, 1H), 1.41 (t, J=7.0 Hz, 3H), 0.84 (s., 9H); LCMS (m/z, ES+)=459.1, 460.4 (M+1).

Step 5: (S)-Ethyl 6-(tert-butyl)-3-hydroxy-2-(hydroxymethyl)-10-oxo-6,10-dihydro-5H-pyrido[1,2-h][1,7]naphthyridine-9-carboxylate

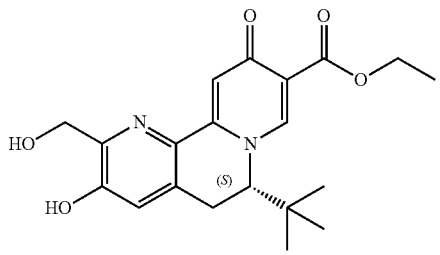

To a solution of ethyl (S)-3-(benzyloxy)-6-(tert-butyl)-10-oxo-2-vinyl-5,10-dihydro-6H-pyrido[1,2-h][1,7]naphthyridine-9-carboxylate (251 mg, 0.55 mmol) in THF (5.5 mL) and water (1.4 mL) at 0° C. was added potassium osmate dihydrate (20.2 mg, 0.055 mmol) followed by sodium periodate (468 mg, 2.19 mmol). After addition was complete, the reaction mixture was stirred at RT for 2 h. The reaction mixture was diluted with CH₂Cl₂ and water, stirred, and filtered through celite. The combined organic phases were dried (Na₂SO₄), filtered, evaporated, and purified by silica gel chromatography (0-100% 3:1 (EtOAc/EtOH) in CH₂Cl₂) to afford ethyl (S)-3-(benzyloxy)-6-(tert-butyl)-2-formyl-10-oxo-5,10-dihydro-6H-pyrido[1,2-h][1,7]naphthyridine-9-carboxylate (assumed quant.). LCMS (m/z, ES+)=461.3 (M+1).

A solution of the above aldehyde and 10% Pd/C (catalytic) in EtOH (20 mL) was stirred under 60 psi H₂ overnight. The reaction mixture was filtered through celite and evaporated to afford ethyl (S)-6-(tert-butyl)-3-hydroxy-2-(hydroxymethyl)-10-oxo-5,10-dihydro-6H-pyrido[1,2-h][1,7]naphthyridine-9-carboxylate (122.1 mg, 60%), which was taken onto the next step without purification. LCMS (m/z, ES+)=373.3 (M+1).

Step 6: Ethyl (S)-6-(tert-butyl)-2-(hydroxymethyl)-3-(3-methoxypropoxy)-10-oxo-5,10-dihydro-6H-pyrido[1,2-h][1,7]naphthyridine-9-carboxylate

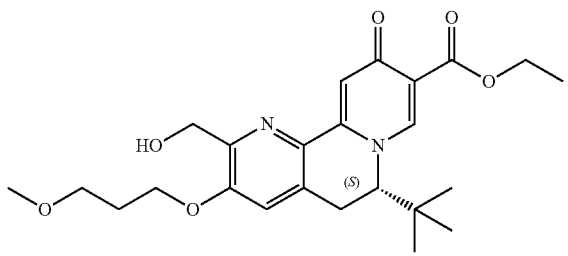

1-Bromo-3-methoxypropane (44.3 µl, 0.39 mmol) was added to a solution of ethyl (S)-6-(tert-butyl)-3-hydroxy-2-(hydroxymethyl)-10-oxo-5,10-dihydro-6H-pyrido[1,2-h][1,7]naphthyridine-9-carboxylate (122.1 mg, 0.33 mmol) and potassium carbonate (136 mg, 0.98 mmol) in DMF (3.3 mL) and the reaction mixture was stirred at RT overnight. Additional potassium carbonate (100 mg, 0.72 mmol) and 1-bromo-3-methoxypropane (44.3 µl, 0.39 mmol) were added and the reaction mixture was heated at 40° C. for 2.5 h, and then stirred at RT overnight. The solvent was evaporated and the residue was diluted with CH₂Cl₂ and brine. The organic layer was dried (Na₂SO₄), filtered, evaporated, and purified by silica gel chromatography (0-100% 3:1 (EtOAc/EtOH) in CH₂Cl₂) to afford ethyl (S)-6-(tert-butyl)-2-(hydroxymethyl)-3-(3-methoxypropoxy)-10-oxo-5,10-dihydro-6H-pyrido[1,2-h][1,7]naphthyridine-9-carboxylate (62.8 mg, 43%) as a yellow oil. ¹H NMR (400 MHz, CDCl₃) δ ppm 8.18 (s, 1H), 7.44 (s, 1H), 6.98 (s, 1H), 4.72 (s, 2H), 4.39 (q, J=7.2 Hz, 2H), 4.22-4.12 (m, 2H), 3.90-4.06 (m, 2H), 3.61-3.53 (m, 3H), 3.37 (s, 3H), 3.21 (d, J=16.8 Hz, 1H), 2.11 (quin, J=6.0 Hz, 2H), 1.40 (t, J=7.2 Hz, 3H), 0.83 (s, 9H); LCMS (m/z, ES+)=445.3 (M+1).

Step 7: (S)-6-(tert-Butyl)-2-(hydroxymethyl)-3-(3-methoxypropoxy)-10-oxo-5,10-dihydro-6H-pyrido[1,2-h][1,7]naphthyridine-9-carboxylic acid

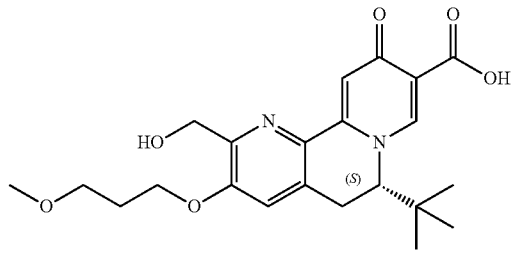

A solution of ethyl (S)-6-(tert-butyl)-2-(hydroxymethyl)-3-(3-methoxypropoxy)-10-oxo-5,10-dihydro-6H-pyrido[1,2-h][1,7]naphthyridine-9-carboxylate (29 mg, 0.065 mmol) in 1 M LiOH (0.65 mL) and MeOH (0.65 mL) was heated at 50° C. for 2 h. 1 M citric acid (1 mL) was added and the reaction mixture was evaporated to dryness. The residue was purified by reverse phase chromatography (5-90% CH₃CN/H₂O (0.1% formic acid)) to afford (S)-6-(tert-butyl)-2-(hydroxymethyl)-3-(3-methoxypropoxy)-10-oxo-5,10-dihydro-6H-pyrido[1,2-h][1,7]naphthyridine-9-carboxylic acid (18.5 mg, 68%) as a white solid. ¹H NMR (400 MHz, CDCl₃) δ ppm 15.96 (s, 1H), 8.49 (s, 1H), 7.74 (s, 1H), 7.02 (s, 1H), 4.79 (d, J=4.4 Hz, 2H), 4.14-4.27 (m, 2H), 4.10 (d, J=6.3 Hz, 1H), 3.90 (t, J=4.9 Hz, 1H), 3.62-3.53 (m, 3H), 3.37 (s, 3H), 3.29 (d, J=17.1 Hz, 1H), 2.13 (quin, J=5.9 Hz, 2H), 0.86 (s, 9H); LCMS (m/z, ES−)=415.3 (M−1).

Example 25: (Compound 244)

(S)-6-(tert-Butyl)-2-cyclopropyl-11-hydroxy-3-(3-methoxypropoxy)-10-oxo-5,10-dihydro-6H-pyrido[1,2-h][1,7]naphthyridine-9-carboxylic acid

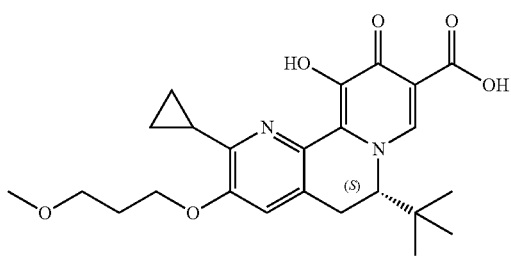

Step 1: Ethyl 4-(benzyloxy)-2-((dimethylamino)methylene)-3-oxobutanoate

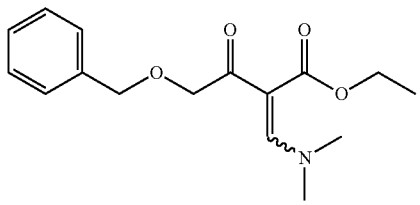 [SMILES: CCOC(=O)C(=CN(C)C)C(=O)COCc1ccccc1]

DMF-DMA (5.70 mL, 42.5 mmol) was added to a solution of ethyl 4-(benzyloxy)-3-oxobutanoate (6.70 g, 28.4 mmol) in toluene (30 mL) and the reaction mixture was stirred overnight and evaporated to dryness. The residue was purified by silica gel chromatography (0-100% EtOAc in hexanes) to afford ethyl 4-(benzyloxy)-2-((dimethylamino)methylene)-3-oxobutanoate (6.78 g, 82%) as a yellow oil. LCMS (m/z, ES+)=292.6 (M+1).

Step 2: Ethyl 5-(benzyloxy)-4-oxo-4H-pyran-3-carboxylate

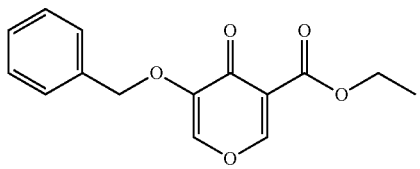 [SMILES: CCOC(=O)c1cocc(OCc2ccccc2)c1=O]

Ethyl formate (10.2 mL, 126 mmol) was slowly added to a suspension of potassium tert-butoxide (3.54 g, 31.6 mmol) in 24 mL THF at 0° C. After addition was complete, the reaction mixture was stirred for another 15 mins at 0° C. and a solution of ethyl 4-(benzyloxy)-2-((dimethylamino)methylene)-3-oxobutanoate (4.6 g, 15.8 mmol) in 24 mL THF was added dropwise using an addition funnel. After addition was complete, the reaction mixture was removed from the ice bath and stirred at RT overnight. 1 M HCl (50 mL) was added and the solution was extracted with EtOAc (2×). The combined organic phases were dried (Na₂SO₄), filtered, evaporated, and purified by silica gel chromatography (0-100% EtOAc in hexanes) to afford ethyl 5-(benzyloxy)-4-oxo-4H-pyran-3-carboxylate (1.48 g, 34%) as a light yellow solid. ¹H NMR (400 MHz, CDCl₃) δ ppm 8.41 (s, 1H), 7.55 (s, 1H), 7.32-7.43 (m, 5H), 5.12 (s, 2H), 4.37 (q, J=7.0 Hz, 2H), 1.38 (t, J=7.2 Hz, 3H); LCMS (m/z, ES+)=275.5 (M+1).

Step 3: (S)-Ethyl 5-(benzyloxy)-1-(1-(6-chloro-2-iodo-5-(3-methoxypropoxy)pyridin-3-yl)-3,3-dimethylbutan-2-yl)-4-oxo-1,4-dihydropyridine-3-carboxylate

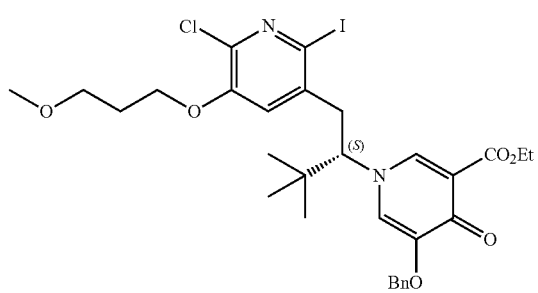

A solution of the (S)-1-(6-chloro-2-iodo-5-(3-methoxypropoxy)pyridin-3-yl)-3,3-dimethylbutan-2-amine, hydrochloride (0.402 g, 0.87 mmol) and ethyl 5-(benzyloxy)-4-oxo-4H-pyran-3-carboxylate (0.38 g, 1.37 mmol) in HOAc (8.7 mL) was stirred at 100° C. for 10 h. The reaction mixture was evaporated to dryness, taken up in CH₂Cl₂ and saturated NaHCO₃ and stirred for 1 h. The aqueous layer was extracted with CH₂Cl₂ and EtOAc (2×). The combined organic phases were dried (Na₂SO₄), filtered and evaporated. The residue was dissolved in EtOH (8 mL) and heated at 80° C. overnight. The reaction mixture was evaporated to dryness and the residue was purified by reverse phase chromatography (5-100% CH₃CN/H₂O (0.1% formic acid)) to afford ethyl (S)-5-(benzyloxy)-1-(1-(6-chloro-2-iodo-5-(3-methoxypropoxy)pyridin-3-yl)-3,3-dimethylbutan-2-yl)-4-oxo-1,4-dihydropyridine-3-carboxylate (89.8 mg, 15%) as a brown solid. LCMS (m/z, ES+)=683.7, 685.7 (M+1).

Step 4: (S)-Ethyl 11-(benzyloxy)-6-(tert-butyl)-2-chloro-3-(3-methoxypropoxy)-10-oxo-6,10-dihydro-5H-pyrido[1,2-h 1,7]naphthyridine-9-carboxylate

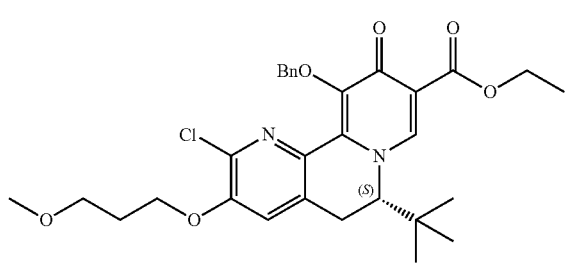

A flask containing ethyl (S)-5-(benzyloxy)-1-(1-(6-chloro-2-iodo-5-(3-methoxypropoxy)pyridin-3-yl)-3,3-dimethylbutan-2-yl)-4-oxo-1,4-dihydropyridine-3-carboxylate (89.8 mg, 0.13 mmol), potassium acetate (26 mg, 0.26 mmol), and palladium(II) bromide (7.0 mg, 0.03 mmol) was purged with nitrogen. Degassed DMF (1.3 mL) was added and the reaction mixture was heated at 90° C. for 24 h. The reaction mixture was filtered through celite, the solvent was removed by evaporation and the residue was purified by silica gel chromatography (0-100% 3:1 (EtOAc/EtOH) in hexanes) to afford ethyl (S)-11-(benzyloxy)-6-(tert-butyl)-2-chloro-3-(3-methoxypropoxy)-10-oxo-5,10-dihydro-6H-pyrido[1,2-h][1,7]naphthyridine-9-carboxylate (47.9 mg, 66%) as a brown oil. ¹H NMR (400 MHz, CDCl₃) δ ppm 8.15 (s, 1H), 7.73 (d, J=6.2 Hz, 2H), 7.28-7.36 (m, 3H), 6.94 (s, 1H), 5.26 (br. s., 2H), 4.35 (q, J=6.4 Hz, 2H), 4.21-4.10 (m, 2H), 3.82-3.92 (m, 1H), 3.56-3.67 (m, 2H), 3.46-3.37 (m, 1H), 3.39 (s, 3H), 2.98 (d, J=16.0 Hz, 1H), 2.13 (quin, J=5.9 Hz, 2H), 1.40-1.31 (m, 3H), 0.71 (s, 9H); LCMS (m/z, ES+)=555.4, 557.3 (M+1).

Step 5: (S)-Ethyl 11-(benzyloxy)-6-(tert-butyl)-2-cyclopropyl-3-(3-methoxypropoxy)-10-oxo-6,10-dihydro-5H-pyrido[1,2-h][1,7]naphthyridine-9-carboxylate

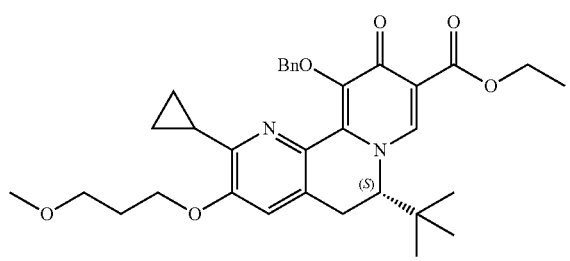

A solution of ethyl (S)-11-(benzyloxy)-6-(tert-butyl)-2-chloro-3-(3-methoxypropoxy)-10-oxo-5,10-dihydro-6H-pyrido[1,2-h][1,7]naphthyridine-9-carboxylate (47.9 mg, 0.086 mmol), Pd(PPh₃)₄ (20 mg, 0.017 mmol), potassium carbonate (36 mg, 0.26 mmol), and cyclopropylboronic acid (15 mg, 0.17 mmol) in 1,4-dioxane (0.9 mL) was heated at 100° C. for 2 days. The reaction mixture was diluted with CH₂Cl₂ and filtered through celite. The filtrate was evaporated and the residue was purified by reverse phase chromatography (5-100% CH₃CN/H₂O (0.1% formic acid)) to afford (S)-ethyl 11-(benzyloxy)-6-(tert-butyl)-2-cyclopropyl-3-(3-methoxypropoxy)-10-oxo-6,10-dihydro-5H-pyrido[1,2-h][1,7]naphthyridine-9-carboxylate (14.7 mg, 30%) as a white solid. ¹H NMR (400 MHz, CDCl₃) δ ppm 8.18 (s, 1H), 7.66 (d, J=7.0 Hz, 2H), 7.27-7.20 (m, 3H), 6.82 (s, 1H), 5.45 (d, J=10.9 Hz, 1H), 5.21 (d, J=10.9 Hz, 1H), 4.46-4.38 (m, 2H), 4.04-4.20 (m, 2H), 3.89 (d, J=5.5 Hz, 1H), 3.65-3.56 (m, 2H), 3.38 (s, 3H), 3.30 (dd, J=16.0, 6.2 Hz, 1H), 3.03 (d, J=16.0 Hz, 1H), 2.39-2.49 (m, 1H), 2.13 (quin, J=6.1 Hz, 2H), 1.42 (t, J=7.2 Hz, 3H), 1.07-1.15 (m, 1H), 0.96-1.04 (m, 1H), 0.88-0.96 (m, 1H), 0.80-0.86 (m, 1H), 0.77 (s, 9H); LCMS (m/z, ES+)=561.8 (M+1).

Step 6: (S)-6-(tert-Butyl)-2-cyclopropyl-11-hydroxy-3-(3-methoxypropoxy)-10-oxo-5,10-dihydro-6H-pyrido[1,2-h][1,7]naphthyridine-9-carboxylic acid

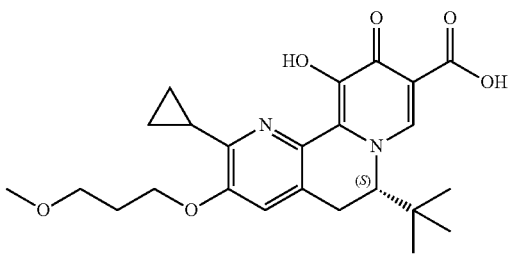

A solution of ethyl (S)-11-(benzyloxy)-6-(tert-butyl)-2-cyclopropyl-3-(3-methoxypropoxy)-10-oxo-5,10-dihydro-6H-pyrido[1,2-h][1,7]naphthyridine-9-carboxylate (14.7 mg, 0.026 mmol) and 10% Pd/C (catalytic) in MeOH (5 mL) was stirred under 1 atm H₂ for 1.5 h. The reaction mixture was filtered through celite and evaporated to dryness. The residue was taken up in MeOH (0.5 mL) and 1 M LiOH (0.5 mL) and the solution was heated at 50° C. for 2 h. 1 M citric acid (1.5 mL) was added, the mixture was evaporated to dryness and the residue was purified by reverse phase chromatography (5-90% CH₃CN/H₂O (0.1% formic acid)) to afford (S)-6-(tert-butyl)-2-cyclopropyl-11-hydroxy-3-(3-methoxypropoxy)-10-oxo-5,10-dihydro-6H-pyrido[1,2-h][1,7]naphthyridine-9-carboxylic acid (6.3 mg, 54%) as a white solid. ¹H NMR (400 MHz, CDCl₃) δ ppm 15.79 (s, 1H), 13.96 (s, 1H), 8.28 (s, 1H), 7.08 (s, 1H), 4.25-4.16 (m, 2H), 4.06 (d, J=6.3 Hz, 1H), 3.58-3.69 (m, 2H), 3.51 (dd, J=17.1, 6.8 Hz, 1H), 3.39 (s, 3H), 3.25 (d, J=17.1 Hz, 1H), 2.49-2.59 (m, 1H), 2.18 (quin, J=6.1 Hz, 2H), 1.06-1.19 (m, 4H), 0.84 (s, 9H); LCMS (m/z, ES+)=443.7 (M+1).

General Scheme 7 for Preparation of Compounds Such as Examples 26, 27

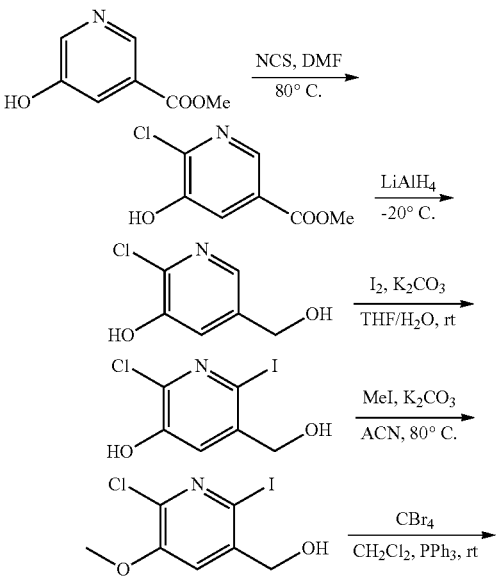

113
-continued
114
-continued
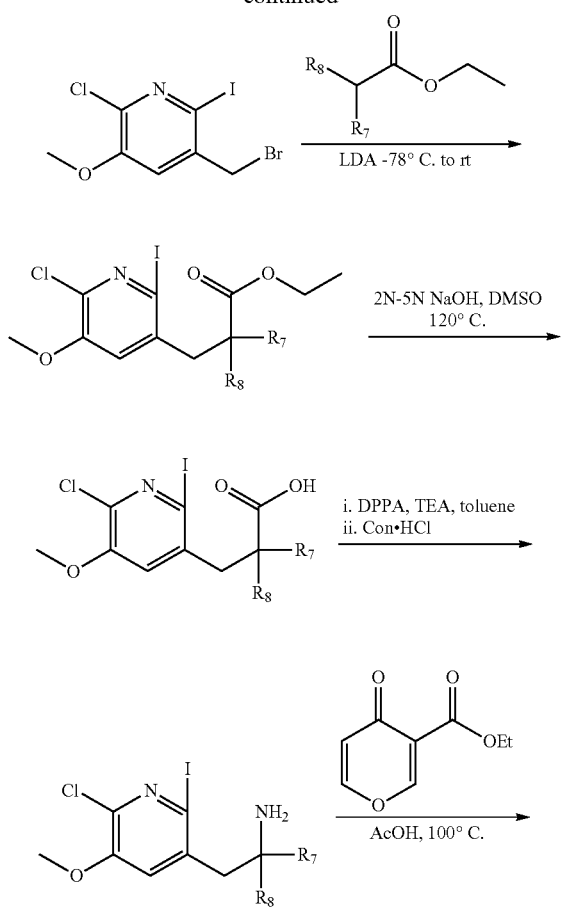
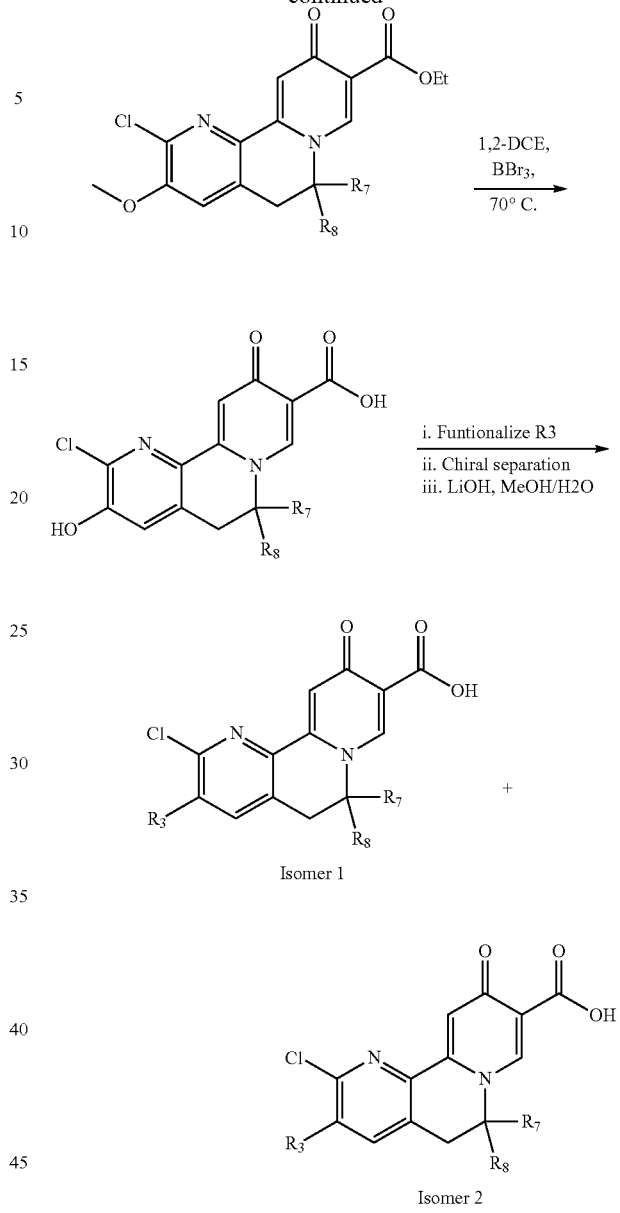
Isomer 1
Isomer 2
Specific Synthetic Scheme 8 for Compounds of Example 26, 2
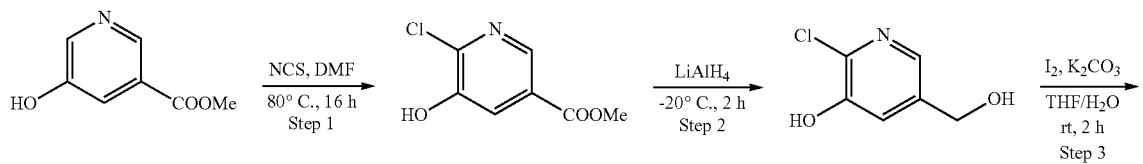
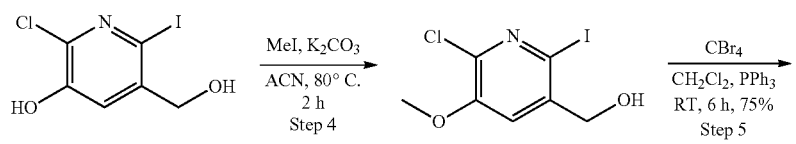

-continued
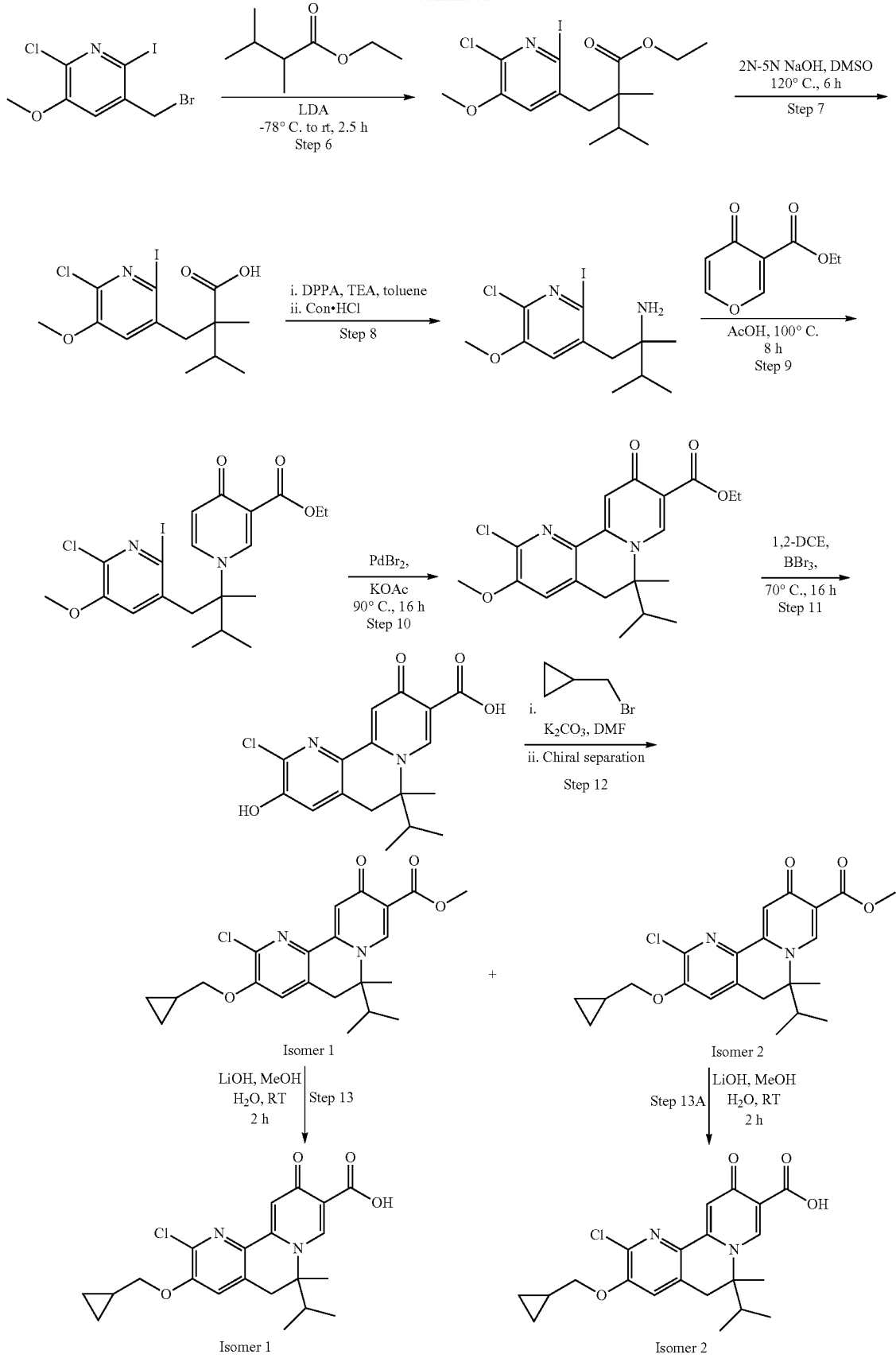

Example 26: (Compound 245)

(2-Chloro-3-(cyclopropylmethoxy)-6-isopropyl-6-methyl-10-oxo-5,10-dihydro-6H-pyrido[1,2-h][1,7]naphthyridine-9-carboxylic acid-Isomer-1

Example 27: (Compound 246)

(2-Chloro-3-(cyclopropylmethoxy)-6-isopropyl-6-methyl-10-oxo-5,10-dihydro-6H-pyrido[1,2-h][1,7]naphthyridine-9-carboxylic acid-Isomer-2

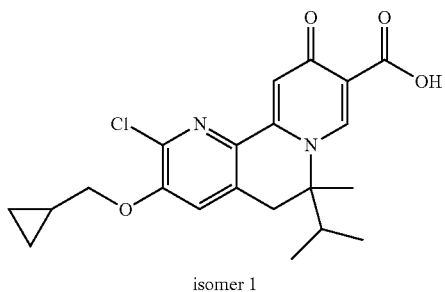

isomer 1

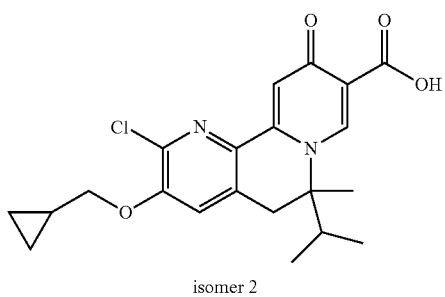

isomer 2

Step 1: Methyl 6-chloro-5-hydroxynicotinate

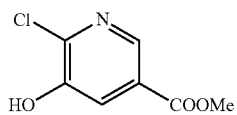

To a solution of methyl 5-hydroxynicotinate (100 g, 0.65 mol) in DMF (1000 mL), NCS (130.5 g, 0.97 mol) was added and the reaction mixture was heated to 80° C. for 16 h. The reaction mixture was cooled to room temperature and the solvent was removed under reduced pressure. The residue was taken in EtOAc (2 L) and washed with saturated sodium chloride solution (500 mL). The organic layer was dried over $Na_2SO_4$ and concentrated. The crude product was purified by column chromatography on 230-400 silica gel using 0-30% ethyl acetate in petroleum ether as an eluent. Fractions were collected and concentrated to afford the title compound as yellow oil (60 g, 49% yield), LCMS (ESI) m/z 187.9 (M+1).

Step 2: 2-Chloro-5-(hydroxymethyl)pyridin-3-ol

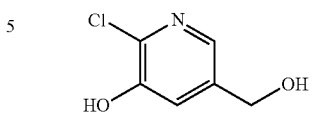

A solution of methyl 6-chloro-5-hydroxynicotinate (60 g, 0.32 mol) in THF (600 mL) was added dropwise to Lithium aluminium hydride (160 ml, 0.32 mol, 2.0 M in THF) at −50° C. under nitrogen atmosphere. The reaction mixture was stirred at −25° C. for 2 h. EtOAc (1000 mL), water (50 ml) and saturated aq. sodium potassium tartrate solution (500 ml) were added to the reaction mixture dropwise at −25° C. The mixture was filtered through celite pad, washed with 20% MeOH in DCM (500 mL). The filtrate was concentrated on reduced pressure to afford as title compound (40 g, 80% yield) as an off-white solid. LCMS (ESI) m/z 157.9 (M−H).

Step 3: 2-Chloro-5-(hydroxymethyl)-6-iodopyridin-3-ol

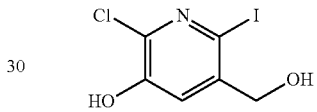

To a solution of 2-chloro-5-(hydroxymethyl)pyridin-3-ol (3.5 g, 22.01 mmol) in THF (35 mL), water (35 mL), $K_2CO_3$ (6.1 g, 44.24 mmol) and Iodine (5.84 g, 23.11 mmol) were added and the reaction mixture was stirred at room temperature for 2 h. The reaction mixture was cooled to 0° C. and quenched with aq. sodium sulfite solution (50 mL). Ethyl acetate (150 mL) was added to it, organic layer was separated and discarded. The aqueous layer was acidified with 1.5N aq. HCl solution up to the pH=6 and extracted with ethyl acetate (150 mL). The organic layer was separated, washed with water (25 mL) and dried over sodium sulphate. Solvent was removed under reduced pressure to afford the title compound as off white solid (4 g, 64.5% yield). LCMS (ESI) m/z: 283.7 (M−H).

Step 4: (6-Chloro-2-iodo-5-methoxypyridin-3-yl)methanol

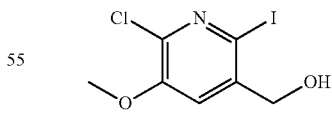

To a solution of 2-chloro-5-(hydroxymethyl)-6-iodopyridin-3-ol (4 g, 14.03 mmol) in acetonitrile (50 mL), $K_2CO_3$ (3.87 g, 28.06 mmol) and methyl iodide (MeI) (5.97 g, 42.10 mmol) were added and the reaction mixture was heated to 80° C. for 2 h in a sealed tube. The reaction mixture was quenched with water (100 mL), acidified with 1.5N HCl (pH=6) and extracted with ethyl acetate (150 mL). The organic layer was washed with brine, dried over $Na_2SO_4$ and concentrated. The crude was purified by column chromatography on 230-400 silica gel using 0-30% ethyl acetate in petroleum ether as an eluent. Fractions were collected and concentrated to afford the title compound as off-white solid (3.3 g, 80% yield). LCMS (ESI) m/z: 299.8 (M+1).

Step 5:
3-(Bromomethyl)-6-chloro-2-iodo-5-methoxypyridine

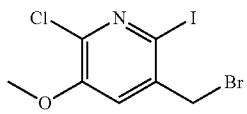

To a solution of (6-chloro-2-iodo-5-methoxypyridin-3-yl)methanol (2.2 g, 7.35 mmol) in DCM (20 mL) was added CBr$_4$ (3.6 g, 11.35 mmol) and PPh$_3$ (2.3 g, 8.82 mmol) in THF (20 mL). The reaction mixture was stirred at room temperature for 6 h. Solvent was removed under reduced pressure to get crude product. This was purified by column chromatography on silica gel 60-120 mesh using 0-20% EtOAc in petroleum ether as an eluent. Fractions were collected and concentrated to afford the title compound as off-white solid (2.4 g, 92% yield). LCMS (ESI) m/z: 363.6 (M+H).

Step 6: Ethyl 2-((6-chloro-2-iodo-5-methoxypyridin-3-yl)methyl)-2,3-dimethylbutanoate

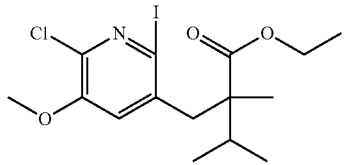 [SMILES: CCOC(=O)C(C)(Cc1cc(OC)c(Cl)nc1I)C(C)C]

To a solution of diisopropyamine (2.43 mL, 17.38 mmol) in dry THF (20 mL) was added n-BuLi (10.86 mL, 17.38 mmol, 1.6M in Hexane) dropwise at −78° C. The reaction mixture was stirred at same temperature for 30 min. Ethyl 2,3-dimethylbutanoate (2.3 g, 16.57 mmol) in THF (20 mL) was added to the reaction mixture and the reaction mixture was stirred at −78° C. for 1 h. 3-(bromomethyl)-6-chloro-2-iodo-5-methoxypyridine (3 g, 8.28 mmol) in THF (20 mL) was added dropwise at same temperature and the reaction mixture was warmed to room temperature and stirred at room temperature for 1 h. The reaction mixture was cooled to 0° C., quenched with saturated NH$_4$Cl solution (50 mL), diluted with water (20 mL) and extracted with EtOAc (3×50 mL). The combined organic layers were washed with brine (20 mL), dried over anhydrous Na$_2$SO$_4$ and filtered. Solvents were removed under reduced pressure to get crude product. The crude product was purified by column chromatography on silica gel 230-400 mesh using 0-10% EtOAc in Petroleum ether as an eluent. Fractions were collected and concentrated to afford the title compound as yellow oil (3 g, 85% yield). LCMS (ESI) m/z: 426 (M+H).

Step 7: 2-((6-Chloro-2-iodo-5-methoxypyridin-3-yl)methyl)-2,3-dimethylbutanoic acid

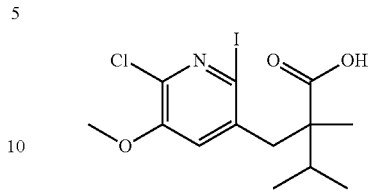

To a solution of ethyl 2-((6-chloro-2-iodo-5-methoxypyridin-3-yl)methyl)-2,3-dimethylbutanoate (3 g, 7.05 mmol) in DMSO (9 mL), 5M NaOH solution (21.6 mL, 98.11 mmol) was added and the reaction mixture was stirred at 120° C. for 6 h. The reaction mixture was cooled to 0° C., acidified with concentrated HCl till pH=1. After diluting with water (50 mL) it was extracted with EtOAc (2×100 L). The combined organic layers were washed with brine (50 mL), dried over anhydrous Na$_2$SO$_4$ and filtered. The solvent was removed under reduced pressure to get the crude product. The crude product was purified by column chromatography on 230-400 silica gel using 0-10% MeOH in DCM to afford 2-((6-chloro-2-iodo-5-methoxypyridin-3-yl)methyl)-2,3-dimethylbutanoic acid (500 mg, 18% yield) (LCMS (ESI) m/z: 397.8 (M+1)).

Step 8: 1-(6-Chloro-2-iodo-5-methoxypyridin-3-yl)-2,3-dimethylbutan-2-amine

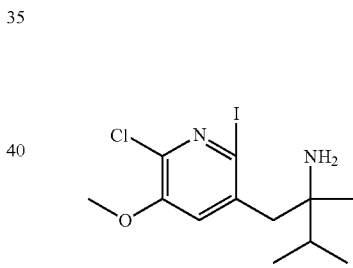

To a solution of 2-((6-chloro-2-iodo-5-methoxypyridin-3-yl)methyl)-2,3-dimethylbutanoic acid (1 g, 2.5 mmol) in toluene (30 mL), triethylamine (0.57 g, 5.5 mmol) and diphenyl phosphoryl azide (1.52 g, 5.5 mmol) were added and the reaction mixture was stirred at 80° C. for 2 h. The reaction mixture was cooled to room temperature and concentrated HCl (8.4 mL) was added to the reaction mixture dropwise over 30 min at 0° C. The reaction mixture was stirred at 60° C. for 2 h. The reaction mixture was cooled to 0° C. and basified with 1N aqueous NaOH solution until pH=10. The reaction mixture was diluted with water (20 mL) and extracted with EtOAc (2×50 mL). The combined organic layers were washed with brine (20 mL), dried over anhydrous Na$_2$SO$_4$, filtered and concentrated to get a brown gummy solid. This was purified by column chromatography on 230-400 silica using 0-3% MeOH in DCM to afford the title compound as yellow oil (800 mg, 87% yield). LCMS (ESI) m/z: 368.8 (M+1).

Step 9: Ethyl 1-(1-(6-chloro-2-iodo-5-methoxypyridin-3-yl)-2,3-dimethylbutan-2-yl)-4-oxo-1,4-dihydropyridine-3-carboxylate

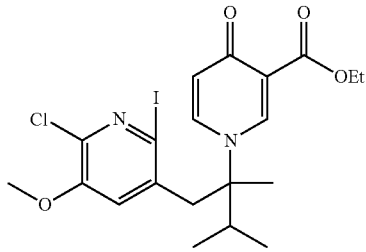 [SMILES: CCOC(=O)c1cn(C(C)(Cc2cc(OC)c(Cl)nc2I)C(C)C)ccc1=O]

To a solution of 1-(6-chloro-2-iodo-5-methoxypyridin-3-yl)-2,3-dimethylbutan-2-amine (800 mg, 2.17 mmol) in acetic acid (25 mL), ethyl 4-oxo-4H-pyran-3-carboxylate (0.547 g, 3.2 mmol) was added and the reaction mixture was stirred at 100° C. for 8 h. The reaction mixture was cooled to room temperature, the solvent was removed under reduced pressure and the residue was purified by column chromatography on 230-400 silica gel using 0-10% MeOH in DCM as an eluent. Fractions were collected and concentrated to afford the title compound (400 mg, 35% yield) as brown solid. LCMS (ESI) m/z: 518.7 (M+1).

Step 10: Ethyl 2-chloro-6-isopropyl-3-methoxy-6-methyl-10-oxo-5,10-dihydro-6H-pyrido[1,2-h][1,7]naphthyridine-9-carboxylate

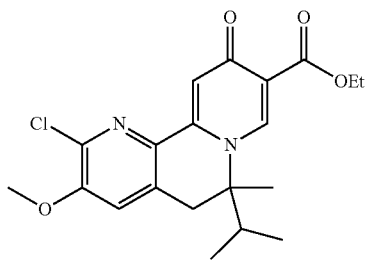 [SMILES: CCOC(=O)c1cn2c(cc1=O)-c1nc(Cl)c(OC)cc1CC2(C)C(C)C]

To a solution of ethyl 1-(1-(6-chloro-2-iodo-5-methoxypyridin-3-yl)-2,3-dimethylbutan-2-yl)-4-oxo-1,4-dihydropyridine-3-carboxylate (300 mg, 0.57 mmol) in N, N-Dimethylformamide (7.5 mL) was added potassium acetate (283 mg, 2.89 mmol). The reaction mixture was degassed with nitrogen for 20 minutes. Palladium (II) bromide (30 mg, 0.11 mmol) was added to the reaction mixture and was stirred at 90° C. for 16 h. The reaction mixture was cooled to room temperature, filtered through celite and washed with DCM. The solvents were removed under reduced pressure and the crude was purified by column chromatography on 230-400 silica gel using 0-10% MeOH in DCM as an eluent. Fractions were collected and concentrated to afford the title compound (150 mg, 68% yield) as brown solid. LCMS (ESI) m/z: 390.9 (M+1).

Step 11: 2-Chloro-3-hydroxy-6-isopropyl-6-methyl-10-oxo-5,10-dihydro-6H-pyrido[1,2-h][1,7]naphthyridine-9-carboxylic acid

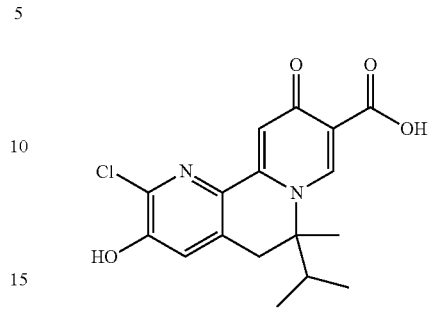

To a solution of ethyl 2-chloro-6-isopropyl-3-methoxy-6-methyl-10-oxo-5,10-dihydro-6H-pyrido[1,2-h][1,7]naphthyridine-9-carboxylate (150 mg, 0.38 mmol) in 1,2-Dichloroethane (DCE) (6.45 mL), $BBr_3$ (288 mg, 1.15 mmol) was added and the reaction mixture was stirred at 70° C. for 16 h. The reaction mixture was cooled to −10° C., methanol (15 mL) was added to reaction mixture dropwise and then stirred at room temperature for 30 minutes. The reaction mixture was concentrated to get the crude compound (150 mg) as a brown solid. LCMS (ESI) m/z: 348.9 (M+1). This crude product was taken for next step.

Step 12: Methyl-2-chloro-3-(cyclopropylmethoxy)-6-isopropyl-6-methyl-10-oxo-5,10-dihydro-6H-pyrido[1,2-h][1,7]naphthyridine-9-carboxylate-Isomer-1 and Methyl-2-chloro-3-(cyclopropylmethoxy)-6-isopropyl-6-methyl-10-oxo-5,10-dihydro-6H-pyrido[1,2-h][1,7]naphthyridine-9-carboxylate-Isomer-2 isomer 1

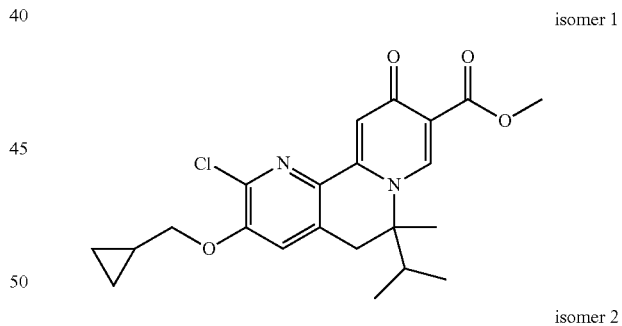

isomer 2

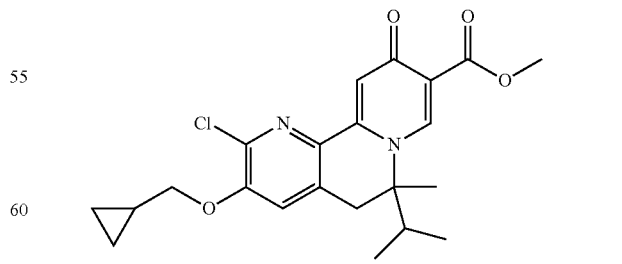

To a solution of 2-chloro-3-hydroxy-6-isopropyl-6-methyl-10-oxo-5,10-dihydro-6H-pyrido[1,2-h][1,7]naphthyridine-9-carboxylic acid (150 mg, 0.43 mmol) in DMF (2 mL), $K_2CO_3$ (594 mg, 4.3 mmol) and (bromomethyl)cyclopropane (464 mg, 3.44 mmol) were added and the reaction mixture was stirred at 80° C. for 5 h. The reaction mixture was cooled to room temperature, the solvent was removed under reduced pressure and the residue was stirred with MeOH (10 mL) at room temperature for 30 min. Solvent was removed under reduced pressure and diluted with DCM (20 mL). Organic layer was washed with water (15 mL) and dried over anhydrous sodium sulphate, filtered and concentrated under reduced pressure to get the compound as mixture of isomers which was separated by chiral supercritical fluid chromatography (SFC). Collected fractions of Isomer-1 (first elution peak) and Isomer-2 (second elution peak) were concentrated under reduced pressure to get methyl-2-chloro-3-(cyclopropylmethoxy)-6-isopropyl-6-methyl-10-oxo-5,10-dihydro-6H-pyrido[1,2-h][1,7]naphthyridine-9-carboxylate-Isomer-1 (50 mg, 28% yield) as off white solid LCMS (ESI) m/z: 417.9 (M+1) and methyl-2-chloro-3-(cyclopropylmethoxy)-6-isopropyl-6-methyl-10-oxo-5,10-dihydro-6H-pyrido[1,2-h][1,7]naphthyridine-9-carboxylate-Isomer-2 (50 mg, 28% yield) as off white solid. LCMS (ESI) m/z: 417.9 (M+1).

Step 13: (2-Chloro-3-(cyclopropylmethoxy)-6-isopropyl-6-methyl-10-oxo-5,10-dihydro-6H-pyrido[1,2-h][1,7]naphthyridine-9-carboxylic acid-Isomer-1

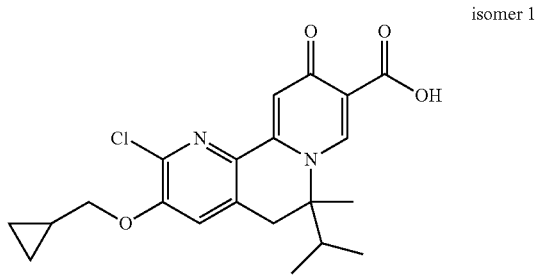 [SMILES: CC(C)C1(C)Cc2cc(OCC3CC3)c(Cl)nc2-c2cc(=O)c(C(=O)O)cn21]

isomer 1

To a solution of methyl-2-chloro-3-(cyclopropylmethoxy)-6-isopropyl-6-methyl-10-oxo-5,10-dihydro-6H-pyrido[1,2-h][1,7]naphthyridine-9-carboxylate-Isomer-1 (50 mg, 0.11 mmol) in Methanol (2 ml) and H₂O (0.5 ml), lithium hydroxide (25 mg, 0.59 mmol) was added and the reaction mixture was stirred at room temperature for 2 h. The solvents were removed under reduced pressure and the residue was taken in water (3 mL) and acidified with 1.5N HCl up to pH ~ 3. The obtained solid was filtered, washed with water (5 ml), dried under vacuum and purified by prep-HPLC to get the title compound (15 mg, yield 31.2%) as off-white solid. LCMS (ESI) m/z: 403.1 (M+1). 1H NMR; 400 MHz, DMSO-d6: δ ppm 8.57 (s, 1H), 7.72 (s, 1H), 7.39 (s, 1H), 4.10-4.07 (m, 2H), 3.36-3.35 (m, 2H), 1.91-1.84 (m, 1H), 1.70 (s, 3H), 1.35-1.25 (m, 1H), 0.85-0.82 (m, 3H), 0.65-0.63 (m, 5H), 0.42-0.39 (m, 2H).

Step 13 A: 2-chloro-3-(cyclopropylmethoxy)-6-isopropyl-6-methyl-10-oxo-5,10-dihydro-6H-pyrido[1,2-h][1,7]naphthyridine-9-carboxylic acid-Isomer-2

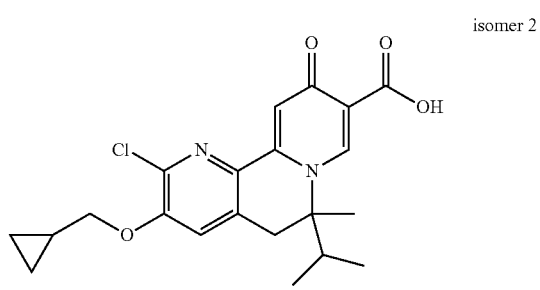 [SMILES: CC(C)C1(C)Cc2cc(OCC3CC3)c(Cl)nc2-c2cc(=O)c(C(=O)O)cn21]

isomer 2

To a solution of methyl 2-chloro-3-(cyclopropylmethoxy)-6-isopropyl-6-methyl-10-oxo-5,10-dihydro-6H-pyrido[1,2-h][1,7]naphthyridine-9-carboxylate-Isomer-2 (50 mg, 0.11 mmol) in Methanol (2 ml) and H₂O (0.5 ml), lithium hydroxide (25 mg, 0.59 mol) was added and the reaction mixture was stirred at room temperature for 2 h. The solvents were removed under reduced pressure and the residue was taken in water (3 mL) and acidified with 1.5N HCl up to pH ~ 3. The obtained solid was filtered, washed with water (5 ml), dried under vacuum for 16 h to get the title compound as off-white solid (30 g, yield 62%). LCMS (ESI) m/z: 402.9 (M+1). 1H NMR; 400 MHz, DMSO-d6: δ ppm 8.57 (s, 1H), 7.71 (s, 1H), 7.39 (s, 1H), 4.09-4.08 (m, 2H), 3.39-3.38 (m, 2H), 1.90-1.87 (m, 1H), 1.70 (s, 3H), 1.32-1.28 (m, 1H), 1.11-1.07 (m, 3H), 0.83-0.81 (m, 5H), 0.63-0.62 (m, 2H).

Example 28: (Compound 247)

2-Cyclopropyl-6-isopropyl-3-(3-methoxypropoxy)-6-methyl-10-oxo-5,10-dihydro-6H-pyrido[1,2-h][1,7]naphthyridine-9-carboxylic acid-Isomer-1

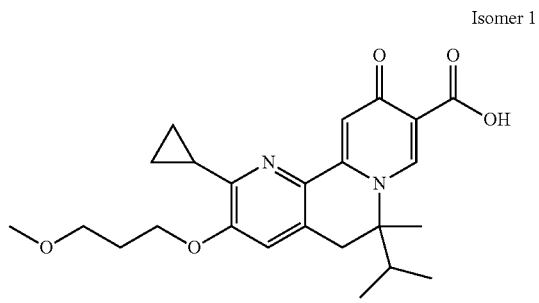 [SMILES: COCCCOc1cc2c(nc1C1CC1)-c1cc(=O)c(C(=O)O)cn1C(C)(C(C)C)C2]

Isomer 1

Example 29: (Compound 248)

2-Cyclopropyl-6-isopropyl-3-(3-methoxypropoxy)-6-methyl-10-oxo-5,10-dihydro-6H-pyrido[1,2-h][1,7]naphthyridine-9-carboxylic acid-Isomer-2

Isomer 2

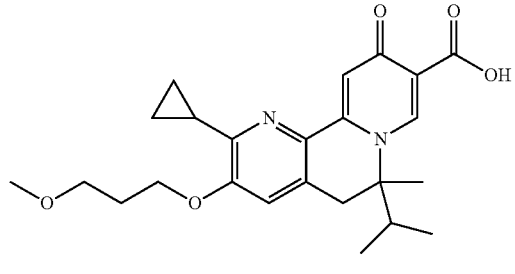

-continued

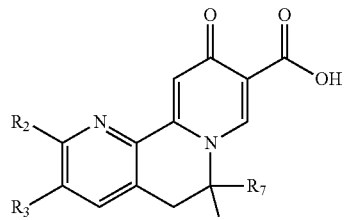

Isomer 1

+

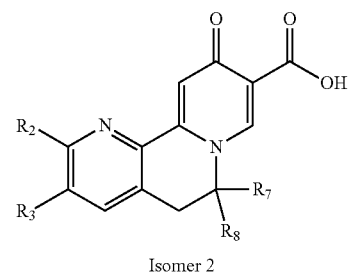

Isomer 2

General Synthetic Scheme 9 for Compounds Such as Example 28, 29

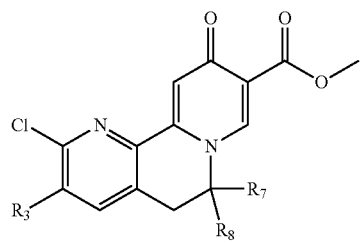

i. Functionalize R2
ii. Chiral separation
iii. LiOH

Step-1

Specific Synthetic Scheme 10 for Compounds of Example 28, 29

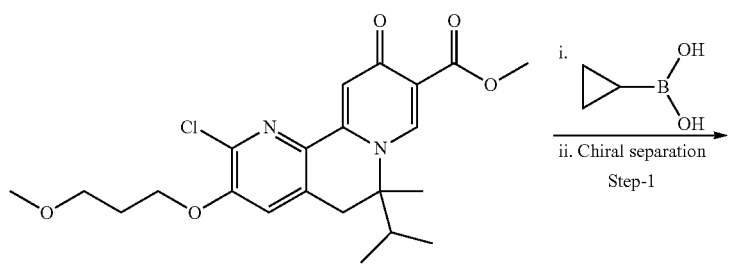

i. cyclopropylboronic acid
ii. Chiral separation

Step-1

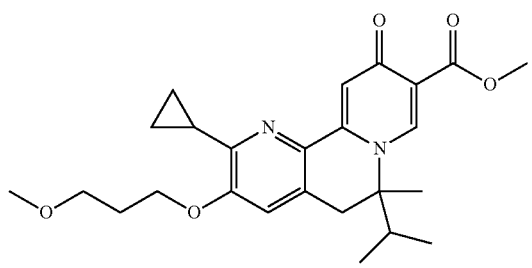

Isomer 1

Step-2 | LiOH

+

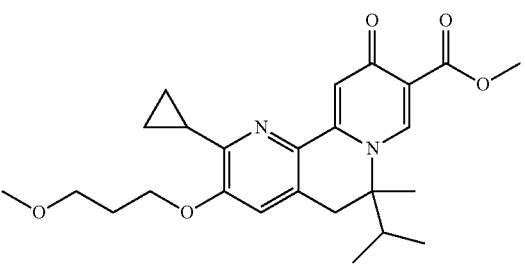

Isomer 2

Step-2A | LiOH

127

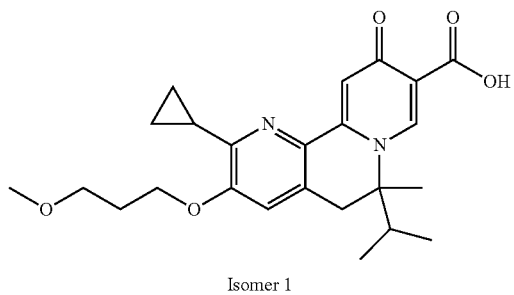

Isomer 1

128

-continued

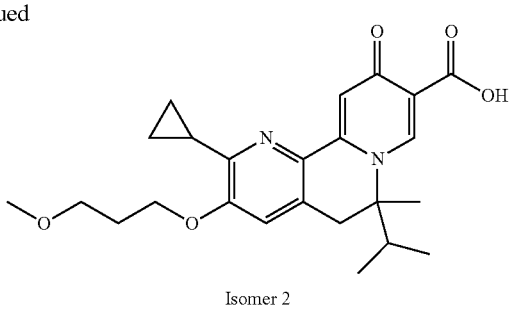

Isomer 2

Step 1: Methyl-2-cyclopropyl-6-isopropyl-3-(3-methoxypropoxy)-6-methyl-10-oxo-5,10-dihydro-6H-pyrido[1,2-h][1,7]naphthyridine-9-carboxylate-Isomer-1 and Methyl-2-cyclopropyl-6-isopropyl-3-(3-methoxypropoxy)-6-methyl-10-oxo-5,10-dihydro-6H-pyrido[1,2-h][1,7]naphthyridine-9-carboxylate-Isomer-2

Isomer 1

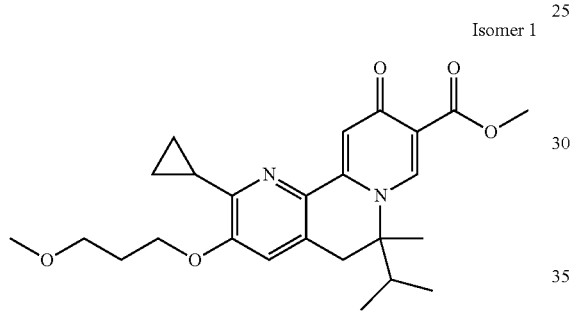

Isomer 2

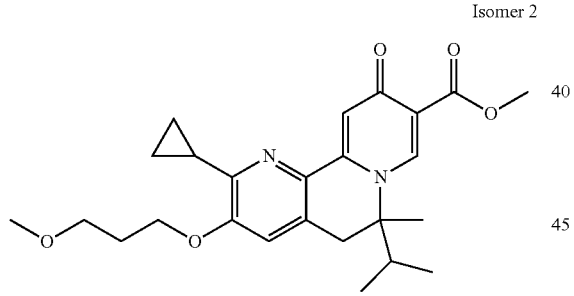

To a stirred solution of methyl 2-chloro-6-isopropyl-3-(3-methoxypropoxy)-6-methyl-10-oxo-5,10-dihydro-6H-pyrido[1,2-h][1,7]naphthyridine-9-carboxylate (570 mg, 1.311 mmol) in 1,4-Dioxane (11.4 mL), was added potassium carbonate (362 mg, 2.62 mmol) and purged with Nitrogen for 5 min. Cyclopropylboronic acid (225 mg, 2.62 mmol) was added followed by Pd(PPh$_3$)$_4$ (303 mg, 0.262 mmol) and purged with nitrogen for 5 min. The reaction mixture was heated to 100° C. in a sealed tube for 16 h. The reaction mixture was concentrated completely under reduced pressure and the residue was diluted with DCM (100 mL), washed with water (40 mL), brine (40 mL). The organic layer was separated, dried over sodium sulfate and concentrated and the crude was purified by Isolera™ silica chromatography and eluted with 3% MeOH in DCM. Collected fractions were concentrated completely to get the compound as mixture of isomers. Then the compound was purified by preparative HPLC followed by chiral SFC.

Collected fractions of Isomer-1 (first elution peak) and Isomer-2 (second elution peak) were concentrated separately under reduced pressure to get methyl-2-cyclopropyl-6-isopropyl-3-(3-methoxypropoxy)-6-methyl-10-oxo-5,10-dihydro-6H-pyrido[1,2-h][1,7]naphthyridine-9-carboxylate-Isomer-1 (60 mg, yield 10.3%) as colorless oil and methyl-2-cyclopropyl-6-isopropyl-3-(3-methoxypropoxy)-6-methyl-10-oxo-5,10-dihydro-6H-pyrido[1,2-h][1,7]naphthyridine-9-carboxylate-Isomer-2 (90 mg, 13.97% yield) as colorless oil. LCMS (ESI) m/z: 441.0 (M+1).

Step 2: 2-Cyclopropyl-6-isopropyl-3-(3-methoxypropoxy)-6-methyl-10-oxo-5,10-dihydro-6H-pyrido[1,2-h][1,7]naphthyridine-9-carboxylic acid-Isomer-1

Isomer 1

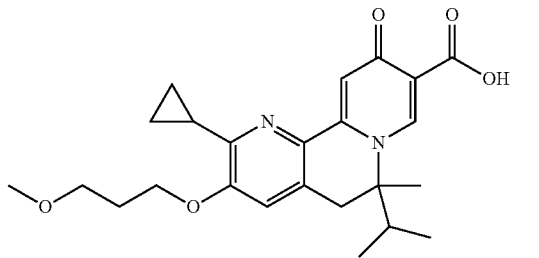

To a solution of methyl-2-cyclopropyl-6-isopropyl-3-(3-methoxypropoxy)-6-methyl-10-oxo-5,10-dihydro-6H-pyrido[1,2-h][1,7]naphthyridine-9-carboxylate, Isomer-1 (60 mg, 0.136 mmol) in methanol (2.4 mL) was added LiOH (16.31 mg, 0.681 mmol) and water (0.60 mL) at room temperature and the reaction mixture was stirred at rt for 2 h. Solvents from the reaction mixture were removed under reduced pressure and the residue was dissolved in water (2 ml). This solution was acidified with 1.5N HCl up to pH 6 at 0° C. The solid obtained was filtered, washed with water, n-pentane and dried to get the title compound as pale brown solid (15 mg, 25.3%). LCMS (ESI) m/z: 427.2 (M+1). 1H NMR (400 MHz, DMSO-d6): δ ppm 8.54 (s, 1H), 7.44 (s, 2H), 4.19-4.18 (m, 2H), 3.53 (t, J=6 Hz, 2H), 3.29-3.27 (m, 5H), 2.05 (t, J=6 Hz, 2H), 1.84-1.82 (m, 1H), 1.68 (s, 3H), 1.03-1.01 (m, 4H), 0.82 (d, J=6.5 Hz 3H), 0.61 (d, J=6.6 Hz, 3H)

Step 2A: 2-Cyclopropyl-6-isopropyl-3-(3-methoxy-propoxy)-6-methyl-10-oxo-5,10-dihydro-6H-pyrido[1,2-h][1,7]naphthyridine-9-carboxylic acid-Isomer-2

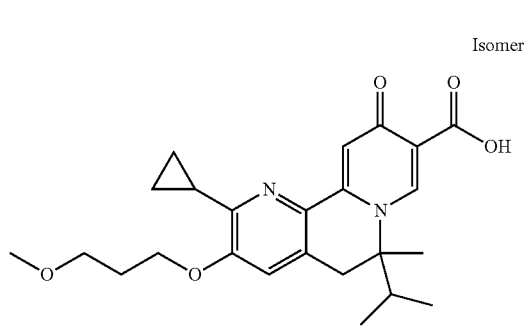

Isomer 2

To a solution of methyl-2-cyclopropyl-6-isopropyl-3-(3-methoxypropoxy)-6-methyl-10-oxo-5,10-dihydro-6H-pyrido[1,2-h][1,7]naphthyridine-9-carboxylate-Isomer-2 (90 mg, 0.204 mmol) in Methanol (3.6 mL) was added LiOH (24.46 mg, 1.021 mmol) and Water (0.90 mL) at room temperature and the reaction mixture was stirred at rt for 2 h. Solvents from the reaction mixture were removed under reduced pressure and the residue was dissolved in water (2 ml). This solution was acidified with 1.5N HCl up to pH 6 at 0° C. The solid obtained was filtered, washed with water, n-pentane and dried to get the title compound as pale brown solid (26 mg, 29.3%). LCMS (ESI) m/z: 427.2 (M+1). 1H NMR (400 MHz, DMSO-d6): δ ppm 8.53 (s, 1H), 7.44 (s, 2H), 4.25-4.12 (m, 2H), 3.56-3.52 (m, 2H), 3.23-3.18 (m, 5H), 2.10-2.01 (m, 3H), 1.81-1.62 (m, 4H), 1.05-0.99 (m, 4H), 0.85-0.81 (m, 3H), 0.65-0.61 (m, 3H).

General Scheme 11 - Preparation of Compounds of Type such as Compound 249

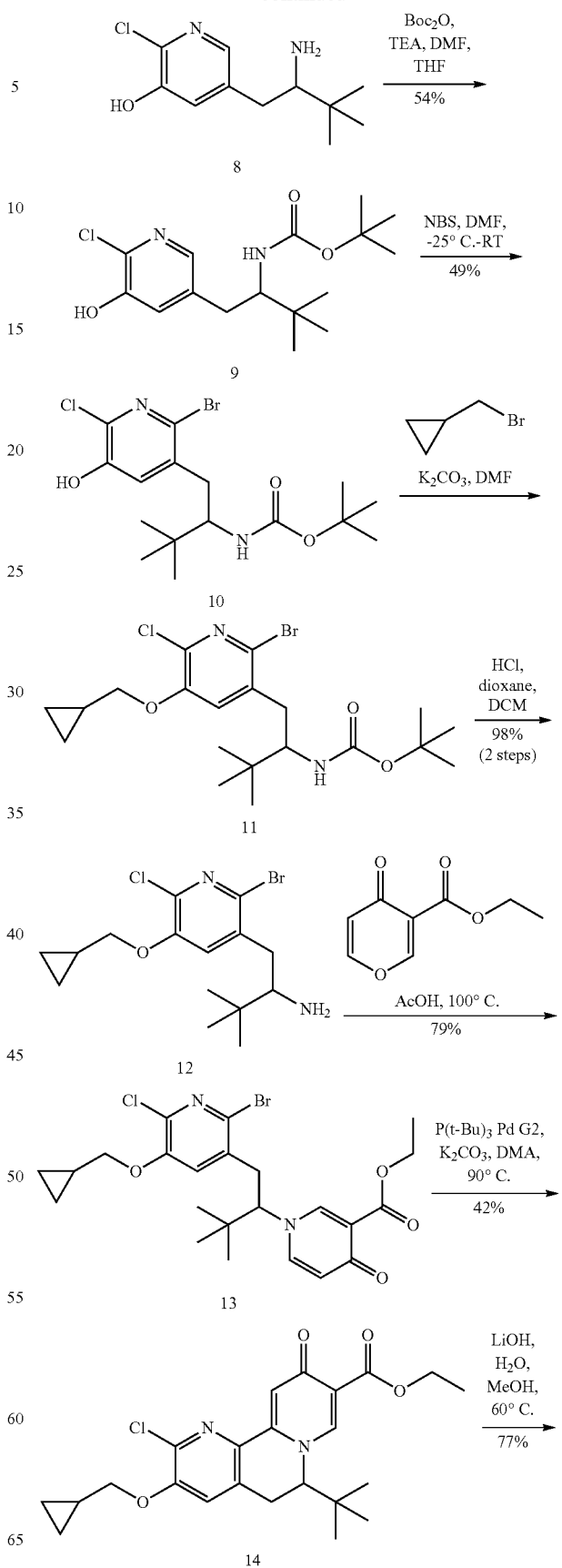

-continued

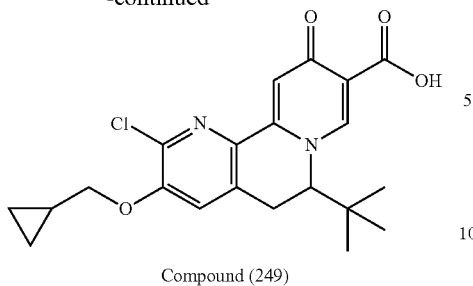

Compound (249)

Compound 249 can be prepared according to the general synthetic procedure outlined in Scheme 11 above, and as described in detail below.

Example 30 (Compound 249 (racemic))

6-(tert-Butyl)-2-chloro-3-(cyclopropylmethoxy)-10-oxo-6,10-dihydro-5H-pyrido[1,2-h][1,7]naphthyridine-9-carboxylic acid

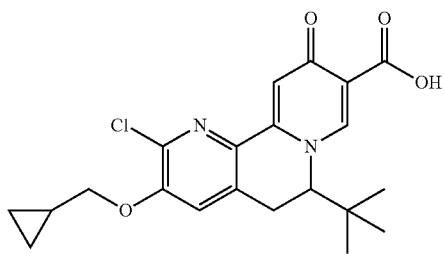

Step 1: 1-(6-Chloro-5-methoxypyridin-3-yl)-3,3-dimethylbutan-2-one

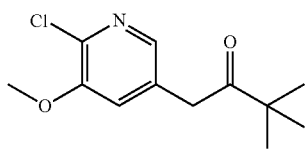 [SMILES: COc1cc(CC(=O)C(C)(C)C)cnc1Cl]

A flask was charged with a stir bar, xantphos (0.225 g, 0.388 mmol), tris(dibenzylideneacetone)dipalladium(0) (0.198 g, 0.216 mmol), and sodium tert-butoxide (2.43 g, 25.3 mmol). The flask was purged with a stream of nitrogen before a solution of 5-bromo-2-chloro-3-methoxypyridine (3.2 g, 14.4 mmol) and 3,3-dimethylbutan-2-one (2.16 ml, 17.3 mmol) in tetrahydrofuran (THF) (50 ml) was added. The mixture was heated at reflux overnight. The mixture was allowed to cool to room temperature and diluted with water. The mixture was extracted 3 times with ethyl acetate. The combined organic layers were washed with brine, dried over sodium sulfate, and concentrated to give 1-(6-chloro-5-methoxypyridin-3-yl)-3,3-dimethylbutan-2-one (3.07 g, 12.7 mmol, 88% yield). $^1$H NMR (400 MHz, CHLOROFORM-d) δ ppm 7.74 (d, J=1.56 Hz, 1H), 7.10 (d, J=1.56 Hz, 1H), 3.89 (s, 3H), 3.77 (s, 2H), 1.20 (s, 9H).

Step 2: 1-(6-Chloro-5-methoxypyridin-3-yl)-3,3-dimethylbutan-2-amine

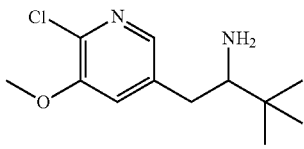 [SMILES: COc1cc(CC(N)C(C)(C)C)cnc1Cl]

A mixture of 1-(6-chloro-5-methoxypyridin-3-yl)-3,3-dimethylbutan-2-one (3.07 g, 12.7 mmol) and ammonium acetate (14.7 g, 191 mmol) in methanol (50 mL) were stirred for 1 hour at room temperature before sodium cyanoborohydride (2.00 g, 31.8 mmol) was added portionwise. The mixture was stirred over the weekend at room temperature before being basified with 1M sodium hydroxide. The mixture was extracted 3 times with dichloromethane. The combined organic layers were washed with brine, dried over sodium sulfate, and concentrated to give 1-(6-chloro-5-methoxypyridin-3-yl)-3,3-dimethylbutan-2-amine (2.82 g) as a clear oil. The material was purified by reverse phase medium pressure chromatography (C18/acetonitrile/water/0.1% formic acid/0% to 100% gradient). Fractions were combined, basified with 1M sodium hydroxide, and extracted 3 times with ethyl acetate. Combined organic layers were washed with brine, dried over sodium sulfate, and concentrated to give 1-(6-chloro-5-methoxypyridin-3-yl)-3,3-dimethylbutan-2-amine (1.45 g, 5.97 mmol, 47.0% yield) as a clear oil. $^1$H NMR (400 MHz, CHLOROFORM-d) δ ppm 7.83 (d, J=1.56 Hz, 1H), 7.08 (d, J=1.56 Hz, 1H), 3.90 (s, 3H), 2.91 (dd, J=13.48, 2.15 Hz, 1H), 2.62 (dd, J=10.94, 1.95 Hz, 1H), 2.22 (dd, J=13.48, 11.13 Hz, 1H), 1.12-1.36 (m, 2H), 0.98 (s, 9H). LCMS(ES+)(m/z): 243, 245 (M+1).

Step 3:
5-(2-Amino-3,3-dimethylbutyl)-2-chloropyridin-3-ol

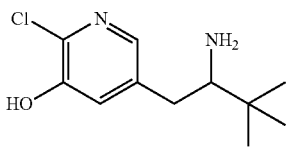

Boron tribromide (2.82 mL, 29.9 mmol) was added dropwise to a solution of 1-(6-chloro-5-methoxypyridin-3-yl)-3,3-dimethylbutan-2-amine (1.45 g, 5.97 mmol) in 1,2-dichloroethane (DCE) (30 mL) at 0° C. The mixture was allowed to warm to room temperature and stirred overnight. LC-MS showed significant conversion to desired product, but starting material was still present. Solids that had formed overnight were broken up and the mixture stirred an additional 24 hours at room temperature. The mixture was cooled to 0° C. and quenched with careful dropwise addition of methanol. After excess BBr$_3$ had been fully quenched, additional methanol (100 mL) was added. The mixture was stirred for 1 hour and concentrated. The residue was purified by medium pressure reverse phase chromatography (C18/acetonitrile/water/0.1% formic acid/0% to 100% gradient). Fractions were lyophilized to give 5-(2-amino-3,3-dimethylbutyl)-2-chloropyridin-3-ol (1.33 g, 5.81 mmol, 97% yield) as a white solid. ¹H NMR (400 MHz, DMSO-d₆) δ ppm 8.21 (s, 1H), 7.83-8.16 (m, 2H), 7.74 (d, J=1.95 Hz, 1H), 7.21 (d, J=1.56 Hz, 1H), 2.82-3.02 (m, 2H), 2.35-2.43 (m, 1H), 0.94 (s, 9H). LCMS(ES⁺)(m/z): 229, 231 (M+1).

Step 4: tert-Butyl (1-(6-chloro-5-hydroxypyridin-3-yl)-3,3-dimethylbutan-2-yl)carbamate

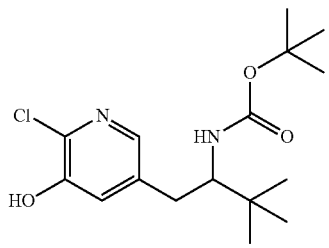 [SMILES: CC(C)(C)OC(=O)NC(Cc1cnc(Cl)c(O)c1)C(C)(C)C]

di-tert-Butyl dicarbonate (1.52 g, 6.98 mmol) was added to a stirring mixture of 5-(2-amino-3,3-dimethylbutyl)-2-chloropyridin-3-ol (1.33 g, 5.81 mmol) and triethylamine (2.43 mL, 17.4 mmol) in N,N-dimethylformamide (DMF) (30 mL). The mixture was stirred at room temperature for 1 hour. LC-MS showed minimal conversion. The solids never fully dissolved. Tetrahydrofuran (THF) (50 mL) was added and the solids went into solution. The mixture was stirred for 2 hours, concentrated, and the residue purified by medium pressure reverse phase chromatography (C18/acetonitrile/water/0.1% formic acid/10% to 100% gradient). Fractions were concentrated and then the residue lyophilized (acetonitrile/water) to give tert-butyl (1-(6-chloro-5-hydroxypyridin-3-yl)-3,3-dimethylbutan-2-yl)carbamate (1.04 g, 3.16 mmol, 54.4% yield). ¹H NMR (400 MHz, Temp.=80 C, DMSO-d₆) δ ppm 9.81-10.14 (m, 1H), 7.68 (d, J=1.56 Hz, 1H), 7.15 (d, J=1.56 Hz, 1H), 6.13-6.46 (m, 1H), 3.24-3.46 (m, 1H), 2.76 (dd, J=14.05, 2.34 Hz, 1H), 2.31-2.42 (m, 1H), 1.21 (br. s., 9H), 0.91 (s, 9H). LCMS(ES⁺)(m/z): 329, 331 (M+1).

Step 5: tert-Butyl (1-(2-bromo-6-chloro-5-hydroxypyridin-3-yl)-3,3-dimethylbutan-2-yl)carbamate

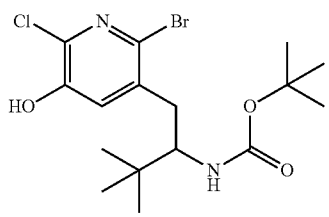 [SMILES: CC(C)(C)OC(=O)NC(Cc1cc(O)c(Cl)nc1Br)C(C)(C)C]

Under nitrogen, a solution of N-bromosuccinimide (471 mg, 2.65 mmol) in 2 mL of DMF was added slowly dropwise to a 0° C. solution of tert-butyl (1-(6-chloro-5-hydroxypyridin-3-yl)-3,3-dimethylbutan-2-yl)carbamate (791 mg, 2.405 mmol) in N,N-dimethylformamide (DMF) (25 mL) and the mixture stirred in a reaction vial that was protected from light by aluminum foil. The cold bath was maintained between −25 C and −20 C for 30 minutes. The mixture was allowed to warm to room temperature and stirred overnight. The mixture was quenched with water and extracted 3 times with ethyl acetate. The combined organic layers were washed with brine and concentrated. The residue was purified by medium pressure reverse phase chromatography (C18/acetonitrile/water/0.1% formic acid/10% to 60% gradient, then isocratic 60%, then 60% to 100% gradient). Fractions were concentrated to give tert-butyl (1-(2-bromo-6-chloro-5-hydroxypyridin-3-yl)-3,3-dimethylbutan-2-yl)carbamate (485 mg, 1.19 mmol, 49.5% yield). ¹H NMR (400 MHz, DMSO-d₆) δ ppm 10.81 (br. s., 1H), 7.23 (s, 1H), 6.60 (d, J=10.15 Hz, 1H), 3.35-3.50 (m, 1H), 2.73-2.89 (m, 1H), 2.18-2.37 (m, 1H), 1.15 (s, 9H), 0.83-0.91 (m, 9H). LCMS (ES+)(m/z): 407, 409, 411 (M+1).

Step 6: 1-(2-Bromo-6-chloro-5-(cyclopropylmethoxy)pyridin-3-yl)-3,3-dimethylbutan-2-amine

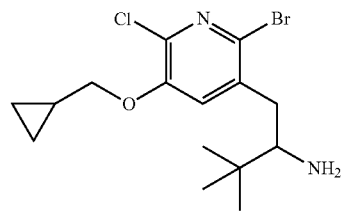 [SMILES: CC(C)(C)C(N)Cc1cc(OCC2CC2)c(Cl)nc1Br]

(Bromomethyl)cyclopropane (0.231 mL, 2.38 mmol) was added to a stirring mixture of tert-butyl (1-(2-bromo-6-chloro-5-hydroxypyridin-3-yl)-3,3-dimethylbutan-2-yl)carbamate (485 mg, 1.19 mmol) and potassium carbonate (658 mg, 4.76 mmol) in N,N-dimethylformamide (DMF) (5 mL). The mixture was stirred at room temperature overnight. The mixture was quenched with water and extracted 2 times with ethyl acetate. The combined organic layers were washed with 5% lithium chloride, washed with brine, dried over sodium sulfate, and concentrated to give crude tert-butyl (1-(2-bromo-6-chloro-5-(cyclopropylmethoxy)pyridin-3-yl)-3,3-dimethylbutan-2-yl)carbamate. The intermediate was dissolved in dichloromethane (DCM) (5.00 mL) before hydrogen chloride (4M in dioxane) (5 mL, 20 mmol) was added. The mixture was stirred for 4 hours and concentrated to give a white solid. Saturated sodium bicarbonate was added and the mixture extracted 2 times with ethyl acetate. The combined organic layers were dried over sodium sulfate and concentrated to give 1-(2-bromo-6-chloro-5-(cyclopropylmethoxy)pyridin-3-yl)-3,3-dimethylbutan-2-amine (423 mg, 1.17 mmol, 98% yield) as a clear oil. ¹H NMR (400 MHz, DMSO-d₆) δ ppm 7.62 (s, 1H), 3.96 (d, J=7.03 Hz, 2H), 2.89 (dd, J=12.88, 1.95 Hz, 1H), 2.43-2.46 (m, 1H), 2.20-2.33 (m, 1H), 1.19-1.36 (m, 3H), 0.92 (s, 9H), 0.52-0.66 (m, 2H), 0.26-0.42 (m, 2H). LCMS(ES+)(m/z): 361, 363, 365 (M+1).

Step 7: Ethyl 1-(1-(2-bromo-6-chloro-5-(cyclopropylmethoxy)pyridin-3-yl)-3,3-dimethylbutan-2-yl)-4-oxo-1,4-dihydropyridine-3-carboxylate

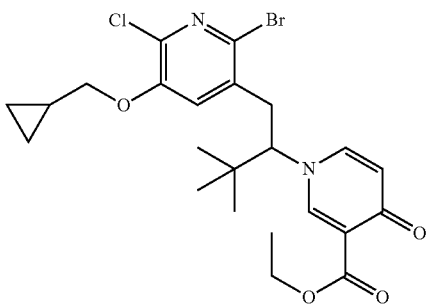 [SMILES: CCOC(=O)c1cn(C(Cc2cc(OCC3CC3)c(Cl)nc2Br)C(C)(C)C)ccc1=O]

1-(2-Bromo-6-chloro-5-(cyclopropylmethoxy)pyridin-3-yl)-3,3-dimethylbutan-2-amine (375 mg, 1.04 mmol) and ethyl 4-oxo-4H-pyran-3-carboxylate (174 mg, 1.04 mmol) in acetic acid (10 mL) were stirred at 100° C. for 4 hours. The mixture was allowed to cool to room temperature and concentrated. The residue was purified by medium pressure reverse phase chromatography (C18/acetonitrile/water/0.1% formic acid/0% to 100% gradient). Fractions were concentrated and the residue lyophilized (water/acetonitrile) to give ethyl 1-(1-(2-bromo-6-chloro-5-(cyclopropylmethoxy)pyridin-3-yl)-3,3-dimethylbutan-2-yl)-4-oxo-1,4-dihydropyridine-3-carboxylate (420 mg, 0.821 mmol, 79% yield) as a white powder. LCMS(ES+)(m/z): 511, 513, 515 (M+1).

Step 8: Ethyl 6-(tert-butyl)-2-chloro-3-(cyclopropylmethoxy)-10-oxo-6,10-dihydro-5H-pyrido[1,2-h][1,7]naphthyridine-9-carboxylate

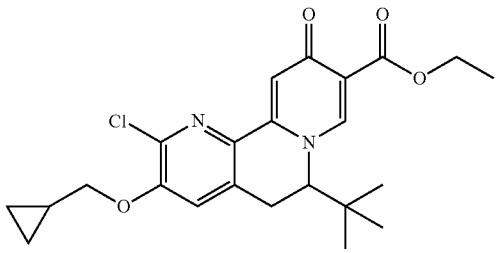 [SMILES: CCOC(=O)c1cn2c(cc1=O)-c1nc(Cl)c(OCC3CC3)cc1CC2C(C)(C)C]

A reaction vial containing a stir bar, ethyl 1-(1-(2-bromo-6-chloro-5-(cyclopropylmethoxy)pyridin-3-yl)-3,3-dimethylbutan-2-yl)-4-oxo-1,4-dihydropyridine-3-carboxylate (395 mg, 0.772 mmol), potassium acetate (151 mg, 1.543 mmol), and chloro[(tri-tert-butylphosphine)-2-(2-aminobiphenyl)] palladium(II) (79 mg, 0.15 mmol) was purged with nitrogen for 15 minutes. N,N-Dimethylacetamide (DMA) (8 mL) was purged with nitrogen for 5 minutes before being added to the reaction vial. The reaction vial was placed into a heating block that was preheated to 90° C. and the mixture stirred overnight. The reaction mixture was allowed to cool to room temperature, filtered through a cotton plug, and purified by reverse phase medium pressure chromatography (C18/acetonitrile/water/0.1% formic acid/10% to 100% gradient). Fractions were concentrated and the residue azeotroped with acetonitrile to help remove any remaining water. The residue was dissolved in dichloromethane and hexanes before being concentrated to give ethyl 6-(tert-butyl)-2-chloro-3-(cyclopropylmethoxy)-10-oxo-5,10-dihydro-6H-pyrido[1,2-h][1,7]naphthyridine-9-carboxylate (140 mg, 0.325 mmol, 42.1% yield) as a pale yellow solid. $^1$H NMR (400 MHz, DMSO-$d_6$) δ ppm 8.38 (s, 1H), 7.66 (s, 1H), 6.90 (s, 1H), 4.40 (d, J=6.25 Hz, 1H), 4.21 (q, J=7.03 Hz, 2H), 3.99-4.10 (m, 2H), 3.37-3.50 (m, 1H), 3.31-3.37 (m, 1H), 1.22-1.37 (m, 4H), 0.74 (s, 9H), 0.59-0.67 (m, 2H), 0.34-0.45 (m, 2H). LCMS(ES$^+$)(m/z): 431, 433 (M+1).

Step 9: 6-(tert-Butyl)-2-chloro-3-(cyclopropylmethoxy)-10-oxo-6,10-dihydro-5H-pyrido[1,2-h][1,7]naphthyridine-9-carboxylic acid

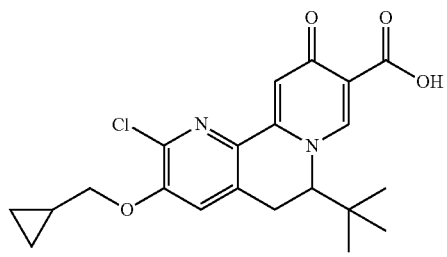 [SMILES: CC(C)(C)C1Cc2cc(OCC3CC3)c(Cl)nc2-c2cc(=O)c(C(=O)O)cn21]

A solution of lithium hydroxide monohydrate (1.6 mg, 0.039 mmol) in water (1 mL) was added to a solution of ethyl 6-(tert-butyl)-2-chloro-3-(cyclopropylmethoxy)-10-oxo-6,10-dihydro-5H-pyrido[1,2-h][1,7]naphthyridine-9-carboxylate (2.0 mg, 3.9 μmol) in methanol (1 mL) and the mixture heated at 60° C. for 3 hours. The mixture was allowed to cool to room temperature and was purified by medium pressure reverse phase chromatography (C18/acetonitrile/water/0.1% formic acid/10% to 100% gradient). Fractions were concentrated and the residue dried to give 6-(tert-butyl)-2-chloro-3-(cyclopropylmethoxy)-10-oxo-6,10-dihydro-5H-pyrido[1,2-h][1,7]naphthyridine-9-carboxylic acid (1.2 mg, 2.9 μmol, 77% yield) as a white solid. $^1$H NMR (400 MHz, METHANOL-$d_4$) δ ppm 8.70 (br. s., 1H), 7.54 (br. s., 1H), 7.47 (br. s., 1H), 4.44-4.55 (m, 1H), 3.97-4.14 (m, 2H), 3.39-3.61 (m, 2H), 1.33 (br. s., 1H), 1.12 (br. s., 1H), 0.83 (s, 9H), 0.63-0.71 (m, 2H), 0.34-0.50 (m, 2H). LCMS(ES$^+$)(m/z): 403, 405 (M+1).

Example 30-a (Compound 249 Isomer 1)

6-(tert-Butyl)-2-chloro-3-(cyclopropylmethoxy)-10-oxo-6,10-dihydro-5H-pyrido[1,2-h][1,7]naphthyridine-9-carboxylic acid (isomer 1)

isomer 1

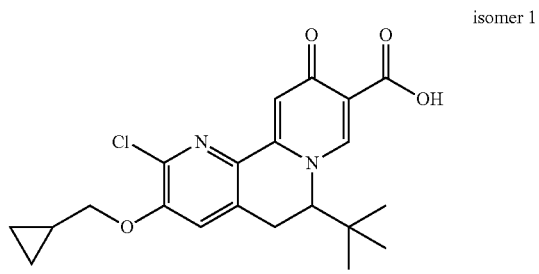 [SMILES: CC(C)(C)C1Cc2cc(OCC3CC3)c(Cl)nc2-c2cc(=O)c(C(=O)O)cn21]

Step 1: Ethyl 6-(tert-butyl)-2-chloro-3-(cyclopropyl-methoxy)-10-oxo-5,10-dihydro-6H-pyrido[1,2-h][1,7]naphthyridine-9-carboxylate (isomer 1)

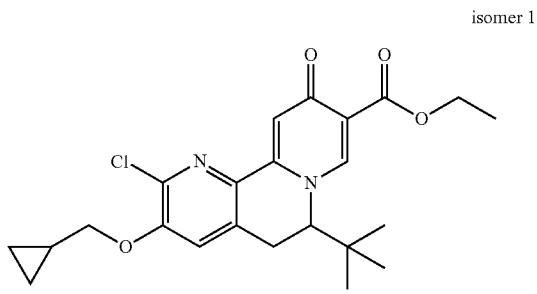 [SMILES: CCOC(=O)c1cn2c(cc1=O)-c1nc(Cl)c(OCC3CC3)cc1CC2C(C)(C)C]

isomer 1

Racemic ethyl 6-(tert-butyl)-2-chloro-3-(cyclopropyl-methoxy)-10-oxo-5,10-dihydro-6H-pyrido[1,2-h][1,7]naphthyridine-9-carboxylate (153 mg) was purified by chiral chromatography using the following conditions: Column=Chiralpak IC, 10 mm×250 mm (5 u); Mobile phase=95:5 MeCN/H$_2$O+0.1% formic acid; Flow rate=10 mL/min: Injection volume=300 uL (18 mg/mL conc.); Collection wavelength: 254 nm. Fractions were concentrated to give ethyl 6-(tert-butyl)-2-chloro-3-(cyclopropylmethoxy)-10-oxo-5,10-dihydro-6H-pyrido[1,2-h][1,7]naphthyridine-9-carboxylate (isomer 1) (48 mg). LCMS(ES$^+$)(m/z): 431, 433 (M+1).

Step 2: 6-(tert-Butyl)-2-chloro-3-(cyclopropyl-methoxy)-10-oxo-6,10-dihydro-5H-pyrido[1,2-h][1,7]naphthyridine-9-carboxylic acid (isomer 1)

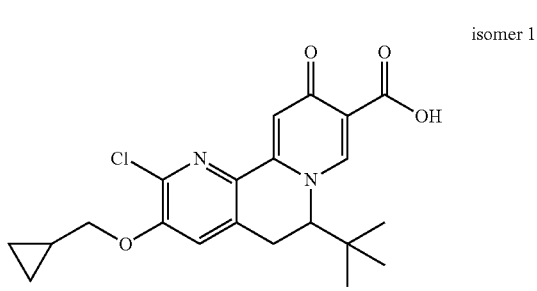 [SMILES: CC(C)(C)C1Cc2cc(OCC3CC3)c(Cl)nc2-c2cc(=O)c(C(=O)O)cn21]

isomer 1

A solution of lithium hydroxide monohydrate (38.8 mg, 0.925 mmol) in water (2 mL) was added to a solution of ethyl 6-(tert-butyl)-2-chloro-3-(cyclopropylmethoxy)-10-oxo-5,10-dihydro-6H-pyrido[1,2-h][1,7]naphthyridine-9-carboxylate (isomer 1) (48 mg, 0.092 mmol) in methanol (2 mL) and the mixture heated at 60° C. for 3 hours. The mixture was cooled to room temperature and acidified with 3 mL of 1 M hydrochloric acid. Solids were collected by filtration. The filtrate was injected onto a medium pressure reverse phase column. The collected solid was dissolved in DMF and injected onto the reverse phase column. The column was eluted (C18/acetonitrile/water/0.1% formic acid/10% to 100% gradient). Fractions were lyophilized to give 6-(tert-butyl)-2-chloro-3-(cyclopropylmethoxy)-10-oxo-5,10-dihydro-6H-pyrido[1,2-h][1,7]naphthyridine-9-carboxylic acid (isomer 1) (33 mg, 0.082 mmol, 89% yield) as a white powder. $^1$H NMR (400 MHz, DMSO-d$_6$) δ ppm 8.75 (br. s., 1H), 7.66 (s, 1H), 7.24 (br. s., 1H), 4.55-4.68 (m, 1H), 3.93-4.10 (m, 2H), 3.39-3.54 (m, 2H), 1.27 (d, J=5.08 Hz, 1H), 0.70 (s, 9H), 0.55-0.62 (m, 2H), 0.30-0.39 (m, 2H). LCMS(ES+)(m/z): 403, 405 (M+1).

Example 30-b (Compound 249 Isomer 2)

6-(tert-Butyl)-2-chloro-3-(cyclopropylmethoxy)-10-oxo-6,10-dihydro-5H-pyrido[1,2-h][1,7]naphthyridine-9-carboxylic acid (isomer 2)

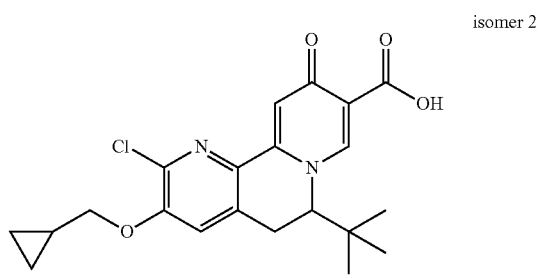 [SMILES: CC(C)(C)C1Cc2cc(OCC3CC3)c(Cl)nc2-c2cc(=O)c(C(=O)O)cn21]

isomer 2

Step 1: Ethyl 6-(tert-butyl)-2-chloro-3-(cyclopropyl-methoxy)-10-oxo-5,10-dihydro-6H-pyrido[1,2-h][1,7]naphthyridine-9-carboxylate (isomer 2)

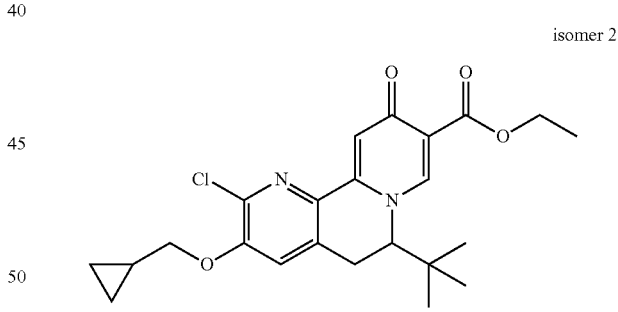

isomer 2

Racemic ethyl 6-(tert-butyl)-2-chloro-3-(cyclopropyl-methoxy)-10-oxo-5,10-dihydro-6H-pyrido[1,2-h][1,7]naphthyridine-9-carboxylate (153 mg) was purified by chiral chromatography using the following conditions: Column=Chiralpak IC, 10 mm×250 mm (5 u); Mobile phase=95:5 MeCN/H$_2$O+0.1% formic acid; Flow rate=10 mL/min: Injection volume=300 uL (18 mg/mL conc.); Collection wavelength: 254 nm. Fractions were concentrated to give ethyl 6-(tert-butyl)-2-chloro-3-(cyclopropylmethoxy)-10-oxo-5,10-dihydro-6H-pyrido[1,2-h][1,7]naphthyridine-9-carboxylate (isomer 2) (46 mg). LCMS(ES$^+$)(m/z): 431, 433 (M+1).

Step 2: 6-(tert-Butyl)-2-chloro-3-(cyclopropylmethoxy)-10-oxo-6,10-dihydro-5H-pyrido[1,2-h][1,7]naphthyridine-9-carboxylic acid (isomer 2)

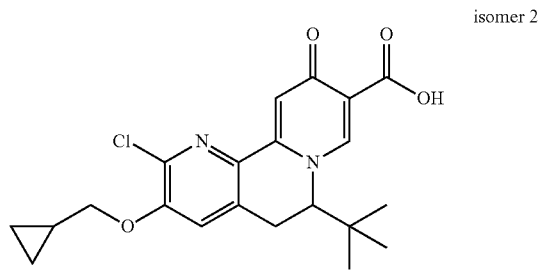

isomer 2

A solution of lithium hydroxide monohydrate (37.2 mg, 0.886 mmol) in water (2 mL) was added to a solution of ethyl 6-(tert-butyl)-2-chloro-3-(cyclopropylmethoxy)-10-oxo-5,10-dihydro-6H-pyrido[1,2-h][1,7]naphthyridine-9-carboxylate (isomer 2) (46 mg, 0.089 mmol) in methanol (2 mL) and the mixture heated at 60° C. for 3 hours. The mixture was allowed to cool to room temperature and was acidified with 3 mL of 1 M hydrochloric acid. Solids were collected by filtration. The filtrate was injected onto a medium pressure reverse phase column. The collected solid was dissolved in DMF and also injected onto the reverse phase column. The column was eluted (C18/acetonitrile/water/0.1% formic acid/10% to 100% gradient). Fractions were lyophilized to give 6-(tert-butyl)-2-chloro-3-(cyclopropylmethoxy)-10-oxo-5,10-dihydro-6H-pyrido[1,2-h][1,7]naphthyridine-9-carboxylic acid (isomer 2) (34 mg, 0.084 mmol, 95% yield) as a white powder. $^1$H NMR (400 MHz, DMSO-$d_6$) δ ppm 8.76 (s, 1H), 7.67 (s, 1H), 7.25 (s, 1H), 4.63 (d, J=6.64 Hz, 1H), 3.96-4.11 (m, 2H), 3.33-3.54 (m, 2H), 1.19-1.33 (m, 1H), 0.70 (s, 9H), 0.56-0.62 (m, 2H), 0.30-0.42 (m, 2H). LCMS(ES+)(m/z): 403, 405 (M+1).

Scheme 12 - Preparation of Compounds of Type YYYY (e.g. Compound 250, 251, 255 and 256)

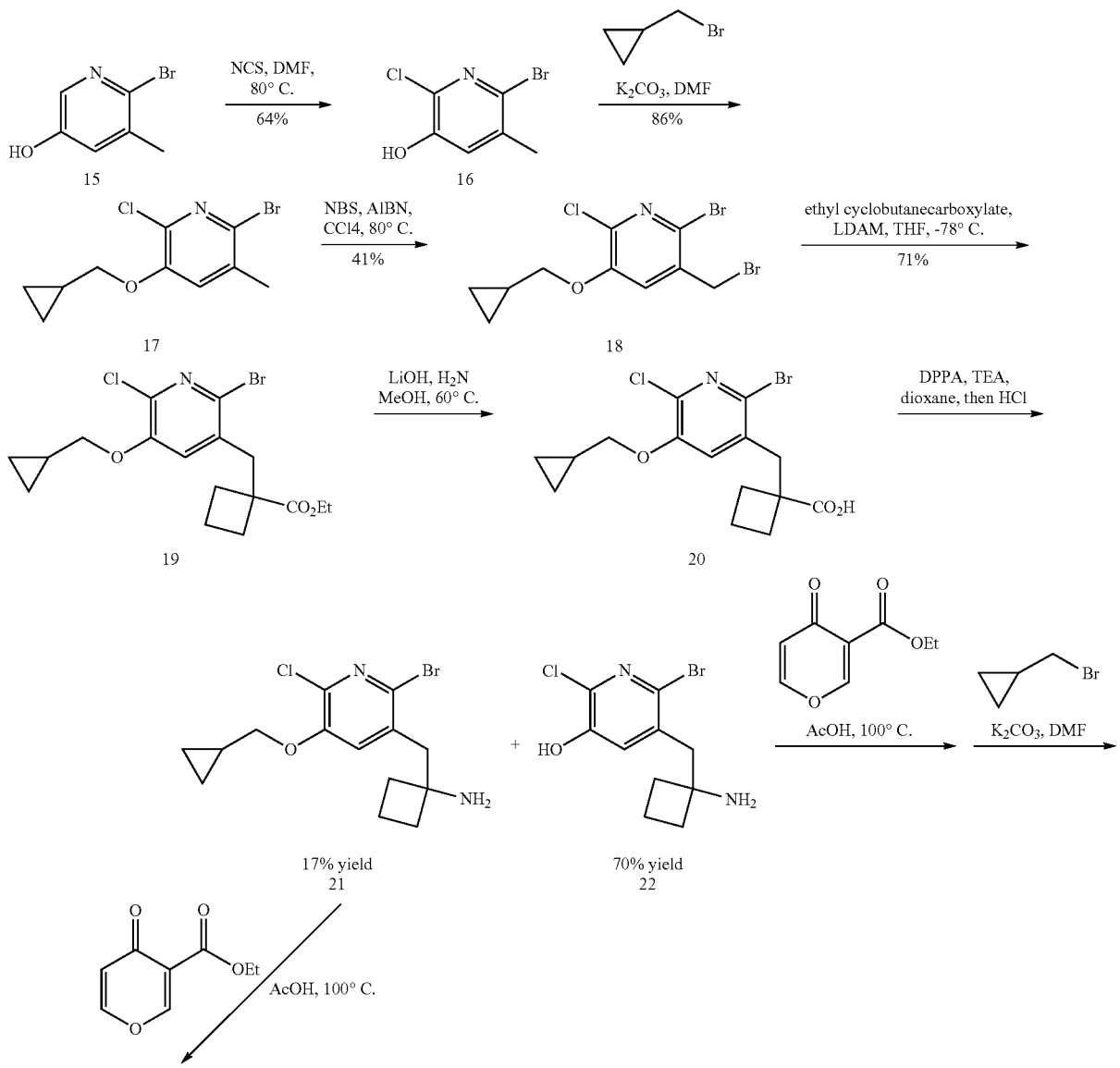

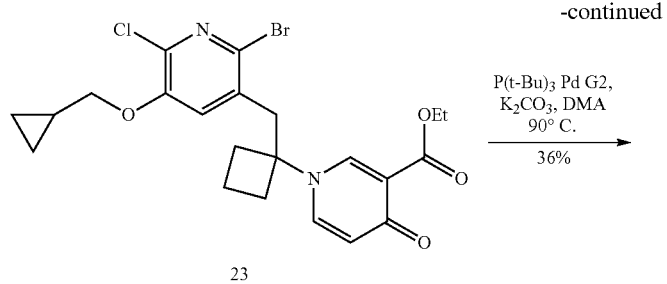

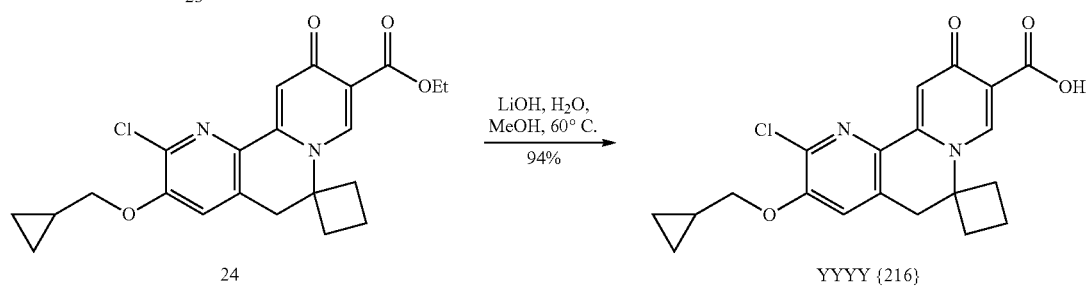

Example 31 (Compound 250)

2'-Chloro-3'-(cyclopropylmethoxy)-10'-oxo-5',10'-dihydrospiro[cyclobutane-1,6'-pyrido[1,2-h][1,7]naphthyridine]-9'-carboxylic acid

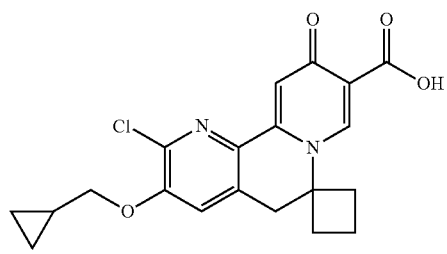 [SMILES: O=C(O)c1cn2c(cc1=O)-c1nc(Cl)c(OCC3CC3)cc1CC21CCC1]

Step 1: 6-Bromo-2-chloro-5-methylpyridin-3-ol

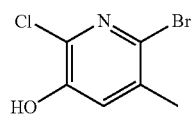

6-Bromo-5-methylpyridin-3-ol (10.4 g, 55.3 mmol) and NCS (8.12 g, 60.8 mmol) in N,N-dimethylformamide (DMF) (150 mL) were heated at 80° C. for 2 hours. The mixture was allowed to cool to room temperature, quenched with brine, and extracted 3 times with ethyl acetate. The combined organic layers were washed with 5% lithium chloride, washed with brine, dried over sodium sulfate, and concentrated. The residue was purified by silica chromatography eluting with a gradient of 0% to 50% ethyl acetate in hexanes. Fractions were concentrated to give 6-bromo-2-chloro-5-methylpyridin-3-ol (7.85 g, 35.3 mmol, 63.8% yield) as a white powder. LCMS(ES⁺)(m/z): 222, 224, 226 (M+1).

Step 2: 2-Bromo-6-chloro-5-(cyclopropylmethoxy)-3-methylpyridine

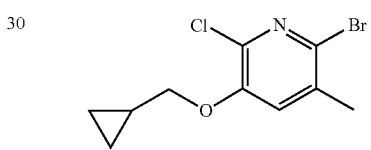

6-Bromo-2-chloro-5-methylpyridin-3-ol (1.1 g, 4.9 mmol), potassium carbonate (2.73 g, 19.8 mmol), and (bromomethyl)cyclopropane (1.01 mL, 10.4 mmol) in N,N-dimethylformamide (DMF) (10 mL) were stirred at room temperature overnight. The mixture was diluted with water and extracted 2 times with ethyl acetate. The combined organic layers were washed with 5% lithium chloride, washed with brine, dried over sodium sulfate, and concentrated to give 2-bromo-6-chloro-5-(cyclopropylmethoxy)-3-methylpyridine (1.18 g, 4.27 mmol, 86% yield) as a white solid. LCMS(ES⁺)(m/z): 276, 278, 280 (M+1).

Step 3: 2-Bromo-3-(bromomethyl)-6-chloro-5-(cyclopropylmethoxy)pyridine

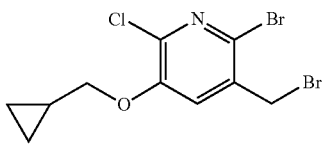 [SMILES: Clc1nc(Br)c(CBr)cc1OCC1CC1]

N-Bromosuccinimide (0.801 g, 4.50 mmol) and AIBN (0.049 g, 0.30 mmol) were added to a stirring solution of 2-bromo-6-chloro-5-(cyclopropylmethoxy)-3-methylpyridine (1.0 g, 3.0 mmol) in carbon tetrachloride (15 mL). The mixture was heated at 85° C. for 5 hours. Additional AIBN (0.049 g, 0.300 mmol) was added and the mixture allowed to heat overnight. The mixture was allowed to cool to room temperature and solids collected by filtration. The filtrate was quenched with water and extracted 2 times with dichloromethane. The combined organic layers were washed with brine, dried over sodium sulfate, and concentrated. The residue was purified by silica chromatography eluting with 10% ethyl acetate in hexanes. Fractions were concentrated to give 2-bromo-3-(bromomethyl)-6-chloro-5-(cyclopropylmethoxy)pyridine (730 mg, 1.23 mmol, 60% pure, 41% yield). The material was ~60:40 mixture of desired product/starting material. LCMS(ES⁺)(m/z): 354, 356, 358 (M+1).

Step 4: Ethyl 1-((2-bromo-6-chloro-5-(cyclopropylmethoxy)pyridin-3-yl)methyl)cyclobutanecarboxylate

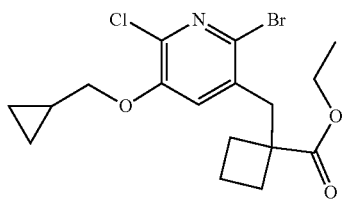 [SMILES: CCOC(=O)C1(Cc2cc(OCC3CC3)c(Cl)nc2Br)CCC1]

n-Butyllithium (2.5 M in hexanes) (1.04 mL, 2.59 mmol) was added dropwise to a −78° C. solution of diisopropylamine (0.369 mL, 2.59 mmol) in tetrahydrofuran (THF) (10 mL). The mixture was allowed to warm to room temperature and stirred for 15 minutes. The mixture was cooled to −78° C. before ethyl cyclobutanecarboxylate (0.317 mL, 2.46 mmol) was added dropwise. The mixture was warmed to 0° C. and stirred for 15 minutes. A solution of 2-bromo-3-(bromomethyl)-6-chloro-5-(cyclopropylmethoxy)pyridine (730 mg, 1.23 mmol) in tetrahydrofuran (THF) (3.33 mL) was added dropwise. The mixture was stirred an additional 10 minutes at 0° C. and then quenched with saturated ammonium chloride. The mixture was extracted 2 times with ethyl acetate. The combined organic layers were washed with brine, dried over sodium sulfate, and concentrated. The residue was purified by medium pressure reverse phase chromatography (C18/acetonitrile/water/0.1% formic acid/10% to 100% gradient). Fractions were concentrated to give ethyl 1-((2-bromo-6-chloro-5-(cyclopropylmethoxy)pyridin-3-yl)methyl)cyclobutane-1-carboxylate (350 mg, 0.869 mmol, 70.5% yield) as an oil. LCMS(ES⁺)(m/z): 402, 404, 406 (M+1).

Step 5: 1-((2-Bromo-6-chloro-5-(cyclopropylmethoxy)pyridin-3-yl)methyl)cyclobutanecarboxylic acid

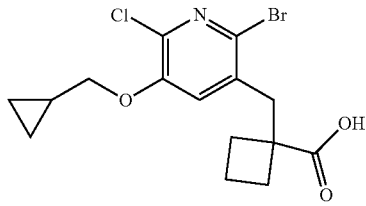 [SMILES: O=C(O)C1(Cc2cc(OCC3CC3)c(Cl)nc2Br)CCC1]

A solution of lithium hydroxide monohydrate (365 mg, 8.69 mmol) in water (3 mL) was added to a solution of ethyl 1-((2-bromo-6-chloro-5-(cyclopropylmethoxy)pyridin-3-yl)methyl)cyclobutane-1-carboxylate (350 mg, 0.869 mmol) in 1,4-dioxane (5 mL) and the mixture heated at 60° C. for 4 hours. The mixture was allowed to cool to room temperature, quenched with saturated ammonium chloride and extracted 3 times with ethyl acetate. The combined organic layers were washed with brine, dried over sodium sulfate, and concentrated to give 1-((2-bromo-6-chloro-5-(cyclopropylmethoxy)pyridin-3-yl)methyl)cyclobutane-1-carboxylic acid (325 mg, 0.867 mmol, quantitative) as a white solid. LCMS(ES+)(m/z): 374, 376, 378 (M+1).

Step 6: 1-((2-Bromo-6-chloro-5-(cyclopropylmethoxy)pyridin-3-yl)methyl)cyclobutanamine and 5-((1-aminocyclobutyl)methyl)-6-bromo-2-chloropyridin-3-ol

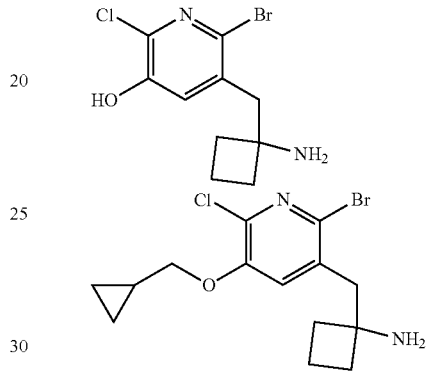

Diphenyl phosphorazidate (0.394 mL, 1.83 mmol) was added dropwise to a 0° C. stirring mixture of 1-((2-bromo-6-chloro-5-(cyclopropylmethoxy)pyridin-3-yl)methyl)cyclobutane-1-carboxylic acid (311 mg, 0.830 mmol) and triethylamine (0.255 mL, 1.83 mmol) in toluene (10 mL). The mixture was allowed to warm to room temperature and stirred for 15 minutes before being heated at 80° C. for 1 hour. LC-MS showed clean conversion to 2-bromo-6-chloro-5-(cyclopropylmethoxy)-3-((1-isocyanatocyclobutyl)methyl)pyridine. The mixture was allowed to cool to room temperature before a 5N hydrogen chloride (5 mL, 25 mmol) and 1,4-dioxane (10 mL) were added. The mixture was heated at 80° C. with vigorous stirring for 3 hours. The mixture was concentrated and the residue purified by medium pressure reverse phase chromatography (C18/acetonitrile/water/0.1% formic acid/10% to 100% gradient). Two sets of fractions were concentrated separately to give the following products:

5-((1-aminocyclobutyl)methyl)-6-bromo-2-chloropyridin-3-ol (170 mg, 0.583 mmol, 70.2% yield). LCMS(ES⁺)(m/z): 291, 293, 295 (M+1)

1-((2-bromo-6-chloro-5-(cyclopropylmethoxy)pyridin-3-yl)methyl)cyclobutan-1-amine (50 mg, 0.145 mmol, 17.43% yield). LCMS(ES⁺)(m/z): 345, 347, 349 (M+1).

Step 7: Ethyl 4-oxo-4H-pyran-3-carboxylate

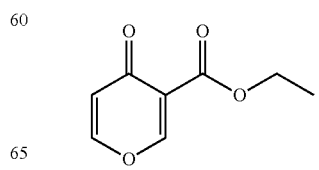

Ethyl formate (23.6 ml, 292 mmol) was slowly added to a suspension of KOtBu (6.06 g, 54.0 mmol) in 50 mL of THF at 0° C. The reaction mixture for stirred for 15 mins at 0° C. and a pre-cooled (0° C.) solution of ethyl 2-((dimethylamino)methylene)-3-oxobutanoate (5 g, 27.0 mmol) in 45 mL of THF was added by cannula transfer. After addition was complete, the solution was removed from the cooling bath, stirred at rt overnight, and quenched by addition of 1M aqueous HCl (80 mL). The mixture was extracted with EtOAc (3×25 mL) and CH$_2$Cl$_2$ (5×25 mL). The organic layers were pooled, dried (Na$_2$SO$_4$), filtered, evaporated, and purified by silica gel chromatography (0-100% EtOAc/hexanes) to afford ethyl 4-oxo-4H-pyran-3-carboxylate (1.8994 g, 41.8% yield) as a brown oil. $^1$H NMR (400 MHz, CDCl$_3$) δ ppm 8.47 (d, J=0.78 Hz, 1H), 7.72 (dd, J=5.86, 0.78 Hz, 1H), 6.47 (d, J=5.86 Hz, 1H), 4.37 (q, J=7.29 Hz, 2H), 1.38 (t, J=7.03 Hz, 3H). LCMS (ESI) m/z: 169.05 (M+1)$^+$.

Step 8: Ethyl 1-(1-((2-bromo-6-chloro-5-(cyclopropylmethoxy)pyridin-3-yl)methyl)cyclobutyl)-4-oxo-1,4-dihydropyridine-3-carboxylate

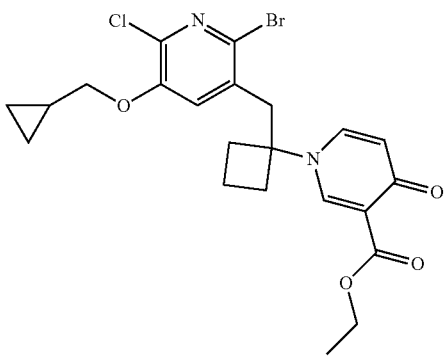 [SMILES: CCOC(=O)c1cn(C2(Cc3cc(OCC4CC4)c(Cl)nc3Br)CCC2)ccc1=O]

5-((1-Aminocyclobutyl)methyl)-6-bromo-2-chloropyridin-3-ol (170 mg, 0.583 mmol) and ethyl 4-oxo-4H-pyran-3-carboxylate (98 mg, 0.58 mmol) in acetic acid (5 mL) were stirred at 100° C. for 4 hours. The mixture was allowed to cool to room temperature and concentrated. The residue was diluted in toluene and the mixture concentrated to remove remaining acetic acid. The residue was dissolved in N,N-dimethylformamide (DMF) (2 mL) before potassium carbonate (322 mg, 2.33 mmol) and (bromomethyl)cyclopropane (0.113 mL, 1.17 mmol) were added. The mixture was stirred at room temperature for 6 hours to give a crude mixture of ethyl 1-(1-((2-bromo-6-chloro-5-(cyclopropylmethoxy)pyridin-3-yl)methyl)cyclobutyl)-4-oxo-1,4-dihydropyridine-3-carboxylate in DMF. In a separate reaction flask, 1-((2-bromo-6-chloro-5-(cyclopropylmethoxy)pyridin-3-yl)methyl)cyclobutan-1-amine (50 mg, 0.145 mmol) and ethyl 4-oxo-4H-pyran-3-carboxylate (24.3 mg, 0.145 mmol) in acetic acid (1 mL) were stirred at 100° C. overnight. The mixture was allowed to cool to room temperature and then combined with the former crude mixture of ethyl 1-(1-((2-bromo-6-chloro-5-(cyclopropylmethoxy)pyridin-3-yl)methyl)cyclobutyl)-4-oxo-1,4-dihydropyridine-3-carboxylate in DMF disclosed above. The mixture was diluted with water and extracted 2 times with ethyl acetate. The combined organic layers were washed with 5% lithium chloride, washed with brine, dried over sodium sulfate, and concentrated. The residue was purified by medium pressure reverse phase chromatography (C18/acetonitrile/water/0.1% formic acid/10% to 100% gradient). Fractions were concentrated until cloudy. Acetonitrile was added to fully dissolve and the solution lyophilized to give ethyl 1-(1-((2-bromo-6-chloro-5-(cyclopropylmethoxy)pyridin-3-yl)methyl) cyclobutyl)-4-oxo-1,4-dihydropyridine-3-carboxylate (100 mg, 0.202 mmol, 26% yield) as a pale yellow solid. LCMS(ES$^+$)(m/z): 495, 497, 499 (M+1).

Step 9: Ethyl 2'-chloro-3'-(cyclopropylmethoxy)-10'-oxo-5',10'-dihydrospiro[cyclobutane-1,6'-pyrido[1,2-h][1,7]naphthyridine]-9'-carboxylate

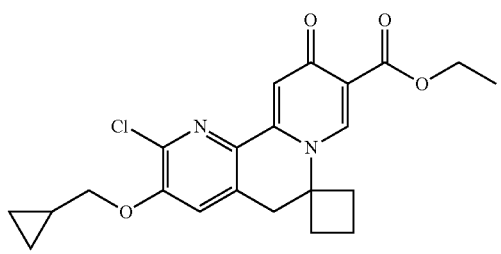 [SMILES: CCOC(=O)c1cn2c(cc1=O)-c1nc(Cl)c(OCC3CC3)cc1CC21CCC1]

A reaction vial containing a stir bar, ethyl 1-(1-((2-bromo-6-chloro-5-(cyclopropylmethoxy)pyridin-3-yl)methyl)cyclobutyl)-4-oxo-1,4-dihydropyridine-3-carboxylate (100 mg, 0.202 mmol), potassium acetate (39.6 mg, 0.403 mmol), and chloro[(tri-tert-butylphosphine)-2-(2-aminobiphenyl)] palladium(II) (20.7 mg, 0.040 mmol) was purged with nitrogen for 15 minutes. N,N-Dimethylacetamide (DMA) (2 mL) was purged with nitrogen for 5 minutes before being added to the reaction vial. The reaction vial was placed into a heating block that was preheated to 90° C. and the mixture stirred overnight. The reaction mixture was allowed to cool to room temperature, filtered through a cotton plug, and purified by reverse phase medium pressure chromatography (C18/acetonitrile/water/0.1% formic acid/10% to 100% gradient). Fractions were lyophilized to give ethyl 2'-chloro-3'-(cyclopropylmethoxy)-10'-oxo-5',10'-dihydrospiro[cyclobutane-1,6'-pyrido[1,2-h][1,7]naphthyridine]-9'-carboxylate (30 mg, 0.072 mmol, 35.9% yield) as an off-white solid. LCMS(ES$^+$)(m/z): 415, 417 (M+1).

Step 10: 2'-Chloro-3'-(cyclopropylmethoxy)-10'-oxo-5',10'-dihydrospiro[cyclobutane-1,6'-pyrido[1,2-h][1,7]naphthyridine]-9'-carboxylic acid

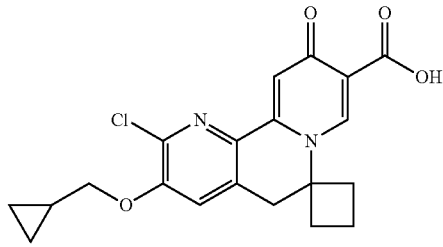 [SMILES: O=C(O)c1cn2c(cc1=O)-c1nc(Cl)c(OCC3CC3)cc1CC21CCC1]

A solution of lithium hydroxide monohydrate (25.2 mg, 0.600 mmol) in water (1 mL) was added to a solution of ethyl 2'-chloro-3'-(cyclopropylmethoxy)-10'-oxo-5',10'-dihydrospiro[cyclobutane-1,6'-pyrido[1,2-h][1,7]naphthyridine]-9'-carboxylate (30 mg, 0.060 mmol) in methanol (1 mL) and the mixture heated at 60° C. for 3 hours. The mixture was allowed to cool to room temperature and acidified with 1M hydrochloric acid. The mixture was diluted with DMF to dissolve the sample and then purified by medium pressure reverse phase chromatography (C18/acetonitrile/water/0.1% formic acid/10% to 100% gradient). Combined fractions were lyophilized to give 2'-chloro-3'-(cyclopropylmethoxy)-10'-oxo-5',10'-dihydrospiro[cyclobutane-1,6'-pyrido[1,2-h][1,7]naphthyridine]-9'-carboxylic acid (22 mg, 0.056 mmol, 94% yield) as an off-white powder. ¹H NMR (400 MHz, DMSO-de) δ ppm 8.79 (s, 1H), 7.68 (s, 1H), 7.27 (s, 1H), 4.07 (d, J=7.03 Hz, 2H), 3.44 (s, 2H), 2.61-2.75 (m, 2H), 2.00-2.12 (m, 2H), 1.78-1.95 (m, 2H), 1.25-1.37 (m, 1H), 0.57-0.68 (m, 2H), 0.33-0.40 (m, 2H). LCMS(ES⁺)(m/z): 387, 389 (M+1).

Example 32 (Compound 251)

2',3'-Dimethoxy-10'-oxo-5',10'-dihydrospiro[cyclobutane-1,6'-pyrido[1,2-h][1,7]naphthyridine]-9'-carboxylic acid

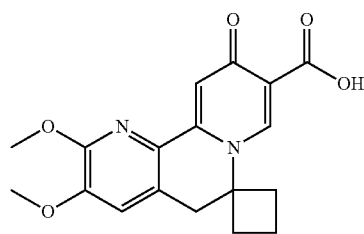 [SMILES: COc1cc2c(nc1OC)-c1cc(=O)c(C(=O)O)cn1C1(CCC1)C2]

Step 1: 2',3'-Dimethoxy-10'-oxo-5',10'-dihydrospiro[cyclobutane-1,6'-pyrido[1,2-h][1,7]naphthyridine]-9'-carboxylic acid

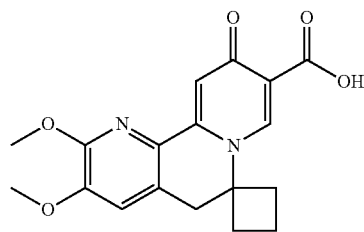 [SMILES: COc1cc2c(nc1OC)-c1cc(=O)c(C(=O)O)cn1C1(CCC1)C2]

2'-Chloro-3'-(cyclopropylmethoxy)-10'-oxo-5',10'-dihydrospiro[cyclobutane-1,6'-pyrido[1,2-h][1,7]naphthyridine]-9'-carboxylic acid (10 mg, 0.026 mmol) and sodium methoxide (0.5M in methanol) (0.517 mL, 0.259 mmol) were heated at 65° C. for 2 hours. Dioxane (0.5 mL) was added and the mixture heated to 100° C. The vial was left uncapped initially so that most the methanol distilled off. The reaction vial was capped and stirred at 100° C. for 1.5 hours. The mixture was allowed to cool to room temperature, acidified with 1N HCl, and purified by medium pressure reverse phase chromatography (C18/acetonitrile/water/0.1% formic acid/10% to 100% gradient). Fractions lyophilized to give 2',3'-dimethoxy-10'-oxo-5',10'-dihydrospiro[cyclobutane-1,6'-pyrido[1,2-h][1,7]naphthyridine]-9'-carboxylic acid (1.5 mg, 4.03 μmol, 15.6% yield) as a white solid. ¹H NMR (400 MHz, CHLOROFORM-d) δ ppm 8.90 (s, 1H), 7.65 (s, 1H), 6.93 (s, 1H), 4.08 (s, 3H), 3.97 (s, 3H), 3.26 (s, 2H), 2.57-2.75 (m, 2H), 2.15-2.29 (m, 2H), 2.00-2.12 (m, 2H). LCMS(ES⁻)(m/z): 341 (M−1)−.

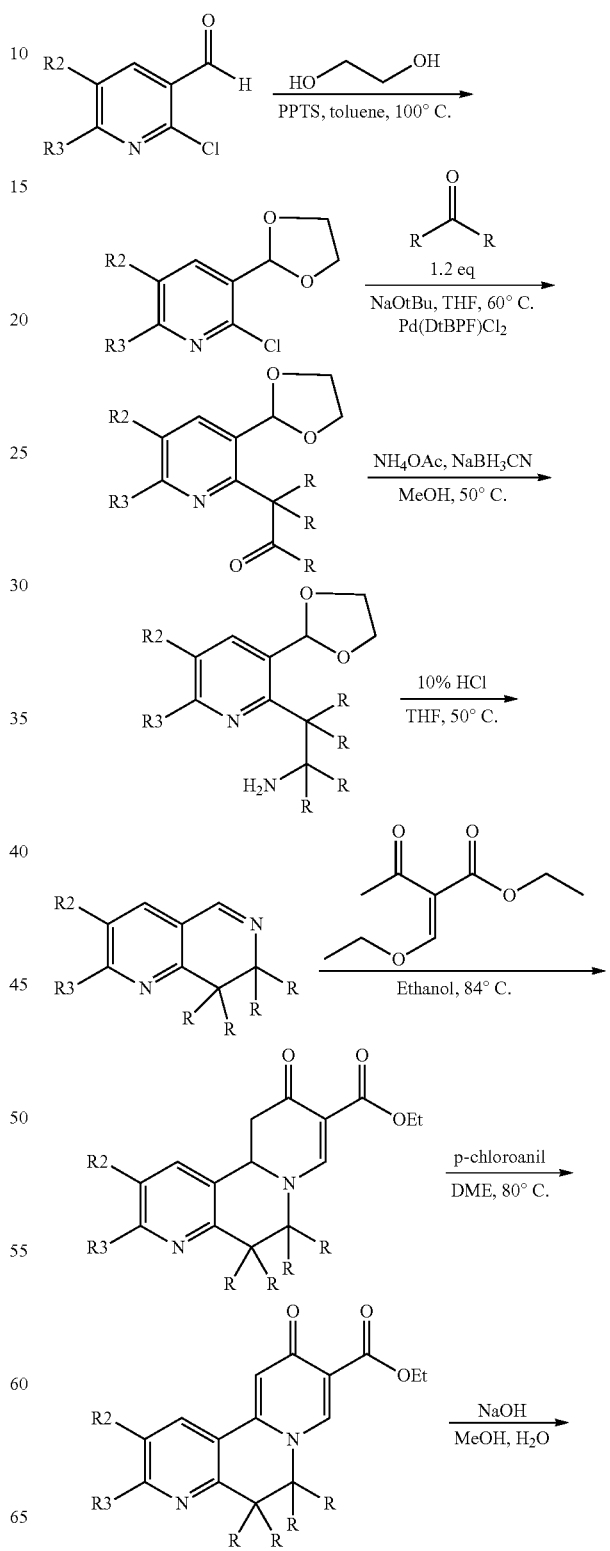

Scheme 13-Preparation of Compounds Such as Example 33 (Compound 252)

149
-continued
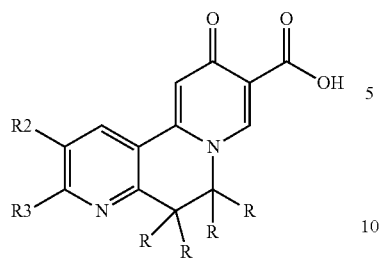
Scheme 14 - Preparation of Example 33 (Compound 252)
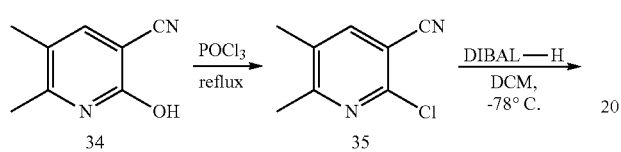
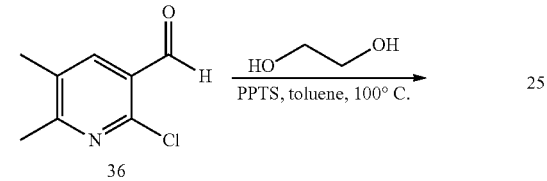
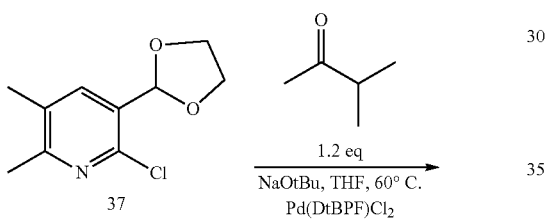
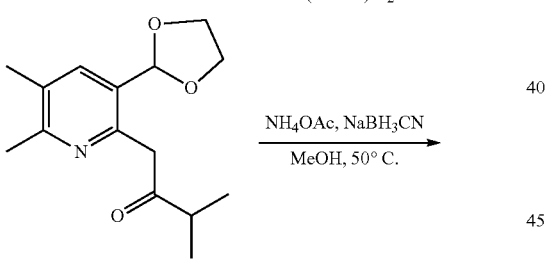
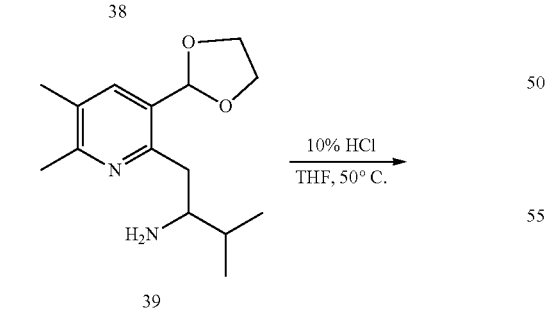
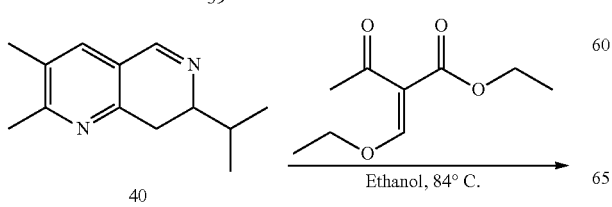
150
-continued
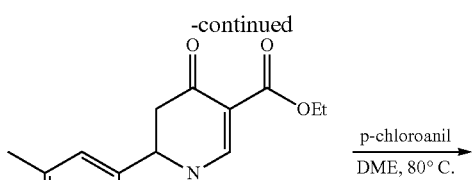
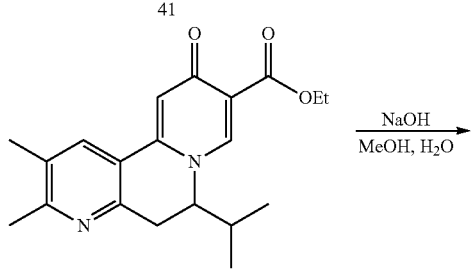
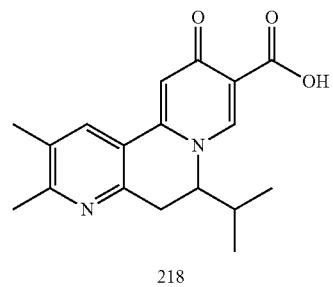
Example 33 (Compound 252)
6-Isopropyl-2,3-dimethyl-10-oxo-5,10-dihydro-6H-pyrido[2,1-f][1,6]naphthyridine-9-carboxylic acid
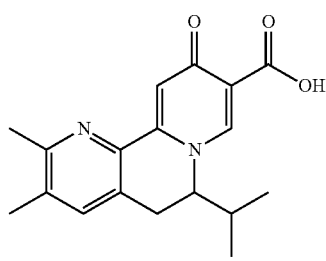 [SMILES: Cc1cc2c(nc1C)-c1cc(=O)c(C(=O)O)cn1C(C(C)C)C2]
Step 1: 2-Chloro-5,6-dimethylnicotinonitrile
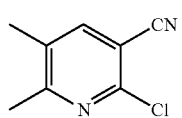
A mixture of 2-hydroxy-5,6-dimethylnicotinonitrile (10 g, 67.5 mmol) in POCl$_3$ (100 ml) was refluxed for 10 h and was concentrated. The residue was basified with 10% NaOH aqueous solution and filtered. The filter cake was washed with H$_2$O. The filtrate was extracted with DCM (200 mL×2). The organic layers were combined, washed with brine (200 mL), dried over anhydrous Na$_2$SO$_4$ and concentrated to give 9.8 g crude 2-chloro-5,6-dimethylnicotinonitrile as a yellow solid. LCMS (ESI) m/z: 167.1, 169.1 (M/M+2)$^+$.

Step 2: 2-Chloro-5,6-dimethylnicotinaldehyde

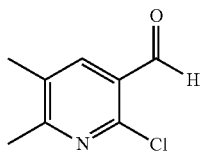

To a −78° C. solution of 2-chloro-5,6-dimethylnicotinonitrile (1.6 g, 9.6 mmol) in DCM (20 ml), DIBAL-H (5.76 ml, 2 mol/L in hexane) was added. The resulting mixture was stirred at the same temperature for 2 h. The reaction was quenched by adding ice water. Then the mixture was acidified with 1N HCl to pH=~6 and extracted with DCM (100 mL×2). The organic layers were combined, washed with brine (50 mL), dried over anhydrous Na$_2$SO$_4$ and concentrated to give 1.5 g crude 2-chloro-5,6-dimethylnicotinaldehyde as a white solid. LCMS (ESI) m/z: 170.1, 172.1 (M/M+2)$^+$.

Step 3: 2-Chloro-3-(1,3-dioxolan-2-yl)-5,6-dimethylpyridine

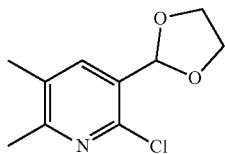

A mixture of 2-chloro-5,6-dimethylnicotinaldehyde (1.5 g, 8.84 mmol), ethane-1,2-diol (1.1 g, 17.68 mmol), PPTS (444.3 mg, 1.768 mmol) in toluene (20 ml) was refluxed for 12 h. The reaction mixture was cooled to r. t. and extracted with EtOAc (100 mL×2). The organic layers were combined, washed with aqueous NaHCO$_3$ solution (50 mL), dried over anhydrous Na$_2$SO$_4$ and concentrated. The residue was purified by flash column chromatography (silica gel, 0-50% EtOAc in PE) to afford 2-chloro-3-(1,3-dioxolan-2-yl)-5,6-dimethylpyridine (1.35 g, 71.5% yield) as a colorless oil. LCMS (ESI) m/z: 214.1, 216.1 (M/M+2)$^+$.

Step 4: 1-(3-(1,3-Dioxolan-2-yl)-5,6-dimethylpyridin-2-yl)-3-methylbutan-2-one

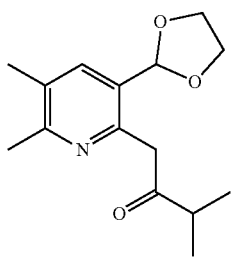 [SMILES: Cc1cc(C2OCCO2)c(CC(=O)C(C)C)nc1C]

A mixture of 2-chloro-3-(1,3-dioxolan-2-yl)-5,6-dimethylpyridine (1.35 g, 6.32 mmol), 3-methylbutan-2-one (653 mg, 7.58 mmol), Pd(dtbpf)Cl$_2$ (411.9 mg, 0.632 mmol) and t-BuONa (1.52 g, 15.8 mmol) in THF (20 ml) was heated at 60° C. for 3 h. The reaction mixture was cooled to r. t. and filtered. The filtrate was concentrated and the residue was purified by the flash column chromatography (silica gel, 0-70% EtOAc in PE) to afford 1-(3-(1,3-dioxolan-2-yl)-5,6-dimethylpyridin-2-yl)-3-methylbutan-2-one (231 mg, 14% yield) as a yellow solid. LCMS (ESI) m/z: 264.3 (M+1)$^+$.

Step 5: 1-(3-(1,3-Dioxolan-2-yl)-5,6-dimethylpyridin-2-yl)-3-methylbutan-2-amine

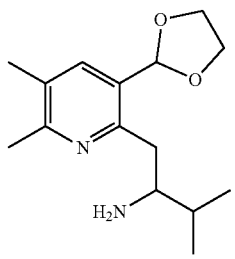 [SMILES: Cc1cc(C2OCCO2)c(CC(N)C(C)C)nc1C]

To a solution of 1-(3-(1,3-dioxolan-2-yl)-5,6-dimethylpyridin-2-yl)-3-methylbutan-2-one (231 mg, 0.878 mmol) in MeOH (10 ml) was added NH$_4$OAc (683.1 mg, 8.78 mmol) at room temperature. After the mixture being stirred for 30 mins, NaBH$_3$CN (82.8 mg, 1.317 mmol) was added to the mixture at 0° C. Then the resulting mixture was stirred at 50° C. for 10 h. The reaction mixture was cooled to r. t. and concentrated. The residue was diluted with H$_2$O (20 ml), basified to ph ~10 with 10% NaOH solution. The aqueous mixture was extracted with DCM (2×). The organic layers were combined, washed with brine (30 ml), dried over anhydrous Na$_2$SO$_4$ and concentrated under reduced pressure to afford 236 mg crude 1-(3-(1,3-dioxolan-2-yl)-5,6-dimethylpyridin-2-yl)-3-methylbutan-2-amine. LCMS (ESI) m/z: 265.3 (M+1)$^+$.

Step 6: 7-Isopropyl-2,3-dimethyl-7,8-dihydro-1,6-naphthyridine

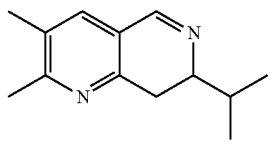

To a solution of 1-(3-(1,3-dioxolan-2-yl)-5,6-dimethylpyridin-2-yl)-3-methylbutan-2-amine (70 mg, 0.264 mmol) in THF (10 mL), 10% HCl aqueous solution (2 mL) was added. The resulting mixture was heated at 50° C. for 10 h. After being cooled to rt, the mixture was concentrated. The residue was purified by column chromatography (silica gel, 0-10% MeOH in DCM) to give 7-isopropyl-2,3-dimethyl-7,8-dihydro-1,6-naphthyridine (20 mg, 37.3% yield). LCMS (ESI) m/z: 203.27 (M+1)$^+$.

Step 7: Ethyl 6-isopropyl-2,3-dimethyl-10-oxo-5,10,11,11a-tetrahydro-6H-pyrido[2,1-f][1,6]naphthyridine-9-carboxylate

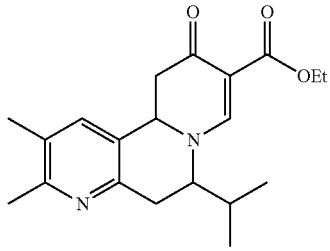 [SMILES: CCOC(=O)C1=CN2C(CC1=O)c1cc(C)c(C)nc1CC2C(C)C]

A solution of 7-isopropyl-2,3-dimethyl-7,8-dihydro-1,6-naphthyridine (20 mg, 0.099 mmol) and ethyl 2-(ethoxymethylene)-3-oxo-butanoate (55.86 mg, 0.3 mmol) in EtOH (5 mL) was heated at 85° C. for 10 h. After being cooled to room temperature, the mixture was concentrated. The residue was purified by column chromatography (silica gel, 0-10% MeOH in DCM) to give ethyl 6-isopropyl-2,3-dimethyl-10-oxo-5,10,11,11a-tetrahydro-6H-pyrido[2,1-f][1,6]naphthyridine-9-carboxylate (20 mg, 58.9% yield). LCMS (ESI) m/z: 343.2 (M+1)+.

Step 8: Ethyl 6-isopropyl-2,3-dimethyl-10-oxo-5,10-dihydro-6H-pyrido[2,1-f][1,6]naphthyridine-9-carboxylate

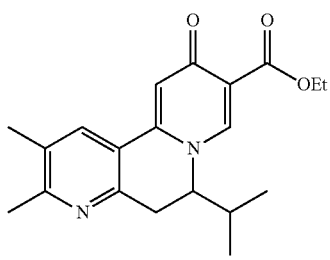 [SMILES: CCOC(=O)c1cn2c(cc1=O)-c1cc(C)c(C)nc1CC2C(C)C]

To a solution of ethyl 6-isopropyl-2,3-dimethyl-10-oxo-5,10,11,11a-tetrahydro-6H-pyrido[2,1-f][1,6]naphthyridine-9-carboxylate (20 mg, 0.058 mmol) in DME (5 mL) was added p-chloranil (12.3 mg, 0.05 mmol). The mixture was heated at 80° C. for 3 h. After being cooled to r. t., the mixture was concentrated. The residue was purified by column chromatography (silica gel, 0-10% MeOH in DCM) to afford ethyl 6-isopropyl-2,3-dimethyl-10-oxo-5,10-dihydro-6H-pyrido[2,1-f][1,6]naphthyridine-9-carboxylate (15 mg, 76% yield). LCMS (ESI) m/z: 341.2 (M+1)+.

Step 9: 6-Isopropyl-2,3-dimethyl-10-oxo-5,10-dihydro-6H-pyrido[2,1-f][1,6]naphthyridine-9-carboxylic acid

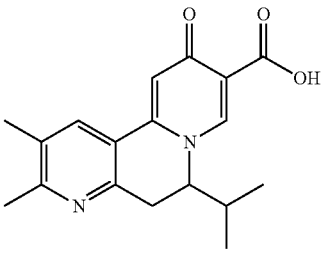 [SMILES: Cc1cc2c(nc1C)CC(C(C)C)n1cc(C(=O)O)c(=O)cc1-2]

To a solution of ethyl 6-isopropyl-2,3-dimethyl-10-oxo-5,10-dihydro-6H-pyrido[2,1-f][1,6]naphthyridine-9-carboxylate (15 mg, 0.044 mmol) in MeOH (5 ml), NaOH (7 mg, 0.176 mmol) dissolved in H₂O (1 ml) was added. The resulting mixture was stirred at room temperature for 2 h. The reaction mixture was acidified to ph ~5 with 1N HCl. Then the mixture was diluted with EtOAc (20 mL) and H₂O (20 mL), and then extracted with EtOAc (20 mL×2). The combined organic layers were dried over anhydrous Na₂SO₄ and concentrated. The residue was purified by reverse phase HPLC (C18 column, 5%-100% MeCN in H₂O, with 0.1% formic acid in H₂O) to give 6-isopropyl-2,3-dimethyl-10-oxo-5,10-dihydro-6H-pyrido[2,1-f][1,6]naphthyridine-9-carboxylic acid (5 mg, 36.3% yield) as a white solid. $^1$H NMR (400 MHz, DMSO-d₆) b 8.87 (s, 1H), 8.25 (s, 1H), 7.43 (s, 1H), 4.63-4.58 (m, 1H), 3.56-3.50 (m, J=16.8, 5.3 Hz, 1H), 3.18 (d, J=16.6 Hz, 1H), 2.48 (s, 3H), 2.31 (s, 3H), 1.64-1.57 (m, 1H), 0.84 (d, J=6.6 Hz, 3H), 0.69 (d, J=6.7 Hz, 3H). LCMS (ESI) m/z: 313.2 (M+1)$^+$.

Example 34 (Compound 253)

2-Chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (racemic cis)

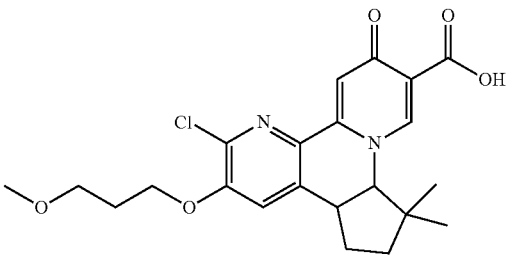 [SMILES: COCCCOc1cc2c(nc1Cl)-c1cc(=O)c(C(=O)O)cn1C1C2CCC1(C)C]

Step 1: 5-(6-Chloro-5-methoxypyridin-3-yl)-2,2-dimethylcyclopentanone

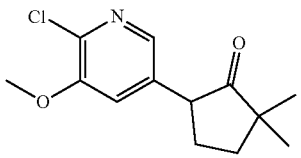

A flask was charged with a stir bar, 5-bromo-2-chloro-3-methoxypyridine (9.9 g, 44 mmol), tris(dibenzylideneacetone)dipalladium(0) (0.611 g, 0.668 mmol), xantphos (0.695 g, 1.202 mmol), and sodium tert-butoxide (7.5 g, 78 mmol). The flask was purged with a stream of nitrogen before 2,2-dimethylcyclopentan-1-one (8.38 ml, 66.8 mmol) in tetrahydrofuran (THF) (200 ml) was added. The mixture was heated to reflux for 3 hours. The mixture was allowed to cool to room temperature, filtered, and the filter cake washed with ethyl acetate. The filtrate was diluted with additional ethyl acetate, washed with brine, concentrated, and the residue purified by silica chromatography eluting with a gradient of 0% to 30% ethyl acetate in hexanes. Fractions were concentrated to give 5-(6-chloro-5-methoxypyridin-3-yl)-2,2-dimethylcyclopentan-1-one (4.6 g, 18 mmol, 41% yield) as an oil. $^1$H NMR (400 MHz, CHLOROFORM-d) δ ppm 7.82 (d, J=1.56 Hz, 1H), 7.13 (d, J=1.95 Hz, 1H), 3.91 (s, 3H), 3.36-3.47 (m, 1H), 2.45 (m, 1H), 1.96-2.17 (m, 2H), 1.79-1.92 (m, 1H), 1.18 (s, 3H), 1.07 (s, 3H). LCMS(ES$^+$)(m/z): 254.2 (M+1).

Step 2: 5-(6-Chloro-5-methoxypyridin-3-yl)-2,2-dimethylcyclopentanamine (cis/trans isomers)

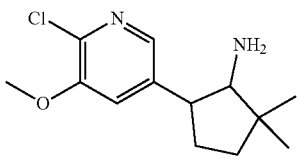

A mixture of 5-(6-chloro-5-methoxypyridin-1-yl)-2,2-dimethylcyclopentan-1-one (4.6 g, 18 mmol) and ammonium acetate (21 g, 270 mmol) in methanol (75 mL) were stirred at room temperature for 1 hour. Sodium cyanoborohydride (2.28 g, 36.3 mmol) was added and the mixture heated at 60° C. overnight and then at 65° C. for an additional 24 hours. The mixture was allowed to cool to room temperature, concentrated to ~20 mL, quenched with 1M sodium hydroxide, and extracted 3 times with 2-methyltetrahydrofuran. The combined organic layers were washed with brine, dried over sodium sulfate, and concentrated. The residue was purified by medium pressure reverse phase chromatography (C18/acetonitrile/water/0.1% formic acid/0% to 100% gradient). Fractions were concentrated to give 5-(6-chloro-5-methoxypyridin-3-yl)-2,2-dimethylcyclopentan-1-amine (2.63 g, 10.3 mmol, 57% yield) as a mixture of cis/trans isomers. LCMS(ES$^+$)(m/z): 255.2 (M+1).

Step 3: 5-(2-Amino-3,3-dimethylcyclopentyl)-2-chloropyridin-3-ol (cis/trans isomers)

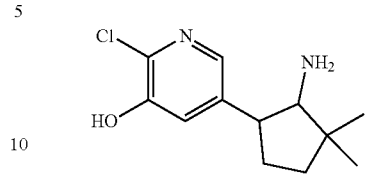

Boron tribromide (4.82 mL, 51.0 mmol) was added slowly dropwise to a vigorously stirring solution of 5-(6-chloro-5-methoxypyridin-3-yl)-2,2-dimethylcyclopentan-1-amine (2.6 g, 10.2 mmol) (cis/trans isomers). The mixture was heated at 70° C. overnight. The mixture was allowed to cool to room temperature and then cooled to 0° C. The mixture was carefully quenched with slow addition of methanol. An additional 50 mL of methanol was added and the mixture stirred for 30 minutes before being concentrated. The residue was purified by medium pressure reverse phase chromatography (C18/acetonitrile/water/0.1% formic acid/ 0% to 100% gradient). Fractions were lyophilized to give 5-(2-amino-3,3-dimethylcyclopentyl)-2-chloropyridin-3-ol (cis/trans isomers) (2.17 g, 9.01 mmol, 88% yield) as a white solid. LCMS(ES$^+$)(m/z) 241.2 (M+1).

Step 4: 5-(2-Amino-3,3-dimethylcyclopentyl)-2-chloro-6-iodopyridin-3-ol (racemic cis) and 5-(2-Amino-3,3-dimethylcyclopentyl)-2-chloro-6-iodopyridin-3-ol (racemic trans)

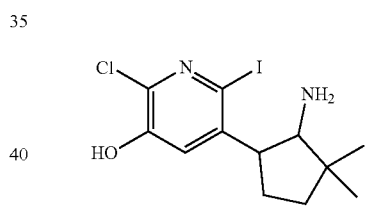

Iodine (2.29 g, 9.01 mmol) was added to a stirring mixture of 5-(2-amino-3,3-dimethylcyclopentyl)-2-chloropyridin-3-ol (2.17 g, 9.01 mmol) and potassium carbonate (3.74 g, 27.0 mmol) in water (40 mL). The mixture was stirred at room temperature for 2 hours. Solid sodium sulfite (2.39 g, 18.9 mmol) was added portion wise and the mixture stirred for 30 minutes. The aqueous mixture was adjusted to pH=~3 with 3N hydrochloric acid. The mixture was filtered. LC-MS showed the solid contained a small amount of product, but was discarded. The wash was concentrated to ~50 mL and injected onto a medium pressure reverse phase C18 ISCO column that was eluted with acetonitrile/water/0.1% formic acid/0% to 100% gradient. 2 sets of fractions were lyophilized separately.

Peak 1=5-(2-amino-3,3-dimethylcyclopentyl)-2-chloro-6-iodopyridin-3-ol (racemic trans) (1.17 g, 3.19 mmol, 35% yield). $^1$H NMR (400 MHz, DMSO-d$_6$) δ ppm 8.23 (s, 1H), 7.26 (s, 1H), 2.99-3.15 (m, 2H), 2.05-2.19 (m, 1H), 1.51-1.64 (m, 2H), 1.22-1.35 (m, 1H), 1.09 (s, 3H), 0.95 (s, 3H). LCMS(ES$^+$)(m/z): 367.1 (M+1).

Peak 2=5-(2-amino-3,3-dimethylcyclopentyl)-2-chloro-6-iodopyridin-3-ol (racemic cis contaminated with ~20% racemic trans) (924 mg, 2.01 mmol, 22% yield). $^1$H NMR (400 MHz, DMSO-d$_6$) δ ppm 8.27 (s, 1H), 7.20 (s, 1H), 3.41-3.53 (m, 1H), 3.28 (d, J=5.86 Hz, 1H), 2.07-2.19 (m, 1H), 1.81-1.95 (m, 1H), 1.68-1.77 (m, 1H), 1.47-1.57 (m, 1H), 1.14 (s, 3H), 1.08 (s, 3H). LCMS(ES⁺)(m/z): 367.1 (M+1).

Step 5: Ethyl 1-(5-(6-chloro-5-hydroxy-2-iodopyridin-3-yl)-2,2-dimethylcyclopentyl)-4-oxo-1,4-dihydropyridine-3-carboxylate (racemic cis)

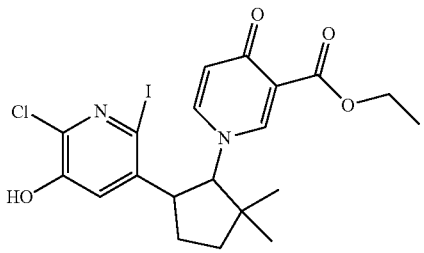 [SMILES: CCOC(=O)c1cn(C2C(c3cc(O)c(Cl)nc3I)CCC2(C)C)ccc1=O]

5-(2-Amino-3,3-dimethylcyclopenty)-2-chloro-6-iodopyridin-3-ol (racemic cis) (924 mg, 2.02 mmol) (contaminated with ~20% trans) and ethyl 4-oxo-4H-pyran-3-carboxylate (466 mg, 2.77 mmol) in acetic acid (13 mL) were stirred at 100° C. for 4 hours. The mixture was allowed to cool to room temperature, diluted with water, and extracted 2 times with dichloromethane. Brine was added to the aqueous phase and the mixture extracted 2 more times with dichloromethane. The combined organic layers were washed with brine, dried over sodium sulfate, and concentrated. The residue was purified by silica chromatography eluting with a gradient of 0% to 10% methanol in dichloromethane. Fractions were concentrated to give ethyl 1-(5-(6-chloro-5-hydroxy-2-iodopyridin-3-yl)-2,2-dimethylcyclopentyl)-4-oxo-1,4-dihydropyridine-3-carboxylate (racemic cis) (346 mg, 0.670 mmol, 33% yield). ¹H NMR (400 MHz, DMSO-d₆) δ ppm 10.92 (br. s., 1H), 7.78 (d, J=1.95 Hz, 1H), 7.43 (dd, J=7.81, 2.34 Hz, 1H), 7.07 (s, 1H), 6.04 (d, J=7.42 Hz, 1H), 4.54 (d, J=7.42 Hz, 1H), 4.03-4.17 (m, 2H), 3.82-3.95 (m, 1H), 2.15-2.27 (m, 2H), 1.99 (dt, J=13.66, 7.22 Hz, 1H), 1.74-1.87 (m, 1H), 1.24-1.31 (m, 3H), 1.14-1.23 (m, 3H), 0.92 (s, 3H). LCMS(ES+)(m/z): 517.1 (M+1).

Step 6: Ethyl 1-(5-(6-chloro-2-iodo-5-(3-methoxypropoxy)pyridin-3-yl)-2,2-dimethylcyclopentyl)-4-oxo-1,4-dihydropyridine-3-carboxylate (racemic cis)

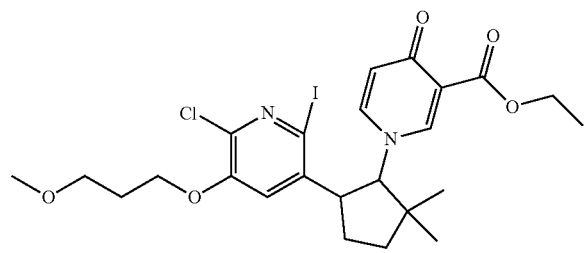 [SMILES: CCOC(=O)c1cn(C2C(c3cc(OCCCOC)c(Cl)nc3I)CCC2(C)C)ccc1=O]

Ethyl 1-(5-(6-chloro-5-hydroxy-2-iodopyridin-3-yl)-2,2-dimethylcyclopentyl)-4-oxo-1,4-dihydropyridine-3-carboxylate (racemic cis) (346 mg, 0.670 mmol), potassium carbonate (463 mg, 3.35 mmol), and 1-bromo-3-methoxypropane (205 mg, 1.34 mmol) in N,N-dimethylformamide (DMF) (5 mL) were stirred at room temperature overnight. The mixture was quenched with water and extracted 3 times with ethyl acetate. The combined organic layers were washed with brine and concentrated. The residue was purified by chromatography to give ethyl 1-(5-(6-chloro-2-iodo-5-(3-methoxypropoxy)pyridin-3-yl)-2,2-dimethylcyclopentyl)-4-oxo-1,4-dihydropyridine-3-carboxylate (341 mg, 0.579 mmol, 86% yield). LCMS(ES+)(m/z): 589.2 (M+1).

Step 7: Ethyl 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylate (racemic cis)

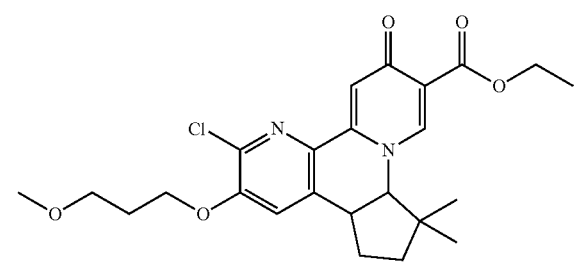 [SMILES: CCOC(=O)c1cn2c(cc1=O)-c1nc(Cl)c(OCCCOC)cc1C1CCC(C)(C)C12]

A septum-capped round bottom flask containing a stir bar, ethyl 1-(5-(6-chloro-2-iodo-5-(3-methoxypropoxy)pyridin-3-yl)-2,2-dimethylcyclopentyl)-4-oxo-1,4-dihydropyridine-3-carboxylate (341 mg, 0.579 mmol), potassium acetate (114 mg, 1.16 mmol), and palladium(II) bromide (30.8 mg, 0.116 mmol) was purged with nitrogen for 15 minutes. N,N-Dimethylacetamide (DMA) (5 mL) was purged with nitrogen for 5 minutes before being added to the reaction vessel. The reaction vessel was placed into an oil bath that was preheated to 90° C. and the mixture stirred for 4 hours. The reaction mixture was allowed to cool to room temperature, diluted with ethyl acetate, and filtered through a cotton plug. The mixture was washed with brine, dried over sodium sulfate, and concentrated. The residue was purified by silica chromatography eluting with a gradient of 0% to 10% methanol in dichloromethane. Fractions were concentrated. Desired product was isolated, but a significant amount of DMA remained. The product was further purified by medium pressure reverse phase chromatography (C18/acetonitrile/water/0.1% formic acid/10% to 100% gradient). Fractions were concentrated to give ethyl 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylate (racemic cis) (150 mg, 0.325 mmol, 56% yield). ¹H NMR (400 MHz, DMSO-d₆) δ ppm 8.21 (s, 1H), 7.55 (s, 1H), 7.00 (s, 1H), 4.43 (d, J=8.98 Hz, 1H), 4.15-4.31 (m, 4H), 3.79-3.88 (m, 1H), 3.47 (t, J=6.05 Hz, 2H), 3.23 (s, 3H), 2.27-2.38 (m, 1H), 2.12-2.25 (m, 1H), 1.99 (quin, J=6.15 Hz, 2H), 1.50-1.60 (m, 1H), 1.35-1.45 (m, 1H), 1.24 (t, J=7.22 Hz, 3H), 1.11 (s, 3H), 0.39 (s, 3H). LCMS(ES⁺) (m/z): 461.3 (M+1).

Step 8: 2-Chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (racemic cis)

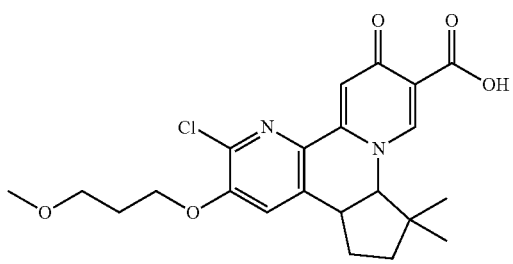 [SMILES: COCCCOc1cc2c(nc1Cl)-c1cc(=O)c(C(=O)O)cn1C1C2CCC1(C)C]

A solution of lithium hydroxide monohydrate (113 mg, 2.70 mmol) in water (2 mL) was added to a solution of ethyl 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylate (racemic cis) (150 mg, 0.270 mmol) in methanol (3 mL) and the mixture heated at 65° C. for 1 hour. The mixture was allowed to cool, diluted with water, acidified with 1 M HCl, and extracted 3 times with 2-methyltetrahydrofuran. The combined organic layers were washed with brine and concentrated. The residue was purified by silica chromatography eluting with a gradient of 0% to 10% methanol in dichloromethane. Fractions were concentrated to give 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid (racemic cis) (95 mg, 0.219 mmol, 81% yield) as a white solid. $^1$H NMR (400 MHz, DMSO-$d_6$) δ ppm 8.62 (s, 1H), 7.63 (s, 1H), 7.43 (s, 1H), 4.72 (d, J=9.37 Hz, 1H), 4.21-4.39 (m, 2H), 3.89-3.99 (m, 1H), 3.51 (t, J=6.05 Hz, 2H), 3.26 (s, 3H), 2.33-2.44 (m, 1H), 2.19-2.31 (m, 1H), 1.96-2.08 (m, 2H), 1.55-1.66 (m, 1H), 1.40-1.51 (m, 1H), 1.15 (s, 3H), 0.40 (s, 3H). LCMS(ES$^+$)(m/z): 433.3 (M+1).

Additional general synthetic protocols for making compounds as described herein are shown below in Scheme 15.

Scheme 15-Compounds of Type Compounds Wherein R10 is from Table 2)

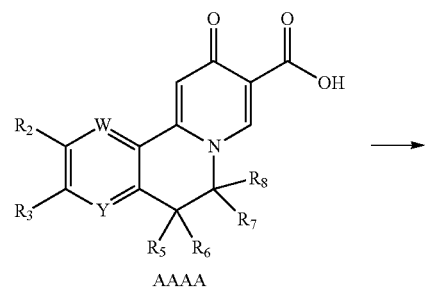

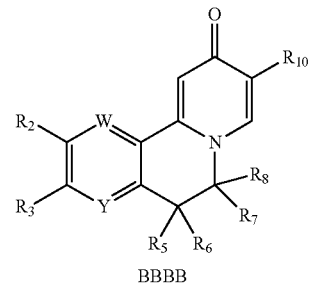

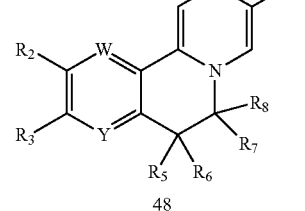

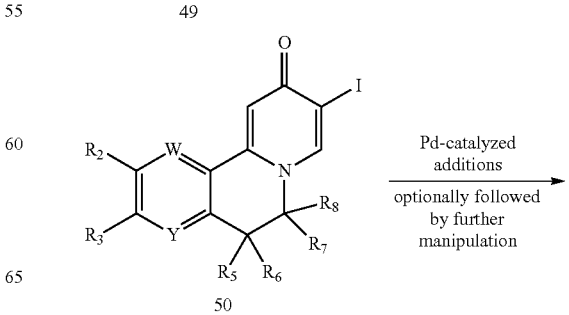

-continued

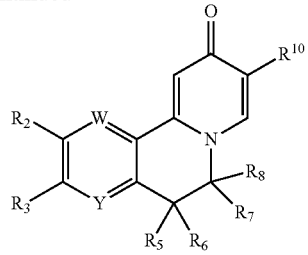

Biological Examples

Example 35—Compound Treatment in Primary Human Hepatocytes Infected with HBV

HBV-Ag Inhibitors

Vials of cryopreserved primary human hepatocytes were placed in a 37° C. water bath just until thawed. The cells were pooled, resuspended gently in differentiation medium (Williams medium containing differentiation supplement, GlutaMax-1™, and penicillin/streptomycin) and counted using a hemacytometer. The cells were pelleted by centrifugation at 1000×g for 10 min and resuspended to a density of $5.5 \times 10^5$ cells/mL in differentiation medium. 100 µL of cell suspension were plated in each well of collagen-coated 96-well plates. The plates were incubated at 37° C. and 5% $CO_2$ for 2 days prior to infection.

HBV stocks were prepared by ultrafiltration of media from HepG2.2.15 cell cultures. To prepare a working virus stock with a multiplicity of infection (MOI) of 100, HBV stock was added to differentiation medium containing 4% polyethylene glycol to achieve a concentration of $5.5 \times 10^7$ HBV DNA copies/mL. The cell media was replaced with 100 µL of the working virus stock in columns 1-11 and with differentiation medium in column 12. The plates were incubated at 37° C. and 5% $C_{O2}$ for approximately 24 hr.

Compounds were resuspended in DMSO and serially diluted 3-fold in DMSO to make a 10-point dilution series at 200× the final desired concentrations. Columns 11 and 12 contained DMSO. Using a Biomek FX, 2.5 µL of each compound dilution was stamped into 96-well U-bottom plates, making 3 copies. The compound plates were sealed and stored at −20° C. After equilibration to room temperature, the compound plates were diluted 200 fold with assay medium (differentiation medium plus 1 mM ABT). The media on the cell plates was replaced with 150 µL of the diluted compounds. The final highest compound concentration was 20 µM. The plates were incubated at 37° C. and 5% $CO_2$. The compound treatments were repeated at days 4 and 9 following the initial treatment. Readouts were done of HBsAg and HBeAg ELISAs at days 9 and 14.

At Days 9 after the initial treatment, the media was transferred from each cell plate to a U-bottom plate and stored at −80° C. At Day 14 after the initial treatment, the cell plates were washed once with PBS and stored at −80° C.

HBs Ag ELISA

Frozen plates containing the collected media were equilibrated to room temperature in a biosafety cabinet for approximately 30 min. The HBsAg ELISA kit was used according to the manufacturer's directions. Briefly, the ELISA plates and solutions were equilibrated to room temperature for approximately 1 hr and the plates were washed once with 300 µL 1× wash buffer. 100 µL 1× enzyme conjugate solution, 120 µL PBS containing 10% FBS, and 30 µL collected media were placed in each well. The assay plates were sealed and incubated at 37° C. for approximately 2 hr. The plates were washed 4 times with 195 mL 1× wash buffer and dried thoroughly inverted on paper towels. 195 µL of chromagen/substrate solution were added to each well and incubated at room temperature for approximately 5 min. 100 µL of stop solution were added to each well and the plates were read on a Molecular Devices SpectraMax® 384 Plus Microplate Reader at 450 nm. $IC_{50}$s were determined using GraphPad Prism: Four-parameter logistic curve with equation Y=Bottom+(Top-Bottom)/(1+10^((Log IC50−X)*HillSlope)).

HBe Ag ELISA

Frozen plates containing the collected media were equilibrated to room temperature in a biosafety cabinet for approximately 30 min. The HBeAg ELISA kit was used according to the manufacturer's directions. Briefly, the ELISA plates and solutions were equilibrated to room temperature for approximately 1 hr and the plates were washed once with 300 µL 1× wash buffer. 80 µL PBS containing 10% FBS, and 20 µL collected media were placed in each well. The assay plates were sealed and incubated at 37° C. for approximately 1 hr. The plates were washed twice with 300 mL 1× wash buffer and dried thoroughly inverted on paper towels. 100 µL 1× enzyme conjugate solution was placed in each well. The assay plates were sealed and incubated at 37° C. for at least 1 hr. The plates were washed 3 times with 300 mL 1× wash buffer and dried thoroughly inverted on paper towels. 100 µL chromagen/substrate solution were added to each well and incubated at room temperature for approximately 5 min. 100 µL of stop solution were added to each well and the plates were read on a Molecular Devices SpectraMax 384 Plus Microplate Reader at 450 nm.

Data Analysis $IC_{50}$S were determined using GraphPad Prism: Four-parameter logistic curve with equation Y=Bottom+(Top-Bottom)/(1+10^((Log IC50−X)*HillSlope)). $IC_{50}$ values for 50% reduction in HBs and HBe antigens for tested compounds are shown in Table 1 for days 9 and 14. As can be seen from the $IC_{50}$ values, the tested compounds exhibited 50% inhibition of HBe and HBs antigens at values between less than ~0.22 µM and 0.0069 µM.

The embodiments of the invention described above are intended to be merely exemplary; numerous variations and modifications will be apparent to those skilled in the art. All such variations and modifications are intended to be within the scope of the present invention as defined in any appended claims.

Example 36 HepAD38 Cells—HBsAg ELISA and Cytotoxicity Assays

HepAD38 cells are maintained in collagen-coated flasks in cell culture medium (DMEM/F12 containing 10% fetal bovine serum (FBS), GlutaMax-1, penicillin/streptomycin, non-essential amino acids, Na pyruvate, 250 µg/mL geneticin, and 1 µg/mL doxycycline). Compound solutions are prepared in DMSO and compound are serially diluted for final concentrations of 4000, 1000, 250, 62.5, 15.6, 3.91, 0.977, 0.244, 0.061, and 0.015 ηM. The cells are then trypsinized and the cells are plate at 10,000 cells per well. Incubate plates are incubated at 37° C., 5% $CO_2$ for 4 days. Media is replaced with new media with compound treatment. The plates are then incubated at 37° C., 5% $CO_2$ for an additional 3 days for a total treatment time of 7 days. For antiviral response, HBsAg was measured using the HBsAg ELISA kit (International Immuno-diagnostics) with instructions provided. 100 uL of cell media samples was used for ELISA. The absorbance was read on the Spectramax® 384 plate reader (Molecular Devices) at 450 nm. For cell toxicity, the cells were used for CellTiter-Glo® Luminescent Cell Viability Assay reagent (Promega). The luminescence was read on Envision Multilabel Reader (Perkin Elmer). The data was analyzed compared to the DMSO control.

% inhibition=(1−(unknown/high control))*100

The average % inhibition values from duplicate assay plates are then plotted in GraphPad Prism to determine one IC value: Four-parameter logistic curve with equation Y=Bottom+(Top−Bottom)/(1+10^((Log IC50−X)*Hill-Slope))

$pIC_{50} = \log(-IC_{50} \text{ in M})$

TABLE 1

| Example/ Scheme No. | Compound No. | Structure | Name |
|---|---|---|---|
| 1 | 220 | 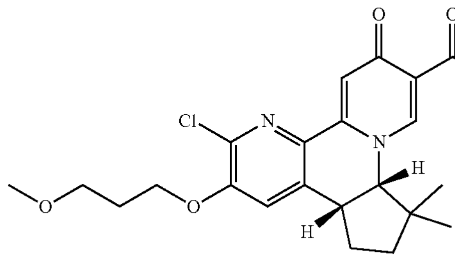 | (4bR,7aS)-2-chloro-3-(3-methoxypropoxy)-7,7-dimethyl-11-oxo-4b,5,6,7,7a, 11-hexahydrocyclopenta[f]pyrido[1,2-h][1,7]naphthyridine-10-carboxylic acid |
| 2 | 221 | 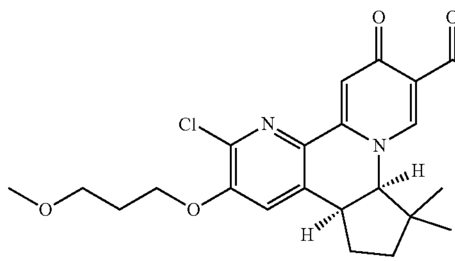 | (4bS,7aR)-2-Chloro-3-(3-methoxypropoxy)-7,7-dimethyl-11-oxo-4b,5,6,7,7a, 11-hexahydrocyclopenta[f]pyrido[1,2-h][1,7]naphthyridine-10-carboxylic acid |
| 3 | 222 | 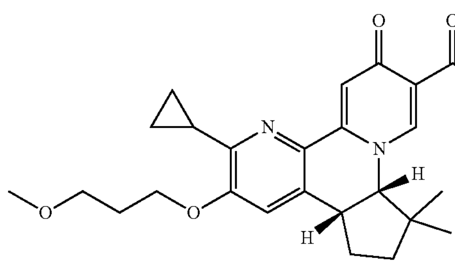 | (4bR,7aS)-2-Cyclopropyl-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid |
| 4 | 223 | 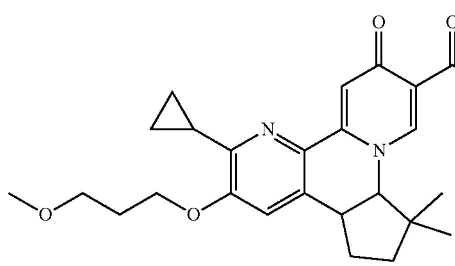 | 2-Cyclopropyl-3-(3-methoxypropoxy)-7,7-dimethyl-11-oxo-4b,5,6,7,7a, 11-hexahydrocyclopenta[f]pyrido[1,2-h][1,7]naphthyridine-10-carboxylic acid (racemic cis) |
| 5 | 224 | 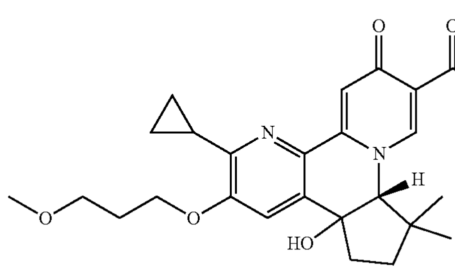 | (7aR)-2-Cyclopropyl-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid |

TABLE 1-continued

| Example/ Scheme No. | Compound No. | Structure | Name |
|---|---|---|---|
| 6 | 225 | 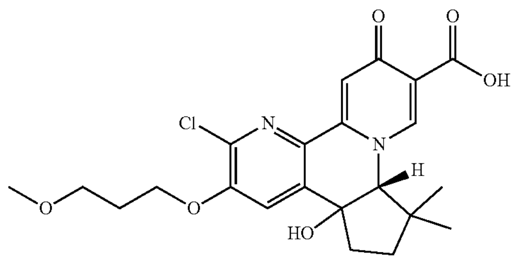 [SMILES: COCCCOc1cc2c(nc1Cl)-c1cc(=O)c(C(=O)O)cn1[C@@H]1C(C)(C)CCC21O] | (7aR)-2-Chloro-4b-hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid |
| 7 | 226 | 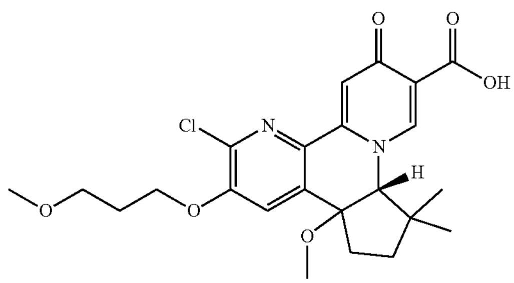 [SMILES: COCCCOc1cc2c(nc1Cl)-c1cc(=O)c(C(=O)O)cn1[C@@H]1C(C)(C)CCC21OC] | (7aR)-2-Chloro-4b-methoxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid |
| 8 | 227 | 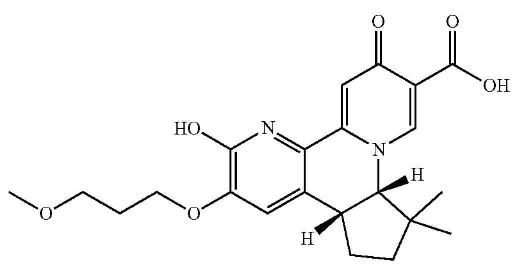 [SMILES: COCCCOc1cc2c(nc1O)-c1cc(=O)c(C(=O)O)cn1[C@H]1[C@@H]2CCC1(C)C] | (4bR,7aS)-2-Hydroxy-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid |
| 9 | 228 | 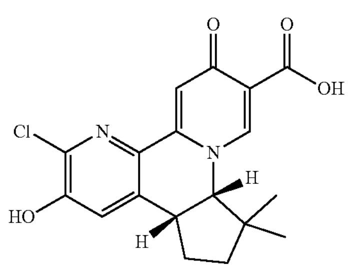 [SMILES: CC1(C)CC[C@@H]2c3cc(O)c(Cl)nc3-c3cc(=O)c(C(=O)O)cn3[C@@H]21] | (4bR,7aS)-2-Chloro-3-hydroxy-7,7-dimethyl-11-oxo-4b,5,6,7,7a,11-hexahydrocyclopenta[f]pyrido[1,2-h][1,7]naphthyridine-10-carboxylic acid |
| 10 | 229 | 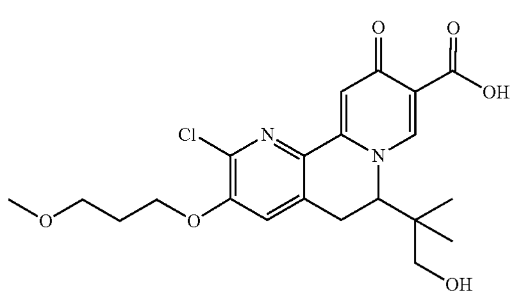 [SMILES: COCCCOc1cc2c(nc1Cl)-c1cc(=O)c(C(=O)O)cn1C(C(C)(C)CO)C2] | 2-Chloro-6-(1-hydroxy-2-methylpropan-2-yl)-3-(3-methoxypropoxy)-10-oxo-6,10-dihydro-5H-pyrido[1,2-h][1,7]naphthyridine-9-carboxylic acid |

TABLE 1-continued

| Example/Scheme No. | Compound No. | Structure | Name |
|---|---|---|---|
| 11 | 230 | 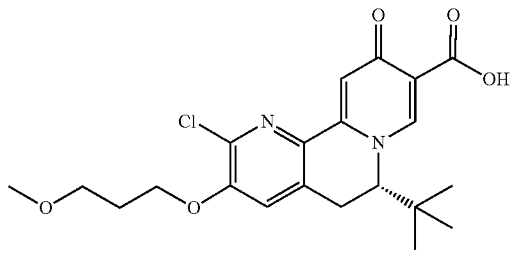 [SMILES: COCCCOc1cc2c(nc1Cl)-c1cc(=O)c(C(=O)O)cn1[C@H](C(C)(C)C)C2] | (S)-6-(tert-butyl)-2-chloro-3-(3-methoxypropoxy)-10-oxo-6, 10-dihydro-5H-pyrido[1,2-h][1,7]naphthyridine-9-carboxylic acid |
| 12 | 231 | 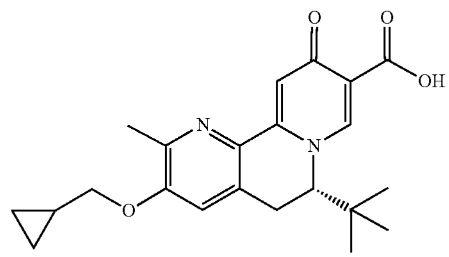 [SMILES: Cc1nc2c(cc1OCC1CC1)C[C@@H](C(C)(C)C)n1cc(C(=O)O)c(=O)cc1-2] | (S)-6-(tert-butyl)-3-(cyclopropylmethoxy)-2-methyl-10-oxo-6, 10-dihydro-5H-pyrido[1,2-h][1,7]naphthyridine-9-carboxylic acid |
| 13 | 232 | 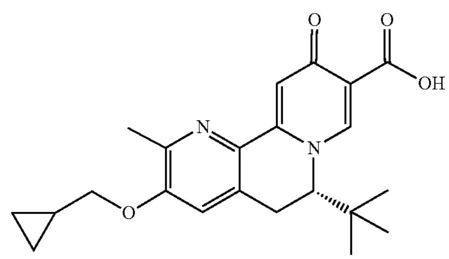 [SMILES: Cc1nc2c(cc1OCC1CC1)C[C@@H](C(C)(C)C)n1cc(C(=O)O)c(=O)cc1-2] | (S)-6-(tert-butyl)-3-(3-methoxypropoxy)-2-methyl-10-oxo-6, 10-dihydro-5H-pyrido[1,2-h][1,7]naphthyridine-9-carboxylic acid |
| 14 | 233 | 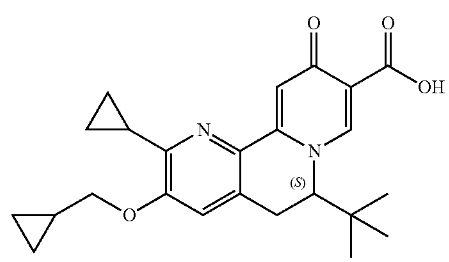 | (S)-6-(tert-butyl)-2-cyclopropyl-3-(cyclopropylmethoxy)-10-oxo-6, 10-dihydro-5H-pyrido[1,2-h][1,7]naphthyridine-9-carboxylic acid |
| 15 | 234 | 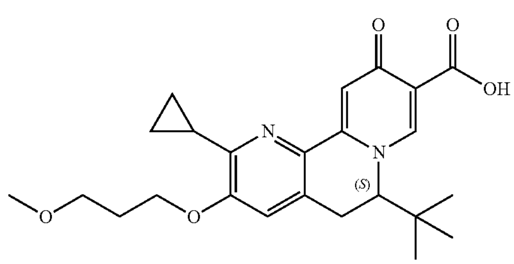 | (S)-6-(tert-butyl)-2-cyclopropyl-3-(3-methoxypropoxy)-10-oxo-6, 10-dihydro-5H-pyrido[1,2-h][1,7]naphthyridine-9-carboxylic acid |
| 16 | 235 | 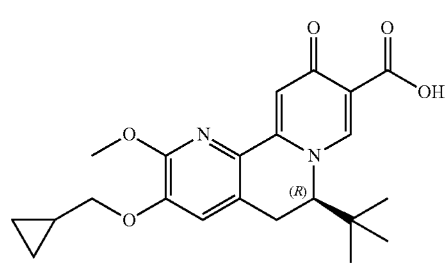 | (R)-6-(tert-butyl)-3-(cyclopropylmethoxy)-2-methoxy-10-oxo-6, 10-dihydro-5H-pyrido[1,2-h][1,7]naphthyridine-9-carboxylic acid |

TABLE 1-continued

| Example/Scheme No. | Compound No. | Structure | Name |
|---|---|---|---|
| 17 | 236 | 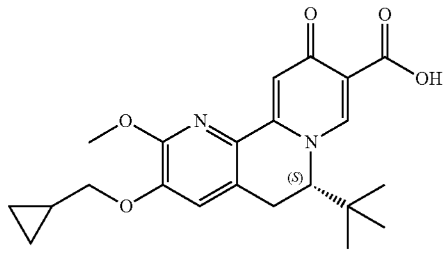 | (S)-6-(tert-butyl)-3-(cyclopropylmethoxy)-2-methoxy-10-oxo-6, 10-dihydro-5H-pyrido[1,2-h][1,7]naphthyridine-9-carboxylic acid |
| 18 | 237 | 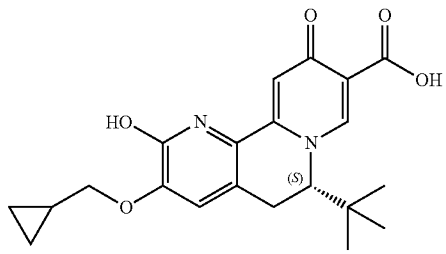 | (S)-6-(tert-butyl)-3-(cyclopropylmethoxy)-2-hydroxy-10-oxo-6, 10-dihydro-5H-pyrido[1,2-h][1,7]naphthyridine-9-carboxylic acid |
| 19 | 238 | 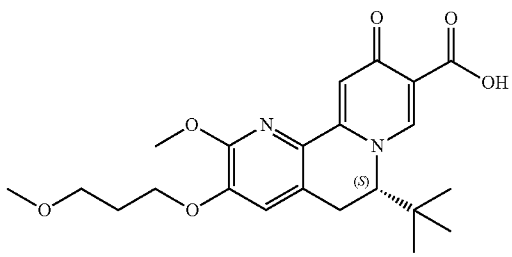 | (S)-6-(tert-butyl)-2-methoxy-3-(3-methoxypropoxy)-10-oxo-6, 10-dihydro-5H-pyrido[1,2-h][1,7]naphthyridine-9-carboxylic acid |
| 20 | 239 | 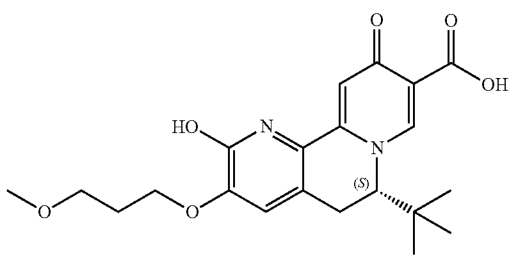 | (S)-6-(tert-butyl)-2-hydroxy-3-(3-methoxypropoxy)-10-oxo-6, 10-dihydro-5H-pyrido[1,2-h][1,7]naphthyridine-9-carboxylic acid |
| 21 | 240 | 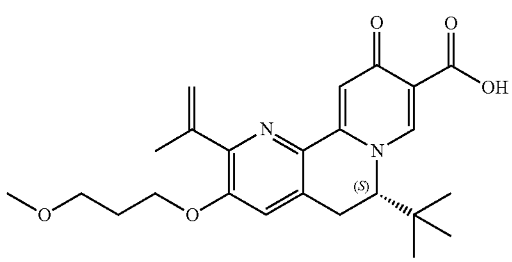 | (S)-6-(tert-butyl)-3-(3-methoxypropoxy)-10-oxo-2-(prop-1-en-2-yl)-6, 10-dihydro-5H-pyrido[1,2-h][1,7]naphthyridine-9-carboxylic acid |
| 22 | 24 | 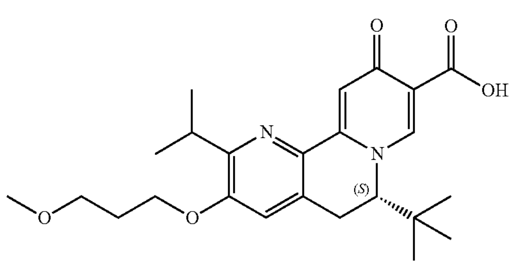 | (S)-6-(tert-butyl)-2-isopropyl-3-(3-methoxypropoxy)-10-oxo-6, 10-dihydro-5H-pyrido[1,2-h][1,7]naphthyridine-9-carboxylic acid |

TABLE 1-continued

| Example/ Scheme No. | Compound No. | Structure | Name |
|---|---|---|---|
| 23 | 242 | 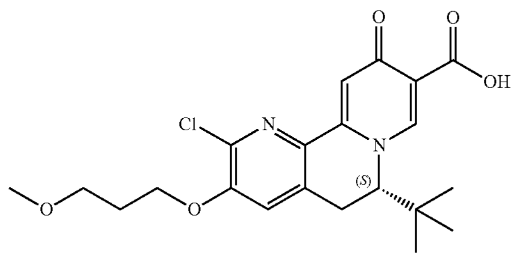 | (S)-6-(tert-butyl)-2-chloro-3-(3-methoxypropoxy)-8-methyl-10-oxo-6, 10-dihydro-5H-pyrido[1,2-h][1,7]naphthyridine-9-carboxylic acid |
| 24 | 243 | 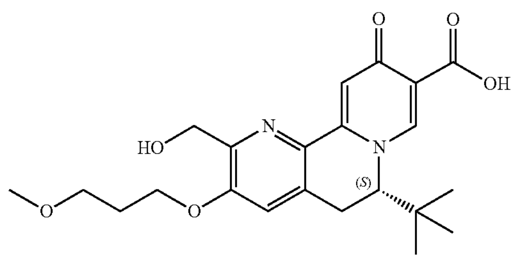 | (S)-6-(tert-butyl)-2-(hydroxymethyl)-3-(3-methoxypropoxy)-10-oxo-5, 10-dihydro-6H-pyrido[1,2-h][1,7]naphthyridine-9-carboxylic acid |
| 25 | 244 | 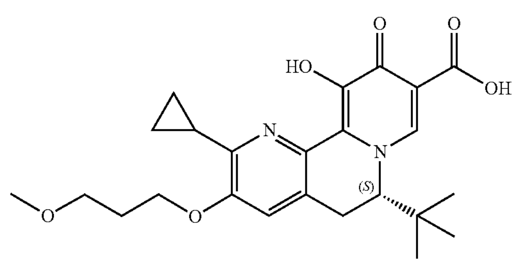 | (S)-6-(tert-butyl)-2-cyclopropyl-11-hydroxy-3-(3-methoxypropoxy)-10-oxo-5, 10-dihydro-6H-pyrido[1,2-h][1,7]naphthyridine-9-carboxylic acid |
| 26 | 245 | isomer 1 | (2-chloro-3-(cyclopropylmethoxy)-6-isopropyl-6-methyl-10-oxo-5, 10-dihydro-6H-pyrido[1,2-h][1,7]naphthyridine-9-carboxylic acid |
| 27 | 246 | isomer 2 | (2-chloro-3-(cyclopropylmethoxy)-6-isopropyl-6-methyl-10-oxo-5,10-dihydro-6H-pyrido[1,2-h][1,7]naphthyridine-9-carboxylic acid |

TABLE 1-continued

| Example/Scheme No. | Compound No. | Structure | Name |
|---|---|---|---|
| 28 | 247 | 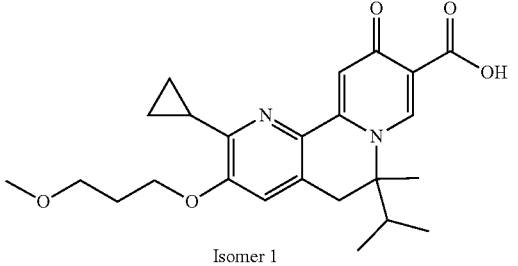 [SMILES: COCCCOc1cc2c(nc1C1CC1)-c1cc(=O)c(C(=O)O)cn1C(C)(C(C)C)C2] Isomer 1 | 2-cyclopropyl-6-isopropyl-3-(3-methoxypropoxy)-6-methyl-10-oxo-5,10-dihydro-6H-pyrido[1,2-h][1,7]naphthyridine-9-carboxylic acid |
| 29 | 248 | 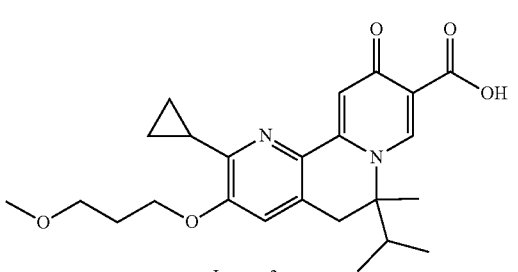 Isomer 2 | 2-cyclopropyl-6-isopropyl-3-(3-methoxypropoxy)-6-methyl-10-oxo-5,10-dihydro-6H-pyrido[1,2-h][1,7]naphthyridine-9-carboxylic acid |
| 30 | 249 | 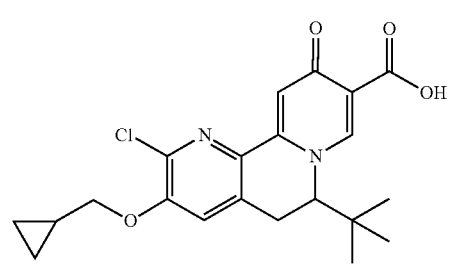 [SMILES: CC(C)(C)C1Cc2cc(OCC3CC3)c(Cl)nc2-c2cc(=O)c(C(=O)O)cn21] | 6-(tert-butyl)-2-chloro-3-(cyclopropylmethoxy)-10-oxo-6,10-dihydro-5H-pyrido[1,2-h][1,7]naphthyridine-9-carboxylic acid (isomers 1 and 2) |
| 31 | 250 | 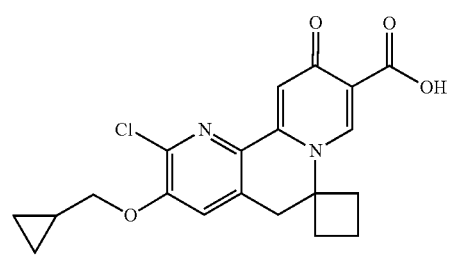 [SMILES: O=C(O)c1cn2c(cc1=O)-c1nc(Cl)c(OCC3CC3)cc1CC21CCC1] | 2'-Chloro-3'-(cyclopropylmethoxy)-10'-oxo-5',10'-dihydrospiro[cyclobutane-1,6'-pyrido[1,2-h][1,7]naphthyridine]-9'-carboxylic acid |
| 32 | 251 | 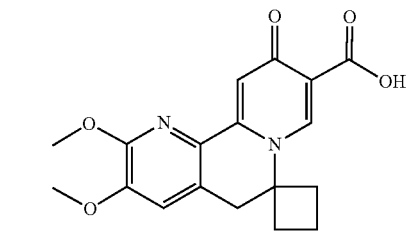 | 2',3'-Dimethoxy-10'-oxo-5',10'-dihydrospiro[cyclobutane-1,6'-pyrido[1,2-h][1,7]naphthyridine]-9'-carboxylic acid |

TABLE 1-continued

| Example/ Scheme No. | Compound No. | Structure | Name |
|---|---|---|---|
| 33 | 252 | 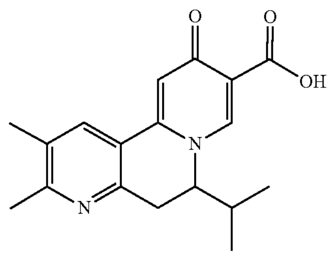 [SMILES: Cc1cc2c(nc1C)CC(C(C)C)n1cc(C(=O)O)c(=O)cc1-2] | 6-Isopropyl-2,3-dimethyl-10-oxo-5, 10-dihydro-6H-pyrido[2, 1-f][1,6]naphthyridine-9-carboxylic acid |
| 34 | 253 | 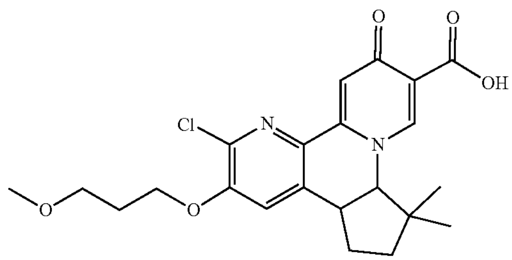 [SMILES: COCCCOc1cc2c(nc1Cl)-c1cc(=O)c(C(=O)O)cn1C1C2CCC1(C)C] | 2-chloro-3-(3-methoxypropoxy)-7,7-dimethyl-11-oxo-4b,5,6,7,7a,11-hexahydrocyclopenta[f]pyrido[1,2-h][1,7]naphthyridine-10-carboxylic acid |
| 35 | 254 | 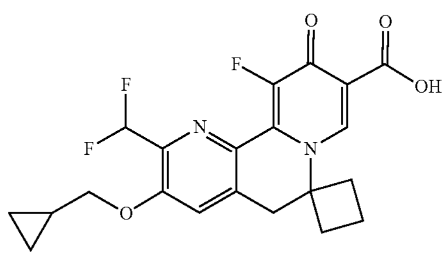 [SMILES: O=C(O)c1cn2c(c(F)c1=O)-c1nc(C(F)F)c(OCC3CC3)cc1CC21CCC1] | 3'-(cyclopropylmethoxy)-2'-(difluoromethyl)-11'-fluoro-10'-oxo-5', 10'-dihydrospiro[cyclobutane-1,6'-pyrido[1,2-h][1,7]naphthyridine]-9'-carboxylic acid |
| 36 | 255 | 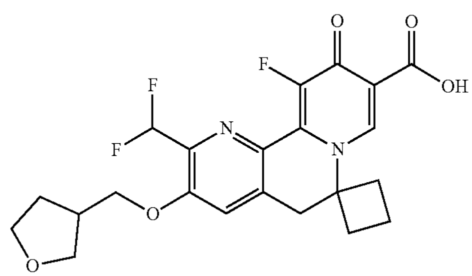 [SMILES: O=C(O)c1cn2c(c(F)c1=O)-c1nc(C(F)F)c(OCC3CCOC3)cc1CC21CCC1] | 2'-(difluoromethyl)-11'-fluoro-10'-oxo-3'-((tetrahydrofuran-3-yl)methoxy)-5', 10'-dihydrospiro[cyclobutane-1,6'-pyrido[1,2-h][1,7]naphthyridine]-9'-carboxylic acid |
| 37 | 256 | 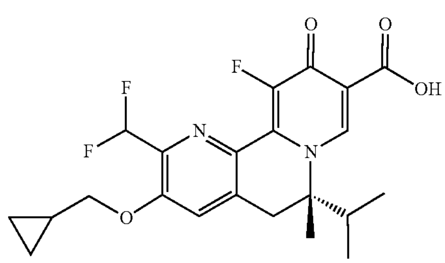 [SMILES: CC(C)[C@]1(C)Cc2cc(OCC3CC3)c(C(F)F)nc2-c2c(F)c(=O)c(C(=O)O)cn21] | (S)-3-(cyclopropylmethoxy)-2-(difluoromethyl)-11-fluoro-6-isopropyl-6-methyl-10-oxo-6,10-dihydro-5H-pyrido[1,2-h][1,7]naphthyridine-9-carboxylic acid |

TABLE 1-continued

| Example/ Scheme No. | Compound No. | Structure | Name |
|---|---|---|---|
| 38 | 257 | 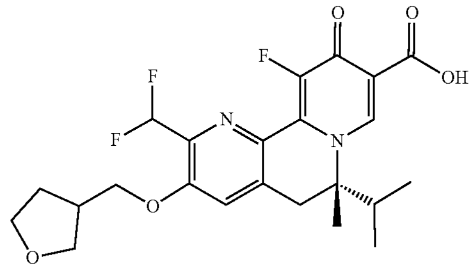 [SMILES: CC(C)[C@]1(C)Cc2cc(OCC3CCOC3)c(C(F)F)nc2-c2c(F)c(=O)c(C(=O)O)cn21] | (6S)-2-(difluoromethyl)-11-fluoro-6-isopropyl-6-methyl-10-oxo-3-((tetrahydrofuran-3-yl)methoxy)-6,10-dihydro-5H-pyrido[1,2-h][1,7]naphthyridine-9-carboxylic acid |

TABLE 2

TABLE 2-continued

| $R^{10} =$ | $R^{10} =$ | $R^{10} =$ | $R^{10} =$ |
|---|---|---|---|

TABLE 2-continued
| $R^{10} =$ | $R^{10} =$ | $R^{10} =$ | $R^{10} =$ |
|---|---|---|---|
| 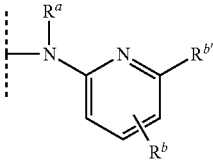 | 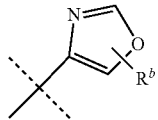 | 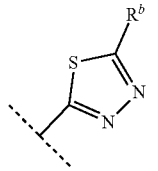 | 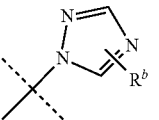 |
| 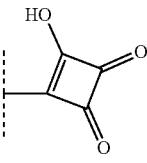 | 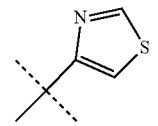 | 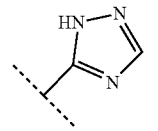 | 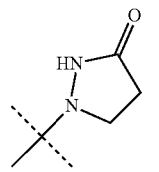 |
| 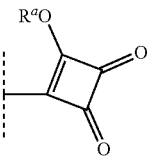 | 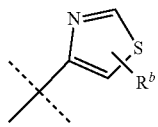 | 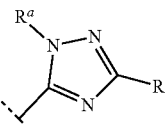 | 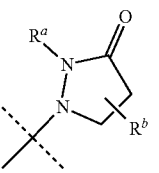 |
| 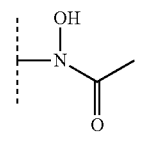 | 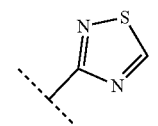 | 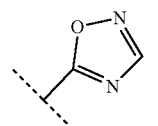 | 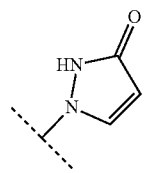 |
| 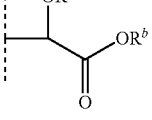 | 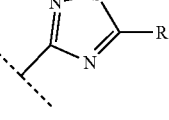 | 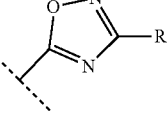 | 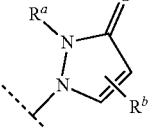 |
| ‡ ($R^9$ forms an oxaborole ring with position $R^{10}$ of the pyridine ring) 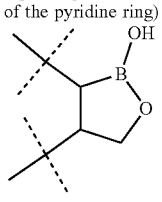 | 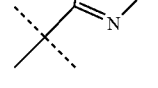 | 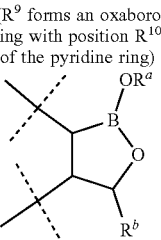 | 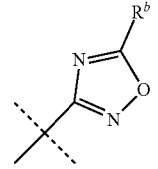 |
| ‡ ($R^9$ forms an oxaborole ring with position $R^{10}$ of the pyridine ring) 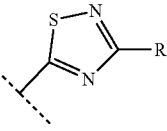 | 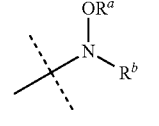 | 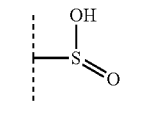 | 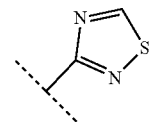 |
| 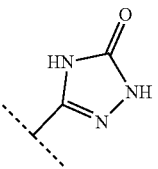 | 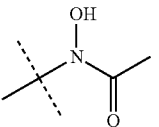 | 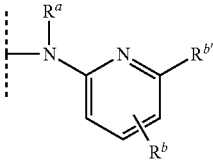 | 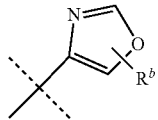 |

TABLE 2-continued

| $R^{10} =$ | $R^{10} =$ | $R^{10} =$ | $R^{10} =$ |
|---|---|---|---|

TABLE 2-continued

| $R^{10} =$ | $R^{10} =$ | $R^{10} =$ | $R^{10} =$ |
|---|---|---|---|

—CO$_2$H     —B(OH)$_2$     —NHSO$_2$R$^{25'}$     —NHSO$_2$R$^{25}$ wherein R$^a$, R$^{a'}$ and R$^{a''}$ are independently selected from hydroxy, alkyl or substituted alkyl, cycloalkyl or substituted cycloalkyl, heterocycloalkyl or substituted heterocycloalkyl, aryl or substituted aryl, heteroaryl or substituted heteroaryl; with the proviso that R$^a$ is not hydroxy when linked to an oxygen group R$^b$, R$^{b'}$ and R$^{b''}$ are independently selected from hydrogen, halo, hydroxy, alkyl or substituted alkyl, alkoxy or substituted alkoxy, cycloalkyl or substituted cycloalkyl, heterocycloalkyl or substituted heterocycloalkyl, thio or thioalkyl, amino or substituted amino, aryl or substituted aryl, heteroaryl or substituted aryl;

R$^{25}$ and R$^{25'}$ are independently selected from H, OH, alkyl or substituted alkyl, cycloalkyl or substituted cycloalkyl, alkenyl or substituted alkenyl, heterocycloalkyl or substituted heterocycloalkyl, aryl or substituted aryl and heteroaryl or substituted heteroaryl;

and wherein the above substituents for R$^{10}$ may exist as tautomers of the structures shown.

TABLE 3

Hep AD38, HBsAg and Cell tox Data - EC$_{50}$ ($\eta$M)

| Example No. | Compound No. | HepAD38, HBsAg (EC50, µM) | Cell tox (EC$_{50}$, $\eta$M) |
|---|---|---|---|
| 1 | 220 | ++++ | − |
| 2 | 221 | ++ | − |
| 3 | 222 | ++++ | − |
| 4 | 223 | ++++ | − |
| 5 | 224 | +++ | − |

TABLE 3-continued

Hep AD38, HBsAg and Cell tox Data - EC$_{50}$ ($\eta$M)

| Example No. | Compound No. | HepAD38, HBsAg (EC50, μM) | Cell tox (EC$_{50}$, $\eta$M) |
|---|---|---|---|
| 6 | 225 | ++ | − |
| 7 | 226 | ++ | − |
| 8 | 227 | + | − |
| 9 | 228 | + | − |
| 10 | 229 | +++ | − |

TABLE 3-continued

Hep AD38, HBsAg and Cell tox Data - EC$_{50}$ ($\eta$M)

| Example No. | Compound No. | HepAD38, HBsAg (EC50, μM) | Cell tox (EC$_{50}$, $\eta$M) |
|---|---|---|---|
| 11 | 230 | ++++ | – |
| 12 | 231 | ++++ | – |
| 13 | 232 | ++++ | – |
| 14 | 233 | ++++ | – |
| 15 | 234 | ++++ | – |

TABLE 3-continued

Hep AD38, HBsAg and Cell tox Data - EC$_{50}$ ($\eta$M)

| Example No. | Compound No. | HepAD38, HBsAg (EC50, μM) | Cell tox (EC$_{50}$, $\eta$M) |
|---|---|---|---|
| 16 | 235 | + | − |
| 17 | 236 | ++++ | − |
| 18 | 237 | + | − |
| 19 | 238 | ++++ | − |
| 20 | 239 | + | − |

TABLE 3-continued

Hep AD38, HBsAg and Cell tox Data - EC$_{50}$ ($\eta$M)

| Example No. | Compound No. | HepAD38, HBsAg (EC50, μM) | Cell tox (EC$_{50}$, $\eta$M) |
|---|---|---|---|
| 21 | 240 | ++++ | − |
| 22 | 241 | ++++ | − |
| 23 | 242 | + | − |
| 24 | 243 | +++ | − |
| 25 | 244 | ++++ | − |

TABLE 3-continued

Hep AD38, HBsAg and Cell tox Data - EC$_{50}$ ($\eta$M)

| Example No. | Compound No. | HepAD38, HBsAg (EC50, μM) | Cell tox (EC$_{50}$, $\eta$M) |
|---|---|---|---|
| 26 | isomer 1<br>245 | +++ | − |
| 27 | isomer 2<br>246 | + | − |
| 28 | Isomer 1<br>247 | ++++ | − |
| 29 | Isomer 2<br>248 | ++ | − |

TABLE 3-continued
Hep AD38, HBsAg and Cell tox Data - EC$_{50}$ ($\eta$M)
| Example No. | Compound No. | HepAD38, HBsAg (EC50, μM) | Cell tox (EC$_{50}$, $\eta$M) |
|---|---|---|---|
| 30 | 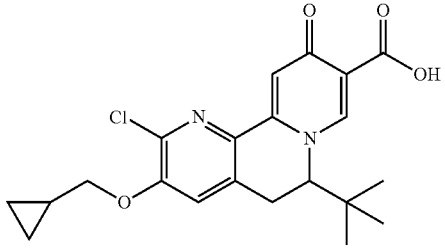<br>(racemate)<br>249-R (racemate) | +++ | – |
| 30-A | 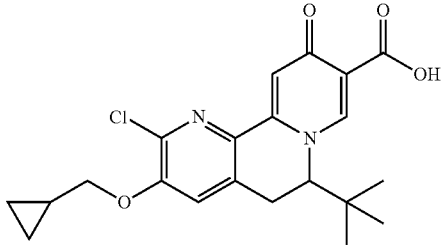<br>isomer 1<br>249 | ++++ | – |
| 30-B | 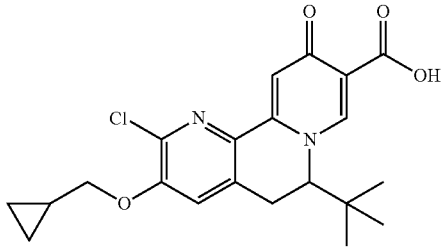<br>isomer 2<br>249 | + | – |
| 31 | 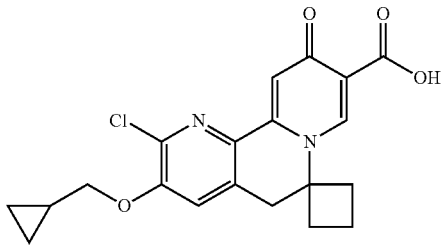 [SMILES: O=C(O)c1cn2c(cc1=O)-c1nc(Cl)c(OCC3CC3)cc1CC21CCC1]<br>250 | +++ | – |
| 32 | 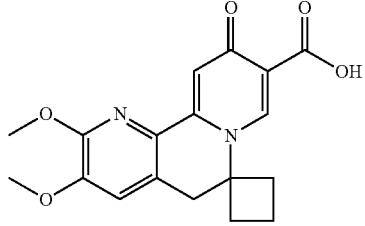 [SMILES: COc1cc2c(nc1OC)-c1cc(=O)c(C(=O)O)cn1C1(CCC1)C2]<br>251 | ++ | – |

TABLE 3-continued

Hep AD38, HBsAg and Cell tox Data - EC$_{50}$ ($\eta$M)

| Example No. | Compound No. | HepAD38, HBsAg (EC50, µM) | Cell tox (EC$_{50}$, $\eta$M) |
|---|---|---|---|
| 33 | 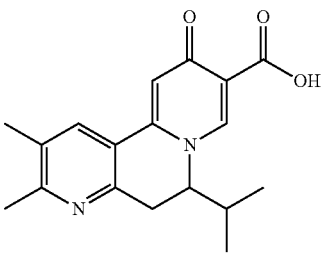 [SMILES: Cc1cc2c(nc1C)CC(C(C)C)n1cc(C(=O)O)c(=O)cc1-2]<br>252 | + | − |
| 34 | 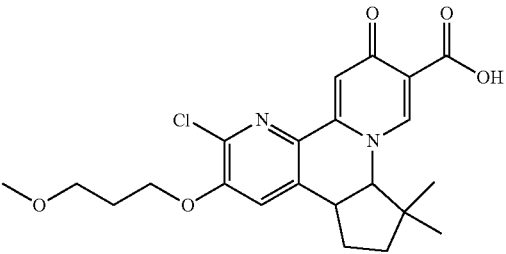 [SMILES: COCCCOc1cc2c(nc1Cl)-c1cc(=O)c(C(=O)O)cn1C1C2CCC1(C)C]<br>253 | ++++ | − | wherein:
− (cell tox) >4000 $\eta$M (4 µM)
+ ≥0.1 µM
++ <0.1 µM, and ≥0.01 µM
+++ <0.01 µM, and ≥0.001 µM
++++ <0.001 µM

What is claimed is:

1. A compound having the structure:

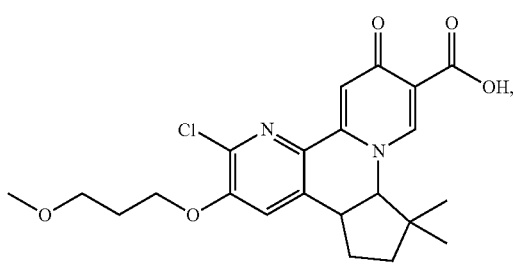 [SMILES: COCCCOc1cc2c(nc1Cl)-c1cc(=O)c(C(=O)O)cn1C1C2CCC1(C)C]

or a pharmaceutically acceptable salt thereof.

2. A compound having the structure:

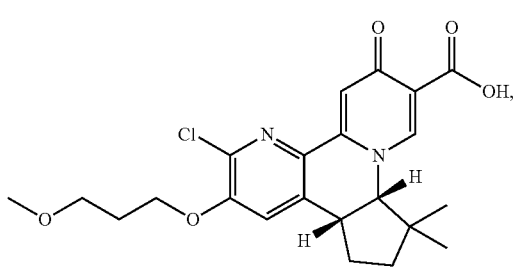 [SMILES: COCCCOc1cc2c(nc1Cl)-c1cc(=O)c(C(=O)O)cn1[C@H]1[C@@H]2CCC1(C)C]

or a pharmaceutically acceptable salt thereof.

3. The compound of claim 2, having the structure:

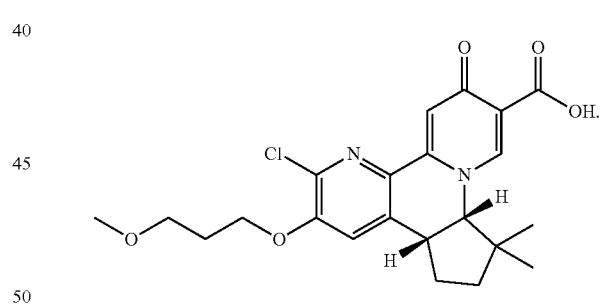

4. A method of treating a hepatitis B virus infection in a subject in need thereof, comprising administering to the subject the compound of claim 1 or a pharmaceutically acceptable salt thereof.

5. A method of treating a hepatitis B virus infection in a subject in need thereof, comprising administering to the subject the compound of claim 2 or a pharmaceutically acceptable salt thereof.

6. A method of treating a hepatitis B virus infection in a subject in need thereof, comprising administering to the subject the compound of claim 3.

7. A pharmaceutical composition comprising a pharmaceutically acceptable diluent and the compound of claim 1 or a pharmaceutically acceptable salt thereof.

8. A pharmaceutical composition comprising a pharmaceutically acceptable diluent and the compound of claim 2 or a pharmaceutically acceptable salt thereof.

9. A pharmaceutical composition comprising a pharmaceutically acceptable diluent and the compound of claim 3.

* * * * *

UNITED STATES PATENT AND TRADEMARK OFFICE
CERTIFICATE OF CORRECTION

| | |
|---|---|
| PATENT NO. | : 12,221,444 B2 |
| APPLICATION NO. | : 17/509769 |
| DATED | : February 11, 2025 |
| INVENTOR(S) | : Catalano et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 705 days.

Signed and Sealed this
Third Day of February, 2026

John A. Squires
*Director of the United States Patent and Trademark Office*